(12) United States Patent
Gall et al.

(10) Patent No.: US 9,725,738 B2
(45) Date of Patent: Aug. 8, 2017

(54) AFFENADENOVIRUS (GORILLA) OR ADENOVIRAL VECTORS AND METHODS OF USE

(71) Applicant: GenVec, Inc., Gaithersburg, MD (US)

(72) Inventors: Jason G. D. Gall, Germantown, MD (US); Duncan McVey, Derwood, MD (US); Douglas E. Brough, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 14/992,152

(22) Filed: Jan. 11, 2016

(65) Prior Publication Data

US 2016/0122781 A1    May 5, 2016

Related U.S. Application Data

(62) Division of application No. 14/349,421, filed as application No. PCT/US2012/058956 on Oct. 5, 2012, now Pat. No. 9,233,153.

(60) Provisional application No. 61/543,638, filed on Oct. 5, 2011.

(51) Int. Cl.
| | |
|---|---|
| C12N 15/86 | (2006.01) |
| C12N 7/00 | (2006.01) |
| A61K 39/155 | (2006.01) |
| C07K 14/005 | (2006.01) |
| A61K 48/00 | (2006.01) |

(52) U.S. Cl.
CPC ............ *C12N 15/86* (2013.01); *A61K 39/155* (2013.01); *C07K 14/005* (2013.01); *C12N 7/00* (2013.01); *A61K 48/00* (2013.01); *C12N 2710/10043* (2013.01); *C12N 2710/10322* (2013.01); *C12N 2710/10333* (2013.01); *C12N 2710/10343* (2013.01)

(58) Field of Classification Search
CPC .................. C07K 14/005; C12N 15/86; C12N 2710/10322; C12N 2710/10333; C12N 2710/10343; C12N 7/00
See application file for complete search history.

(56) References Cited

U.S. PATENT DOCUMENTS

| | | | |
|---|---|---|---|
| 5,837,511 A | 11/1998 | Falck-Pedersen et al. | |
| 5,851,806 A | 12/1998 | Kovesdi et al. | |
| 5,994,106 A | 11/1999 | Kovesdi et al. | |
| 5,994,128 A | 11/1999 | Fallaux et al. | |
| 5,998,205 A | 12/1999 | Hallenbeck et al. | |
| 6,033,908 A | 3/2000 | Bout et al. | |
| 6,127,175 A | 10/2000 | Vigne et al. | |
| 6,225,289 B1 | 5/2001 | Kovesdi et al. | |
| 6,482,616 B1 | 11/2002 | Kovesdi et al. | |
| 6,514,943 B2 | 2/2003 | Kovesdi et al. | |
| 6,551,586 B1 | 4/2003 | Davidson et al. | |
| 6,677,156 B2 | 1/2004 | Brough et al. | |
| 6,682,929 B2 | 1/2004 | Brough et al. | |
| 7,195,896 B2 | 3/2007 | Kovesdi et al. | |
| 8,940,290 B2 | 1/2015 | Roy et al. | |
| 2003/0165820 A1 | 9/2003 | Day et al. | |
| 2004/0136963 A1 | 7/2004 | Wilson et al. | |
| 2008/0233650 A1 | 9/2008 | Gall et al. | |
| 2011/0223135 A1 | 9/2011 | Roy et al. | |
| 2014/0248307 A1 | 9/2014 | Gall et al. | |
| 2014/0248308 A1 | 9/2014 | McVey et al. | |
| 2014/0271711 A1 | 9/2014 | Brough et al. | |
| 2014/0314717 A1 | 10/2014 | Brough et al. | |
| 2015/0140025 A1 | 5/2015 | Wei et al. | |
| 2015/0152434 A1 | 6/2015 | Roy et al. | |
| 2015/0157700 A1 | 6/2015 | Bruder et al. | |

FOREIGN PATENT DOCUMENTS

| | | |
|---|---|---|
| WO | WO 94/28152 A1 | 12/1994 |
| WO | WO 95/02697 A2 | 1/1995 |
| WO | WO 95/16772 A1 | 6/1995 |
| WO | WO 95/34671 A1 | 12/1995 |
| WO | WO 96/22378 A1 | 7/1996 |
| WO | WO 97/00326 A1 | 1/1997 |
| WO | WO 97/12986 A2 | 4/1997 |
| WO | WO 97/21826 A2 | 6/1997 |
| WO | WO 00/00628 A1 | 1/2000 |
| WO | WO 00/34444 A2 | 6/2000 |
| WO | WO 03/020879 A2 | 3/2003 |
| WO | WO 03/022311 A1 | 3/2003 |
| WO | WO 2007/027860 A2 | 3/2007 |
| WO | WO 2008/011609 A2 | 1/2008 |
| WO | WO 2010/051367 A1 | 5/2010 |
| WO | WO 2011/057248 A2 | 5/2011 |
| WO | WO 2012/021730 A2 | 2/2012 |

OTHER PUBLICATIONS

Altschul et al., "Basic Local Alignment Search Tool," *J. Molecular Biol.*, 215(3): 403-410 (1990).
Altschul et al., "Gapped BLAST and PSI-BLAST: a new generation of protein database search programs," *Nucleic Acids Res.*, 25(17): 3389-3402 (1997).
Bai et al., "Mutations that alter an Arg-Gly-Asp (RGD) sequence in the adenovirus type 2 penton base protein abolish its cell-rounding activity and delay virus reproduction in flat cells," *J. Virol.*, 67(9): 5198-5205 (1993).
Biegert et al., "Sequence context-specific profiles for homology searching," *Proc. Natl. Acad. Sci. USA*, 106(10): 3770-3775 (2009).
Boulanger et al., "Characterization of adenovirus protein IX," *J. Gen. Virol.*, 44(3): 783-800 (1979).

(Continued)

*Primary Examiner* — Rachel B Gill
(74) *Attorney, Agent, or Firm* — Leydig, Voit & Mayer, Ltd.

(57) ABSTRACT

The invention provides an adenovirus or adenoviral vector characterized by comprising one or more particular nucleic acid sequences or one or more particular amino acid sequences, or portions thereof, pertaining to, for example, an adenoviral pIX protein, DNA polymerase protein, penton protein, hexon protein, and/or fiber protein.

37 Claims, No Drawings

(56) References Cited

OTHER PUBLICATIONS

Brough et al., "Activation of transgene expression by early region 4 is responsible for a high level of persistent transgene expression from adenovirus vectors in vivo," J. Virol., 71(12): 9206-9213 (1997).
Cartier et al., "Hematopoietic stem cell gene therapy with a lentiviral vector in X-linked adrenoleukodystrophy," Science, 326(5954): 818-823 (2009).
Cavazzana-Calvo et al., "Gene therapy of human severe combined immunodeficiency (SCID)-X1 disease," Science, 288(5466): 669-672 (2000).
Chen et al., "Persistence in muscle of an adenoviral vector that lacks all viral genes," Proc. Natl. Acad. Sci. USA, 94(5): 1645-1650 (1997).
Chroboczek et al., "The sequence of the genome of adenovirus type 5 and its comparison with the genome of adenovirus type 2," Virology, 186(1): 280-285 (1992).
Crawford-Miksza et al., "Analysis of 15 adenovirus hexon proteins reveals the location and structure of seven hypervariable regions containing serotype-specific residues," J. Virol., 70(3): 1836-1844 (1996).
Curiel et al., "High-efficiency gene transfer mediated by adenovirus coupled to DNA-polylysine complexes," Hum. Gene Ther., 3(2): 147-154 (1992).
Devaux et al., "Structure of adenovirus fibre. I. Analysis of crystals of fibre from adenovirus serotypes 2 and 5 by electron microscopy and X-ray crystallography," J. Molec. Biol., 215(4): 567-588 (1990).
Dey et al., "Molecular epidemiology of adenovirus infection among infants and children with acute gastroenteritis in Dhaka City, Bangladesh," Infect. Genet. Evol., 9(4) 518-522 (2009).
Field et al., "Properties of the adenovirus DNA polymerase," J. Biol. Chem., 259(15): 9487-9495 (1984).
Gall et al., "Construction and characterization of hexon-chimeric adenoviruses: specification of adenovirus serotype," J. Virol., 72(12): 10260-10264 (1998).
GENBANK Accession No. ABU95388.1, "hexon, partial [Human adenovirus 9]," (Jun. 2009).
GENBANK Accession No. EDA88859.1, "hypothetical protein GOS_1918841, partial [marine metagenome]," (Apr. 2007).
GENBANK Accession No. FJ025900, "simian adenovirus 43, complete genome," (Jul. 2009).
GENBANK Accession No. FJ025900.1, "Simian adenovirus 43, complete genome," (Mar. 2012).
GENBANK Accession No. FJ025901, "Simian adenovirus 45, complete genome," (Jul. 2009).
GENBANK Accession No. FJ025901.1, "Simian adenovirus 45, complete genome," (Mar. 2012).
GENBANK Accession No. JN163990.1, "Gorilla gorilla beringei adenovirus 6 hexon gene, partial cds," (Dec. 2011).
GENBANK Accession No. KC702816, "Gorilla beringei beringei adenovirus 7 isolate GC44 DNA polymerase gene, complete cds.," (Sep. 2013).
GENBANK Accession No. KC702813.1, "Beringei beringei adenovirus 7 isolate GC44 hexon gene, complete cds.," (Sep. 2013).
Ghosh-Choudhury et al., "Protein IX, a minor component of the human adenovirus capsid, is essential for the packaging of full length genomes," EMBO J., 6(6): 1733-1739 (1987).
Ginsberg et al., "A proposed terminology for the adenovirus antigens and virion morphological subunits," Virology, 28(4): 782-783 (1966).
Goins et al., "Herpes simplex virus vector-mediated gene delivery for the treatment of lower urinary tract pain," Gene Ther., 16(4): 558-569 (2009).
Graham et al., "Characteristics of a human cell line transformed by DNA from human adenovirus type 5," J. Gen. Virol., 36(1): 59-72 (1977).
Green et al., "Evidence for a repeating cross-beta sheet structure in the adenovirus fibre," EMBO J., 2(8): 1357-1365 (1983).
Hacein-Bey-Abina et al., "A serious adverse event after successful gene therapy for X-linked severe combined immunodeficiency," N. Engl. J. Med., 348(3): 255-256 (2003).
Henry et al., "Characterization of the knob domain of the adenovirus type 5 fiber protein expressed in Escherichia coli," J. Virol., 68(8): 5239-5246 (1994).
Horvath et al., "Nonpermissivity of human peripheral blood lymphocytes to adenovirus type 2 infection," J. Virology, 62(1): 341-345 (1988).
Jornvall et al., "The adenovirus hexon protein. The primary structure of the polypeptide and its correlation with the hexon gene," J. Biol. Chem., 256(12): 6181-6186 (1981).
Kannan et al., "Structural and functional diversity of the microbial kinome," PLoS Biol., 5(3) E17 (2007).
Kay et al., "Viral vectors for gene therapy: the art of turning infectious agents into vehicles of therapeutics," Nature Medicine, 7(1): 33-40 (2001).
Kochanek et al., "High-capacity adenoviral vectors for gene transfer and somatic gene therapy," Hum. Gene Ther., 10(15): 2451-2459 (1999).
Kohlmann et al., "Protective efficacy and immunogenicity of an adenoviral vector vaccine encoding the codon-optimized F protein of respiratory syncytial virus," J Virol., 83(23): 12601-10 (2009).
Lasaro et al., "New insights on adenovirus as vaccine vectors," Molecular Therapy, 17(8): 1333-1339 (2009).
Lutz et al., "The product of the adenovirus intermediate gene IX is a transcriptional activator," J. Virol., 71(7): 5102-5109 (1997).
Mayrhofer et al., "Nonreplicating vaccinia virus vectors expressing the H5 influenza virus hemagglutinin produced in modified Vero cells induce robust protection," J. Virol., 83(10): 5192-5203 (2009).
Mease et al., "Safety, tolerability, and clinical outcomes after intraarticular injection of a recombinant adeno-associated vector containing a tumor necrosis factor antagonist gene: results of a phase 1/2 Study," Journal of Rheumatology, 37(4): 692-703 (2010).
Morsy et al., An adenoviral vector deleted for all viral coding sequences results in enhanced safety and extended expression of a leptin transgene, Proc. Natl. Acad. Sci. USA, 95: 7866-7871 (1998).
NCBI reference sequence AP_000218, "E3 12.5K [Human adenovirus 5]," (Dec. 2008).
NCBI reference sequence AP_000224.1, "Homo sapiens genomic DNA, chromosome 21q21.2, LL56-APP region, clone:B2017A3, complete sequence," (Nov. 1991).
Neumann et al., "Determination of the nucleotide sequence for the penton-base gene of human adenovirus type 5," Gene, 69(1) 153-157 (1988).
Novelli et al., "Deletion analysis of functional domains in baculovirus-expressed adenovirus type 2 fiber," Virology, 185(1): 365-376 (1991).
Roberts et al., "Three-dimensional structure of the adenovirus major coat protein hexon," Science, 232(4754): 1148-1151 (1986).
Roy et al., "Isolation and Characterization of Adenoviruses Persistently Shed from the Gastrointestinal Tract of Non-Human Primates," PLOS Pathogens, 5(7): E1000503, 1-9, (2009).
Rusch et al., "The Sorcerer II Global Ocean Sampling expedition: northwest Atlantic through eastern tropical Pacific," PLoS Biol., 5(3) E77 (2007).
Rux et al., "Structural and phylogenetic analysis of adenovirus hexons by use of high-resolution x-ray crystallographic, molecular modeling, and sequence-based methods," J. Virol., 77(17): 9553-9566 (2003).
Signas et al., Adenovirus 3 Fiber Polypeptide Gene: Implications for the Structure of the Fiber Protein,J. Virol., 53(2): 672-678 (1985).
Silver et al., "Interaction of human adenovirus serotype 2 with human lymphoid cells," Virology, 165(2): 377-387 (1988).
Soding, "Protein homology detection by HMM-HMM comparison," Bioinformatics, 21(7): 951-960 (2005).
Stewart et al., "Image reconstruction reveals the complex molecular organization of adenovirus," Cell, 67(1): 145-154 (1991).
Stewart et al., "Difference imaging of adenovirus: bridging the resolution gap between X-ray crystallography and electron microscopy," EMBO J., 12(7): 2589-99 (1993).

(56) References Cited

OTHER PUBLICATIONS

Thomas et al., "Progress and problems with the use of viral vectors for gene therapy," *Nature Review Genetics*, 4(5): 346-358 (2003).
Van Oostrum et al, "Molecular composition of the adenovirus type 2 virion," *J. Virol.*, 56(2): 439-448 (1985).
Wevers et al., "A novel adenovirus of Western lowland gorillas (*Gorilla gorilla gorilla*)," *J. Virology*, 7(1): 1-8 (2010).
Wevers et al., "Novel Adenoviruses in Wild Primates: a High Level of Genetic Diversity and Evidence of Zoonotic Transmissions," *J. Virology*, 85(20): 10774-10784, (2011).
Yeh et al., "Human adenovirus type 41 contains two fibers," *Virus Res.*, 33(2): 179-198 (1991).
Yooseph et al., "The Sorcerer II Global Ocean Sampling expedition: expanding the universe of protein families," *PLoS Biol.*, 5(3) E16, (2007).
Aubert et al., "Accumulation of Herpes Simplex Virus Type 1 Early and Leaky-Late Proteins Correlates with Apoptosis Prevention in infected Human Hep-2 Cells," *J. Virol.*, 75(2): 1013-1030 (2001).
Dolan et al., "The genome sequence of herpes simplex virus type 2," *J. Virol.*, 72(3): 2010-2021 (1998).
European Patent Office, International Search Report in International Patent Application No. PCT/US/2013/041358 (Dec. 11, 2014).
GENBANK Accession No. ABX79578, "UL47 [Human herpesvirus 2]" (Apr. 14, 2009).
GENBANK Accession No. CAB06743.1, "major capsid protein [Human herpesvirus 2]" (Nov. 14, 2006).
GENBANK Accession No. EDL20708.1, "mCG1048340," (Jun. 2007).
GENBANK Accession No. KC702815.1, "Gorilla beringei graueri adenovirus 9 isolate GC46 hexon gene, complete cds," (Sep. 2013).
GENBANK Accession No. P89442.1, "Major capsid protein" (Nov. 2005).
GENBANK Accession No. P89467, "Tegument protien and transactivator of immediate early genes," (Oct. 2006).
Koelle et al., "CD4 T-cell responses to herpes simplex virus type 2 major capsid protein VP5: Comparison with responses to tegument and envelope glycoproteins", *J. Virol.*, 74(23):11422-11425 (2000).
Muller et al., "Herpes simplex virus type 2 tegument proteins contain subdominant T-cell epitopes detectable in BALB/c mice after DNA immunization and infection", *J. Virol.*, 90 (5): 1153-1163 (2009).
Narum et al., "Codon Optimization of Gene Fragments Encoding Plasmodium falciparum Merzoite Proteins Enhances Dna Vaccine Protein Expression and Immunogenicity in Mice," *Infect Immun*, 69(12): 7250-7253 (2001).
Roy et al., "Generation of an adenoviral vaccine vector based on simian adenovirus 21," *Journal of General Virology* 87: 2477-2485 (2006).
Subak-Sharpe et al., "HSV Molecular Biology: General Aspects of Herpes Simplex Virus Molecular Biology", *Virus Genes*, 16(3): 239-251 (1998).

AFFENADENOVIRUS (GORILLA) OR ADENOVIRAL VECTORS AND METHODS OF USE

CROSS-REFERENCE TO RELATED APPLICATIONS

This patent application is a divisional of U.S. patent application Ser. No. 14/349,421, filed on Apr. 3, 2014, which issued as U.S. Pat. No. 9,233,153 on Jan. 12, 2016, which is the U.S. national phase application of PCT/US2012/058956, filed on Oct. 5, 2012, which claims the benefit of U.S. Provisional Patent Application No. 61/543,638, filed Oct. 5, 2011, all of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 285,356 Byte ASCII (Text) file named "722627 ST25.TXT," created on Jan. 11, 2016.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the delivery of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics*, 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine*, 7(1): 33-40 (2001).

Viral vectors that have been used with some success to deliver exogenous proteins to mammalian cells for therapeutic purposes include, for example, Retrovirus (see, e.g., Cavazzana-Calvo et al., *Science*, 288 (5466): 669-672 (2000)), Lentivirus (see, e.g., Cartier et al., *Science*, 326: 818-823 (2009)), Adeno-associated virus (AAV) (see, e.g., Mease et al., *Journal of Rheumatology*, 27(4): 692-703 (2010)), Herpes Simplex Virus (HSV) (see, e.g., Goins et al., *Gene Ther.*, 16(4): 558-569 (2009)), Vaccinia Virus (see, e.g., Mayrhofer et al., *J. Virol.*, 83(10): 5192-5203 (2009)), and Adenovirus (see, e.g., Lasaro and Ertl, *Molecular Therapy*, 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology*, 165: 377-387 (1988), and Horvath et al., *J. Virology*, 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.*, 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides an adenovirus or adenoviral vector. The adenovirus or adenoviral vector comprises one or more of the nucleic acid sequences selected from the group consisting of (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5.

The invention provides an adenovirus or adenoviral vector comprising one or more of the nucleic acid sequences selected from the group consisting of (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10.

The invention provides an adenovirus or adenoviral vector comprising one or more of the nucleic acid sequences selected from the group consisting of (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

The invention provides an adenovirus or adenoviral vector comprising one or more of the amino acid sequences selected from the group consisting of (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15.

The invention provides an adenovirus or adenoviral vector comprising one or more of the nucleic acid sequences selected from the group consisting of (a) a nucleic acid sequence encoding the amino acid sequence of SEQ ID NO: 11, (b) a nucleic acid sequence encoding an amino acid sequence that is at least 99% identical to SEQ ID NO: 12, (c) a nucleic acid sequence encoding an amino acid sequence that is at least 82% identical to SEQ ID NO: 13, (d) a nucleic acid sequence encoding an amino acid sequence that is at least 80% identical to SEQ ID NO: 14, and (e) a nucleic acid sequence encoding an amino acid sequence that is at least 83% identical to SEQ ID NO: 15.

The invention provides an adenovirus or adenoviral vector comprising one or more of the amino acid sequences selected from the group consisting of (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20.

The invention provides an adenovirus or adenoviral vector comprising one or more of the nucleic acid sequences selected from the group consisting of (a) a nucleic acid sequence encoding the amino acid sequence of SEQ ID NO: 16, (b) a nucleic acid sequence encoding an amino acid sequence that is at least 99.78% identical to SEQ ID NO: 17, (c) a nucleic acid sequence encoding an amino acid sequence that is at least 97.8% identical to SEQ ID NO: 18, (d) a nucleic acid sequence encoding an amino acid that is at least 93.4% identical to SEQ ID NO: 19, and (e) a nucleic acid sequence encoding an amino acid sequence that is at least 98.2% identical to SEQ ID NO: 20.

The invention provides an adenovirus or adenoviral vector comprising one or more of the amino acid sequences selected from the group consisting of (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The invention provides an adenovirus or adenoviral vector comprising one or more of the nucleic acid sequences selected from the group consisting of (a) a nucleic acid sequence encoding an amino acid sequence comprising at least 89 contiguous amino acid residues of SEQ ID NO: 16, (b) a nucleic acid sequence encoding an amino acid sequence comprising at least 428 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 370 contiguous amino acid residues of SEQ ID NO: 19, and (e) a nucleic acid sequence encoding an amino acid sequence comprising at least 192 contiguous amino acid residues of SEQ ID NO: 20.

DETAILED DESCRIPTION OF THE INVENTION

Adenoviruses are generally associated with benign pathologies in humans, and the genomes of adenoviruses isolated from a variety of species, including humans, have been extensively studied. Adenovirus is a medium-sized (90-100 nm), nonenveloped icosohedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology*, 28: 782-83 (1966)). The hexon comprises three identical proteins, namely polypeptide II (Roberts et al., *Science*, 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell*, 67: 145-54 (1991), and Stewart et al., *EMBO J.*, 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"), or for use as antigen delivery systems for vaccine applications. For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.*, 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The invention is predicated, at least in part, on the discovery and isolation of an adenovirus that has not previously been identified or isolated. The adenovirus described herein was isolated from a gorilla. There are four widely recognized gorilla subspecies within the two species of Eastern Gorilla (*Gorilla beringei*) and Western Gorilla (*Gorilla gorilla*). The Western Gorilla species includes the subspecies Western Lowland Gorilla (*Gorilla gorilla gorilla*) and Cross River Gorilla (*Gorilla gorilla diehli*). The Eastern Gorilla species includes the subspecies Mountain Gorilla (*Gorilla beringei beringei*) and Eastern Lowland Gorilla (*Gorilla beringei graueri*) (see, e.g., Wilson and Reeder, eds., *Mammalian Species of the World*, 3$^{rd}$ ed., Johns Hopkins University Press, Baltimore, Md. (2005)). The adenovirus of the invention was isolated from Mountain Gorilla (*Gorilla beringei beringei*).

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, 5$^{th}$ ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.*, 44: 783-800 (1979); Horwitz M. S., "Adenoviridae and their replication" in *Virology*, 2nd ed., B. N. Fields et al. (eds.), Raven Press, Ltd., New York, pp. 1679-1721 (1990), Ghosh-Choudhury et al., *EMBO J.*, 6: 1733-1739 (1987), and van Oostrum et al, *J. Virol.*, 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.*, 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.*, 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO: 2. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.*, 72: 10260-264 (1998), and Rux et al., *J. Virol.*, 77(17): 9553-9566 (2003)). The major structural features of the hexon protein are shared by adenoviruses across serotypes, but the hexon protein differs in size and immunological properties between serotypes (Jornvall et al., *J. Biol. Chem.*, 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.*, 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.*, 215: 567-88 (1990), Yeh et al., *Virus Res.*, 33: 179-98 (1991)). The fiber protein mediates primary viral binding to receptors on the cell surface via the knob and the shaft domains (Henry et al., *J. Virol.*, 68(8): 5239-46 (1994)). The amino acid sequences for trimerization are located in the knob, which appears necessary for the amino terminus of the fiber (the tail) to properly associate with the penton base (Novelli et al., *Virology*, 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.*, 2: 1357-65 (1983), Chroboczek et al., *Virology*, 186: 280-85 (1992), and Signas et al., *J. Virol.*, 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene*, 69: 153-157 (1988)). The RGD tripeptide mediates binding to αv integrins and adenoviruses that have point mutations in the RGD sequence of the penton base are restricted in their ability to infect cells (Bai et al., *J. Virol.*, 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences,* Cambridge University Press, Cambridge UK (1997)).

In one embodiment, the adenovirus or adenoviral vector comprises one or more of the following nucleic acid sequences: (a) the nucleic acid sequence of SEQ ID NO: 1, (b) a nucleic acid sequence that is at least 98.5% identical (e.g., at least 98.73%, at least 98.96%, at least 99.18%, at least 99.41%, at least 99.64%, at least 99.87%, or 100% identical) to SEQ ID NO: 2, (c) a nucleic acid sequence that is at least 90% identical (e.g., at least 92.94%, at least 95.88%, 98.82%, or 100% identical) to SEQ ID NO: 3, (d) a nucleic acid sequence that is at least 80% identical (e.g., at least 80.83%, at least 83.06%, at least 85.28%, at least 87.50%, at least 89.72%, at least 91.94%, at least 94.17%, at least 96.39%, at least 98.61%, or 100% identical) to SEQ ID NO: 4, and (e) a nucleic acid sequence that is at least 89% identical (e.g., at least 92.33%, at least 95.67%, at least 99%, or 100% identical) to SEQ ID NO: 5.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise the nucleic acid sequence of SEQ ID NO: 1. The adenovirus or adenoviral vector can comprise a nucleic acid sequence that is at least 98.5% identical to SEQ ID NO: 2 and a nucleic acid sequence that is at least 90% identical to SEQ ID NO: 3. The adenovirus or adenoviral vector can comprise the nucleic acid sequence of SEQ ID NO: 1, a nucleic acid sequence that is at least 90% identical to SEQ ID NO: 3, and a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, or (e) the nucleic acid sequence of SEQ ID NO: 5. The adenovirus or adenoviral vector can comprise (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, and (e) the nucleic acid sequence of SEQ ID NO: 5.

In another embodiment, the adenovirus or adenoviral vector comprises one or more of the following nucleic acid sequences: (a) a nucleic acid sequence that is at least 98.6% identical (e.g., at least 98.85%, at least 99.10%, at least 99.35%, at least 99.60%, or 100% identical) to SEQ ID NO: 6, (b) a nucleic acid sequence that is at least 99.06% identical (e.g., at least 99.09%, at least 99.12%, at least 99.15%, at least 99.19%, at least 99.22%, at least 99.25%, at least 99.28%, at least 99.31%, at least 99.34%, at least 99.38%, at least 99.41%, at least 99.44%, at least 99.47%, at least 99.50%, at least 99.53%, at least 99.57%, at least 99.60%, at least 99.63%, at least 99.66%, at least 99.69%, at least 99.72%, at least 99.75%, at least 99.79%, at least 99.82%, at least 99.85%, at least 99.88%, at least 99.91%, at least 99.94%, at least 99.98%, or 100% identical) to SEQ ID NO: 7, (c) a nucleic acid sequence that is at least 97.13% identical (e.g., at least 97.18%, at least 97.23%, at least 97.28%, at least 97.33%, at least 97.38%, at least 97.43%, at least 97.48%, at least 97.5% at least 97.54%, at least 97.59%, at least 97.6%, at least 97.64%, at least 97.69%, at least 97.7%, at least 97.74%, at least 97.79%, at least 97.8%, at least 97.84%, at least 97.89%, at least 97.9%, at least 97.94%, at least 97.99%, at least 98%, at least 98.04%, at least 98.09%, at least 98.1%, at least 98.14%, at least 98.19%, at least 98.2%, at least 98.24%, at least 98.30%, at least 98.35%, at least 98.40%, at least 98.45%, at least 98.50%, at least 98.55%, at least 98.60%, at least 98.70%, at least 98.75%, at least 98.80%, at least 98.85%, at least 98.90%, at least 98.95%, at least 99.00%, at least 99.06%, at least 99.11%, at least 99.16%, at least 99.2%, at least 99.21%, at least 99.26%, at least 99.3%, at least 99.31%, at least 99.36%, at least 99.4%, at least 99.41%, at least 99.46%, at least 99.5%, at least 99.51%, at least 99.56%, at least 99.6%, at least 99.61%, at least 99.66%, at least 99.7%, at least 99.71%, at least 99.76%, at least 99.8%, at least 99.81%, at least 99.87%, at least 99.9%, at least 99.92%, at least 99.95%, at least 99.97%, or 100% identical) to SEQ ID NO: 8, (d) a nucleic acid sequence that is at least 90.7% identical (e.g., at least 90.73%, at least 90.77%, at least 90.80%, at least 90.84%, at least 90.87%, at least 90.91%, at least 90.94%, at least 90.98%, at least 91.01%, at least 91.05%, at least 91.08%, at least 91.12%, at least 91.15%, at least 91.19%, at least 91.22%, at least 91.26%, at least 91.29%, at least 91.33%, at least 91.36%, at least 91.40%, at least 91.43%, at least 91.46%, at least 91.50%, at least 91.53%, at least 91.57%, at least 91.60%, at least 91.64%, at least 91.67%, at least 91.71%, at least 91.74%, at least 91.78%, at least 91.81%, at least 91.85%, at least 91.88%, at least 91.92%, at least 91.95%, at least 91.99%, at least 92.02%, at least 92.06%, at least 92.09%, at least 92.13%, at least 92.16%, at least 92.19%, at least 92.23%, at least 92.26%, at least 92.30%, at least 92.33%, at least 92.37%, at least 92.40%, at least 92.44%, at least 92.47%, at least 92.51%, at least 92.54%, at least 92.58%, at least 92.61%, at least 92.65%, at least 92.68%, at least 92.72%, at least 92.75%, at least 92.79%, at least 92.82%, at least 92.86%, at least 92.89%, at least 92.92%, at least 92.96%, at least 92.99%, at least 93.03%, at least 93.06%, at least 93.10%, at least 93.13%, at least 93.17%, at least 93.20%, at least 93.24%, at least 93.27%, at least 93.31%, at least 93.34%, at least 93.38%, at least 93.41%, at least 93.45%, at least 93.48%, at least 93.52%, at least 93.55%, at least 93.58%, at least 93.62%, at least 93.65%, at least 93.69%, at least 93.72%, at least 93.76%, at least 93.79%, at least 93.83%, at least 93.86%, at least 93.90%, at least 93.93%, at least 93.97%, at least 94.00%, at least 94.04%, at least 94.07%, at least 94.11%, at least 94.14%, at least 94.18%, at least 94.21%, at least 94.25%, at least 94.28%, at least 94.31%, at least 94.35%, at least 94.38%, at least 94.42%, at least 94.45%, at least 94.49%, at least 94.52%, at least 94.56%, at least 94.59%, at least 94.63%, at least 94.66%, at least 94.70%, at least 94.73%, at least 94.77%, at least 94.80%, at least 94.84%, at least 94.87%, at least 94.91%, at least 94.94%, at least 94.98%, at least 95.01%, at least 95.04%, at least 95.08%, at least 95.11%, at least 95.15%, at least 95.18%, at least 95.22%, at least 95.25%, at least 95.29%, at least 95.32%, at least 95.36%, at least 95.39%, at least 95.43%, at least 95.46%, at least 95.50%, at least 95.53%, at least 95.57%, at least 95.60%, at least 95.64%, at least 95.67%, at least 95.71%, at least 95.74%, at least 95.77%, at least 95.81%, at least 95.84%, at least 95.88%, at least 95.91%, at least 95.95%, at least 95.98%, at least 96.02%, at least 96.05%, at least 96.09%, at least 96.12%, at least 96.16%, at least 96.19%, at least 96.23%, at least 96.26%, at least 96.30%, at least 96.33%, at least 96.37%, at least 96.40%, at least 96.44%, at least 96.47%, at least 96.50%, at least 96.54%, at least 96.57%, at least 96.61%, at least 96.64%, at least 96.68%, at least 96.71%, at least 96.75%, at least 96.78%, at least 96.82%, at least 96.85%, at least 96.89%, at least 96.92%, at least 96.96%, at least 96.99%, at least 97.03%, at least 97.06%, at least 97.10%, at least 97.13%, at least 97.17%, at least 97.20%, at least 97.23%, at least 97.27%, at least 97.30%, at least 97.34%, at least 97.37%, at least 97.41%, at least 97.44%, at least 97.48%, at least 97.51%, at least 97.55%, at least 97.58%, at least 97.62%, at least 97.65%, at least 97.69%, at least 97.72%, at least 97.76%, at least 97.79%, at least 97.83%, at least 97.86%, at least 97.89%, at least 97.93%, at least 97.96%, at least 98.00%, at least 98.03%, at least 98.07%, at least 98.10%, at least 98.14%, at least 98.17%, at least 98.21%, at least 98.24%, at least 98.28%, at least 98.31%, at least 98.35%, at least 98.38%, at least 98.42%, at least 98.45%, at least 98.49%, at least 98.52%, at least 98.56%, at least 98.59%, at least 98.62%, at least 98.66%, at least 98.69%, at least 98.73%, at least 98.76%, at least 98.80%, at least 98.83%, at least 98.87%, at least 98.90%, at least 98.94%, at least 98.97%, at least 99.01%, at least 99.04%, at least 99.08%, at least 99.11%, at least 99.15%, at least 99.18%, at least 99.22%, at least 99.25%, at least 99.29%, at least 99.32%, at least 99.35%, at least 99.39%, at least 99.42%, at least 99.46%, at least 99.49%, at least 99.53%, at least 99.56%, at least 99.60%, at least 99.63%, at least 99.67%, at least 99.70%, at least 99.74%, at least 99.77%, at least 99.81%, at least 99.84%, at least 99.88%, at least 99.91%, at least 99.95%, at least 99.98%, or 100% identical) to SEQ ID NO: 9, and (e) a nucleic acid sequence that is at least 96.6% identical (e.g., at least 96.66%, at least 96.71%, at least 96.77%, at least 96.83%, at least 96.89%, at least 96.94%, at least 97.00%, at least 97.06%, at least 97.11%, at least 97.17%, at least 97.23%, at least 97.29%, at least 97.34%, at least 97.40%, at least 97.46%, at least 97.51%, at least 97.57%, at least 97.63%, at least 97.69%, at least 97.74%, at least 97.80%, at least 97.86%, at least 97.92%, at least 97.97%, at least 98.03%, at least 98.09%, at least 98.14%, at least 98.20%, at least 98.26%, at least 98.32%, at least 98.37%, at least 98.43%, at least 98.49%, at least 98.54%, at least 98.60%, at least 98.66%, at least 98.72%, at least 98.77%, at least 98.83%, at least 98.89%, at least 98.94%, at least 99.00%, at least 99.06%, at least 99.12%, at least 99.17%, at least 99.23%, at least 99.29%, at least 99.34%, at least 99.40%, at least 99.46%, at least 99.52%, at least 99.57%, at least 99.63%, at least 99.69%, at least 99.74%, at least at least 99.80%, at least 99.86%, at least 99.92%, at least 99.97%, or 100% identical) to SEQ ID NO: 10.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 98.6% identical to SEQ ID NO: 6. The adenovirus or adenoviral vector can comprise a nucleic acid sequence that is at least 99.06% identical to SEQ ID NO: 7 and a nucleic acid sequence that is at least 97.13% identical to SEQ ID NO: 8. The adenovirus or adenoviral vector can comprise a nucleic acid sequence that is at least 97.13% identical to SEQ ID NO: 8, a nucleic acid sequence that is at least 90.7% identical to SEQ ID NO: 9, and a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, or (e) the nucleic acid sequence of SEQ ID NO: 10. The adenovirus or adenoviral vector can comprise (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, and (e) the nucleic acid sequence of SEQ ID NO: 10.

In another embodiment, the adenovirus or adenoviral vector comprises one or more of the following nucleic acid sequences: (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, or (e) a nucleic acid sequence comprising at least 188 contiguous nucleotides of SEQ ID NO: 10.

The adenovirus or adenoviral vector can comprise a nucleic acid sequence comprising at least 121 (e.g., 125 or more, 130 or more, 150 or more, 200 or more, 250 or more, or 300 or more) contiguous nucleotides of SEQ ID NO: 6, but no more than 399 (e.g., 398 or less, 350 or less, or 275 or less) contiguous nucleotides of SEQ ID NO: 6. Preferably, the adenovirus or adenoviral vector comprises a nucleic acid sequence comprising 121 to 300 contiguous nucleotides (e.g., 125, 150, 175, 200, 250, or 275 contiguous nucleotides), 121 to 200 contiguous nucleotides (e.g., 130, 140, 145, 160, 165, 170, 180, 185, 190, 195, or 199 contiguous nucleotides), or 121 to 150 contiguous nucleotides (e.g., 122, 123, 124, 125, 126, 127, 128, 129, 130, 131, 132, 133, 134, 135, 136, 137, 138, 139, 140, 141, 142, 143, 144, 145, 146, 147, 148, or 149 contiguous nucleotides) of SEQ ID NO: 6, or a range defined by any two of the foregoing values.

The adenovirus or adenoviral vector can comprise a nucleic acid sequence comprising at least 462 (e.g., 470 or more, 500 or more, 600 or more, 700 or more, 800 or more, 900 or more, or 1,000 or more) contiguous nucleotides of SEQ ID NO: 7, but no more than 3168 (e.g., 3,100 or less, 3,000 or less, 2,500 or less, 2,000 or less, or 1,500 or less) contiguous nucleotides of SEQ ID NO: 7. Preferably, the adenovirus or adenoviral vector comprises a nucleic acid sequence comprising 462 to 2,000 contiguous nucleotides (e.g., 475, 500, 700, 1,000, 1,200, 1,500, or 1,700 contiguous nucleotides), 462 to 1,000 contiguous nucleotides (e.g., 490, 525, 575, 600, 650, 675, 725, 750, 800, 850, 900, or 950 contiguous nucleotides), or 462 to 800 contiguous nucleotides (e.g., 480, 485, 490, 495, 499, 510, 515, 530, 540, 550, 560, 565, 570, 580, 585, 590, 595, 615, 625, 630, 640, 660, 665, 670, 680, 685, 690, 695, 705, 715, 730, 740, 755, 760, 765, 770, 775, 780, 785, 790, 795, or 799 contiguous nucleotides) of SEQ ID NO: 7, or a range defined by any two of the foregoing values.

The adenovirus or adenoviral vector can comprise a nucleic acid sequence comprising at least 234 (e.g., 235 or more, 250 or more, 300 or more, 350 or more, 400 or more, 450 or more, or 500 or more) contiguous nucleotides of SEQ ID NO: 8, but no more than 1,974 (e.g., 1,900 or less, 1,800 or less, 1,500 or less, 1,200 or less, 1,000 or less, 850 or less, 800 or less, 750 or less, or 700 or less) contiguous nucleotides of SEQ ID NO: 8. Preferably, the adenovirus or adenoviral vector comprises a nucleic acid sequence comprising 234 to 1,500 contiguous nucleotides (e.g., 290, 300, 400, 500, 600, 700, 800, 900, 1,000, or 1,200 contiguous nucleotides), 234 to 1,000 contiguous nucleotides (e.g., 295, 350, 450, 550, 650, 750, 850, or 950 contiguous nucleotides), or 234 to 500 contiguous nucleotides (e.g., 290, 305, 310, 315, 325, 340, 345, 360, 365, 370, 375, 380, 385, 390, 395, 405, 425, 430, 440, 455, 460, 465, 470, 475, 480, 485, 490, 495, or 499 contiguous nucleotides) of SEQ ID NO: 8, or a range defined by any two of the foregoing values.

The adenovirus or adenoviral vector can comprise a nucleic acid sequence comprising at least 606 (e.g., 610 or more, 650 or more, 700 or more, 800 or more, or 1,000 or more) contiguous nucleotides of SEQ ID NO: 9, but no more than 2877 (2,800 or less, 2,500 or less, 2,000 or less, 1,800 or less, or 1,500 or less) contiguous nucleotides of SEQ ID NO: 9. Preferably, the adenovirus or adenoviral vector comprises a nucleic acid sequence comprising 606 to 2,000 contiguous nucleotides (e.g., 615, 650, 700, 800, 900, 1,000, 1,200, 1,500, 1,700, or 1,900 contiguous nucleotides), 606 to 1,000 contiguous nucleotides (e.g., 630, 645, 665, 675, 725, 750, 775, 825, 850, 875, 925, 950, or 975 contiguous nucleotides), or 606 to 800 contiguous nucleotides (e.g., 620, 635, 640, 655, 660, 670, 680, 685, 690, 695, 699, 705, 715, 730, 735, 740, 745, 755, 760, 765, 770, 785, 790, 795, or 799 contiguous nucleotides) of SEQ ID NO: 9, or a range defined by any two of the foregoing values.

The adenovirus or adenoviral vector can comprise a nucleic acid sequence comprising at least 188 (e.g., 189 or more, 200 or more, 300 or more, 500 or more, 700 or more, or 900 or more) contiguous nucleotides of SEQ ID NO: 10, but no more than 1,749 (1,700 or less, 1,500 or less, 1,200 or less, or 1,000 or less) contiguous nucleotides of SEQ ID NO: 10. Preferably, the adenovirus or adenoviral vector comprises a nucleic acid sequence comprising 188 to 1,500 contiguous nucleotides (e.g., 200, 400, 600, 800, 1,000, 1,200, or 1,400 contiguous nucleotides), 188 to 1,000 contiguous nucleotides (e.g., 195, 250, 350, 450, 550, 650, 750, 850, or 950 contiguous nucleotides), or 188 to 500 contiguous nucleotides (e.g., 190, 225, 230, 240, 255, 260, 265, 270, 275, 315, 325, 330, 340, 355, 360, 365, 370, 375, 380, 385, 390, 395, 415, 425, 430, 440, 455, 460, 465, 470, 475, 480, 485, 490, 495, or 499 contiguous nucleotides) of SEQ ID NO: 10, or a range defined by any two of the foregoing values.

The adenovirus or adenoviral vector can comprise one, two, three, four, or all five of the aforementioned sequences alone, or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence comprising at least 121 contiguous nucleotides of SEQ ID NO: 6. The adenovirus or adenoviral vector can comprise a nucleic acid sequence comprising at least 234 contiguous nucleotides of SEQ ID NO: 8, and a nucleic acid sequence comprising at least 188 contiguous nucleotides of SEQ ID NO: 10. The adenovirus or adenoviral vector can comprise a nucleic acid sequence comprising at least 462 contiguous nucleotides of SEQ ID NO: 7, a nucleic acid sequence comprising at least 606 contiguous nucleotides of SEQ ID NO: 9, and a nucleic acid sequence comprising at least 188 contiguous nucleotides of SEQ ID NO: 10. The adenovirus or adenoviral vector can comprise a nucleic acid sequence comprising at least 121 contiguous nucleotides of SEQ ID NO: 6, a nucleic acid sequence comprising at least 462 contiguous nucleotides of SEQ ID NO: 7, a nucleic acid sequence comprising at least 234 contiguous nucleotides of SEQ ID NO: 8, and a nucleic acid sequence comprising at least 606 contiguous nucleotides of SEQ ID NO: 9. The adenovirus or adenoviral vector can comprise (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

In another embodiment, the adenovirus or adenoviral vector comprises one or more of the following amino acid sequences: (a) the amino acid sequence of SEQ ID NO: 11, (b) an amino acid sequence that is at least 82% identical (e.g., at least 88.67%, at least 95.33%, or 100% identical) to SEQ ID NO: 13, (c) an amino acid sequence that is at least 80% identical (e.g., at least 81%, at least 82%, at least 83%, at least 83.06%, at least 84%, at least 85%, at least 85.28%, at least 86%, at least 87%, at least 87.5%, at least 88%, at least 88.67%, at least 89%, at least 89.72% at least 90%, at least 91%, at least 91.94%, at least 92%, at least 92.33%, at least 93%, at least 94%, at least 94.17%, at least 95%, at least 95.33%, at least 95.67%, at least 96%, at least 96.39%, at least 97%, at least 98%, at least 98.61%, at least 99%, at least 99.5%, or 100% identical) to SEQ ID NO: 14, and (d) an amino acid sequence that is at least 83% identical (e.g., at least 89.67%, at least 96.33%, or 100% identical) to SEQ ID NO: 15.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 11. The adenovirus or adenoviral vector can comprise an amino acid sequence of SEQ ID NO: 11, and an amino acid sequence that is at least 82% identical to SEQ ID NO: 13. The adenovirus or adenoviral vector can comprise the amino acid sequence of SEQ ID NO: 11, an amino acid sequence that is at least 82% identical to SEQ ID NO: 13, and an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, or (d) the amino acid sequence of SEQ ID NO: 15. The adenovirus or adenoviral vector can comprise (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, and (d) the amino acid sequence of SEQ ID NO: 15.

In another embodiment, the adenovirus or adenoviral vector comprises one or more of the following amino acid sequences: (a) the amino acid sequence of SEQ ID NO: 16, (b) an amino acid sequence that is at least 97.8% identical (e.g., at least 97.95%, at least 98.10%, at least 98.26%, at least 98.41%, at least 98.56%, at least 98.71%, at least 98.86%, at least 99.02%, at least 99.17%, at least 99.32%, at least 99.47%, at least 99.62%, at least 99.78%, or 100% identical) to SEQ ID NO: 18, (c) an amino acid sequence that is at least 93.4% identical (e.g., at least 93.50%, at least 93.61%, at least 93.71%, at least 93.82%, at least 93.92%, at least 94.03%, at least 94.13%, at least 94.23%, at least 94.34%, at least 94.44%, at least 94.55%, at least 94.65%, at least 94.76%, at least 94.86%, at least 94.96%, at least 95.07%, at least 95.17%, at least 95.28%, at least 95.38%, at least 95.49%, at least 95.59%, at least 95.69%, at least 95.80%, at least 95.90%, at least 96.01%, at least 96.11%, at least 96.22%, at least 96.32%, at least 96.42%, at least 96.53%, at least 96.63%, at least 96.74%, at least 96.84%, at least 96.95%, at least 97.05%, at least 97.15%, at least 97.26%, at least 97.36%, at least 97.47%, at least 97.57%, at least 97.68%, at least 97.78%, at least 97.88%, at least 97.99%, at least 98.09%, at least 98.20%, at least 98.30%, at least 98.41%, at least 98.51%, at least 98.61%, at least 98.72%, at least 98.82%, at least 98.93%, at least 99.03%, at least 99.14%, at least 99.24%, at least 99.34%, at least 99.45%, at least 99.55%, at least 99.66%, at least 99.76%, at least 99.87%, at least 99.97%, or 100% identical) to SEQ ID NO: 19, and (d) an amino acid sequence that is at least 98.2% identical (e.g., at least 98.37%, at least 98.54%, at least 98.71%, at least 98.89%, at least 99.06%, at least 99.23%, at least 99.40%, at least 99.57%, at least 99.74%, at least 99.92%, or 100% identical) to SEQ ID NO: 20.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 16. The adenovirus or adenoviral vector can comprise the amino acid sequence of SEQ ID NO: 16, and an amino acid sequence that is at least 93.4% identical to SEQ ID NO: 19. The adenovirus or adenoviral vector can comprise the amino acid sequence of SEQ ID NO: 16, an amino acid sequence that is at least 93.4% identical to SEQ ID NO: 19, and an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, or (d) the amino acid sequence of SEQ ID NO: 20. The adenovirus or adenoviral vector can comprise (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, and (d) the amino acid sequence of SEQ ID NO: 20.

In another embodiment, the adenovirus or adenoviral vector comprises one or more of the following amino acid sequences: (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The adenovirus or adenoviral vector can comprise an amino acid sequence comprising at least 89 (e.g., 90 or more, 100 or more, or 110 or more) contiguous amino acid residues of SEQ ID NO: 16, but no more than 133 (e.g., 130 or less, 125 or less, 120 or less, or 115 or less) contiguous amino acid residues of SEQ ID NO: 16. Preferably, the adenovirus or adenoviral vector comprises an amino acid sequence comprising 89 to 130 contiguous amino acid residues (e.g., 90, 100, 110, 115, 120, or 125 contiguous amino acid residues) of SEQ ID NO: 16, 89 to 115 contiguous amino acid residues of SEQ ID NO: 16 (e.g., 95, 110, or 112 contiguous amino acid residues), or 89 to 100 contiguous amino acid residues (e.g., 89, 90, 91, 92, 93, 94, 95, 96, 97, 98, or 99 contiguous amino acid residues) of SEQ ID NO: 16, or a range defined by any two of the foregoing values.

The adenovirus or adenoviral vector can comprise an amino acid sequence comprising at least 247 (e.g., 250 or more, 275 or more, 300 or more, or 400 or more) contiguous amino acid residues of SEQ ID NO: 18, but no more than 658 (e.g., 650 or less, 550 or less, or 450 or less) contiguous amino acid residues of SEQ ID NO: 18. Preferably, the adenovirus or adenoviral vector comprises an acid sequence comprising 247 to 600 contiguous amino acid residues (e.g., 255, 275, 300, 400, or 500 contiguous amino acid residues) of SEQ ID NO: 18, 247 to 500 contiguous amino acid residues of SEQ ID NO: 18 (e.g., 325, 350, 375, 425, 450, or 475 contiguous amino acid residues), or 247 to 400 contiguous amino acid residues (e.g., 265, 280, 285, 290, 295, 360, 365, 380, 385, 390, 395, or 399 contiguous amino acid residues) of SEQ ID NO: 18, or a range defined by any two of the foregoing values.

The adenovirus or adenoviral vector can comprise an amino acid sequence comprising at least 370 (e.g., 380 or more, 400 or more, or 500 or more) contiguous amino acid residues of SEQ ID NO: 19, but no more than 959 (e.g., 950 or less, 900 or less, 800 or less, 700 or less, or 600 or less) contiguous amino acid residues of SEQ ID NO: 19. Preferably, the adenovirus or adenoviral vector comprises an acid sequence comprising 370 to 800 contiguous amino acid residues (e.g., 390, 400, 500, 600, or 700 contiguous amino acid residues) of SEQ ID NO: 19, 370 to 600 contiguous amino acid residues (e.g., 375, 385, 395, 425, 445, 450, 465, 475, 525, 545, 550, 565 or 575 contiguous amino acid residues) of SEQ ID NO: 19, or 370 to 500 contiguous amino acid residues (e.g., 385, 389, 395, 399, 415, 435, 440, 460, 470, 480, or 499 contiguous amino acid residues) of SEQ ID NO: 19, or a range defined by any two of the foregoing values.

The adenovirus or adenoviral vector can comprise an amino acid sequence comprising at least 192 (e.g., 193 or more, 200 or more, or 300 or more) contiguous amino acid residues of SEQ ID NO: 20, but no more than 583 (e.g., 580 or less, 550 or less, 500 or less, 450 or less, or 400 or less) contiguous amino acid residues of SEQ ID NO: 20. Preferably, the adenovirus or adenoviral vector comprises an acid sequence comprising 192 to 500 contiguous amino acid residues (e.g., 198, 200, 300, or 400 contiguous amino acid residues) of SEQ ID NO: 20, 192 to 300 contiguous amino acid residues (e.g., 194, 196, 200, 210, 220, 230, 240, 250, 260, 270, 280, or 290 contiguous amino acid residues) of SEQ ID NO: 20, or 192 to 250 contiguous amino acid residues (e.g., 195, 199, 215, 225, 235, or 245 contiguous amino acid residues) of SEQ ID NO: 20, or a range defined by any two of the foregoing values.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence comprising at least 89 contiguous amino acid residues of SEQ ID NO: 16. The adenovirus or adenoviral vector can comprise an amino acid sequence comprising at least 89 contiguous amino acid residues of SEQ ID NO: 16, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 192 contiguous amino acid residues of SEQ ID NO: 20. The adenovirus or adenoviral vector can comprise (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

In other embodiments, the adenovirus or adenoviral vector comprises one or more nucleic acid sequences that encode one or more of any of the aforementioned amino acid sequences, e.g., the amino acid sequences of any of SEQ ID NOs: 11-20 or any of the variants and/or portions thereof as described herein. For example, the adenovirus or adenoviral vector can comprise a nucleic acid sequence encoding an amino acid sequence that is at least 99.78% identical (e.g., at least 99.87%, at least 99.97%, or 100% identical) to SEQ ID NO: 17, or a nucleic acid sequence encoding an amino acid sequence that is at least 99% identical (e.g., at least 99.68% or 100% identical) to SEQ ID NO: 12.

The adenovirus or adenoviral vector can comprise the nucleic acid sequence of, for example, SEQ ID NO: 21, SEQ ID NO: 22, SEQ ID NO: 23, SEQ ID NO: 24, or SEQ ID NO: 25.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region may be deleted in whole or in part, or retained in whole or in part. The size of the deletion may be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the invention, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.*, 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Other suitable complementing cell lines to produce the replication-deficient adenovirus or adenoviral vector of the invention include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

The invention provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. No. 6,225,289, U.S. Pat. No. 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the present invention and, of course, should not be construed as in any way limiting its scope.

EXAMPLE 1

This example demonstrates the immunogenicity of an adenoviral vector encoding a Respiratory Syncytial Virus (RSV) F protein in cotton rats.

A gorilla adenovirus having the nucleic acid sequence of SEQ ID NO: 22 was modified by genetic engineering to (1) be rendered replication-deficient by deletion of the E1 region, and (2) express the human Respiratory Syncytial Virus (RSV) Fusion (F) glycoprotein. Because RSV replicates in the cytoplasm of cells, the gene encoding the F protein was modified for expression in a cell nucleus by removing RNA processing signals (e.g., RNA splicing sites), and was codon-optimized for expression in a mammalian cell. The expression of the F protein from the adenoviral vector was verified by infection of HEK-293 cells in vitro, and by a Western blot assay using protein extracts of the infected cells and a commercially available anti-RSV polyclonal antibody (Pab7133P, Maine Biotechnology, Portland, Me.).

Cotton rats (*Sigmodon hispidus*) were injected in the tibialis muscle with a single administration of $10^7$ particle units (pu) of the E1-deleted adenoviral vector expressing the RSV F glycoprotein. The animals were then challenged 28 days later with live human RSV ($10^6$ particle forming units (pfu) administered intranasally). At 5 days post-challenge, the viral load of RSV in the lungs of the animals was measured. The animals that were immunized with the adenoviral vector expressing the F protein did not have detectable RSV in the lungs (limit of detection 70 pfu/gram of lung tissue).

The results of this example demonstrate that the inventive adenoviral vector encoding an RSV F protein is immunogenic in vivo and can confer complete protection against RSV infection in cotton rats.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adenovirus or adenoviral vector comprising a non-native nucleic acid sequence and one or more of the nucleic acid sequences selected from the group consisting of:
   (a) the nucleic acid sequence of SEQ ID NO: 1,
   (b) a nucleic acid sequence that is at least 98.5% identical to SEQ ID NO: 2,
   (c) a nucleic acid sequence that is at least 90% identical to SEQ ID NO: 3,
   (d) a nucleic acid sequence that is at least 80% identical to SEQ ID NO: 4, and
   (e) a nucleic acid sequence that is at least 89% identical to SEQ ID NO: 5.

2. The adenovirus or adenoviral vector of claim 1, which comprises the nucleic acid sequence of SEQ ID NO: 1.

3. The adenovirus or adenoviral vector of claim 1, which comprises a nucleic acid sequence that is at least 98.5% identical to SEQ ID NO: 2.

4. The adenovirus or adenoviral vector of claim 3, which comprises the nucleic acid sequence of SEQ ID NO: 2.

5. The adenovirus or adenoviral vector of claim 1, which comprises a nucleic acid sequence that is at least 90% identical to SEQ ID NO: 3.

6. The adenovirus or adenoviral vector of claim 5, which comprises the nucleic acid sequence of SEQ ID NO: 3.

7. The adenovirus or adenoviral vector of claim 1, which comprises a nucleic acid sequence that is at least 80% identical to SEQ ID NO: 4.

8. The adenovirus or adenoviral vector of claim 7, which comprises the nucleic acid sequence of SEQ ID NO: 4.

9. The adenovirus or adenoviral vector of claim 1, which comprises a nucleic acid sequence that is at least 89% identical to SEQ ID NO: 5.

10. The adenovirus or adenoviral vector of claim 9, which comprises the nucleic acid sequence of SEQ ID NO: 5.

11. An adenovirus or adenoviral vector comprising a non-native nucleic acid sequence and one or more of the amino acid sequences selected from the group consisting of:
    (a) the amino acid sequence of SEQ ID NO: 11,
    (b) an amino acid sequence that is at least 82% identical to SEQ ID NO: 13,
    (c) an amino acid sequence that is at least 80% identical to SEQ ID NO: 14, and
    (d) an amino acid sequence that is at least 83% identical to SEQ ID NO: 15.

12. The adenovirus or adenoviral vector of claim 11, which comprises the amino acid sequence of SEQ ID NO: 11.

13. The adenovirus or adenoviral vector of claim 11, which comprises an amino acid sequence that is at least 82% identical to SEQ ID NO: 13.

14. The adenovirus or adenoviral vector of claim 13, which comprises the amino acid sequence of SEQ ID NO: 13.

15. The adenovirus or adenoviral vector of claim 11, which comprises an amino acid sequence that is at least 80% identical to SEQ ID NO: 14.

16. The adenovirus or adenoviral vector of claim 15, which comprises the amino acid sequence of SEQ ID NO: 14.

17. The adenovirus or adenoviral vector of claim 11, which comprises an amino acid sequence that is at least 83% identical to SEQ ID NO: 15.

18. The adenovirus or adenoviral vector of claim 17, which comprises the amino acid sequence of SEQ ID NO: 15.

19. An adenovirus or adenoviral vector comprising a non-native nucleic acid sequence and one or more of the nucleic acid sequences selected from the group consisting of:
    (a) a nucleic acid sequence encoding the amino acid sequence of SEQ ID NO: 11,
    (b) a nucleic acid sequence encoding an amino acid sequence that is at least 99% identical to SEQ ID NO: 12,
    (c) a nucleic acid sequence encoding an amino acid sequence that is at least 82% identical to SEQ ID NO: 13,
    (d) a nucleic acid sequence encoding an amino acid sequence that is at least 80% identical to SEQ ID NO: 14, and
    (e) a nucleic acid sequence encoding an amino acid sequence that is at least 83% identical to SEQ ID NO: 15.

20. The adenovirus or adenoviral vector of claim 19, which comprises a nucleic acid sequence encoding the amino acid sequence of SEQ ID NO: 11.

21. The adenovirus or adenoviral vector of claim 19, which comprises a nucleic acid sequence encoding an amino acid sequence that is at least 99% identical to SEQ ID NO: 12.

22. The adenovirus or adenoviral vector of claim 21, which comprises a nucleic acid sequence encoding the amino acid sequence of SEQ ID NO: 12.

23. The adenovirus or adenoviral vector of claim 19, which comprises a nucleic acid sequence encoding an amino acid sequence that is at least 82% identical to SEQ ID NO: 13.

24. The adenovirus or adenoviral vector of claim 23, which comprises a nucleic acid sequence encoding the amino acid sequence of SEQ ID NO: 13.

25. The adenovirus or adenoviral vector of claim 19, which comprises a nucleic acid sequence encoding an amino acid sequence that is at least 80% identical to SEQ ID NO: 14.

26. The adenovirus or adenoviral vector of claim 25, which comprises a nucleic acid sequence encoding the amino acid sequence of SEQ ID NO: 14.

27. The adenovirus or adenoviral vector of claim 19, which comprises a nucleic acid sequence encoding an amino acid sequence that is at least 83% identical to SEQ ID NO: 15.

28. The adenovirus or adenoviral vector of claim 27, which comprises a nucleic acid sequence encoding the amino acid sequence of SEQ ID NO: 15.

29. The adenovirus or adenoviral vector of claim 1, wherein the adenovirus or adenoviral vector requires complementation of a deficiency in one or more early regions of the adenoviral genome for propagation and does not require complementation of any other deficiency of the adenoviral genome for propagation.

30. The adenovirus or adenoviral vector of claim 1 further comprising a transgene.

31. A composition comprising the adenovirus or adenoviral vector of claim 1 and a pharmaceutically acceptable carrier.

32. The adenovirus or adenoviral vector of claim 11, wherein the adenovirus or adenoviral vector requires complementation of a deficiency in one or more early regions of the adenoviral genome for propagation and does not require complementation of any other deficiency of the adenoviral genome for propagation.

33. The adenovirus or adenoviral vector of claim 19, wherein the adenovirus or adenoviral vector requires complementation of a deficiency in one or more early regions of the adenoviral genome for propagation and does not require complementation of any other deficiency of the adenoviral genome for propagation.

34. The adenovirus or adenoviral vector of claim 11 further comprising a transgene.

35. The adenovirus or adenoviral vector of claim 19 further comprising a transgene.

36. A composition comprising the adenovirus or adenoviral vector of claim 11 and a pharmaceutically acceptable carrier.

37. A composition comprising the adenovirus or adenoviral vector of claim 19 and a pharmaceutically acceptable carrier.

* * * * *

SEQUENCE LISTING

```
<160> NUMBER OF SEQ ID NOS: 25

<210> SEQ ID NO 1
<211> LENGTH: 30
<212> TYPE: DNA
<213> ORGANISM: Gorilla beringei beringei

<400> SEQUENCE: 1
agctctttgg tggcgagcgg cgcggcctct                                       30
```

```
<210> SEQ ID NO 2
<211> LENGTH: 439
<212> TYPE: DNA
<213> ORGANISM: Gorilla beringei beringei

<400> SEQUENCE: 2
aacatcaata cctcaaagtc atggtcaggg acactttcgc cctcacccac acctccctcc     60
gcaaggcggc gcaggcctac gcgctgcccg tggagaaggg ctgttgcccc taccaggccg    120
tcaaccagtt ctacatgcta ggctcttacc gttcggacac ggacgggttt ccctccaag    180 agtactggaa agaccgcgaa gagttcgtcc tcaaccgcga gctgtggaaa agaaggggg    240 aggataagta tgcatcatc cgcgagaccc tcgactactg cgcgctcgac gtccaggtca    300
ccgccgagct ggtgcacaag ctgcgcgagt cctacgcctc cttcgtcagg gactcggtgg    360
gcttgcaaga agcaagcttc aacgtcttcc agcggccac catctcctcc aactcccatg    420
ccatcttcag gcagatcgc                                                  439

<210> SEQ ID NO 3
<211> LENGTH: 34
<212> TYPE: DNA
<213> ORGANISM: Gorilla beringei beringei

<400> SEQUENCE: 3
actgaggctg cggctaaggc tgaggtcgaa gcca                                  34

<210> SEQ ID NO 4
<211> LENGTH: 45
<212> TYPE: DNA
<213> ORGANISM: Gorilla beringei beringei

<400> SEQUENCE: 4
ataggtgtgg atgccacaca ggcgggagat aaccctatat atgct                      45

<210> SEQ ID NO 5
<211> LENGTH: 30
<212> TYPE: DNA
<213> ORGANISM: Gorilla beringei beringei

<400> SEQUENCE: 5
gtagcaggcc ccctagctgt ggccaatggc                                       30

<210> SEQ ID NO 6
<211> LENGTH: 399
<212> TYPE: DNA
<213> ORGANISM: Gorilla beringei beringei

<400> SEQUENCE: 6
atgagcgaca ccggcaacag ctttgatgga agcatcttta gccctatct gacagtgcgc      60 atgcctcact gggctggagt gcgtcagaat gtgatgggtt ccaacgtgga tggacgcccc    120
gttctgcctt caaattcgtc tacaatggcc tacgcgaccg tggaggaac tccgctggac     180 gccgcgacct ccgccgccgc ctccgccgcc gccgcgaccg cgcagcat ggctacggac      240 ctttacagct ctttggtggc gagcggcgcg gcctctcgcg cgtctgctcg ggatgagaaa    300
ctgaccgctc tgctgcttaa actggaagac ttgacccggg agctgggtca actgacccag    360
caggtctcca gcttgcgtga gagcagcctt gcctccccc                            399

<210> SEQ ID NO 7
<211> LENGTH: 3168
<212> TYPE: DNA
```

<213> ORGANISM: Gorilla beringei beringei

<400> SEQUENCE: 7

| | | | | | |
|---|---|---|---|---|---|
| atggacagct | ccaatgtgcg | cgatgtcgtc | atcaaactcc | gcccgccgag | cgccgagatc | 60 |
| tggacctgcg | gctctcgcgg | cgtggtggtc | tgctccacca | tcgccctcca | ggagacagat | 120 |
| gctggcggcc | agacaaccaa | agtagaagac | caccagccac | acgggacccc | aggcggggga | 180 |
| cttagattcc | cgctgcgctt | cctcgtcaga | ggtcgccagg | ttcacctcgt | gcaagatata | 240 |
| caacccgtgc | agcgctgcca | gtactgcggt | cgcttttaca | aaagccagca | cgagtgctcg | 300 |
| gcccgcagac | gggacttcta | ctttcaccac | atcaacagcc | aatcctccaa | ctggtggcgg | 360 |
| gagatccagt | tcttcccgat | cggctctcat | cctcgcacgg | agcgcctctt | tgtcacctac | 420 |
| gatgtagaga | cctacacttg | gatgggagcc | tttggcaagc | agctcgtgcc | cttcatgctg | 480 |
| gtcatgaaac | tgggggggcga | cgaggctctg | gtcgccgccg | cgcgcgacct | cgcccgagag | 540 |
| ctcagatggg | accctgggaa | gaaagaccc | ctcaccttct | actgcatcac | ccccgaaaag | 600 |
| atggccgtgg | ggcgacagtt | cagaaccttc | gcgaccgcc | tgcagaccct | catggcccgc | 660 |
| gacctctggc | gatccttcct | ggcggccaac | cctcacttgc | aagactgggc | cctggaggag | 720 |
| cacggcctgg | aatcgcccga | ggagctcacc | tacgaggaac | tcaaaaagct | cccctccatc | 780 |
| aagggccagc | cccgcttttt | ggagctctac | atcgtgggcc | acaacataaa | cggctttgac | 840 |
| gagatcgtcc | tggccgccca | ggtcatcaac | aaccgctcct | cggtcccagg | gcccttttcgc | 900 |
| atcaccagaa | acttcatgcc | tcgagcgggg | aagatcctct | tcaatgacct | caccttctcc | 960 |
| ctgcccaacc | cgcgctccaa | aaagcgcacg | gactacaccc | tgtgggaaca | gggcggctgc | 1020 |
| gatgacacag | acttcaaaca | tcaataccctc | aaagtcatgg | tcaggacac | tttcgccctc | 1080 |
| acccacacct | ccctccgcaa | ggcggcgcag | gcctacgcgc | tgcccgtgga | aagggctgt | 1140 |
| tgccccctacc | aggccgtcaa | ccagttctac | atgctaggct | cttaccgttc | ggacacggac | 1200 |
| gggtttcccc | tccaagagta | ctggaaagac | cgcgaagagt | tcgtcctcaa | ccgcgagctg | 1260 |
| tggaaaaaga | agggggagga | taagtatgac | atcatccgcg | agaccctcga | ctactgcgcg | 1320 |
| ctcgacgtcc | aggtcaccgc | cgagctggtg | cacaagctgc | gcgagtccta | cgcctccttc | 1380 |
| gtcagggact | cggtgggctt | gcaagaagca | agcttcaacg | tcttccagcg | gcccaccatc | 1440 |
| tcctccaact | cccatgccat | cttcaggcag | atcgccttcc | gcgccgagcg | ccccccagcgc | 1500 |
| accaacctcg | ggcccaacat | gctggccccc | tcccacgagc | tctatgacta | cgtgcgcgcc | 1560 |
| agcatccgcg | gggggcgctg | ctacccccacc | tacctcggca | tcctcaggga | acccctgtac | 1620 |
| gtgtatgaca | tctgcggcat | gtacgcctcc | gcgctcaccc | accccatgcc | ctggggcccg | 1680 |
| cccctcaacc | cctacgagcg | cgcgctcgcc | gcccgcgaat | ggcagcgggc | tctggacatg | 1740 |
| caagcttgca | agatcgacta | ctttgacccg | cgcttgctcc | ccggggtctt | caccatcgac | 1800 |
| gcggaccccc | caaacgagga | ccagctggac | ccccctaccccc | ccttctgctc | cgcaagggc | 1860 |
| ggccgcctct | gctggaccaa | cgagcgcctg | cgcggcgagg | tcgccaccag | cgtcgacatg | 1920 |
| gtcaccctgc | acaaccgagg | ctggagggtg | cgcctaatcc | cagacgagcg | caccaccgtc | 1980 |
| ttccccgagt | ggaagtgcgt | ggcccgcgag | tacgtgcaac | tcaacatcgc | ggccaaggag | 2040 |
| cgagccgacc | gcgacaaaaa | ccagaccctg | cgctccatcg | ccaagctgct | ctccaacgcc | 2100 |
| ctctacgggt | cgttcgccac | caagcttgac | aacaaaaaaa | tagtgttttc | tgaccagatg | 2160 |
| gacccaggta | ccctcaaagg | tatcacctcc | ggacaggtga | acatcaaatc | ctcctcattt | 2220 |
| ttagaaactg | acaacctgag | cgctgaggtc | atgcccgcct | tcgagaggga | atacttaccc | 2280 |

```
cagcagctgg ccctcgcaga cagcgatgcg gaagagagtg aagatgaaag ggcgcccacc      2340
cccttttata cccccccgtc gggaacccc ggtcacgtgt cctacaccta caagccaatc       2400 actttctgg acgcggagga gggggacatg tgcctgcaca ccctggagaa ggtggacccg       2460
ctagtggaca cgaccgcta ccctcccac gtggcctcct tcgtcctggc ctggacgcgg        2520
gccttcgtct cagagtggtc agagtttctc tacgaggagg acagaggcac tccgctggaa     2580
gacaggcccc tgaagtcggt ctacggggac acggacagcc tcttcgtcac cgagaaggga     2640
caccgcctca tggagagccg aggtaagaaa cgcatcaaaa agcatggggg caacctggtt      2700
tttgaccctg accgcccgga gctcacttgg ctggtggaat gcgagacggt ctgcgcttcc     2760
tgcggcgcgg acgcctactc cccagagtcc gtgtttctcg ctcccaagct ctacgccctg     2820
aagagcctgc agtgccctc gtgcggcgcc acctccaagg gaaagctccg cgccaagggg      2880
cacgccgccg agggtctcga ctacgagacc atggtcaaat gctacctggc cgacgcgcag     2940
ggcgaagagc ggcagcgatt cagcaccagc agaaccagcc tcaagcgcac cctggccagc     3000
gcccaacccg gagcgcaccc cttcaccgtg acccagacca ccctgacgag gaccctgcgc     3060
ccatggaagg acatgactct ggccccgctg gacgcccatc ggctggtgcc ctacagcgaa     3120
agccgcccca acccgcgaaa cgaggagatc tgctggatcg agatgccg                  3168
```

<210> SEQ ID NO 8
<211> LENGTH: 1974
<212> TYPE: DNA
<213> ORGANISM: Gorilla beringei beringei

<400> SEQUENCE: 8

```
atgcggcgcg cggcgatgtt cgaggagggg cctccccct cttacgagag cgcgatgggg        60
atttctcctg cggcgcccct gcagcctccc tacgtgcctc ctcggtacct gcaacctaca      120 gggggagaa atagcatctg ttactctgag ctgcagcccc tgtacgatac caccagactg       180
tacctggtgg acaacaagtc cgcggacgtg gcctccctga actaccagaa cgaccacagc     240
gattttttga ccacggtgat ccaaaacaac gacttcaccc caaccgaggc cagcacccag     300
accataaacc tggataacag gtcgaactgg ggcggcgacc tgaagaccat cttgcacacc     360
aacatgccca acgtgaacga gttcatgttc accaactctt ttaaggcgcg ggtgatggtg    420
gcgcgcgagc agggggaggc gaagtacgag tgggtggact tcacgctgcc cgagggcaac     480
tactcagaga ccatgactct cgacctgatg aacaatgcga tcgtggaaca ctatctgaaa     540
gtgggcaggg agaacggggt gaaggaaagc gatatcgggg tcaagtttga caccagaaac    600
ttccgtctgg gctgggaccc cgtgaccggg ctggtcatgc cggggtctca caccaacgag    660
gcctttcatc ccgacatagt gcttctgccc ggctgtgggg tggacttcac ccagagccgg    720
ctgagcaacc tgctgggcat cgcaagcgg cagcctttcc aggagggttt caagatcacc     780
tatgaggatc tgaaggggg caacattccc gcgctccttg atctggacgc ctacgaggag     840
agcttgaaac ccgaggagag cgctggcgac agcggcgaga gtggcgagga caagccggc     900 ggcggtggcg gcgcgtcggt agaaaacgaa agtacgcccg cagtggcggc ggacgctgcg    960
gaggtcgagc cggaggccat gcagcaggac gcagaggagg cgcacagga gggcgcgcag    1020 aaggacatga cgatgggga gatcagggga gacacattcg ccaccggggg cgaagaaaaa    1080
gaggcagagg cggcggcggc ggcgacggcg gaggccgaaa ccgaggttga ggcagaggca    1140
gagcccgaga ccgaagttat ggaagacatg aatgatggag aacgtagggg cgacacgttc    1200
```

| | |
|---|---|
| gccacccggg gcgaagagaa ggcggcggag gcagaagccg cggctgagga ggcggctgcg | 1260 |
| gctgcggcca agactgaggc tgcggctaag gctgaggtcg aagccaatgt tgcggttgag | 1320 |
| gctcaggctg aggaggaggc ggcggctgaa gcagttaagg aaaaggccca ggcagagcag | 1380 |
| gaagagaaaa aacctgtcat tcaacctcta aagaagata gcaaaaagcg cagttacaac | 1440 |
| gtcatcgagg gcagcacctt tacccagtac cgcagctggt acctggcgta caactacggc | 1500 |
| gacccggtca aggggtgcg ctcgtggacc ctgctctgca cgccgacgt cacctgcggc | 1560 |
| tccgagcaga tgtactggtc gctgccgaac atgatgcaag acccggtgac cttccgctcc | 1620 |
| acgcggcagg ttagcaactt cccggtggtg ggcgccgaac tgctgcccgt gcactccaag | 1680 |
| agttttttaca acgagcaggc cgtctactcc cagctgatcc gccaggccac ctctctgacc | 1740 |
| cacgtgttca atcgctttcc cgagaaccag atttttggcgc gcccgccggc ccccaccatc | 1800 |
| accaccgtga gtgaaaacgt tcctgccctc acagatcacg ggacgctacc gctgcgcaac | 1860 |
| agcatctcag gagtccagcg agtgaccatt actgacgcca gacgccggac ctgcccctac | 1920 |
| gtttacaagg ccttgggcat agtctcgccg cgcgtcctct ccagtcgcac tttt | 1974 |

```
<210> SEQ ID NO 9
<211> LENGTH: 2877
<212> TYPE: DNA
<213> ORGANISM: Gorilla beringei beringei

<400> SEQUENCE: 9
```

| | |
|---|---|
| atggcgaccc catcgatgat gcctcagtgg tcgtacatgc acatctcggg ccaggacgct | 60 |
| tcggagtacc tgagccccgg gctggtgcag ttcgcccgcg ccacagacac ctacttcaac | 120 |
| atgagtaaca agttcaggaa ccccactgtg gcgcccaccc acgatgtgac cacggaccgg | 180 |
| tcgcagcgcc tgacgctgcg gttcatcccc gtggatcggg aggacaccgc ctactcttac | 240 |
| aaggcgcggt tcacgctggc cgtgggcgac aaccgcgtgc tggacatggc ctccacttac | 300 |
| tttgacatca ggggggtgct ggacaggggc cccaccttca gccctactc gggtactgcc | 360 |
| tacaactccc tggcccccaa gggcgctccc aattcttgcg agtgggaaca agatgaacca | 420 |
| gctcaggcag caatagctga agatgaagaa gaacttgaag aagaacaagc tcaggacgaa | 480 |
| caggcgccca ctaagaaaac ccatgtatac gcccaggcac ctctttctgg tgaaaaaatt | 540 |
| actaaggatg gtttgcaaat aggtgtggat gccacacagg cgggagataa ccctatatat | 600 |
| gctgataaaa cattccaacc cgaacctcag ataggtgagt ctcagtggaa cgaggctgat | 660 |
| gccacagtag caggaggcag agtcttaaaa aagaccaccc ctatgagacc ttgctatgga | 720 |
| tcctatgcca aacctactaa tgccaatggc ggtcaaggga tcatggtggc caatgatcag | 780 |
| ggagcgcttg aatctaaagt tgagatgcaa ttttttctcca ccacaacgtc tcttaatgta | 840 |
| agggaaggtg aaaacaatct tcagccaaaa gtagtgctat acagcgaaga tgttaacttg | 900 |
| gaatccctg acactcattt gtcttacaaa cctaaaaagg atgacaccaa ctctaaaatc | 960 |
| atgttgggtc agcaagccat gcccaacaga cccaacctca ttgcttttag ggacaacttt | 1020 |
| attggactta tgtactacaa cagcacaggc aacatgggag tgctggcagg acaggcctcc | 1080 |
| cagctaaacg ctgtggtaga cttgcaagac agaaacacag agctgtcata ccaactgatg | 1140 |
| cttgattcca ttggagacag atcaagatac ttttccatgt ggaaccaggc agtggacagc | 1200 |
| tatgacccag atgtcagaat cattgaaaac catggggttg aagatgagct gcccaactat | 1260 |
| tgctttcccc tgggcggtat tggaattaca gacacatacc agtgcataaa accaccgca | 1320 |
| gctgctaata acactacatg gtctaaggat gaagaattta gtgatcgcaa tgaaataggg | 1380 |

```
gtgggaaaca acttcgccat ggagatcaac atccaggcca acctctggag gaacttcctc    1440
tatgcgaacg tggggctcta cctgccagac aagctcaagt acaaccccac caacgtggac    1500
atctctgaca accccaacac ctatgactac atgaacaagc gtgtggtggc tcccggcctg    1560
gtggactgct tgtcaatgt gggagccagg tggtccctgg actacatgga caacgtcaac    1620
cccttcaacc accaccgcaa tgcgggtctg cgctaccgct ccatgatcct gggcaacggg    1680
cgctacgtgc ccttccacat tcaggtgccc cagaagttct tgccatcaa gaacctcctc    1740 ctcctgccgg gctcctacac ttacgagtgg aacttcagga aggatgtcaa catggtcctg    1800
cagagctctc tgggcaatga ccttagggtg acgggggcca gcatcaagtt tgacagcgtc    1860
accctctatg ctaccttctt ccccatggct cacaacaccg cctccacgct cgaggccatg    1920
ctgaggaacg acaccaacga ccagtccttc aatgactacc tctctggggc caacatgctc    1980
taccccatcc ccgccaaggc caccaacgtg cccatctcca ttccctctcg caactgggcc    2040
gccttcagag gctgggcctt acccgccctt aagaccaagg aaaccccctc cctgggctcg    2100
ggttttgacc cctactttgt ctactcggga tccatcccct acctggatgg caccttctac    2160
ctcaaccaca cttttaagaa gatatccatc atgtatgact cctccgtcag ctggccgggc    2220
aatgaccgcc tgctcacccc caatgagttc gaggtcaagc gcgccgtgga cggcgagggc    2280
tacaacgtgg cccagtgcaa catgaccaag gactggttcc tggtgcagat gctgccaac    2340 tacaacatag gctaccaggg cttctacatc ccagagagct acaaggacag gatgtactcc    2400
ttcttcagaa atttccaacc catgagcagg caggtggtgg acgagaccaa atacaaggac    2460
tatcaggcca ttggcatcac tcaccagcac aacaactcgg gattcgtggg ctacctggct    2520
cccaccatgc gcgaggggca ggcctacccc gccaacttcc cctacccgtt gataggcaaa    2580
accgcggtcg acagcgtcac ccagaaaaag ttcctctgcg accgcaccct ctggcgcatc    2640
cccttctcta gcaacttcat gtccatgggt gcgctcacgg acctgggcca gaacctgctc    2700
tatgccaact ccgcccatgc gctggacatg acttttgagg tggaccccat ggacgagccc    2760 accctttctct atattgtgtt tgaagtgttc gacgtggtca gagtgcacca gccgcaccgc    2820
ggtgtcatcg agaccgtgta cctgcgcacg cccttctcgg ccggcaacgc caccacc      2877
```

<210> SEQ ID NO 10
<211> LENGTH: 1749
<212> TYPE: DNA
<213> ORGANISM: Gorilla beringei beringei

<400> SEQUENCE: 10

```
atgaaacgcg cgagatcgtc tgacgagacc ttcaaccccg tgtaccccta cgataccgag      60
atcgctccga cttctgtccc tttccttacc cctcccttg tgtcatccgc aggaatgcaa     120
gaaaatccag ctggggtgct gtccctgcac ttgtcagagc ccttaccac ccacaatggg     180 gccctgactc taaaaatggg gggcggcctg accctggaca aggaagggaa tctcacttcc     240
caaaacatca ccagtgtcga tccccctctc aaaaaaagca gaacaacat cagccttcag     300 accgccgcac ccctcgccgt cagctccggg gccctaacac tttttgccac tcccccccta     360
gcggtcagtg gtgacaacct tactgtgcag tctcaggccc ctctcacttt ggaagactca     420
aaactaactc tggccaccaa aggacccta actgtgtccg aaggcaaact tgtcctagaa     480
acagaggctc ccctgcatgc aagtgacagc agcagcctgg ccttagcgt tacgccccca     540 cttagcatta caatgacag cctaggacta gatctgcagg cacccattgt ctctcaaaat     600
```

```
ggaaaactgg ctctaaatgt agcaggcccc ctagctgtgg ccaatggcat taatgctttg    660
acagtaggca caggcaaagg tattggtcta aatgaaacca gcactcactt gcaagcaaag    720
ttggtcgccc ccctaggctt tgataccaat ggcaacatta agctaagcgt tgcaggaggc    780
atgagactaa ataatgacac acttatacta gatgtaaact acccatttga agctcaaggc    840
caactaagtc taagagtggg ccagggtccg ctgtatgtag attctagcag ccataacctg    900
accattagat gccttagagg attatacata acatcgtcta ataaccaaac cggtctagag    960
gccaacataa aactaacaaa aggccttgtc tatgatggaa atgccatagc agtcaatgtt   1020
ggtcaaggat tgcaatacag cactactgcc acatcggaag gtgtgtatcc tatacagtct   1080
aagataggtt tgggaatgga atatgatacc aacggagcca tgatgacaaa actaggctct   1140
ggactaagct ttgacaattc aggagccatt gtagtgggaa acaaaaatga tgacaggctt   1200
actctgtgga ctacaccaga cccatctcct aactgtagaa tttattctga aaaagatact   1260
aaactaacct tggtgctgac taagtgtggc agccaaatcc taggcacagt atctgccctt   1320
gctgtcagag gcagccttgc gcccatcact aatgcatcca gcatagtcca aatatttcta   1380
agatttgatg aaaatggact attgatgagc aactcatcgc tagacggtga ttactggaat   1440
tacagaaatg gggactccac taatagcaca ccatatacaa atgcagtagg ctttatgcct   1500
aatctagcag cctatcctaa aggtcaggct acagctgcaa aaagcagtat tgtaagccag   1560
gtatacatgg atggtgacac tactaaacct ataacactaa aaataaactt caatggcatt   1620
gatgaaacaa cagaaaatac ccctgttagt aaatattcca tgacattctc atggagctgg   1680
cccaccgcaa gctacatagg ccacactttt gcaacaaact cttttacttt ctcctacatc   1740
gcccaagaa                                                            1749
```

<210> SEQ ID NO 11
<211> LENGTH: 10
<212> TYPE: PRT
<213> ORGANISM: Gorilla beringei beringei

<400> SEQUENCE: 11

Ser Ser Leu Val Ala Ser Gly Ala Ala Ser
1               5                   10

<210> SEQ ID NO 12
<211> LENGTH: 147
<212> TYPE: PRT
<213> ORGANISM: Gorilla beringei beringei

<400> SEQUENCE: 12

Lys His Gln Tyr Leu Lys Val Met Val Arg Asp Thr Phe Ala Leu Thr
1               5                   10                  15

His Thr Ser Leu Arg Lys Ala Ala Gln Ala Tyr Ala Leu Pro Val Glu
            20                  25                  30

Lys Gly Cys Cys Pro Tyr Gln Ala Val Asn Gln Phe Tyr Met Leu Gly
        35                  40                  45

Ser Tyr Arg Ser Asp Thr Asp Gly Phe Pro Leu Gln Glu Tyr Trp Lys
    50                  55                  60

Asp Arg Glu Glu Phe Val Leu Asn Arg Glu Leu Trp Lys Lys Lys Gly
65                  70                  75                  80

Glu Asp Lys Tyr Asp Ile Ile Arg Glu Thr Leu Asp Tyr Cys Ala Leu
                85                  90                  95

Asp Val Gln Val Thr Ala Glu Leu Val His Lys Leu Arg Glu Ser Tyr
            100                 105                 110

-continued

```
Ala Ser Phe Val Arg Asp Ser Val Gly Leu Gln Glu Ala Ser Phe Asn
        115                 120                 125

Val Phe Gln Arg Pro Thr Ile Ser Ser Asn Ser His Ala Ile Phe Arg
    130                 135                 140

Gln Ile Ala
145

<210> SEQ ID NO 13
<211> LENGTH: 15
<212> TYPE: PRT
<213> ORGANISM: Gorilla beringei beringei

<400> SEQUENCE: 13

Lys Thr Glu Ala Ala Lys Ala Glu Val Glu Ala Asn Val Ala
1               5                   10                  15

<210> SEQ ID NO 14
<211> LENGTH: 15
<212> TYPE: PRT
<213> ORGANISM: Gorilla beringei beringei

<400> SEQUENCE: 14

Ile Gly Val Asp Ala Thr Gln Ala Gly Asp Asn Pro Ile Tyr Ala
1               5                   10                  15

<210> SEQ ID NO 15
<211> LENGTH: 15
<212> TYPE: PRT
<213> ORGANISM: Gorilla beringei beringei

<400> SEQUENCE: 15

Leu Asn Val Ala Gly Pro Leu Ala Val Ala Asn Gly Ile Asn Ala
1               5                   10                  15

<210> SEQ ID NO 16
<211> LENGTH: 133
<212> TYPE: PRT
<213> ORGANISM: Gorilla beringei beringei

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
            20                  25                  30

Gly Ser Asn Val Asp Gly Arg Pro Val Leu Pro Ser Asn Ser Ser Thr
        35                  40                  45

Met Ala Tyr Ala Thr Val Gly Gly Thr Pro Leu Asp Ala Ala Thr Ser
    50                  55                  60

Ala Ala Ala Ser Ala Ala Ala Thr Ala Arg Ser Met Ala Thr Asp
65                  70                  75                  80

Leu Tyr Ser Ser Leu Val Ala Ser Gly Ala Ala Ser Arg Ala Ser Ala
                85                  90                  95

Arg Asp Glu Lys Leu Thr Ala Leu Leu Lys Leu Glu Asp Leu Thr
            100                 105                 110

Arg Glu Leu Gly Gln Leu Thr Gln Gln Val Ser Ser Leu Arg Glu Ser
        115                 120                 125

Ser Leu Ala Ser Pro
    130
```

<210> SEQ ID NO 17
<211> LENGTH: 1056
<212> TYPE: PRT
<213> ORGANISM: Gorilla beringei beringei

<400> SEQUENCE: 17

```
Met Asp Ser Ser Asn Val Arg Asp Val Val Ile Lys Leu Arg Pro Pro
1               5                   10                  15

Ser Ala Glu Ile Trp Thr Cys Gly Ser Arg Gly Val Val Cys Ser
            20                  25                  30

Thr Ile Ala Leu Gln Glu Thr Asp Ala Gly Gly Gln Thr Thr Lys Val
                35                  40                  45

Glu Asp His Gln Pro His Gly Thr Pro Gly Gly Leu Arg Phe Pro
 50                  55                  60

Leu Arg Phe Leu Val Arg Gly Arg Gln Val His Leu Val Gln Asp Ile
 65                  70                  75                  80

Gln Pro Val Gln Arg Cys Gln Tyr Cys Gly Arg Phe Tyr Lys Ser Gln
                85                  90                  95

His Glu Cys Ser Ala Arg Arg Arg Asp Phe Tyr Phe His His Ile Asn
            100                 105                 110

Ser Gln Ser Ser Asn Trp Trp Arg Glu Ile Gln Phe Pro Ile Gly
            115                 120                 125

Ser His Pro Arg Thr Glu Arg Leu Phe Val Thr Tyr Asp Val Glu Thr
130                 135                 140

Tyr Thr Trp Met Gly Ala Phe Gly Lys Gln Leu Val Pro Phe Met Leu
145                 150                 155                 160

Val Met Lys Leu Gly Gly Asp Glu Ala Leu Val Ala Ala Ala Arg Asp
                165                 170                 175

Leu Ala Arg Glu Leu Arg Trp Asp Pro Trp Glu Lys Asp Pro Leu Thr
            180                 185                 190

Phe Tyr Cys Ile Thr Pro Glu Lys Met Ala Val Gly Arg Gln Phe Arg
        195                 200                 205

Thr Phe Arg Asp Arg Leu Gln Thr Leu Met Ala Arg Asp Leu Trp Arg
210                 215                 220

Ser Phe Leu Ala Ala Asn Pro His Leu Gln Asp Trp Ala Leu Glu Glu
225                 230                 235                 240

His Gly Leu Glu Ser Pro Glu Glu Leu Thr Tyr Glu Glu Leu Lys Lys
                245                 250                 255

Leu Pro Ser Ile Lys Gly Gln Pro Arg Phe Leu Glu Leu Tyr Ile Val
            260                 265                 270

Gly His Asn Ile Asn Gly Phe Asp Glu Ile Val Leu Ala Ala Gln Val
        275                 280                 285

Ile Asn Asn Arg Ser Ser Val Pro Gly Pro Phe Arg Ile Thr Arg Asn
290                 295                 300

Phe Met Pro Arg Ala Gly Lys Ile Leu Phe Asn Asp Leu Thr Phe Ser
305                 310                 315                 320

Leu Pro Asn Pro Arg Ser Lys Lys Arg Thr Asp Tyr Thr Leu Trp Glu
                325                 330                 335

Gln Gly Gly Cys Asp Asp Thr Asp Phe Lys His Gln Tyr Leu Lys Val
            340                 345                 350

Met Val Arg Asp Thr Phe Ala Leu Thr His Thr Ser Leu Arg Lys Ala
        355                 360                 365

Ala Gln Ala Tyr Ala Leu Pro Val Glu Lys Gly Cys Cys Pro Tyr Gln
370                 375                 380
```

```
Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Glu Phe Val Leu
            405                 410                 415

Asn Arg Glu Leu Trp Lys Lys Lys Gly Glu Asp Lys Tyr Asp Ile Ile
            420                 425                 430

Arg Glu Thr Leu Asp Tyr Cys Ala Leu Asp Val Gln Val Thr Ala Glu
            435                 440                 445

Leu Val His Lys Leu Arg Glu Ser Tyr Ala Ser Phe Val Arg Asp Ser
            450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
            485                 490                 495

Arg Pro Gln Arg Thr Asn Leu Gly Pro Asn Met Leu Ala Pro Ser His
            500                 505                 510

Glu Leu Tyr Asp Tyr Val Arg Ala Ser Ile Arg Gly Gly Arg Cys Tyr
            515                 520                 525

Pro Thr Tyr Leu Gly Ile Leu Arg Glu Pro Leu Tyr Val Tyr Asp Ile
            530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
            565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
            595                 600                 605

Leu Asp Pro Leu Pro Pro Phe Cys Ser Arg Lys Gly Gly Arg Leu Cys
            610                 615                 620

Trp Thr Asn Glu Arg Leu Arg Gly Glu Val Ala Thr Ser Val Asp Met
625                 630                 635                 640

Val Thr Leu His Asn Arg Gly Trp Arg Val Arg Leu Ile Pro Asp Glu
            645                 650                 655

Arg Thr Thr Val Phe Pro Glu Trp Lys Cys Val Ala Arg Glu Tyr Val
            660                 665                 670

Gln Leu Asn Ile Ala Ala Lys Glu Arg Ala Asp Arg Asp Lys Asn Gln
            675                 680                 685

Thr Leu Arg Ser Ile Ala Lys Leu Leu Ser Asn Ala Leu Tyr Gly Ser
            690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
            725                 730                 735

Ser Ser Ser Phe Leu Glu Thr Asp Asn Leu Ser Ala Glu Val Met Pro
            740                 745                 750

Ala Phe Glu Arg Glu Tyr Leu Pro Gln Gln Leu Ala Leu Ala Asp Ser
            755                 760                 765

Asp Ala Glu Glu Ser Glu Asp Glu Arg Ala Pro Thr Pro Phe Tyr Thr
            770                 775                 780

Pro Pro Ser Gly Thr Pro Gly His Val Ser Tyr Thr Tyr Lys Pro Ile
785                 790                 795                 800

Thr Phe Leu Asp Ala Glu Glu Gly Asp Met Cys Leu His Thr Leu Glu
```

```
            805                 810                 815
Lys Val Asp Pro Leu Val Asp Asn Asp Arg Tyr Pro Ser His Val Ala
            820                 825                 830

Ser Phe Val Leu Ala Trp Thr Arg Ala Phe Val Ser Glu Trp Ser Glu
            835                 840                 845

Phe Leu Tyr Glu Glu Asp Arg Gly Thr Pro Leu Glu Asp Arg Pro Leu
            850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
                900                 905                 910

Glu Cys Glu Thr Val Cys Ala Ser Cys Gly Ala Asp Ala Tyr Ser Pro
            915                 920                 925

Glu Ser Val Phe Leu Ala Pro Lys Leu Tyr Ala Leu Lys Ser Leu Gln
            930                 935                 940

Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Glu Arg Gln Arg Phe Ser Thr Ser Arg Thr
            980                 985                 990

Ser Leu Lys Arg Thr Leu Ala Ser Ala Gln Pro Gly Ala His Pro Phe
            995                1000                1005

Thr Val Thr Gln Thr Thr Leu Thr Arg Thr Leu Arg Pro Trp Lys
1010                1015                1020

Asp Met Thr Leu Ala Pro Leu Asp Ala His Arg Leu Val Pro Tyr
    1025                1030                1035

Ser Glu Ser Arg Pro Asn Pro Arg Asn Glu Glu Ile Cys Trp Ile
    1040                1045                1050

Glu Met Pro
    1055

<210> SEQ ID NO 18
<211> LENGTH: 658
<212> TYPE: PRT
<213> ORGANISM: Gorilla beringei beringei

<400> SEQUENCE: 18

Met Arg Arg Ala Ala Met Phe Glu Glu Gly Pro Pro Ser Tyr Glu
1               5                   10                  15

Ser Ala Met Gly Ile Ser Pro Ala Pro Leu Gln Pro Pro Tyr Val
            20                  25                  30

Pro Pro Arg Tyr Leu Gln Pro Thr Gly Gly Arg Asn Ser Ile Cys Tyr
            35                  40                  45

Ser Glu Leu Gln Pro Leu Tyr Asp Thr Thr Arg Leu Tyr Leu Val Asp
            50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Thr Pro Thr Glu
                85                  90                  95

Ala Ser Thr Gln Thr Ile Asn Leu Asp Asn Arg Ser Asn Trp Gly Gly
            100                 105                 110
```

-continued

```
Asp Leu Lys Thr Ile Leu His Thr Asn Met Pro Asn Val Asn Glu Phe
            115                 120                 125

Met Phe Thr Asn Ser Phe Lys Ala Arg Val Met Val Ala Arg Glu Gln
130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
            180                 185                 190

Gly Val Lys Phe Asp Thr Arg Asn Phe Arg Leu Gly Trp Asp Pro Val
            195                 200                 205

Thr Gly Leu Val Met Pro Gly Val Tyr Thr Asn Glu Ala Phe His Pro
210                 215                 220

Asp Ile Val Leu Leu Pro Gly Cys Gly Val Asp Phe Thr Gln Ser Arg
225                 230                 235                 240

Leu Ser Asn Leu Leu Gly Ile Arg Lys Arg Gln Pro Phe Gln Glu Gly
            245                 250                 255

Phe Lys Ile Thr Tyr Glu Asp Leu Lys Gly Asn Ile Pro Ala Leu
            260                 265                 270

Leu Asp Leu Asp Ala Tyr Glu Glu Ser Leu Lys Pro Glu Glu Ser Ala
275                 280                 285

Gly Asp Ser Gly Glu Ser Glu Glu Gln Ala Gly Gly Gly Gly
            290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala
            355                 360                 365

Thr Ala Glu Ala Glu Thr Glu Val Glu Ala Glu Ala Glu Pro Glu Thr
370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Ala Ala Ala Glu
                405                 410                 415

Glu Ala Ala Ala Ala Ala Lys Thr Glu Ala Ala Lys Ala Glu
            420                 425                 430

Val Glu Ala Asn Val Ala Val Glu Ala Gln Ala Glu Glu Glu Ala Ala
            435                 440                 445

Ala Glu Ala Val Lys Glu Lys Ala Gln Ala Glu Gln Glu Glu Lys Lys
450                 455                 460

Pro Val Ile Gln Pro Leu Lys Glu Asp Ser Lys Lys Arg Ser Tyr Asn
465                 470                 475                 480

Val Ile Glu Gly Ser Thr Phe Thr Gln Tyr Arg Ser Trp Tyr Leu Ala
                485                 490                 495

Tyr Asn Tyr Gly Asp Pro Val Lys Gly Val Arg Ser Trp Thr Leu Leu
            500                 505                 510

Cys Thr Pro Asp Val Thr Cys Gly Ser Glu Gln Met Tyr Trp Ser Leu
            515                 520                 525

Pro Asn Met Met Gln Asp Pro Val Thr Phe Arg Ser Thr Arg Gln Val
```

```
                530                 535                 540
Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
                580                 585                 590

Ala Arg Pro Pro Ala Pro Thr Ile Thr Thr Val Ser Glu Asn Val Pro
                595                 600                 605

Ala Leu Thr Asp His Gly Thr Leu Pro Leu Arg Asn Ser Ile Ser Gly
                610                 615                 620

Val Gln Arg Val Thr Ile Thr Asp Ala Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe

<210> SEQ ID NO 19
<211> LENGTH: 959
<212> TYPE: PRT
<213> ORGANISM: Gorilla beringei beringei

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Asn Met Ser Asn Lys Phe Arg Asn Pro
                35                  40                  45

Thr Val Ala Pro Thr His Asp Val Thr Thr Asp Arg Ser Gln Arg Leu
                50                  55                  60

Thr Leu Arg Phe Ile Pro Val Asp Arg Glu Asp Thr Ala Tyr Ser Tyr
65              70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ser Leu Ala Pro Lys Gly
                115                 120                 125

Ala Pro Asn Ser Cys Glu Trp Glu Gln Asp Glu Pro Ala Gln Ala Ala
                130                 135                 140

Ile Ala Glu Asp Glu Glu Glu Leu Glu Glu Glu Gln Ala Gln Asp Glu
145                 150                 155                 160

Gln Ala Pro Thr Lys Lys Thr His Val Tyr Ala Gln Ala Pro Leu Ser
                165                 170                 175

Gly Glu Lys Ile Thr Lys Asp Gly Leu Gln Ile Gly Val Asp Ala Thr
                180                 185                 190

Gln Ala Gly Asp Asn Pro Ile Tyr Ala Asp Lys Thr Phe Gln Pro Glu
                195                 200                 205

Pro Gln Ile Gly Glu Ser Gln Trp Asn Glu Ala Asp Ala Thr Val Ala
                210                 215                 220

Gly Gly Arg Val Leu Lys Lys Thr Thr Pro Met Arg Pro Cys Tyr Gly
225                 230                 235                 240

Ser Tyr Ala Lys Pro Thr Asn Ala Asn Gly Gly Gln Gly Ile Met Val
```

```
                    245                 250                 255
Ala Asn Asp Gln Gly Ala Leu Glu Ser Lys Val Glu Met Gln Phe Phe
                260                 265                 270

Ser Thr Thr Thr Ser Leu Asn Val Arg Glu Gly Glu Asn Asn Leu Gln
            275                 280                 285

Pro Lys Val Val Leu Tyr Ser Glu Asp Val Asn Leu Glu Ser Pro Asp
        290                 295                 300

Thr His Leu Ser Tyr Lys Pro Lys Asp Asp Thr Asn Ser Lys Ile
305                 310                 315                 320

Met Leu Gly Gln Gln Ala Met Pro Asn Arg Pro Asn Leu Ile Ala Phe
                325                 330                 335

Arg Asp Asn Phe Ile Gly Leu Met Tyr Tyr Asn Ser Thr Gly Asn Met
            340                 345                 350

Gly Val Leu Ala Gly Gln Ala Ser Gln Leu Asn Ala Val Val Asp Leu
        355                 360                 365

Gln Asp Arg Asn Thr Glu Leu Ser Tyr Gln Leu Met Leu Asp Ser Ile
    370                 375                 380

Gly Asp Arg Ser Arg Tyr Phe Ser Met Trp Asn Gln Ala Val Asp Ser
385                 390                 395                 400

Tyr Asp Pro Asp Val Arg Ile Ile Glu Asn His Gly Val Glu Asp Glu
                405                 410                 415

Leu Pro Asn Tyr Cys Phe Pro Leu Gly Gly Ile Gly Ile Thr Asp Thr
            420                 425                 430

Tyr Gln Cys Ile Lys Pro Thr Ala Ala Ala Asn Asn Thr Thr Trp Ser
        435                 440                 445

Lys Asp Glu Glu Phe Ser Asp Arg Asn Glu Ile Gly Val Gly Asn Asn
    450                 455                 460

Phe Ala Met Glu Ile Asn Ile Gln Ala Asn Leu Trp Arg Asn Phe Leu
465                 470                 475                 480

Tyr Ala Asn Val Gly Leu Tyr Leu Pro Asp Lys Leu Lys Tyr Asn Pro
                485                 490                 495

Thr Asn Val Asp Ile Ser Asp Asn Pro Asn Thr Tyr Asp Tyr Met Asn
            500                 505                 510

Lys Arg Val Val Ala Pro Gly Leu Val Asp Cys Phe Val Asn Val Gly
        515                 520                 525

Ala Arg Trp Ser Leu Asp Tyr Met Asp Asn Val Asn Pro Phe Asn His
    530                 535                 540

His Arg Asn Ala Gly Leu Arg Tyr Arg Ser Met Ile Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Pro Gly Ser Tyr Thr Tyr Glu Trp Asn Phe
            580                 585                 590

Arg Lys Asp Val Asn Met Val Leu Gln Ser Ser Leu Gly Asn Asp Leu
        595                 600                 605

Arg Val Asp Gly Ala Ser Ile Lys Phe Asp Ser Val Thr Leu Tyr Ala
    610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Gly
                645                 650                 655

Ala Asn Met Leu Tyr Pro Ile Pro Ala Lys Ala Thr Asn Val Pro Ile
            660                 665                 670
```

```
Ser Ile Pro Ser Arg Asn Trp Ala Ala Phe Arg Gly Trp Ala Phe Thr
            675                 680                 685

Arg Leu Lys Thr Lys Glu Thr Pro Ser Leu Gly Ser Gly Phe Asp Pro
    690                 695                 700

Tyr Phe Val Tyr Ser Gly Ser Ile Pro Tyr Leu Asp Gly Thr Phe Tyr
705                 710                 715                 720

Leu Asn His Thr Phe Lys Lys Ile Ser Ile Met Tyr Asp Ser Val
                725                 730                 735

Ser Trp Pro Gly Asn Asp Arg Leu Leu Thr Pro Asn Glu Phe Glu Val
            740                 745                 750

Lys Arg Ala Val Asp Gly Glu Gly Tyr Asn Val Ala Gln Cys Asn Met
                755                 760                 765

Thr Lys Asp Trp Phe Leu Val Gln Met Leu Ala Asn Tyr Asn Ile Gly
            770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Glu Thr
                805                 810                 815

Lys Tyr Lys Asp Tyr Gln Ala Ile Gly Ile Thr His Gln His Asn Asn
            820                 825                 830

Ser Gly Phe Val Gly Tyr Leu Ala Pro Thr Met Arg Glu Gly Gln Ala
            835                 840                 845

Tyr Pro Ala Asn Phe Pro Tyr Pro Leu Ile Gly Lys Thr Ala Val Asp
            850                 855                 860

Ser Val Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Ile Val Phe Glu
            915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955

<210> SEQ ID NO 20
<211> LENGTH: 583
<212> TYPE: PRT
<213> ORGANISM: Gorilla beringei beringei

<400> SEQUENCE: 20

Met Lys Arg Ala Arg Ser Ser Asp Glu Thr Phe Asn Pro Val Tyr Pro
1               5                   10                  15

Tyr Asp Thr Glu Ile Ala Pro Ser Val Pro Phe Leu Thr Pro Pro
                20                  25                  30

Phe Val Ser Ser Ala Gly Met Gln Glu Asn Pro Ala Gly Val Leu Ser
            35                  40                  45

Leu His Leu Ser Glu Pro Leu Thr Thr His Asn Gly Ala Leu Thr Leu
        50                  55                  60

Lys Met Gly Gly Gly Leu Thr Leu Asp Lys Glu Gly Asn Leu Thr Ser
65                  70                  75                  80

Gln Asn Ile Thr Ser Val Asp Pro Pro Leu Lys Lys Ser Lys Asn Asn
```

```
                    85                  90                  95
Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Leu Thr Leu Glu Asp Ser Lys Leu Thr Leu
    130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Leu Gly Leu Ser
                165                 170                 175

Val Thr Ala Pro Leu Ser Ile Asn Asn Asp Ser Leu Gly Leu Asp Leu
                180                 185                 190

Gln Ala Pro Ile Val Ser Gln Asn Gly Lys Leu Ala Leu Asn Val Ala
            195                 200                 205

Gly Pro Leu Ala Val Ala Asn Gly Ile Asn Ala Leu Thr Val Gly Thr
        210                 215                 220

Gly Lys Gly Ile Gly Leu Asn Glu Thr Ser Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asp Thr Leu Ile Leu Asp Val
            260                 265                 270

Asn Tyr Pro Phe Glu Ala Gln Gly Gln Leu Ser Leu Arg Val Gly Gln
        275                 280                 285

Gly Pro Leu Tyr Val Asp Ser Ser His Asn Leu Thr Ile Arg Cys
    290                 295                 300

Leu Arg Gly Leu Tyr Ile Thr Ser Ser Asn Asn Gln Thr Gly Leu Glu
305                 310                 315                 320

Ala Asn Ile Lys Leu Thr Lys Gly Leu Val Tyr Asp Gly Asn Ala Ile
                325                 330                 335

Ala Val Asn Val Gly Gln Gly Leu Gln Tyr Ser Thr Thr Ala Thr Ser
            340                 345                 350

Glu Gly Val Tyr Pro Ile Gln Ser Lys Ile Gly Leu Gly Met Glu Tyr
        355                 360                 365

Asp Thr Asn Gly Ala Met Met Thr Lys Leu Gly Ser Gly Leu Ser Phe
    370                 375                 380

Asp Asn Ser Gly Ala Ile Val Val Gly Asn Lys Asn Asp Asp Arg Leu
385                 390                 395                 400

Thr Leu Trp Thr Thr Pro Asp Pro Ser Pro Asn Cys Arg Ile Tyr Ser
                405                 410                 415

Glu Lys Asp Thr Lys Leu Thr Leu Val Leu Thr Lys Cys Gly Ser Gln
            420                 425                 430

Ile Leu Gly Thr Val Ser Ala Leu Ala Val Arg Gly Ser Leu Ala Pro
        435                 440                 445

Ile Thr Asn Ala Ser Ser Ile Val Gln Ile Phe Leu Arg Phe Asp Glu
    450                 455                 460

Asn Gly Leu Leu Met Ser Asn Ser Ser Leu Asp Gly Asp Tyr Trp Asn
465                 470                 475                 480

Tyr Arg Asn Gly Asp Ser Thr Asn Ser Thr Pro Tyr Thr Asn Ala Val
                485                 490                 495

Gly Phe Met Pro Asn Leu Ala Ala Tyr Pro Lys Gly Gln Ala Thr Ala
            500                 505                 510
```

```
Ala Lys Ser Ser Ile Val Ser Gln Val Tyr Met Asp Gly Asp Thr Thr
        515                 520                 525

Lys Pro Ile Thr Leu Lys Ile Asn Phe Asn Gly Ile Asp Glu Thr Thr
    530                 535                 540

Glu Asn Thr Pro Val Ser Lys Tyr Ser Met Thr Phe Ser Trp Ser Trp
545                 550                 555                 560

Pro Thr Ala Ser Tyr Ile Gly His Thr Phe Ala Thr Asn Ser Phe Thr
            565                 570                 575

Phe Ser Tyr Ile Ala Gln Glu
            580
```

<210> SEQ ID NO 21
<211> LENGTH: 37229
<212> TYPE: DNA
<213> ORGANISM: Gorilla beringei beringei

<400> SEQUENCE: 21

| | | |
|---|---|---:|
| catcatcaat aatataccct attttggatt gtggccaata tgataatgag gtgggcgggg | | 60 |
| agaggcgggg cgggtgacgt aggacgcgcg agtagggttg ggaggtgtgg cggaagtgtg | | 120 |
| gcatttgcaa gtgggaggag ctcacatgca agcttccgtc gcggaaaatg tgacgttttt | | 180 |
| gatgagcgcc gcctacctcc ggaagtgcca attttcgcgc gcttttcacc ggatatcgta | | 240 |
| gtaattttgg gcgggaccat gtaagatttg gccattttcg cgcgaaaagt gaaacgggga | | 300 |
| agtgaaaact gaataatagg gcgttagtca tagcgcgtaa tatttaccga gggccgaggg | | 360 |
| actttgaccg attacgtgga ggactcgccc aggtgttttt tacgtgaatt ccgcgttcc | | 420 |
| gggtcaaagt ctccgttttt attgtcaccg tcatttgacg cggagggtat ttaaacccgc | | 480 |
| tgcgctcctc aagaggccac tcttgagtgc cagcgagaag agttttctcc tctgctccgc | | 540 |
| ttcggtgatc gaaaaatgag acacatagcc tgcactccgg gtcttttgtc cggtcgggcg | | 600 |
| gcggccgagc ttttggacgc tttgatcaat gatgtcctaa gcgatgattt tccgtctact | | 660 |
| acccacttta gcccacctac tcttcacgaa ctgtacgatc tggatgtact ggtggatgtg | | 720 |
| aacgatccca acgaggaggc ggtttctgcg ttttttcccg agtctgcgct gttggccgct | | 780 |
| caggagggat ttgacctaca cactccgccg cctattttag agtctccgct gccggagccc | | 840 |
| agtggtatac cttatatgcc tgaactgctt cccgaagtgg tagacctgac ctgccacgag | | 900 |
| cctggctttc cgcccagcga cgatgagggt gagccttttg ttttagactt tgctgagata | | 960 |
| cctgggcacg gttgcaggtc ttgtgcatat catcagaggg ttaccggaga ccccgaggtt | | 1020 |
| aagtgttcgc tgtgctatat gaggatgacc tcttccttta tctacagtaa gttttttgtct | | 1080 |
| aggtgggctt tgggtaggt gggttttgtg tcagaacagg tgtaaacgtt gcttgtgttt | | 1140 |
| tttgtacctg taggtccggt gtccgagcca gacccggagc ccgaccgcga tcccgagccg | | 1200 |
| gatcccgagc tcctcgcag gacaaggaaa ctaccttcca ttctgtgcaa gtctcagaca | | 1260 |
| cctgtaagga ccagcgaggc agacagcacc gactctggca cttctacctc tcccctgaa | | 1320 |
| attcacccag tggttcctct gggtatacat aaacctgttg ctgttaaagt ttgcgggcga | | 1380 |
| cgccctgcag tacagtgcat tgaggacttg cttcacgatc ccgaggaacc tttgacttg | | 1440 |
| agccttaaac gccctaggca ataaacccca cctaagtaat aaacccacc taagtaataa | | 1500 |
| accctgccgc ccttggttat tgagatgacg cccaatgttt gcttttgaat gacttcatgt | | 1560 |
| gtgtaataaa agtgagtgtg atcataggtc tcttgtttgt ctgggcgggg cttaaggta | | 1620 |
| tataagtctc ttggggctaa acttggttac acttgacccc aatggaggcg tgggggtgct | | 1680 |

```
tggaggagtt tgcggacgtg cgccgtttgc tggacgagag ctctagcaat acctatacta    1740
tttggaggta tctgtggggc tctactcagg ccaagttggt ttccagaatt aagcaggatt    1800
acaagtgcga ttttgaagag cttttagtt cctgcggtga gcttttgcaa tccttgaatc     1860
tgggccatca ggctattttc caggaaaagg ttctctcgac tttggatttt tccactcccg    1920
ggcgcaccgc cgcttgtgtg gcttttgtgt cttttgtgca agataaatgg agcgaggaga    1980
cccacctgag tcacggctac gtactggatt tcatggcgat ggctctttgg agggctcaca    2040
acaaatggaa gattcagaag gaactgtacg gttccgccct acgtcgtcca cttctgtcgc    2100
gacaggggct gaggtttccc gaccatcggc agcatcagaa tctggaagac gagtcggagg    2160
agcgagcgga ggagaagatc agcttgagag ccggcctgga ccctcctcag gaggaatgaa    2220
tctcccgcag gtggttgacc tgtttccaga actgagacgg gtcctgacta tcagggagga    2280
tggtcagttt gtgaagaagt ttaagaggga tcggggtgag ggagatgatg aggcggctag    2340
caatttagct tttagtctga tgactcgcca ccgaccggaa tgtattacct atcagcagat    2400
taaggagagt tgtgccaacg agctggatct tttgggtcag aagtatagca tagaacagct    2460
taccacttac tggcttcagc ctggggatga ttgggaagag gcgatcaggg tgtatgcaaa    2520
ggtggccctg cggcccgatt gcaagtataa gattactaag ttggttaata ttagaaactg    2580
ctgctatatt tctgggaacg gggccgaagt ggagatagat actcaggaca gggtggcttt    2640
taggtgttgc atgataaaca tgtggcccgg gatactgggg atggatgggg tggtattcat    2700
gaatgtgagg tttacgggcc ccaactttaa tggcacggtg ttcatgggca acaccaactt    2760
gctcctgcat ggtgcgagtt tctatgggtt taataacacc tgtatagagg cctggaccga    2820
tgtaaaggtt cgaggttgtt cctttatag ctgttggaag gcggtggtgt gtcgccctaa     2880
aagcaggggt tctgtgaaaa aatgcttgtt tgaaaggtgc accttaggca tcctctctga    2940
gggcaactcc agggtgcgcc ataatgtggc ttcgaactgc ggttgcttca tgcaagtgaa    3000
gggggtgagc gttatcaagc ataactcggt gtgtggaaac tgcgaggatc gcgcctccca    3060
gatgctgacc tgctttgatg gcaactgtca cctgttgaag accattcata taagcagcca    3120
ccccagaaag gcctggcccg tgtttgagca taacatcttg acccgctgct ccttgcatct    3180
gggggtcagg aggggtatgt tcctgcctta ccagtgtaac tttagccaca ctaaaatcct    3240
gctggaaccc gagtgcatga ccaaggtcag cctgaatggt gtgtttgatg tgactctgaa    3300
aatctggaag gtgctgaggt atgatgagac caggaccagg tgccgaccct gcgagtgcgg    3360
cggcaagcac atgagaaatc agcctgtgat gttggatgtg accgaggagc ttaggcctga    3420
ccatctggtg ctggcctgca ccagggccga gtttgggtct agcgatgagg ataccgattg    3480
aggtgggtaa ggtgggcgtg gctagaaggg tgggcgtgt ataaattggg ggtctaaggg     3540
tctctctgtt ttgtcttgca acagccgccg ccatgagcga caccggcaac agctttgatg    3600
gaagcatctt tagcccctat ctgacagtgc gcatgcctca ctgggctgga gtgcgtcaga    3660
atgtgatggg ttccaacgtg gatggacgcc ccgttctgcc ttcaaattcg tctacaatgg    3720
cctacgcgac cgtgggagga actccgctgg acgccgcgac ctcgccgcc gcctccgccg     3780 ccgccgcgac cgcgcgcagc atggctacgg acctttacag ctctttggtg gcgagcggcg    3840
cggcctctcg cgcgtctgct cgggatgaga aactgaccgc tctgctgctt aaactggaag    3900
acttgacccg ggagctgggt caactgaccc agcaggtctc cagcttgcgt gagagcagcc    3960
ttgcctcccc ctaatggccc ataatataaa taaaagccag tctgtttgga ttaagcaagt    4020
```

-continued

```
gtatgttctt tatttaactc tccgcgcgcg gtaagcccgg gaccagcggt ctcggtcgtt    4080
tagggtgcgg tggattcttt ccaacacgtg gtacaggtgg ctctggatgt ttagatacat    4140
gggcatgagt ccatccctgg ggtggaggta gcaccactgc agagcttcgt gctcgggggt    4200
ggtgttgtat atgatccagt cgtagcagga gcgctgggcg tggtgctgaa aaatgtcctt    4260
aagcaagagg cttatagcta gggggaggcc cttggtgtaa gtgtttacaa atctgctcag    4320
ttgggagggg tgcatccggg gggatataat gtgcatcttg gactggattt ttaggttggc    4380
tatgttccca cccagatccc ttctgggatt catgttgtgc aggaccacca gcacggtata    4440
tccagtgcac ttgggaaatt tatcgtggag cttagacggg aatgcatgga agaacttgga    4500
gacgcccttg tggcctccca gattttccat acattcgtcc atgatgatgg caatgggccc    4560
gtgggaagct gcctgagcaa aaatgtttct gggatcgctc acatcgtagt tatgttccag    4620
ggtgaggtca tcataggaca tctttacgaa tcggggcgg agggtcccgg actgggggat    4680
gatggtaccc tcgggccccg gggcgtagtt cccctcacag atctgcatct cccaggcttt    4740
catttcagag ggagggatca tatccacctg cggagcgatg aaaaacacag tttctggcgc    4800 agggagatt aactgggatg agagcaggtt tctgagcagc tgtgactttc cacagccggt    4860
gggcccatat atcacgccta tcaccggctg cagctggtag ttaagagagc tgcagctgcc    4920
gtcctcccgg agcaggggg ccacctcgtt cagcatatcc ctgacgtgga tgttctccct    4980
gaccaattcc gccagaaggc gctcgccgcc cagcgaaagc agctcttgca aggaagcaaa    5040 attttttcagc ggttttaggc cgtcggccgt gggcatgttt ttcagcgtct gggtcagcag    5100
ttccagcctg tcccacagct cggtgatgtg ctctacggca tctcgatcca gcagatctcc    5160
tcgtttcgcg ggttggggcg gctttcgctg tagggcacca gccgatgggc gtccagcggg    5220
gccagagtca tgtccttcca tgggcgcagg gtcctcgtca gggtggtctg ggtcacggtg    5280
aaggggtgcg ctccggggttg ggcgctggcc agggtgcgct tgaggctggt tctgctggtg    5340
ctgaatcgct gccgctcttc gccctgcgcg tcggccaggt agcatttgac catggtctcg    5400
tagtcgagac cctcggcggc gtgccccttg gcgcggagct ttcccttgga ggtggcgccg    5460
cacgaggggc actgcaggct cttcagggcg tagagcttgg gagcgagaaa cacggactct    5520
ggggagtagg cgtccgcgcc gcaggaagcg cagaccgtct cgcattccac cagccaagtg    5580
agctccgggc ggtcagggtc aaaaaccagg ttgcccccat gcttttttgat gcgtttctta    5640 cctcggctct ccatgaggcg gtgtcccttc tcggtgacga agaggctgtc cgtgtccccg    5700
tagaccgact tcaggggcct gtcttccagc ggagtgcctc tgtcctcctc gtagagaaac    5760
tctgaccact ctgagacgaa ggcccgcgtc caggccagga cgaaggaggc cacgtgggag    5820
gggtagcggt cgttgtccac tagcgggtcc accttctcca gggtgtgcag gcacatgtcc    5880
ccctcctccg cgtccagaaa agtgattggc ttgtaggtgt aggacacgtg accgggggtt    5940
cccgacgggg gggtataaaa gggggtgggc gccctttcat cttcactctc ttccgcatcg    6000
ctgtctgcga gggccagctg ctggggtaag tattccctct cgaaggcggg catgacctca    6060
gcgctcaggt tgtcagtttc taaaaatgag gaggatttga tgttcacctg tccggaggtg    6120
atacctttga gggtacctgg gtccatctgg tcagaaaaca ctattttttt gttgtcaagc    6180
ttggtggcga acgacccgta gagggcgttg agagcagct tggcgatgga gcgcagggtc    6240 tggttttgt cgcggtcggc tcgtccttg gccgcgatgt tgagttgcac gtactcgcgg    6300
gccacgcact tccactcggg gaagacggtg gtgcgctcgt ctgggattag gcgcaccctc    6360
cagcctcggt tgtgcagggt gaccatgtcg acgctggtgg cgacctcgcc gcgcaggcgc    6420
```

```
tcgttggtcc agcagaggcg gccgcccttg cgcgagcaga agggggtag gggtccagc    6480 tggtcctcgt ttgggggtc cgcgtcgatg gtgaagaccc cggggagcaa gcgcgggtca    6540
aagtagtcga tcttgcaagc ttgcatgtcc agagcccgct gccattcgcg ggcggcgagc    6600
gcgcgctcgt aggggttgag gggcgggccc cagggcatgg ggtgggtgag cgcggaggcg    6660
tacatgccgc agatgtcata cacgtacagg ggttccctga ggatgccgag gtaggtgggg    6720
tagcagcgcc ccccgcggat gctggcgcgc acgtagtcat agagctcgtg ggaggggcc    6780 agcatgttgg gcccgaggtt ggtgcgctgg gggcgctcgg cgcggaaggc gatctgcctg    6840
aagatggcat gggagttgga ggagatggtg ggccgctgga agacgttgaa gcttgcttct    6900
tgcaagccca ccgagtccct gacgaaggag gcgtaggact cgcgcagctt gtgcaccagc    6960
tcggcggtga cctggacgtc gagcgcgcag tagtcgaggg tctcgcggat gatgtcatac    7020
ttatcctccc ccttctttt ccacagctcg cggttgagga cgaactcttc gcggtctttc    7080
cagtactctt ggaggggaaa cccgtccgtg tccgaacggt aagagcctag catgtagaac    7140
tggttgacgg cctggtaggg gcaacagccc ttctccacgg gcagcgcgta ggcctgcgcc    7200
gccttgcgga gggaggtgtg ggtgagggcg aaagtgtccc tgaccatgac tttgaggtat    7260
tgatgtttga agtctgtgtc atcgcagccg ccctgttccc acagggtgta gtccgtgcgc    7320
tttttggagc gcgggttggg cagggagaag gtgaggtcat tgaagaggat cttccccgct    7380
cgaggcatga agtttctggt gatgcgaaag ggccctggga ccgaggagcg gttgttgatg    7440
acctgggcgg ccaggacgat ctcgtcaaag ccgtttatgt tgtggcccac gatgtagagc    7500
tccaaaaagc ggggctggcc cttgatggag gggagctttt tgagttcctc gtaggtgagc    7560
tcctcgggcg attccaggcc gtgctcctcc agggcccagt cttgcaagtg agggttggcc    7620
gccaggaagg atcgccagag gtcgcgggcc atgagggtct gcaggcggtc gcggaaggtt    7680
ctgaactgtc gccccacggc catcttttcg ggggtgatgc agtagaaggt gaggggtct    7740 ttctcccagg ggtcccatct gagctctcgg gcgaggtcgc gcgcggcggc gaccagagcc    7800
tcgtcgcccc ccagtttcat gaccagcatg aagggcacga gctgcttgcc aaaggctccc    7860
atccaagtgt aggtctctac atcgtaggtg acaaagaggc gctccgtgcg aggatgagag    7920
ccgatcggga agaactggat ctcccgccac cagttggagg attggctgtt gatgtggtga    7980
aagtagaagt cccgtctgcg ggccgagcac tcgtgctggc ttttgtaaaa gcgaccgcag    8040
tactggcagc gctgcacggg ttgtatatct tgcacgaggt gaacctggcg acctctgacg    8100
aggaagcgca gcgggaatct aagtccccg cctggggtcc cgtgtggctg gtggtcttct    8160
actttggttg tctggccgcc agcatctgtc tcctggaggg cgatggtgga gcagaccacc    8220
acgccgcgag agccgcaggt ccagatctcg gcgctcggcg ggcggagttt gatgacgaca    8280
tcgcgcacat tggagctgtc catggtctcc agctcccgcg gcggcaggtc agctgggagt    8340
tcctggaggt tcacctcgca gagacgggtc aaggcgcggg cagtgttgag atggtatctg    8400
atttcaaggg gcgtgttggc ggcggagtcg atggcttgca ggaggccgca gccccggggg    8460
gccacgatgg ttccccgcgg ggcgcgaggg gaggcggaag ctgggggtgt gttcagaagc    8520
ggtgacgcgg gcgggccccc ggaggtaggg ggggttccgg ccccacaggc atgggcggca    8580
ggggcacgtc ttcgccgcgc gcgggcaggg gctggtgctg gctccgaaga gcgcttgcgt    8640
gcgcgacgac gcgacggttg gtgtcctgta tctgacgcct ctgagtgaag accacgggtc    8700
ccgtgacctt gaacctgaaa gagagttcga cagaatcaat ctcggcatcg ttgacagcgg    8760
```

```
cctggcgcag gatctcctgc acgtcgcccg agttgtcctg gtaggcgatc tctgccatga    8820
actgctcgat ctcttcttcc tggagatctc ctcgtccggc gcgctccacg gtggccgcca    8880
ggtcgttgga gatgcgaccc atgagctgtg agaaggcgtt gagcccgccc tcgttccaga    8940
cccggctgta gaccacgccc ccctcggcgt cgcgagcgcg catgaccacc tgggccaggt    9000
tgagctccac gtgtcgcgtg aagacggcgt agttgcgcag gcgctggaaa aggtagttca    9060
gggtggtggc ggtgtgctcg gcgacgaaga agtacatgac ccagcgccgc aacgtggatt    9120
cattgatgtc ccccaaggcc tccaggcgct ccatggcctc gtagaagtcc acggcgaagt    9180
tgaaaaactg ggagttgcga gcggacacgg tcaactcctc ctccagaaga cggatgagct    9240
cggcgacagt gttgcgcacc tcgcgctcga aggccacggg gggcgcttct tcctcttcca    9300
cctcttcttc catgatcgct tcttcttctt cctcagccgg gacgggaggg ggcggcggcg    9360 gcggggagg ggcgcggcgg cggcggcggc gcaccgggag gcggtcgatg aagcgctcga    9420
tcatctcccc ccgcatgcgg cgcatggtct cggtgacggc gcggccgttc tcccggggc    9480 gcagctcgaa gacgccgcct ctcatctcgc cgcggggcga gcggccgtga ggtagcgaga    9540
cggcgctgac tatgcatctt aacaattgct gtgtaggtac accgccgagg gacctgattg    9600
agtccagatc caccggatcc gaaaaccttt ggaggaaagc gtctatccag tcgcagtcgc    9660
aaggtaggct gagcaccgtg gcgggcgggg gcgggtctgg agagttcctg gcggagatgc    9720
tgctgatgat gtaattaaag taggcggtct tgagaaggcg gatggtggac aggagcacca    9780
tgtctttggg tccggcctgt tggatgcgga ggcggtcggc catgcccag gcctcgttct    9840 gacaccggcg caggtctttg tagtagtctt gcatgagtct ttccaccggc acctcttctc    9900
cttcctcttc tccatctcgc cggtggtttc tcgcgccgcc catgcgcgtg accccaaagc    9960
ccctgagcgg ctgcagcagg gccaggtcgg cgaccacgcg ctcggccaag atggcctgct    10020
gcacctgagt gagggtcctc tcgaagtcat ccatgtccac gaagcggtgg taggcgcccg    10080
tgttgatggt gtaggtgcag ttggccatga cggaccagtt gacggtctgg tgtcccggct    10140
gcgagagctc cgtgtaccgc aggcgcgaga aggcgcggga atcgaacacg tagtcgttgc    10200
aagtccgcac cagatactgg tagcccacca ggaagtgcgg cggaggttgg cgatagaggg    10260
gccagcgctg ggtggcgggg gcgccgggcg ccaggtcttc cagcatgagg cggtggtatc    10320
cgtagatgta cctggacatc caggtgatgc cggcggcggt ggtggtggcg cgcgcgtagt    10380
cgcggacccg gttccagatg tttcgcaggg gcgagaagtg ttccatggtc ggcacgctct    10440
ggccggtgag gcgcgcgcag tcgttgacgc tctatacaca cacaaaaacg aaagcgttta    10500
cagggctttc gttctgtagc ctggaggaaa gtaaatgggt tgggttgcgg tgtgccccgg    10560
ttcgagacca agctgagctc ggccggctga agccgcagct aacgtggtat tggcagtccc    10620
gtctcgaccc aggccctgta tcctccagga tacggtcgag agcccttttg ctttcttggc    10680
caagcgcccg tggcgcgatc tgggatagat ggtcgcgatg agaggacaaa agcggctcgc    10740
ttccgtagtc tggagaaaca atcgccaggg ttgcgttgcg gcgtaccccg gttcgagccc    10800
ctatggcggc ttgaatcggc cggaaccgcg gctaacgagg gccgtggcag ccccgtcctc    10860 aggacccgc cagccgactt ctccagttac gggagcgagc ccctttttgtt ttttattttt    10920 tagatgcatc ccgtgctgcg gcagatgcgc ccctcgcccc ggcccgatca gcagcagcaa    10980
cagcaggcat gcagaccccc ctctcccctt tccgccccgg tcaccacggc gcggcggcc    11040 gtgtcgggcg cggggggcgc gctggagtca gatgagccac cgcggcggcg acctaggcag    11100
tatctggact tggaagaggg cgagggactg gcgcggctgg gggcgaactc tccagagcgc    11160
```

```
cacccgcgggg tgcagttgaa aagggacgcg cgcgaggcgt acctgccgcg gcagaacctg   11220
tttcgcgacc gcggggggcga ggagcccgag gagatgcgag actgcaggtt ccaagcgggg   11280
cgcgagctgc ggcgcgggct ggacagacag cgcctgctgc gcgaggagga ctttgagccc   11340
gacacgcaga cgggcatcag ccccgcgcgc gcgcacgtag ccgcggccga cctggtgacc   11400
gcctacgagc agacggtaaa ccaggagcgc aacttccaaa agagcttcaa caaccacgtg   11460
cgcacgctgt tggcgcgcga ggaggtgacc ctgggtctca tgcatctgtg ggacctggtg   11520
gaggcgatcg tgcagaaccc cagcagcaag ccctgaccg cgcagctgtt cctggtggtg   11580
cagcacagca gggacaacga ggccttcagg gaggcgctgc tgaacatcac cgagccggag   11640
gggcgctggc tcctggacct gataaacatc ctgcagagca tagtggtgca ggagcgcagc   11700
ctgagcctgg ccgagaaggt ggcggccatc aactactcta tgctgagcct gggcaagttc   11760
tacgcccgca agatctacaa gaccccctac gtgcccatag acaaggaggt gaagatagac   11820
agcttctaca tgcgcatggc gctgaaggtg ctgaccctga gcgacgacct gggagtgtac   11880
cgcaacgagc gcatccacaa ggccgtgagc gccagccggc ggcgcgagct gagcgaccgc   11940
gagctgatgc acagtctgca gcgcgcgctg accggcgcgg gcgagggcga cagggaggtc   12000
gagtcctact tcgacatggg ggccgacctg cactggcagc cgagccgccg cgccctggag   12060
gcggcggggg cgtacggcgg cccctggcg gccgatgacc aggaagagga ggactatgag   12120
ctagaggagg gcgagtacct ggaggactga cctggctggt ggtgttttgg tatagatgca   12180
agatccgaac gtggcggacc cggcggtccg ggcggcgctg caaagccagc cgtccggcat   12240
taactcctct gacgactggg ccgcggccat gggtcgcatc atgggcctga ccgcgcgcaa   12300
ccccgaggct ttcaggcagc agcctcaggc caaccggctg gcggccatct tggaagcggt   12360
agtgcccgcg cgctccaacc ccacccacga gaaggtgctg gccatagtca acgcgctggc   12420
ggagagcagg gccatccgcg cggacgaggc cggactggtg tacgatgcgc tgctgcagcg   12480
ggtggcgcgg tacaacagcg gcaacgtgca gaccaacctg gaccgcctgg tgacggacgt   12540
gcgcgaggcc gtggcgcagc gcgagcgctt gcatcaggac ggtaacctgg gctcgctggt   12600
ggcgctaaac gccttcctca gcacccagcc ggccaacgta ccgcgggggc aggaggacta   12660
caccaacttt ttgagcgcgc tgcggctgat ggtgaccgag gtccctcaga gcgaggtgta   12720
ccagtcgggg cccgactact tcttccagac cagcagacag ggcttgcaaa ccgtgaacct   12780
gagccaggct ttcaagaacc tgcgggggct gtggggagtg aaggcgccca ccggcgaccg   12840
ggctacggtg tccagcctgc taaccccaa ctcgcgcctg ctgctgctgc tgatcgcgcc   12900
cttcacggac agcgggagcg tctcgcggga gacctatctg ggccacctgc tgacgctgta   12960
ccgcgaggcc atcgggcagg cgcaggtgga cgagcacacc ttccaagaga tcaccagcgt   13020
gagccacgcg ctggggcagg aggacacggg cagcctgcag gcgaccctga actacctgct   13080
gaccaacagg cggcagaaga ttcccacgct gcacagcctg acccaggagg aggagcgcat   13140
cttgcgctac gtgcagcaga gcgtgagcct gaacctgatg cgcgacggcg tgacgcccag   13200
cgtggcgctg gacatgaccg cgcgcaacat ggaaccgggc atgtacgcct cccaccggcc   13260
gtttatcaac cgcctgatgg actacttgca tcgggcggcg gccgtgaacc ccgagtactt   13320
cactaatgcc attctgaatc cccactggat gccccctccg ggtttctaca cgggggactt   13380
tgaggtgccc gaggtcaacg acgggttcct ctgggatgac atggatgaca gtgtgttctc   13440
acccaacccg ctgcgcgccg cgtctctgcg attgaaggag ggctctgaca gggaaggacc   13500
```

```
gaggagtctg gcctcctccc tggctctggg agcggtgggc gccacgggcg cggcggcgcg    13560
gggcagtagc cccttcccca gcctggcaga ctctctgaac agcgggcggg tgagcaggcc    13620
ccgcttgcta ggcgaggagg agtatctgaa caactccctg ctgcagcccg cgagggacaa    13680
gaacgctcag cggcagcagt ttcccaacaa tgggatagag agcctggtgg acaagatgtc    13740
cagatggaag acgtatgcgc aggagtacaa ggagtgggag gaccgccagc cgcggccctt    13800
gccgccccct aggcagcgct ggcagcgcg cgcgtccaac cgccgctgga ggcaggggcc    13860
cgaggacgat gatgactctg cagatgacag cagcgtgttg gacctgggcg ggagcgggaa    13920 cccctttttcg cacctgcgcc cacgcctggg caagatgttt taaaagaaaa aaaaaataaa    13980
actcaccaag gccatggcga cgagcgttgg ttttttgttc ccttccttag tatgcggcgc    14040
gcggcgatgt tcgaggaggg gcctcccccc tcttacgaga gcgcgatggg gatttctcct    14100
gcggcgcccc tgcagcctcc ctacgtgcct cctcggtacc tgcaacctac aggggggaga    14160
aatagcatct gttactctga gctgcagccc ctgtacgata ccaccagact gtacctggtg    14220
gacaacaagt ccgcggacgt ggcctccctg aactaccaga cgaccacag cgattttttg    14280 accacggtga tccaaaacaa cgacttcacc ccaaccgagg ccagcaccca gaccataaac    14340
ctggataaca ggtcgaactg gggcggcgac ctgaagacca tcttgcacac caacatgccc    14400
aacgtgaacg agttcatgtt caccaactct tttaaggcgc gggtgatggt ggcgcgcgag    14460 caggggggagg cgaagtacga gtgggtggac ttcacgctgc ccgagggcaa ctactcagag    14520
accatgactc tcgacctgat gaacaatgcg atcgtggaac actatctgaa agtgggcagg    14580
cagaacgggg tgaaggaaag cgatatcggg gtcaagtttg acaccagaaa cttccgtctg    14640
ggctgggacc ccgtgaccgg gctggtcatg ccggggggtct acaccaacga ggcctttcat    14700
cccgacatag tgcttctgcc cggctgtggg gtggacttca cccagagccg gctgagcaac    14760
ctgctgggca ttcgcaagcg gcagcctttc caggagggtt tcaagatcac ctatgaggat    14820 ctgaagggggg gcaacattcc cgcgctcctt gatctggacg cctacgagga gagcttgaaa    14880
cccgaggaga gcgctggcga cagcggcgag agtggcgagg agcaagccgg cggcggtggc    14940
ggcgcgtcgg tagaaaacga aagtacgccc gcagtggcgg cggacgctgc ggaggtcgag    15000
ccggaggcca tgcagcagga cgcagaggag ggcgcacagg agggcgcgca aaggacatg    15060 aacgatgggg agatcagggg agacacattc gccacccggg gcgaagaaaa agaggcagag    15120
gcggcggcgg cggcgacggc ggaggccgaa accgaggttg aggcagaggc agagcccgag    15180
accgaagtta tggaagacat gaatgatgga gaacgtaggg gcgacacgtt cgccacccgg    15240
ggcgaagaga aggcggcgga ggcagaagcc gcggctgagg aggcggctgc ggctgcggcc    15300
aagactgagg ctgcggctaa ggctgaggtc gaagccaatg ttgcggttga ggctcaggct    15360
gaggaggagg cggcggctga agcagttaag gaaaaggccc aggcagagca ggaagagaaa    15420
aaacctgtca ttcaacctct aaagaagat agcaaaaagc gcagttacaa cgtcatcgag    15480
ggcagcacct ttacccagta ccgcagctgg tacctggcgt acaactacgg cgacccggtc    15540
aagggggtgc gctcgtggac cctgctctgc acgccggacg tcacctgcgg ctccgagcag    15600
atgtactggt cgctgccgaa catgatgcaa gacccggtga ccttccgctc cacgcggcag    15660
gttagcaact tccccggtggt gggcgccgaa ctgctgcccg tgcactccaa gagttttttac    15720 aacgagcagg ccgtctactc ccagctgatc cgccaggcca cctctctgac ccacgtgttc    15780
aatcgctttc ccgagaacca gattttggcg cgcccgccgg ccccaccat caccaccgtg    15840 agtgaaaacg ttcctgccct cacagatcac gggacgctac cgctgcgcaa cagcatctca    15900
```

```
ggagtccagc gagtgaccat tactgacgcc agacgccgga cctgccccta cgtttacaag   15960
gccttgggca tagtctcgcc gcgcgtcctc tccagtcgca cttttttaaaa cacatctacc   16020 cacacgttcc aaaatcatgt ccgtactcat ctcacccagc aacaacaccg gctgggggct   16080
gcgcgcgccc agcaagatgt ttggagggggc gaggaagcgc tccgaccagc accctgtgcg   16140
cgtgcgcggc cactaccgcg cgccctgggg agcgcacaag cgcgggcgca cagggcgcac   16200
cactgtggac gacgtcattg actccgtagt ggagcaagcg cgccactaca cacccggcgc   16260
gccgaccgcc cccgccgtgt ccaccgtgga ccaggcgatc gaaagcgtgg tacagggcgc   16320
gcggcactat gccaacctta aaagtcgccg ccgccgcgtg ccccgccgcc atcgccggag   16380
accccgggcc accgccgccg cgcgccttac taaggctctg ctcaggcgcg ccaggcgaac   16440
tggccaccgg gccgccatga gggcgcacg gcgggctgcc gctgccgcaa gcgtcgtggc   16500
cccgcgggca cgaaggcgcg cggccgctgc cgccgccgcc gccatttcca gcttggcctc   16560
gacgcggcgc ggtaacatat actgggtgcg cgactcggta accggcacgc gggtacccgt   16620
gcgctttcgc cccccgcgga attagcacaa gacaacatac acactgagtc tcctgctgtt   16680
gtgtatccca gcgcgaccg tcagcagcgg cgacatgtcc aagcgcaaaa ttaaagaaga   16740
gatgctccag gtcatcgcgc cggagatcta tgggcccccg aagaaggagg aggatgatta   16800 caagcccgc aagctaaagc gggtcaaaaa gaaaaagaaa gatgatgatg acgaggcggt   16860
ggagtttgtc cgccgcatgg cacccaggcg ccccgtgcag tggaagggcc ggcgcgtgca   16920
gcgcgttttg cgccccggca ccgcggtggt cttcacgccc ggcgagcgct ccacgcgcac   16980
tttcaagcgg gtgtacgatg aggtgtacgg cgacgaggac ctgttggagc aggccaacca   17040
gcgctttggg gagtttgcat atgggaaacg ccccgcgag agtctaaaag aggacctgct   17100
ggcgctaccg ctggacgagg gcaatcccac cccgagtctg aagccggtaa ccctgcaaca   17160
ggtgctgcct ttgagcgcgc ccagcgagca taagcgaggg ttgaagcgcg aaggcgggga   17220
cctggcgccc accgtgcagt tgatggtgcc caagcggcag aagctggagg acgtgctgga   17280
gaaaatgaaa gtagagcccg ggatccagcc cgagatcaag gtccgcccca tcaagcaggt   17340
ggcgcccggc gtgggagtcc agaccgtgga cgttaggatt cccacggagg agatggaaac   17400
ccaaaccgcc actccctctt cggcggccag cgccaccacc ggcaccgctt cggtagaggt   17460
gcagacggac ccctggctac ccgccaccgc tgttgccgcc gccgcccccc gttcgcgcgg   17520
gcgcaagaga aattatccag cggccagcgc gctcatgccc cagtacgcac tgcatccatc   17580
catcgtgccc acccccggct accgcgggta ctcgtaccgc ccgcgcagat cagccggcac   17640
tcgcggccgc cgccgccgtg cgaccacaac cagccgccgc cgtcgccgcc gccgccagcc   17700
agtgctgacc cccgtgtctg taaggaaggt ggctcgctcg gggagcacgc tggtggtgcc   17760
cagagcgcgc taccacccca gcatcgttta aagccggtct ctgtatggtt cttgcagata   17820
tggccctcac ttgtcgcctc cgcttcccgg tgccgggata ccgaggaaga actcaccgcc   17880
gcagaggcat ggcgggcagc ggtctccgcg gcggccgtcg ccatcgccgg cgcgcaaaaa   17940
gcaggcgcat gcgcggcggt gtgctgcctc tgctaatccc gctaatcgcc gcggcgatcg   18000
gtgccgtacc cgggatcgcc tccgtggccc tgcaggcgtc ccagaaacgt tgactcttgc   18060
aaccttgcaa gcttgcattt tttggaggaa aaataaaaaa aagtctagac tctcacgctc   18120
gcttggtcct gtgactattt tgtagaaaaa aagatggaag acatcaactt tgcgtcgctg   18180 gcccccgcgtc acggctcgcg cccgttcatg ggagactgga cagatatcgg caccagcaat   18240
```

```
atgagcggtg gcgccttcag ctggggcagt ctgtggagcg gccttaaaaa ttttggttcc    18300
accattaaga actatggcaa caaagcgtgg aacagcagca cgggccagat gctgagagac    18360
aagttgaaag agcagaactt ccaggagaag gtggcgcagg gcctggcctc tggcatcagc    18420 gggtggtgg acatagctaa ccaggccgtg cagaaaaaga taaacagtca tctggaccc     18480 cgtcctcagg tggaggaaat gcctccagcg atggagacgg tgtctcccga gggcaaaggc    18540
gaaaagcgcc cgcggcccga cagagaagag accctggtgt cacacaccga ggagccgccc    18600
tcttacgagg aggcagtcaa ggccggcctg cccaccactc gccccatagc ccccatggcc    18660
accggtgtgg tgggccacag gcaacacact cccgcaacac tagatctgcc cccgccgtcc    18720
gagccgccgc gccagccaaa ggcggcgacg gtgcccgctc cctccacttc cgccgccaac    18780
agagtgcccc tgcgccgcgc cgcgagcggc ccccgggcct cgcgagttag cggcaactgg    18840
cagagcacac tgaacagcat cgtgggcctg ggagtgagga gtgtgaagcg ccgccgttgc    18900
tactgaatga gcaagctagc taacgtgttg tatgtgtgta tgcgtcctat gtcgccgcca    18960
gaggagctgt tgagccgccg gcgccgtctg cactccagcg aatttcaaga tggcgacccc    19020
atcgatgatg cctcagtggt cgtacatgca catctcgggc caggacgctt cggagtacct    19080
gagccccggg ctggtgcagt tcgccgcgc cacagacacc tacttcaaca tgagtaacaa    19140
gttcaggaac cccactgtgg cgcccaccca cgatgtgacc acggaccggt cgcagcgcct    19200
gacgctgcgg ttcatccccg tggatcggga ggacaccgcc tactcttaca aggcgcggtt    19260
cacgctggcc gtgggcgaca accgcgtgct ggacatggcc tccacttact ttgacatcag    19320 ggggtgctg gacaggggcc ccaccttcaa gccctactcg ggtactgcct acaactccct    19380
ggcccccaag ggcgctccca attcttgcga gtgggaacaa gatgaaccag ctcaggcagc    19440
aatagctgaa gatgaagaag aacttgaaga agaacaagct caggacgaac aggcgcccac    19500
taagaaaacc catgtatacg cccaggcacc tctttctggt gaaaaaatta ctaaggatgg    19560
tttgcaaata ggtgtggatg ccacacaggc gggagataac cctatatatg ctgataaaac    19620
attccaaccc gaacctcaga taggtgagtc tcagtggaac gaggctgatg ccacagtagc    19680
aggaggcaga gtcttaaaaa agaccacccc tatgagacct tgctatggat cctatgccaa    19740
acctactaat gccaatggcg gtcaagggat catggtggcc aatgatcagg gagcgcttga    19800
atctaaagtt gagatgcaat ttttctccac cacaacgtct cttaatgtaa gggaaggtga    19860
aaacaatctt cagccaaaag tagtgctata cagcgaagat gttaacttgg aatcccctga    19920
cactcatttg tcttacaaac ctaaaaagga tgacaccaac tctaaaatca tgttgggtca    19980
gcaagccatg cccaacagac ccaacctcat tgcttttagg gacaaccttta ttggacttat    20040 gtactacaac agcacaggca acatgggagt gctggcagga caggcctccc agctaaacgc    20100
tgtggtagac ttgcaagaca gaaacacaga gctgtcatac caactgatgc ttgattccat    20160
tggagacaga tcaagatact tttccatgtg gaaccaggca gtggacagct atgcccaga    20220 tgtcagaatc attgaaaacc atggggttga agatgagctg cccaactatt gctttcccct    20280
gggcggtatt ggaattacag acacatacca gtgcataaaa ccaaccgcag ctgctaataa    20340
cactacatgg tctaaggatg aagaatttag tgatcgcaat gaaatagggg tgggaaacaa    20400
cttcgccatg gagatcaaca tccaggccaa cctctggagg aacttcctct atgcgaacgt    20460
ggggctctac ctgccagaca agctcaagta caacccccac aacgtggaca tctctgacaa    20520
ccccaacacc tatgactaca tgaacaagcg tgtggtggct cccggcctgg tggactgctt    20580
tgtcaatgtg ggagccaggt ggtccctgga ctacatggac aacgtcaacc ccttcaacca    20640
```

```
ccaccgcaat gcgggtctgc gctaccgctc catgatcctg ggcaacgggc gctacgtgcc   20700
cttccacatt caggtgcccc agaagttctt tgccatcaag aacctcctcc tcctgccggg   20760
ctcctacact tacgagtgga acttcaggaa ggatgtcaac atggtcctgc agagctctct   20820
gggcaatgac cttagggtgg acggggccag catcaagttt gacagcgtca ccctctatgc   20880
taccttcttc cccatggctc acaacaccgc ctccacgctc gaggccatgc tgaggaacga   20940
caccaacgac cagtccttca atgactacct ctctggggcc aacatgctct accccatccc   21000
cgccaaggcc accaacgtgc ccatctccat tccctctcgc aactgggccg ccttcagagg   21060
ctgggccttt acccgcctta agaccaagga aacccctcc ctgggctcgg gttttgaccc   21120
ctactttgtc tactcgggat ccatcccta cctggatggc accttctacc tcaaccacac   21180
ttttaagaag atatccatca tgtatgactc ctccgtcagc tggccgggca atgaccgcct   21240
gctcaccccc aatgagttcg aggtcaagcg cgccgtggac ggcgagggct acaacgtggc   21300
ccagtgcaac atgaccaagg actggttcct ggtgcagatg ctggccaact acaacatagg   21360
ctaccagggc ttctacatcc agagagcta caaggacagg atgtactcct tcttcagaaa   21420
tttccaaccc atgagcaggc aggtggtgga cgagaccaaa tacaaggact atcaggccat   21480
tggcatcact caccagcaca caactcggg attcgtgggc tacctggctc ccaccatgcg   21540
cgaggggcag gcctaccccg ccaacttccc ctaccgttg ataggcaaaa ccgcggtcga   21600
cagcgtcacc cagaaaaagt tcctctgcga ccgcacctc tggcgcatcc ccttctctag   21660
caacttcatg tccatgggtg cgctcacgga cctgggccag aacctgctct atgccaactc   21720
cgcccatgcg ctggacatga cttttgaggt ggaccccatg gacgagccca ccttctcta   21780 tattgtgttt gaagtgttcg acgtggtcag agtgcaccag ccgcaccgcg gtgtcatcga   21840
gaccgtgtac ctgcgcacgc ccttctcggc cggcaacgcc accacctaag gagacagcgc   21900
cgccgcctgc atgacgggtt ccaccgagca agagctcagg gccatcgcca gagacctggg   21960
atgcggaccc tattttttgg gcacctatga caaacgcttc ccgggcttca tctcccgaga   22020
caagctcgcc tgcgccatcg tcaacacggc cgcgcgcgag accgggggcg tgcactggct   22080
ggcctttggc tgggacccgc gctccaaaac ctgctacctc ttcgacccct ttggcttctc   22140
cgatcagcgc ctcagacaga tctatgagtt tgagtacgag gggctgctgc ccgcagcgc   22200 gcttgcctcc tcgcccgacc gctgcatcac ccttgagaag tccaccgaga ccgtgcaggg   22260
gccccactcg gccgcctgcg gtctcttctg ctgcatgttt ttgcacgcct ttgtgcgctg   22320
gccccagagt cccatggatc gcaaccccac catgaacttg ctcaagggag tgcccaacgc   22380
catgctccag agcccccagg tccagcccac cctgcgccac aaccaggaac agctctaccg   22440
cttcctggag cgccactccc cctacttccg cagtcacagc gcgcacatcc ggggggccac   22500
ctctttctgc cacttgcaag aaaacatgca agacggaaaa tgatgtacag ctcgcttttt   22560
aataaatgta aagactgtgc actttatttta tacacgggct cttttctggtt atttattcaa   22620 caccgccgtc gccatctaga aatcgaaagg gttctgccgc gcgtcgccgt gcgccacggg   22680
cagagacacg ttgcgatact ggaagcggct cgcccactta aactcgggca ccaccatgcg   22740
gggcagtggt tcctcgggga agttctcgcc ccacagggtg cgggtcagct gcagcgcgct   22800
caggaggtcg ggagccgaga tcttgaagtc gcagttgggg ccggaaccct gcgcgcgcga   22860
gttgcggtac acgggttgc agcactggaa caccagcagg gccggattat gcacgctggc   22920
cagcaggctc tcgtcgctga tcatgtcgct gtccagatcc tccgcgttgc tcagggcgaa   22980
```

```
cggggtcatc ttgcagacct gcctgcccag gaaaggcggc agcccgggct tgccgttgca   23040
gtcgcagcgc aggggcatca gcaggtgccc gcggcccgac tgcgcctgcg ggtacagcgc   23100
gcgcatgaag gcttcgatct gcctgaaagc cacctgcgtc ttggctccct ccgaaaagaa   23160
catcccacag gacttgctgg agaactggtt cgcgggacag ctggcatcgt gcaggcagca   23220
gcgcgcgtcg gtgttggcga tctgcaccac gttgcgaccc caccggttct tcactatctt   23280
ggccttggaa gcctgctcct tcagcgcgcg ctggccgttc tcgctggtca catccatctc   23340
tatcacctgc tccttgttga tcatgtttgt accgtgcaga cacttcaggt cgccctccgt   23400
ctgggtgcag cggtgctccc acagcgcgca accggtgggc tcccaatttt tgtgggtcac   23460
ccccgcgtag gcctgcaggt aggcctgcaa gaagcgcccc atcatggcca caaaggtctt   23520
ctggctcgta aaggtcagct gcaggccgcg atgctcttcg ttcagccagg tcttgcagat   23580
ggcggccagc gcctcggtct gctcgggcag catcctaaaa tttgtcttca ggtcgttatc   23640
cacgtggtac ttgtccatca tggcgcgcgc cgcctccatg cccttctccc aggcggacac   23700
catgggcagg cttaggggggt ttatcacttc caccggcgag gacaccgtac tttcgatttc   23760
ttcttcctcc ccctcttccc ggcgcgcgcc cacgctgctg cgcgctctca ccgcctgcac   23820
caaggggtcg tcttcaggca agcgccgcac cgagcgcttg ccgcccttga cctgcttaat   23880
cagcaccggc gggttgctga gcccaccat ggtcagcgcc gcctgctctt cttcgtcttc   23940
gctgtctacc actatctctg ggaagggct tctccgctct gcggcggcgc gcttcttttt   24000
tttcttggga gcggccgtga tggagtccgc cacggcgacg gaggtcgagg gcgtggggct   24060
gggggtgcgc ggtaccaggg cctcgtcgcc ctcggactct tcctctgact ccaggcggcg   24120
gcggagtcgc ttctttgggg gcgcgcgcgt cagcggcggc ggagacgggg acggggacgg   24180
ggacgggacg ccctccacag ggggtggtct tcgcgcagac ccgcggccgc gctcgggggt   24240
cttctcgagc tggtcttggt cccgactggc cattgtatcc tcctcctcct aggcagagag   24300
acataaggag tctatcatgc aagtcgagaa ggaggagagc ttaaccaccc cctctgagac   24360
cgccgatgcg cccgccgtcg ccgtcgcccc cgctgccgcc gacgcgcccg ccacaccgag   24420
cgacaccccc gcggacccccc ccgccgacgc accctgttc gaggaagcgg ccgtggagca   24480
ggacccgggc tttgtctcgg cagaggagga tttgcgagag gaggaggata aggagaagaa   24540
gccctcagtg ccaaaagatg ataaagagca agacgagcac gacgcagatg cacaccaggg   24600
tgaagtcggg cggggggacg gagggcatga cggcgccgac tacctagacg aagggaacga   24660
cgtgctcttg aagcacctgc atcgtcagtg cgccattgtt tgcgacgctc tgcaggagcg   24720
cagcgaagtg ccccctcagcg tggcggaggt cagccacgcc tacgagctca gcctcttctc   24780
cccccgggtg ccccccgcc gccgcgaaaa cggcacatgc gagcccaacc cgcgcctcaa   24840
cttctacccc gcctttgtgg tacccgaggt cctggccacc tatcacatct tctttcaaaa   24900
ttgcaagatc cccctctcgt gccgcgccaa ccgtagccgc gccgataaga tgctggccct   24960
gcgccagggc gaccacatac ctgatatcgc cgctttggaa gatgtaccaa agatcttcga   25020
gggtctgggt cgcaacgaga agcgggcagc aaactctctg caacaggaaa acagcgaaaa   25080
tgagagtcac accggggtac tggtggagct cgagggcgac aacgcccgcc tggcggtggt   25140
caagcgcagc atcgaggtca cccactttgc ctaccccgcg ctaaacctgc cccccaaagt   25200
catgaacgcg gccatggacg ggctgatcat gcgccgcggc cggcccctcg ctccagatgc   25260
aaacttgcat gaggagaccg aggacggcca gcccgtggtc agcgacgagc agctggcgcg   25320
ctggctggag accgcggacc ccgccgaact ggaggagcgg cgcaagatga tgatggccgt   25380
```

```
ggtgctggtc accgtagagc tggagtgtct gcagcgcttc ttcggcgacc ccgagatgca    25440
gagaaaggtc gaggagaccc tgcactacac cttccgccag ggctacgtgc gccaggcttg    25500
caagatctcc aacgtggagc tcagcaacct ggtgtcctac ctgggcatct tgcatgagaa    25560
ccgcctcggg cagagcgtgc tgcactccac cctgcgcggg gaggcgcgcc gcgactacgt    25620
gcgcgactgc gtttacctct tcctctgcta cacctggcag acggccatgg gggtctggca    25680
gcagtgcctg gaggagcgca acctcaagga gctggagaag ctcctgcagc gcgcgctcaa    25740
agatctctgg acgggctaca acgagcgctc ggtggccgcc gcgctggccg acctcatctt    25800
ccccgagcgc ctgctcaaaa ccctccagca ggggctgccc gacttcacca gccaaagcat    25860
gttgcaaaac ttcaggaact ttatcctgga gcgttctggc atcctacccg ccacctgctg    25920
cgccctgccc agcgactttg tccccctcgt gtaccgcgag tgccccccgc cgctgtgggg    25980
tcactgctac ctgttccaac tggccaacta cctgtcctac cacgcggacc tcatggagga    26040
ctccagcggc gaggggctca tggagtgcca ctgccgctgc aacctctgca cgccccaccg    26100
ctccctggtc tgcaacaccc aactgctcag cgagagtcag attatcggta ccttcgagct    26160
acagggtccg tcctcctcag acgagaagtc cgcggctccg gggctaaaac tcactccggg    26220
gctgtggact tccgcctacc tgcgcaaatt tgtacctgaa gactaccacg cccacgagat    26280
caggttttac gaagaccaat cccgcccgcc caaggcggag ctgaccgcct gcgtcatcac    26340
ccagggcgag atcctaggcc aattgcaagc catccaaaaa gcccgccaag acttttttgct    26400 gaagaagggt cgggggggtgt atctggaccc ccagtcgggt gaggagctca acccggttcc    26460
cccgctgccg ccgccgcggg accttgcttc ccaggataag catcgccatg gctcccagaa    26520
agaagcagca gcggccgcca ctgccgccac cccacatgct ggaggaagag gaggaatact    26580
gggacagtca ggcagaggag gtttcggacg aggaggagcc ggagacggag atggaagagt    26640
gggaggagga cagcttagac gaggaggctt ccgaagccga agaggcagac gcaacaccgt    26700
caccctcggc cgcagccccc tcgcaggcgc ccccgaagtc cgctcccagc atcagcagca    26760
acagcagcgc tataacctcc gctcctccac cgccgcgacc cacggccgac cgcagaccca    26820
accgtagatg ggacaccacc ggaaccgggg ccggtaagtc ctccgggaga ggcaagcaag    26880
cgcagcgcca aggctaccgc tcgtggcgcg ctcacaagaa cgccatagtc gcttgcttgc    26940
aagactgcgg ggggaacatc tccttcgccc gccgcttcct gctcttccac cacggtgtgg    27000
ccttcccccg taacgtcctg cattactacc gtcatctcta cagcccctac tgcggcggca    27060
gtgagccaga gacggtcggc ggcggcggcg gcgcccgttt cggcgcctag gaagaccag    27120 ggcaagactt cagccaagaa actcgcggcg gccgcggcga acgcggtcgc gggggccctg    27180
cgcctgacgg tgaacgaacc cctgtcgacc gcgaactga ggaaccgaat cttccccact    27240
ctctatgcca tcttccagca gagcagaggg caggatcagg aactgaaagt aaaaaacagg    27300
tctctgcgct ccctcacccg cagctgtctg tatcacaaga gcgaagacca gcttcggcgc    27360
acgctggagg acgctgaggc actcttcagc aaatactgcg cgctcactct taaggactag    27420
ctccgcgccc ttctcgaatt taggcgggaa cgcctacgtc atcgcagcgc cgccgtcatg    27480
agcaaggaca ttcccacgcc atacatgtgg agctatcagc cgcagatggg actcgcggcg    27540
ggcgcctccc aagactactc caccccgcatg aactggctca gtgccggccc acacatgatc    27600
tcacaggtta atgatatccg cacccatcga aaccaaatat tggtggagca ggcggcaatt    27660
accaccacgc cccgcaataa tcccaacccc agggagtggc ccgcgtccct ggtgtatcag    27720
```

-continued

| | |
|---|---|
| gaaattcccg gcccccaccac cgtactactt ccgcgtgatt cccaggccga agtccaaatg | 27780 |
| actaactcag gggcacagct cgcgggcggc tgtcgtcaca gggtgcggcc tcctcgccag | 27840 |
| ggtataactc acctggagat ccgaggcaga ggtattcagc tcaacgacga gtcggtgagc | 27900 |
| tcctcgctcg gtctcagacc tgacgggacc ttccagatag ccggagccgg ccgatcttcc | 27960 |
| ttcacgcccc gccaggcgta cctgactctg caaagctcgt cctcggcgcc gcgctcgggc | 28020 |
| ggcatcggga ctctccagtt cgtgcaggag tttgtgccct cggtctactt caacccttc | 28080 |
| tcgggctctc ccggtcgcta cccggaccag ttcatctcga actttgacgc cgcgagggac | 28140 |
| tcggtggacg gctacgactg aatgtcgggt ggacccggtg cagagcaact cgcctgaag | 28200 |
| cacctcgacc actgccgccg ccctcagtgc tttgcccgct gtcagaccgg tgagttccag | 28260 |
| tactttccc tgcccgactc gcacccggac ggccggcgc acggggtgcg cttttcatc | 28320 |
| ccgagtcagg tgcgctctac cctaatcagg gagtttaccg cccgtcccct actggcggag | 28380 |
| ttggaaaagg ggccttctat cctaaccatt gcctgcatct gctctaaccc tggattgcac | 28440 |
| caagatcttt gctgtcattt gtgtgctgag tataataaag gctgagatca gaatctactc | 28500 |
| gggctcctgt cgccatcctg tcaacgccac cgtccaagcc cggcccgatc agcccgaggt | 28560 |
| gaacctcacc tgccggtctgc accggcgcct gaggaaatac ctagcttggt actacaacag | 28620 |
| cactcccttt gtggtttaca acagctttga ccaggacggg gtctcactga gggataacct | 28680 |
| ctcgaacctg agctactcca tcaggaagaa cagcaccctc gagctactc ctccttacct | 28740 |
| gcccgggact taccagtgtg tcaccggtcc ctgcacccac acccacctgt tgatcgtaaa | 28800 |
| cgactctctt ccgagaacag acctcaataa ctcctcttcg cagttcccca gaacaggagg | 28860 |
| tgagctcagg aaaccccggg taaagaaggg tggacgagag ttaacacttg tggggtttct | 28920 |
| ggtgtatgtg acgctggtgg tggctctttt gattaaggct tttccttcca tgtctgaact | 28980 |
| ctccctcttc ttttatgaac aactcgacta gtgctaacgg gaccctaccc aacgaatcgg | 29040 |
| gattgaatat cggtaaccag gttgcagttt cacttttgat taccttcata gtcctcttcc | 29100 |
| tgctagtgct gtcgcttctg tgcctgcgga tcggggctg ctgcatccac gtttatatct | 29160 |
| ggtgctggct gtttagaagg ttcggagacc atcgcaggta gaataaacat gctgctgctt | 29220 |
| accctctttg tcctggcgct ggccgccagc tgccaagcct tttccgaggc tgactttata | 29280 |
| gagcccagt gtaatgtgac ttttaaagcc catgcacagc gttgtcatac tataatcaaa | 29340 |
| tgtgccaccg aacacgatga ataccttatc cagtataaag ataaatcaca caaagtggca | 29400 |
| cttgttgaca tctggaaacc cgaagaccct ttggaataca atgtgaccgt tttccagggt | 29460 |
| gacctcttca aaatttacaa ttacactttc ccatttgacc agatgtgtga ctttgtcatg | 29520 |
| tacatggaaa agcagcacaa gctgtggcct ccgactcccc agggctgtgt ggaaaatcca | 29580 |
| ggctctttct gcatgatctc tctctgtgta actgtgctgg cactaatact cacgcttttg | 29640 |
| tatatcagat ttaaatcaag gcaaagcttc attgatgaaa agaaaatgcc ttaatcgctt | 29700 |
| tcacgcttga ttgctaacac cggggttttta tccgcagaat gattggaatc accctactaa | 29760 |
| tcacctccct ccttgcgatt gcccatgggt tggaacgaat cgaagtccct gtggggcca | 29820 |
| atgttaccct ggtggggcct gtcggcaatg ctacattaat gtgggaaaaa tatactaaaa | 29880 |
| atcaatgggt ctcttactgc actaacaaaa atagccacaa gcccagagcc atctgcgatg | 29940 |
| ggcaaaatct aaccttgatt gatgttcaat tgctggatgc gggctactat tatgggcagc | 30000 |
| tgggtacaat gattaattac tggagacccc acagagatta catgctccac gtagtaaagg | 30060 |
| gtccccttag cagcccaccc actaccacct ctactacccc cactaccacc actactccca | 30120 |

```
ccaccagcac tgccgcccag cctcctcata gcagaacaac cacttttatc aattccaagt   30180
cccactcccc ccacattgcc ggcgggccct ccgcctcaga ctccgaaacc accgagatct   30240
gcttctgcaa atgctctgac gccattgccc aggatttgga agatcacgag gaagatgagc   30300
atgacttcgc agatgcatgc caggcatcag agccagaagc gctgccggtg ccctcaaac    30360 agtatgcaga cccccacacc acccccgacc ttcctccacc ttcccagaag ccaagtttcc   30420
tgggggaaaa tgaaactctg cctctctcca tactcgctct gacatctgtt gctatgttga   30480
ccgctctgct ggtgcttcta tgctctatat gctacctgat ctgctgcaga aagaaaaaat   30540
ctcacggcca tgctcaccag cccctcatgc acttcccctta ccctccagag ctgggcgacc  30600
acaaacttta agtctgcagt aactatctgc ccatcccttg tcagtcgaca gcgatgagcc   30660
ccactaatct aacggcctct ggacttacaa catcgtctct taatgagacc accgctcctc   30720
aagacctgta cgatggtgtc tccgcgctgg ttaaccagtg ggatcacctg gcatatggt    30780 ggctcctcat aggagcagtg accctgtgcc taatcctggt ctggatcatc tgctgcatca   30840
aaagcagaag acccaggcgg cggcccatct acaggccctt tgtcatcaca cctgaagatg   30900
atgatgacac cacttccagg ctgcagaggc taaagcagct actcttctct tttacagcat   30960
ggtaaattga atcatgcctc gcattttcat ctacttgtct ctccttccac tttttctggg   31020
ctcttctaca ttggccgctg tgtcccacat cgaggtagac tgcctcacgc ccttcacagt   31080
ctacctgctt ttcggcttttg tcatctgcac ctttgtctgc agcgttatca ctgtagtgat   31140
ctgcttcata cagtgcatcg actacgtctg cgtgcgggtg gcttacttta gacaccaccc   31200
ccagtatcgc aacagggaca tagcggctct cctaagactt gtttaaaatc atggccaaat   31260
taactgtgat tggtcttctg atcatctgct gcgtcctagc cgcgattggg actcaagctc   31320
ctaccaccac cagcgctccc agaaagagac atgtatcctg cagcttcaag cgtccctgga   31380 atataccccca atgctttact gatgaacctg aaatctcttt ggcttggtac ttcagcgtca   31440
ccgcccttct tatcttctgc agtacggtta ttgcccttgc catctaccct tcccttgacc   31500
tgggctggaa tgctgtcaac tctatggaat atcccacctt cccagaacca gacctgccag   31560
acctggttgt tctaaacgcg tttcctcctc ctgctcccgt tcaaaatcag tttcgccctc   31620
cgtcccccac gcccactgag gtcagctact ttaatctaac aggcggagat gactgaaaac   31680
ctagacctag aaatggacgg tctctgcagc gagcaacgca cactagagag gcgccggcaa   31740
aaagagctcg agcgtcttaa acaagagctc caagacgcgg tggccataca ccagtgcaaa   31800
aaaggtgtct tctgtctggt aaaacaggcc acgctcacct atgaaaaaac aggtgacacc   31860
caccgcctag gatacaagct gcccacacag cgccaaaagt tcgccctcat gataggcgaa   31920
caacccatca ccgtgaccca gcactccgtg gagacagaag gctgcataca tgctccctgt   31980
aggggcgctg actgcctcta caccttgatc aaaaccctct gcggtctcag agaccttatc   32040
cctttcaatt aatcataact gtaatcaata aaaaatcact tacttgaaat ctgatagcaa   32100
gcctctgtcc aatttttttca gcaacacttc cttcccctcc tcccaactct ggtactctag   32160
gcgcctccta gctgcaaact tcctccacag tctgaaggga atgtcagatt cctcctcctg   32220
tccctccgca cccacgatct tcatgttgtt gcagatgaaa cgcgcgagat cgtctgacga   32280
gaccttcaac cccgtgtacc cctacgatac cgagatcgct ccgacttctg tcccttctcct  32340 taccccctccc tttgtgtcat ccgcaggaat gcaagaaaat ccagctgggg tgctgtccct   32400
gcacttgtca gagcccctta ccacccacaa tggggccctg actctaaaaa tgggggggcgg  32460
```

```
cctgaccctg gacaaggaag ggaatctcac ttcccaaaac atcaccagtg tcgatccccc   32520
tctcaaaaaa agcaagaaca acatcagcct tcagaccgcc gcacccctcg ccgtcagctc   32580
cggggcccta acactttttg ccactcccc cctagcggtc agtggtgaca accttactgt   32640
gcagtctcag gcccctctca ctttggaaga ctcaaaacta actctggcca ccaaaggacc   32700
cctaactgtg tccgaaggca aacttgtcct agaaacagag gctcccctgc atgcaagtga   32760
cagcagcagc ctgggcctta gcgttacggc cccacttagc attaacaatg acagcctagg   32820
actagatctg caggcaccca ttgtctctca aaatggaaaa ctggctctaa atgtagcagg   32880
ccccctagct gtggccaatg gcattaatgc tttgacagta ggcacaggca aggtattgg    32940 tctaaatgaa accagcactc acttgcaagc aaagttggtc gccccctag gctttgatac    33000 caatggcaac attaagctaa gcgttgcagg aggcatgaga ctaaataatg acacacttat   33060
actagatgta aactacccat tgaagctca aggccaacta agtctaagag tgggccaggg    33120
tccgctgtat gtagattcta gcagccataa cctgaccatt agatgcctta gaggattata   33180
cataacatcg tctaataacc aaaccggtct agaggccaac ataaaactaa caaaggcct    33240 tgtctatgat ggaaatgcca tagcagtcaa tgttggtcaa ggattgcaat acagcactac   33300
tgccacatcg gaaggtgtgt atcctataca gtcaagata ggtttgggaa tggaatga     33360 taccaacgga gccatgatga caaaactagg ctctggacta agctttgaca attcaggagc   33420
cattgtagtg ggaaacaaaa atgatgacag gcttactctg tggactacac cagacccatc   33480
tcctaactgt agaatttatt ctgaaaaaga tactaaacta accttggtgc tgactaagtg   33540
tggcagccaa atcctaggca cagtatctgc ccttgctgtc agaggcagcc ttgcgcccat   33600
cactaatgca tccagcatag tccaaatatt tctaagattt gatgaaaatg gactattgat   33660
gagcaactca tcgctagacg gtgattactg gaattacaga aatggggact ccactaatag   33720
cacaccatat acaaatgcag taggctttat gcctaatcta gcagcctatc ctaaaggtca   33780
ggctacagct gcaaaagca gtattgtaag ccaggtatac atggatggtg acactactaa   33840
acctataaca ctaaaaataa acttcaatgg cattgatgaa acaacagaaa ataccctgt    33900 tagtaaatat tccatgacat tctcatggag ctggcccacc gcaagctaca taggccacac   33960
ttttgcaaca aactcttta ctttctccta catcgcccaa gaataaagaa agcacagaga    34020
tgcttgtttt gatttcaaaa ttgtgtgctt ttatttattt tcagcttaca gtatttccag   34080
tagtcattcg aataaagctt aatcaaactg catgagaacc cttccacata gcttaaatta   34140
gcaccagtgc aaatggagaa aattcaacat acctttttta tccagatatc agagaactct   34200
agtggtcagt tttcccccac cctcccagct cacagaatac acagtccttt ccccccggct   34260
ggctttaaac aacactatct cattggtaac agacatattc ttaggtgtaa taatccacac   34320
ggtctcttgg cgggccaagc gctggtcggt gatgttaata aactcccag gcagctcttt    34380 caagttcacg tcgctgtcca actgctgaag cgctcgcggc tccgactgcg cctctagcgg   34440
aggcaacggc aacacccgat ccttgatcta taaaggagta gagtcataat ccccataag    34500 aatagggcgg tgatgcagca acaaggcgcg cagcaactcc tgccgccgcc tctccgtacg   34560
acaggaatgc aacggcgtgg tggtctcctc cgcgataatc cgcaccgctc gcagcatcag   34620
catcctcgtc ctccgggcac agcagcgcat cctgatctca ctgagatcgg cgcagtaagt   34680
gcagcacaaa accaagatgt tatttaagat cccacagtgc aaagcactgt acccaaagct   34740
catggcggga aggacagccc ccacgtgacc atcataccag atccttaggt aaatcaaatg   34800
acgacctctc ataaacacgc tggacatgta catcacctcc ttgggcatgc gctgattcac   34860
```

```
cacctctcga taccacaagc atcgctgatt aattaaagac ccctcaagca ccatcctgaa   34920
ccaggaagcc agcacctgac cccccgccag gcactgcagg gaccccggtg aattgcagtg   34980
gcagtgaaga ctccagcgct cgtagccgtg aaccatagag ccggtcatta tatccacatt   35040
ggcacaacac aaacacactt tcatacactt tttcatgatt agcagctcct ctctagtcag   35100
gaccatatcc caaggaatca cccactcttg aatcaaggta aatcccacac agcagggcag   35160
gcctctcaca taactcacgt tatgcatagt gagcgtgtcg caatctggaa ataccggatg   35220
atcttccatc accgaagctc gcgtctccgt ctcaaaggga ggtaaacggt ccctcgtgta   35280
gggacagtgg cgggataatc gagatcgtgt tgaacgtaga gtcatgccaa agggaacagc   35340
ggacgtactc atatttcctc cagcagaacc aagtgcgcgc gtggcagcta tccctgcgtc   35400
ttctgtctcg ccgcctgccc cgctcggtgt agtagttgta atacagccac tccctcagac   35460
cgtcaaggcg ctccctggcg tccggatcta taacaacacc gtcctgcagc gccgccctga   35520
tgacatccac caccgtagag tatgccaagc ccagccagga aatgcattca ctttgacagc   35580
gagagatagg aggagcggga agagatggaa gaaccatgat agtaaaagac ttttattcca   35640
atcgatcctc tacaatgtca aagtgtagat ctataagatg acactggtct cctccgctga   35700
gtcgatcaaa ataacagct aaaccacaaa caacacgatt ggtcaaatgc tccacaaggg   35760
cttgcagcat aaaatcgcct cgaaagtcca ccgcaagcat aacatcaaag ccaccgcccc   35820
tatcatgatc tataataaaa accccacagc tatccaccag acccataaag ttttcatctc   35880
tccatcgtga aaaaatattt acaagctcct cctttaaatc acctccaacc aattgaaaaa   35940
gttgagccaa accgccctcc accttcattt tcagcaagcg catcatgatt gcaaaaattc   36000
aggctcctga gacacctgta taagattgag aagcggaacg ttaacgtcaa tgtttcgctc   36060
gcgaagatcg cgcctcagtg caagcatgat ataatcccac aggtcggagc ggatcagcga   36120
ggacatctcc ccgccaggaa ccaactcaac ggagcctatg ctgattataa tacgcatatt   36180
cggggctatg ctgaccagca cggcccccaa ataggcgtac tgcataggcg gcgacaaaaa   36240
gtgaacagtt tgggttaaaa aatcaggcaa acagtcgcgc aaaaaagcaa gaacatcata   36300
accatgctca tgcaaataga tgcaagtaag ctcaggaacg accacagaaa aatgcacaat   36360
ttttctctca aacatgactg cgagccctgc aaaaaataaa aaagaaacat tacacaagag   36420
tagcctgtct tacgatggga tagactactc taaccaacat aagacgggcc acaacatcgc   36480
ccgcgtggcc ataaaaaaaa ttgtccgtgt gattaaaaag aagcacagat agctggccag   36540
tcatatccgg agtcatcacg tgtgaacccg tgtagacccc cggggttggac acatcggcca   36600 aacaaagaaa gcggccaatg tacccaggag gaatcataac actaagacga agatacaaca   36660
gaataacccc atgaggggga ataacaaagt tagtaggtga ataaaaacga taaacacccg   36720
aaactccctc ctgcgtaggc aaaatagcac cctccccttc caaaacaaca tatagcgctt   36780
ccacagcagc catgacaaaa gactcaaaac actcaaaaga ctcagtctta ccaggaaaat   36840
aaaagcactc tcacagcacc agcactaatc agagtgtgaa gagggccaag tgccgaacga   36900
gtatatatag gaataaaaaa tgacgtaaat gtgtaaaggt cagaaaacgc ccagaaaaat   36960
acacagacca acgcccgaaa cgaaacccg cgaaaaaata cccagaactt cctcaacaac   37020
cgccacttcc ggtttctcac ggtacgtcac ttccgcaaga aaagcaaaac tacatttccc   37080
acatgtgtaa aaacgaaacc ccgccccttg taactgccca caacttacat catcaaaaca   37140
taaactccta cgtcacccgc cccgcctctc cccgcccacc tcattatcat attggccaca   37200
```

| atccaaaata aggtatatta ttgatgatg | 37229 |

<210> SEQ ID NO 22
<211> LENGTH: 37232
<212> TYPE: DNA
<213> ORGANISM: Gorilla beringei beringei

<400> SEQUENCE: 22

| catcatcaat aatatacctt attttggatt gtggccaata tgataatgag gtgggcgggg | 60 |
| agaggcgggg cggtgacgt aggacgcgcg agtagggttg ggaggtgtgg cggaagtgtg | 120 |
| gcatttgcaa gtgggaggag ctcacatgca agcttccgtc gcggaaaatg tgacgttttt | 180 |
| gatgagcgcc gcctacctcc ggaagtgcca attttcgcgc gcttttcacc ggatatcgta | 240 |
| gtaattttgg gcgggaccat gtaagatttg gccattttcg cgcgaaaagt gaaacgggga | 300 |
| agtgaaaact gaataatagg gcgttagtca tagcgcgtaa tatttaccga gggccgaggg | 360 |
| actttgaccg attacgtgga ggactcgccc aggtgttttt tacgtgaatt ccgcgttcc | 420 |
| gggtcaaagt ctccgttttt attgtcaccg tcatttgacg cggagggtat ttaaacccgc | 480 |
| tgcgctcctc aagaggccac tcttgagtgc cagcgagaag agttttctcc tctgctccgc | 540 |
| ttcggtgatc gaaaaatgag acacatagcc tgcactccgg gtcttttgtc cggtcgggcg | 600 |
| gcggccgagc ttttggacgc tttgatcaat gatgtcctaa gcgatgattt tccgtctact | 660 |
| acccacttta gcccacctac tcttcacgaa ctgtacgatc tggatgtact ggtggatgtg | 720 |
| aacgatccca acgaggaggc ggtttctgcg tttttttccg agtctgcgct gttggccgct | 780 |
| caggagggat ttgacctaca cactccgccg cctattttag agtctccgct gccggagccc | 840 |
| agtggtatac cttatatgcc tgaactgctt cccgaagtgg tagacctgac ctgccacgag | 900 |
| cctggctttc cgcccagcga cgatgagggt gagccttttg ttttagactt tgctgagata | 960 |
| cctgggcacg gttgcaggtc ttgtgcatat catcagaggg ttaccggaga ccccgaggtt | 1020 |
| aagtgttcgc tgtgctatat gaggatgacc tcttccttta tctacagtaa gttttttgtct | 1080 |
| aggtgggctt ttgggtaggt gggttttgtg tcagaacagg tgtaaacgtt gcttgtgttt | 1140 |
| tttgtacctg taggtccggt gtccgagcca gacccggagc ccgaccgcga tcccgagccg | 1200 |
| gatcccgagc ctcctcgcag gacaaggaaa ctaccttcca ttctgtgcaa gtctcagaca | 1260 |
| cctgtaagga ccagcgaggc agacagcacc gactctggca cttctacctc tcccctgaa | 1320 |
| attcacccag tggttcctct gggtatacat aaacctgttg ctgttaaagt tgcgggcga | 1380 |
| cgccctgcag tacagtgcat tgaggacttg cttcacgatc ccgaggaacc tttgacttg | 1440 |
| agccttaaac gccctaggca ataaaccccca cctaagtaat aaacccccacc taagtaataa | 1500 |
| accctgccgc ccttggttat tgagatgacg cccaatgttt gcttttgaat gacttcatgt | 1560 |
| gtgtaataaa agtgagtgtg atcataggtc tcttgtttgt ctgggcgggg cttaagggta | 1620 |
| tataagtctc ttggggctaa acttggttac acttgacccc aatggaggcg tgggggtgct | 1680 |
| tggaggagtt tgcggacgtg cgccgtttgc tggacgagag ctctagcaat acctatacta | 1740 |
| tttggaggta tctgtggggc tctactcagg ccaagttggt ttccagaatt aagcaggatt | 1800 |
| acaagtgcga ttttgaagag ctttttagtt cctgcggtga gcttttgcaa tccttgaatc | 1860 |
| tgggccatca ggctattttc caggaaaagg ttctctcgac tttggatttt tccactcccg | 1920 |
| ggcgcaccgc cgcttgtgtg gcttttgtgt cttttgtgca agataaatgg agcgaggaga | 1980 |
| cccacctgag tcacggctac gtactggatt tcatggcgat ggctctttgg agggctcaca | 2040 |
| acaaatggaa gattcagaag gaactgtacg gttccgccct acgtcgtcca cttctgtcgc | 2100 |

```
gacagggact gaggtttccc gaccatcggc agcatcagaa tctggaagac gagtcggagg    2160
agcgagcgga ggagaagatc agcttgagag ccggcctgga ccctcctcag gaggaatgaa    2220
tctcccgcag gtggttgacc tgtttccaga actgagacgg gtcctgacta tcagggagga    2280
tggtcagttt gtgaagaagt ttaagaggga tcggggtgag ggagatgatg aggcggctag    2340
caatttagct tttagtctga tgactcgcca ccgaccggaa tgtattaccct atcagcagat    2400 taaggagagt tgtgccaacg agctggatct tttgggtcag aagtatagca tagaacagct    2460
taccacttac tggcttcagc ctggggatga ttgggaagag gcgatcaggg tgtatgcaaa    2520
ggtggccctg cggcccgatt gcaagtataa gattactaag ttggttaata ttagaaactg    2580
ctgctatatt tctgggaacg gggccgaagt ggagatagat actcaggaca gggtggcttt    2640
taggtgttgc atgataaaca tgtggcccgg gatactgggg atggatgggg tggtattcat    2700
gaatgtgagg tttacgggcc ccaactttaa tggcacggtg ttcatgggca acaccaactt    2760
gctcctgcat ggtgcgagtt tctatgggtt taataacacc tgtatagagg cctggaccga    2820
tgtaaaggtt cgaggttgtt cctttttatag ctgttggaag gcggtggtgt gtcgccctaa    2880
aagcaggggt tctgtgaaaa aatgcttgtt tgaaaggtgc accttaggca tcctctctga    2940
gggcaactcc agggtgcgcc ataatgtggc ttcgaactgc ggttgcttca tgcaagtgaa    3000
gggggtgagc gttatcaagc ataactcggt gtgtggaaac tgcgaggatc gcgcctccca    3060
gatgctgacc tgctttgatg gcaactgtca cctgttgaag accattcata taagcagcca    3120
ccccagaaag gcctggcccg tgtttgagca taacatcttg acccgctgct ccttgcatct    3180
gggggtcagg aggggtatgt tcctgcctta ccagtgtaac tttagccaca ctaaaatcct    3240
gctggaaccc gagtgcatga ccaaggtcag cctgaatggt gtgtttgatg tgactctgaa    3300
aatctggaag gtgctgaggt atgatgagac caggaccagg tgccgaccct gcgagtgcgg    3360
cggcaagcac atgagaaatc agcctgtgat gttggatgtg accgaggagc ttaggcctga    3420
ccatctggtg ctggcctgca ccagggccga gtttgggtct agcgatgagg ataccgattg    3480
aggtgggtaa ggtgggcgtg gctagaaggg tgggggcgtgt ataaattggg ggtctaaggg    3540
tctctctgtt ttgtcttgca acagccgccg ccatgagcga caccggcaac agctttgatg    3600
gaagcatctt tagcccctat ctgacagtgc gcatgcctca ctgggctgga gtgcgtcaga    3660
atgtgatggg ttccaacgtg gatggacgcc ccgttctgcc ttcaaaatcg tctacaatgg    3720
cctacgcgac cgtgggagga actccgctgg acgccgcgac ctccgccgcc gcctccgccg    3780
ccgccgcgac cgcgcgcagc atggctacgg acctttacag ctcttttggtg gcgagcggcg    3840 cggcctctcg cgcgtctgct cgggatgaga aactgaccgc tctgctgctt aaactggaag    3900
acttgacccg ggagctgggt caactgaccc agcaggtctc cagcttgcgt gagagcagcc    3960
ttgcctcccc ctaatggccc ataatataaa taaaagccag tctgtttgga ttaagcaagt    4020
gtatgttctt tatttaactc tccgcgcgcg gtaagcccgg gaccagcggt ctcggtcgtt    4080
tagggtgcgg tggattcttt ccaacacgtg gtacaggtgg ctctggatgt ttagatacat    4140
gggcatgagt ccatccctgg ggtggaggta gcaccactgc agagcttcgt gctcgggggt    4200
ggtgttgtat atgatccagt cgtagcagga gcgctgggcg tggtgctgaa aaatgtcctt    4260
aagcaagagg cttatagcta gggggaggcc cttggtgtaa gtgtttacaa atctgctcag    4320
ttgggagggg tgcatccggg gggatataat gtgcatcttg gactgatttt ttaggttggc    4380
tatgttccca cccagatccc ttctgggatt catgttgtgc aggaccacca gcacggtata    4440
```

| | |
|---|---|
| tccagtgcac ttgggaaatt tatcgtggag cttagacggg aatgcatgga agaacttgga | 4500 |
| gacgcccttg tggcctccca gatttccat acattcgtcc atgatgatgg caatgggccc | 4560 |
| gtgggaagct gcctgagcaa aaatgtttct gggatcgctc acatcgtagt tatgttccag | 4620 |
| ggtgaggtca tcataggaca tctttacgaa tcggggcgg agggtcccgg actgggggat | 4680 |
| gatggtaccc tcgggccccg gggcgtagtt cccctcacag atctgcatct cccaggcttt | 4740 |
| catttcagag ggagggatca tatccacctg cggagcgatg aaaaacacag tttctggcgc | 4800 |
| aggggagatt aactgggatg agagcaggtt tctgagcagc tgtgactttc cacagccggt | 4860 |
| gggcccatat atcacgccta tcaccggctg cagctggtag ttaagagagc tgcagctgcc | 4920 |
| gtcctcccgg agcagggggg ccacctcgtt cagcatatcc ctgacgtgga tgttctccct | 4980 |
| gaccaattcc gccagaaggc gctcgccgcc cagcgaaagc agctcttgca aggaagcaaa | 5040 |
| attttcagc ggttttaggc cgtcggccgt gggcatgttt ttcagcgtct gggtcagcag | 5100 |
| ttccagcctg tcccacagct cggtgatgtg ctctacggca tctcgatcca gcagatctcc | 5160 |
| tcgtttcgcg ggttggggcg gctttcgctg tagggcacca gccgatgggc gtccagcggg | 5220 |
| gccagagtca tgtccttcca tgggcgcagg gtcctcgtca gggtggtctg ggtcacggtg | 5280 |
| aaggggtgcg ctccggggttg ggcgctggcc agggtgcgct tgaggctggt tctgctggtg | 5340 |
| ctgaatcgct gccgctcttc gccctgcgcg tcggccaggt agcatttgac catggtctcg | 5400 |
| tagtcgagac cctcggcggc gtgccccttg gcgcggagct ttcccttgga ggtggcgccg | 5460 |
| cacgaggggc actgcaggct cttcagggcg tagagcttgg gagcgagaaa cacggactct | 5520 |
| ggggagtagg cgtccgcgcc gcaggaagcg cagaccgtct cgcattccac cagccaagtg | 5580 |
| agctccgggc ggtcagggtc aaaaaccagg ttgcccccat gctttttgat gcgtttctta | 5640 |
| cctcggctct ccatgaggcg gtgtcccttc tcggtgacga agaggctgtc cgtgtccccg | 5700 |
| tagaccgact tcaggggcct gtcttccagc ggagtgcctc tgtcctcctc gtagagaaac | 5760 |
| tctgaccact ctgagacgaa ggcccgcgtc caggccagga cgaaggaggc cacgtgggag | 5820 |
| gggtagcggt cgttgtccac tagcgggtcc accttctcca gggtgtgcag gcacatgtcc | 5880 |
| ccctcctccg cgtccagaaa agtgattggc ttgtaggtgt aggacacgtg accgggggtt | 5940 |
| cccgacgggg gggtataaaa gggggtgggc gcccttttcat cttcactctc ttccgcatcg | 6000 |
| ctgtctgcga gggccagctg ctggggtaag tattccctct cgaaggcggg catgacctca | 6060 |
| gcgctcaggt tgtcagtttc taaaaatgag gaggatttga tgttcacctg tccggaggtg | 6120 |
| atacctttga gggtacctgg gtccatctgg tcagaaaaca ctatttttt gttgtcaagc | 6180 |
| ttggtggcga acgacccgta gagggcgttg agagcagct tggcgatgga gcgcagggtc | 6240 |
| tggttttgt cgcggtcggc tcgctccttg gccgcgatgt tgagttgcac gtactcgcgg | 6300 |
| gccacgcact tccactcggg gaagacggtg gtgcgctcgt ctgggattag gcgcacccct | 6360 |
| cagcctcggt tgtgcagggt gaccatgtcg acgctggtgg cgacctcgcc gcgcaggcgc | 6420 |
| tcgttggtcc agcagaggcg gccgcccttg cgcgagcaga aggggggtag ggggtccagc | 6480 |
| tggtcctcgt ttgggggtc cgcgtcgatg gtgaagaccc cggggagcaa gcgcgggtca | 6540 |
| aagtagtcga tcttgcaagc ttgcatgtcc agagcccgct gccattcgcg ggcggcgagc | 6600 |
| gcgcgctcgt aggggttgag gggcgggccc cagggcatgg ggtgggtgag cgcggaggcg | 6660 |
| tacatgccgc agatgtcata cacgtacagg ggttccctga ggatgccgag gtaggtgggg | 6720 |
| tagcagcgcc ccccgcggat gctggcgcgc acgtagtcat agagctcgtg ggaggggggc | 6780 |
| agcatgttgg gcccgaggtt ggtgcgctgg gggcgctcgg cgcggaaggc gatctgcctg | 6840 |

```
aagatggcat gggagttgga ggagatggtg ggccgctgga agacgttgaa gcttgcttct    6900
tgcaagccca ccgagtccct gacgaaggag gcgtaggact cgcgcagctt gtgcaccagc    6960
tcggcggtga cctggacgtc gagcgcgcag tagtcgaggg tctcgcggat gatgtcatac    7020
ttatcctccc ccttcttttt ccacagctcg cggttgagga cgaactcttc gcggtctttc    7080
cagtactctt ggaggggaaa cccgtccgtg tccgaacggt aagagcctag catgtagaac    7140
tggttgacgg cctggtaggg gcaacagccc ttctccacgg gcagcgcgta ggcctgcgcc    7200
gccttgcgga gggaggtgtg ggtgagggcg aaagtgtccc tgaccatgac tttgaggtat    7260
tgatgtttga agtctgtgtc atcgcagccg ccctgttccc acagggtgta gtccgtgcgc    7320
tttttggagc gcgggttggg cagggagaag gtgaggtcat tgaagaggat cttccccgct    7380
cgaggcatga agtttctggt gatgcgaaag ggccctggga ccgaggagcg gttgttgatg    7440
acctgggcgg ccaggacgat ctcgtcaaag ccgtttatgt tgtggcccac gatgtagagc    7500
tccaaaaagc ggggctggcc cttgatggag gggagctttt tgagttcctc gtaggtgagc    7560
tcctcgggcg attccaggcc gtgctcctcc agggcccagt cttgcaagtg agggttggcc    7620
gccaggaagg atcgccagag gtcgcgggcc atgagggtct gcaggcggtc gcggaaggtt    7680
ctgaactgtc gccccacggc catcttttcg ggggtgatgc agtagaaggt gaggggtct    7740 ttctcccagg ggtcccatct gagctctcgg gcgaggtcgc gcgcggcggc gaccagagcc    7800
tcgtcgcccc ccagtttcat gaccagcatg aagggcacga gctgcttgcc aaaggctccc    7860
atccaagtgt aggtctctac atcgtaggtg acaaagaggc gctccgtgcg aggatgagag    7920
ccgatcggga agaactggat ctcccgccac cagttggagg attggctgtt gatgtggtga    7980
aagtagaagt cccgtctgcg ggccgagcac tcgtgctggc ttttgtaaaa gcgaccgcag    8040
tactggcagc gctgcacggg ttgtatatct tgcacgaggt gaacctggcg acctctgacg    8100
aggaagcgca gcgggaatct aagtcccccg cctgggggtcc cgtgtggctg gtggtcttct    8160
actttggttg tctggccgcc agcatctgtc tcctggaggg cgatggtgga gcagaccacc    8220
acgccgcgag agccgcaggt ccagatctcg gcgctcggcg ggcggagttt gatgacgaca    8280
tcgcgcacat tggagctgtc catggtctcc agctcccgcg gcggcaggtc agctgggagt    8340
tcctggaggt tcacctcgca gagacgggtc aaggcgcggg cagtgttgag atggtatctg    8400
atttcaaggg gcgtgttggc ggcggagtcg atggcttgca ggaggccgca gccccggggg    8460
gccacgatgg ttccccgcgg ggcgcgaggg gaggcggaag ctgggggtgt gttcagaagc    8520
ggtgacgcgc gcgggccccc ggaggtaggg ggggttccgg ccccacaggc atgggcggca    8580
ggggcacgtc ttcgccgcgc gcgggcaggg gctggtgctg gctccgaaga gcgcttgcgt    8640
gcgcgacgac gcgacggttg gtgtcctgta tctgacgcct ctgagtgaag accacgggtc    8700
ccgtgacctt gaacctgaaa gagagttcga cagaatcaat ctcggcatcg ttgacagcgg    8760
cctggcgcag gatctcctgc acgtcgcccg agttgtcctg gtaggcgatc tctgccatga    8820
actgctcgat ctcttcttcc tggagatctc ctcgtccggc gcgctccacg gtggccgcca    8880
ggtcgttgga gatgcgaccc atgagctgtg agaaggcgtt gagcccgccc tcgttccaga    8940
cccggctgta gaccacgccc ccctcggcgt cgcgagcgcg catgaccacc tgggccaggt    9000
tgagctccac gtgtcgcgtg aagacggcgt agttgcgcag gcgctggaaa aggtagttca    9060
gggtggtggc ggtgtgctcg gcgacgaaga agtacatgac ccagcgccgc aacgtggatt    9120
cattgatgtc ccccaaggcc tccaggcgct ccatggcctc gtagaagtcc acggcgaagt    9180
```

```
tgaaaaactg ggagttgcga gcggacacgg tcaactcctc ctccagaaga cggatgagct      9240
cggcgacagt gttgcgcacc tcgcgctcga aggccacggg gggcgcttct tcctcttcca      9300
cctcttcttc catgatcgct tcttcttctt cctcagccgg gacgggaggg ggcggcggcg      9360 gcggggagg ggcgcggcgg cggcggcggc gcaccgggag gcggtcgatg aagcgctcga      9420
tcatctcccc ccgcatgcgg cgcatggtct cggtgacggc gcggccgttc tcccggggc      9480 gcagctcgaa gacgccgcct ctcatctcgc cgcggggcga gcggccgtga ggtagcgaga      9540
cggcgctgac tatgcatctt aacaattgct gtgtaggtac accgccgagg gacctgattg      9600
agtccagatc caccggatcc gaaaacctttt ggaggaaagc gtctatccag tcgcagtcgc     9660
aaggtaggct gagcaccgtg gcgggcgggg gcgggtctgg agagttcctg gcggagatgc      9720
tgctgatgat gtaattaaag taggcggtct tgagaaggcg gatggtggac aggagcacca      9780
tgtctttggg tccggcctgt tggatgcgga ggcggtcggc catgccccag gcctcgttct      9840
gacaccggcg caggtctttg tagtagtctt gcatgagtct ttccaccggc acctcttctc      9900
cttcctcttc tccatctcgc cggtggtttc tcgcgccgcc catgcgcgtg accccaaagc      9960
ccctgagcgg ctgcagcagg gccaggtcgg cgaccacgcg ctcggccaag atggcctgct     10020
gcacctgagt gagggtcctc tcgaagtcat ccatgtccac gaagcggtgg taggcgcccg     10080
tgttgatggt gtaggtgcag ttggccatga cggaccagtt gacggtctgg tgtcccggct     10140
gcgagagctc cgtgtaccgc aggcgcgaga aggcgcggga atcgaacacg tagtcgttgc     10200
aagtccgcac cagatactgg tagcccacca ggaagtgcgg cggaggttgg cgatagaggg     10260
gccagcgctg ggtggcgggg gcgccgggcg ccaggtcttc cagcatgagg cggtggtatc     10320
cgtagatgta cctggacatc caggtgatgc cggcggcggt ggtggtggcg cgcgcgtagt     10380
cgcggacccg gttccagatg tttcgcaggg gcgagaagtg ttccatggtc ggcacgctct     10440
ggccggtgag gcgcgcgcag tcgttgacgc tctatacaca cacaaaaacg aaagcgttta     10500
cagggctttc gttctgtagc ctggaggaaa gtaaatgggt tgggttgcgg tgtgccccgg     10560
ttcgagacca agctgagctc ggccggctga agccgcagct aacgtggtat tggcagtccc     10620
gtctcgaccc aggccctgta tcctccagga tacggtcgag agcccttttg ctttcttggc     10680
caagcgcccg tggcgcgatc tgggatagat ggtcgcgatg agaggacaaa agcggctcgc     10740
ttccgtagtc tggagaaaca atcgccaggg ttgcgttgcg gcgtacccg gttcgagccc      10800 ctatggcggc ttgaatcggc cggaaccgcg gctaacgagg gccgtggcag ccccgtcctc     10860 aggacccgc cagccgactt ctccagttac gggagcgagc ccctttgtt ttttattttt       10920 tagatgcatc ccgtgctgcg gcagatgcgc ccctcgcccc ggcccgatca gcagcagcaa     10980
cagcaggcat gcagaccccc ctctcccctt tccgccccgg tcaccacggc cgcggcggcc     11040
gtgtcgggcg cggggggcgc gctggagtca gatgagccac cgcggcggcg acctaggcag     11100
tatctggact tggaagaggg cgagggactg gcgcggctgg gggcgaactc tccagagcgc     11160
cacccgcggg tgcagttgaa aagggacgcg cgcgaggcgt acctgccgcg gcagaacctg     11220
tttcgcgacc gcggggggcga ggagcccgag gagatgcgag actgcaggtt ccaagcgggg    11280
cgcgagctgc ggcgcgggct ggacagacag cgcctgctgc gcgaggagga ctttgagccc     11340
gacacgcaga cgggcatcag ccccgcgcgc gcgcacgtag ccgcggccga cctggtgacc     11400
gcctacgagc agacggtaaa ccaggagcgc aacttccaaa agagcttcaa caaccacgtg     11460
cgcacgctgt ggcgcgcgga ggaggtgacc ctggtctca tgcatctgtg ggacctggtg      11520
gaggcgatcg tgcagaaccc cagcagcaag ccctgaccg cgcagctgtt cctggtggtg      11580
```

```
cagcacagca gggacaacga ggccttcagg gaggcgctgc tgaacatcac cgagccggag   11640
gggcgctggc tcctggacct gataaacatc ctgcagagca tagtggtgca ggagcgcagc   11700
ctgagcctgg ccgagaaggt ggcggccatc aactactcta tgctgagcct gggcaagttc   11760
tacgcccgca agatctacaa gacccccac gtgcccatag acaaggaggt gaagatagac   11820
agcttctaca tgcgcatggc gctgaaggtg ctgaccctga gcgacgacct gggagtgtac   11880
cgcaacgagc gcatccacaa ggccgtgagc gccagccggc ggcgcgagct gagcgaccgc   11940
gagctgatgc acagtctgca gcgcgcgctg accggcgcgg gcgagggcga cagggaggtc   12000
gagtcctact tcgacatggg ggccgacctg cactggcagc cgagccgccg cgccctggag   12060
gcggcggggg cgtacggcgg cccctggcg gccgatgacc aggaagagga ggactatgag   12120
ctagaggagg gcgagtacct ggaggactga cctggctggt ggtgttttgg tatagatgca   12180
agatccgaac gtggcggacc cggcggtccg ggcggcgctg caaagccagc cgtccggcat   12240
taactcctct gacgactggg ccgcggccat gggtcgcatc atggccctga ccgcgcgcaa   12300
ccccgaggct ttcaggcagc agcctcaggc caaccggctg gcggccatct tggaagcggt   12360
agtgcccgcg cgctccaacc ccacccacga gaaggtgctg gccatagtca acgcgctggc   12420
ggagagcagg gccatccgcg cggacgaggc cggactggtg tacgatgcgc tgctgcagcg   12480
ggtggcgcgg tacaacagcg gcaacgtgca gaccaacctg gaccgcctgg tgacggacgt   12540
gcgcgaggcc gtggcgcagc gcgagcgctt gcatcaggac ggtaacctgg gctcgctggt   12600
ggcgctaaac gccttcctca gcacccagcc ggccaacgta ccgcggggc aggaggacta   12660 caccaacttt ttgagcgcgc tgcggctgat ggtgaccgag gtccctcaga gcgaggtgta   12720
ccagtcgggg cccgactact tcttccagac cagcagacag ggcttgcaaa ccgtgaacct   12780
gagccaggct ttcaagaacc tgcgggggct gtggggagtg aaggcgccca ccggcgaccg   12840
ggctacggtg tccagcctgc taaccccaa ctcgcgcctg ctgctgctgc tgatcgcgcc   12900
cttcacggac agcgggagcg tctcgcggga gacctatctg ggccacctgc tgacgctgta   12960
ccgcgaggcc atcgggcagg cgcaggtgga cgagcacacc ttccaagaga tcaccagcgt   13020
gagccacgcg ctggggcagg aggacacggg cagcctgcag gcgaccctga actacctgct   13080
gaccaacagg cggcagaaga ttcccacgct gcacagcctg acccaggagg aggagcgcat   13140
cttgcgctac gtgcagcaga gcgtgagcct gaacctgatg cgcgacggcg tgacgcccag   13200
cgtggcgctg gacatgaccg cgcgcaacat ggaaccgggc atgtacgcct cccaccggcc   13260
gtttatcaac cgcctgatgg actacttgca tcgggcggcg gccgtgaacc ccgagtactt   13320
cactaatgcc attctgaatc cccactggat gcccctccg ggttctaca acggggactt   13380 tgaggtgccc gaggtcaacg acgggttcct ctgggatgac atggatgaca gtgtgttctc   13440
acccaacccg ctgcgcgccg cgtctctgcg attgaaggag ggctctgaca gggaaggacc   13500
gaggagtctg gcctcctccc tggctctggg agcggtgggc gccacgggcg cggcggcgcg   13560
gggcagtagc cccttcccca gcctggcaga ctctctgaac agcgggcggg tgagcaggcc   13620
ccgcttgcta ggcgaggagg agtatctgaa caactccctg ctgcagcccg cgagggacaa   13680
gaacgctcag cggcagcagt ttcccaacaa tgggatagag agcctggtgg acaagatgtc   13740
cagatggaag acgtatgcgc aggagtacaa ggagtgggag gaccgccagc gcggccctt   13800 gccgccccct aggcagcgct ggcagcggcg gcgcgtccaa ccgccgctgga ggcaggggcc   13860 cgaggacgat gatgactctg cagatgacag cagcgtgttg gacctgggcg ggagcgggaa   13920
```

```
cccctttttcg cacctgcgcc cacgcctggg caagatgttt taaaagaaaa aaaaaaataa   13980
aactcaccaa ggccatggcg acgagcgttg gttttttgtt cccttcctta gtatgcggcg   14040
cgcggcgatg ttcgaggagg ggcctccccc ctcttacgag agcgcgatgg ggatttctcc   14100
tgcgcgcccc ctgcagcctc cctacgtgcc tcctcggtac ctgcaaccta caggggggag   14160
aaatagcatc tgttactctg agctgcagcc cctgtacgat accaccagac tgtacctggt   14220
ggacaacaag tccgcggacg tggcctccct gaactaccag aacgaccaca gcgattttt    14280 gaccacggtg atccaaaaca acgacttcac cccaaccgag gccagcaccc agaccataaa   14340
cctggataac aggtcgaact ggggcggcga cctgaagacc atcttgcaca ccaacatgcc   14400
caacgtgaac gagttcatgt tcaccaactc ttttaaggcg cgggtgatgg tggcgcgcga   14460 gcaggggggag gcgaagtacg agtgggtgga cttcacgctg cccgagggca actactcaga   14520
gaccatgact ctcgacctga tgaacaatgc gatcgtggaa cactatctga aagtgggcag   14580
gcagaacggg gtgaaggaaa gcgatatcgg ggtcaagttt gacaccagaa acttccgtct   14640
gggctgggac cccgtgaccg ggctggtcat gccggggtc tacaccaacg aggcctttca    14700
tcccgacata gtgcttctgc ccggctgtgg ggtggacttc acccagagcc ggctgagcaa   14760
cctgctgggc attcgcaagc ggcagccttt ccaggagggt ttcaagatca cctatgagga   14820
tctgaagggg ggcaacattc ccgcgctcct tgatctggac gcctacgagg agagcttgaa   14880
acccgaggag agcgctggcg acagcggcga gagtggcgag gagcaagccg gcggcggtgg   14940
cggcgcgtcg gtagaaaacg aaagtacgcc cgcagtggcg gcggacgctg cggaggtcga   15000 gccgaggcc atgcagcagg acgcagagga gggcgcacag gagggcgcgc agaaggacat    15060
gaacgatggg gagatcaggg gagacacatt cgccacccgg ggcgaagaaa agaggcaga    15120 ggcggcggcg gcggcgacgg cggaggccga aaccgaggtt gaggcagagg cagagcccga   15180
gaccgaagtt atggaagaca tgaatgatgg agaacgtagg ggcgacacgt tcgccacccg   15240
gggcgaagag aaggcggcgg aggcagaagc cgcggctgag gaggcggctg cggctgcggc   15300
caagactgag gctgcggcta aggctgaggt cgaagccaat gttgcggttg aggctcaggc   15360
tgaggaggag gcggcggctg aagcagttaa ggaaaaggcc caggcagagc aggaagagaa   15420
aaaacctgtc attcaacctc taaaagaaga tagcaaaaag cgcagttaca acgtcatcga   15480
gggcagcacc tttacccagt accgcagctg gtacctggcg tacaactacg gcgacccggt   15540
caagggggtg cgctcgtgga ccctgctctg cacgccggac gtcacctgcg gctccgagca   15600
gatgtactgg tcgctgccga acatgatgca agacccggtg accttccgct ccacgcggca   15660
ggttagcaac ttcccggtgg tgggcgccga actgctgccc gtgcactcca gagtttttta   15720
caacgagcag gccgtctact cccagctgat ccgccaggcc acctctctga cccacgtgtt   15780
caatcgcttt cccgagaacc agatttttggc gcgcccgccg gccccccacca tcaccaccgt   15840 gagtgaaaac gttcctgccc tcacagatca cgggacgcta ccgctgcgca acagcatctc   15900
aggagtccag cgagtgacca ttactgacgc cagacgccgg acctgcccct acgtttacaa   15960
ggccttgggc atagtctcgc cgcgcgtcct ctccagtcgc acttttttaaa acacatctac   16020 ccacacgttc caaaatcatg tccgtactca tctcacccag caacaacacc ggctggggc    16080 tgcgcgcgcc cagcaagatg tttggagggg cgaggaagcg ctccgaccag caccctgtgc   16140
gcgtgcgcgg ccactaccgc gcgccctggg gagcgcacaa gcgcgggcgc acagggcgca   16200
ccactgtgga cgacgtcatt gactccgtag tggagcaagc gcgccactac acacccggcg   16260
cgccgaccgc ccccgccgtg tccaccgtgg accaggcgat cgaaagcgtg gtacagggcg   16320
```

```
cgcggcacta tgccaacctt aaaagtcgcc gccgccgcgt ggcccgccgc catcgccgga   16380
gaccccgggc caccgccgcc gcgcgcctta ctaaggctct gctcaggcgc gccaggcgaa   16440
ctggccaccg ggccgccatg agggccgcac ggcgggctgc cgctgccgca agcgtcgtgg   16500
ccccgcgggc acgaaggcgc gcggccgctg ccgccgccgc cgccatttcc agcttggcct   16560
cgacgcggcg cggtaacata tactgggtgc gcgactcggt aaccggcacg cgggtacccg   16620
tgcgctttcg ccccccgcgg aattagcaca agacaacata cacactgagt ctcctgctgt   16680
tgtgtatccc agcggcgacc gtcagcagcg gcgacatgtc caagcgcaaa attaaagaag   16740
agatgctcca ggtcatcgcg ccggagatct atgggccccc gaagaaggag gaggatgatt   16800
acaagccccg caagctaaag cgggtcaaaa agaaaaagaa agatgatgat gacgaggcgg   16860
tggagtttgt ccgccgcatg gcacccaggc gccccgtgca gtggaagggc cggcgcgtgc   16920
agcgcgtttt gcgccccggc accgcggtgg tcttcacgcc cggcgagcgc tccacgcgca   16980
ctttcaagcg ggtgtacgat gaggtgtacg gcgacgagga cctgttggag caggccaacc   17040
agcgctttgg ggagtttgca tatgggaaac ggccccgcga gagtctaaaa gaggacctgc   17100
tggcgctacc gctggacgag ggcaatccca ccccgagtct gaagccggta accctgcaac   17160
aggtgctgcc tttgagcgcg cccagcgagc ataagcgagg gttgaagcgc gaaggcgggg   17220
acctggcgcc caccgtgcag ttgatggtgc ccaagcggca gaagctggag gacgtgctgg   17280
agaaaatgaa gtagagcccg ggatccagcc cgagatcaag gtccgccccc atcaagcagg   17340
tggcgcccgg cgtgggagtc cagaccgtgg acgttaggat ccccacggag gagatggaaa   17400
cccaaaccgc cactccctct tcggcggcca gcgccaccac cggcaccgct tcggtagagg   17460
tgcagacgga cccctggcta cccgccaccg ctgttgccgc cgccgccccc cgttcgcgcg   17520
ggcgcaagag aaattatcca gcggccagcg cgctcatgcc ccagtacgca ctgcatccat   17580
ccatcgtgcc cacccccggc taccgcgggt actcgtaccg cccgcgcaga tcagccggca   17640
ctcgcggccg ccgccgccgt gcgaccacaa ccagccgccg ccgtcgccgc cgccgccagc   17700
cagtgctgac ccccgtgtct gtaaggaagg tggctcgctc ggggagcacg ctggtggtgc   17760
ccagagcgcg ctaccacccc agcatcgttt aaagccggtc tctgtatggt tcttgcagat   17820
atggccctca cttgtcgcct ccgcttcccg gtgccgggat accgaggaag aactcaccgc   17880
cgcagaggca tggcgggcag cggtctccgc ggcggccgtc gccatcgccg gcgcgcaaaa   17940
agcaggcgca tgcgcggcgg tgtgctgcct ctgctaatcc cgctaatcgc gcggcgatc   18000 ggtgccgtac ccgggatcgc ctccgtggcc ctgcaggcgt cccagaaacg ttgactcttg   18060
caaccttgca agcttgcatt ttttggagga aaaataaaa aaaagtcta gactctcacg   18120 ctcgcttggt cctgtgacta ttttgtagaa aaaagatgg aagacatcaa ctttgcgtcg   18180
ctggccccgc gtcacggctc gcgcccgttc atgggagact ggacagatat cggcaccagc   18240
aatatgagcg gtgcgccttt cagctgggc agtctgtgga gcggcttaa aaattttggt   18300 tccaccatta agaactatgg caacaaagcg tggaacagca gcacgggcca gatgctgaga   18360
gacaagttga agagcagaa cttccaggag aaggtggcgc agggcctggc ctctggcatc   18420
agcggggtgg tggacatagc taaccaggcc gtgcagaaaa agataaacag tcatctggac   18480
ccccgtcctc aggtggagga aatgcctcca gcgatggaga cggtgtctcc cgagggcaaa   18540
ggcgaaaagc gcccgcggcc cgacagaaa gagaccctgg tgtcacacac cgaggagccg   18600
ccctcttacg aggaggcagt caaggccggc ctgcccacca ctcgccccat agccccatg   18660
```

```
gccaccggtg tggtgggcca caggcaacac actcccgcaa cactagatct gcccccgccg   18720
tccgagccgc cgcgccagcc aaaggcggcg acggtgcccg ctccctccac ttccgccgcc   18780
aacagagtgc ccctgcgccg cgccgcgagc ggcccccggg cctcgcgagt tagcggcaac   18840
tggcagagca cactgaacag catcgtgggc ctgggagtga ggagtgtgaa gcgccgccgt   18900
tgctactgaa tgagcaagct agctaacgtg ttgtatgtgt gtatgcgtcc tatgtcgccg   18960
ccagaggagc tgttgagccg ccggcgccgt ctgcactcca gcgaatttca agatggcgac   19020
cccatcgatg atgcctcagt ggtcgtacat gcacatctcg ggccaggacg cttcggagta   19080
cctgagcccc gggctggtgc agttcgcccg cgccacagac acctacttca acatgagtaa   19140
caagttcagg aaccccactg tggcgcccac ccacgatgtg accacggacc ggtcgcagcg   19200
cctgacgctg cggttcatcc ccgtggatcg ggaggacacc gcctactctt acaaggcgcg   19260
gttcacgctg gccgtgggcg acaaccgcgt gctggacatg gcctccactt actttgacat   19320 cagggggtg ctggacaggg gccccacctt caagccctac tcgggtactg cctacaactc   19380
cctggccccc aagggcgctc ccaattcttg cgagtgggaa caagatgaac cagctcaggc   19440
agcaatagct gaagatgaag aagaacttga agaagaacaa gctcaggacg aacaggcgcc   19500
cactaagaaa acccatgtat acgcccaggc acctctttct ggtgaaaaaa ttactaagga   19560
tggtttgcaa ataggtgtgg atgccacaca ggcgggagat aaccctatat atgctgataa   19620
aacattccaa cccgaacctc agataggtga gtctcagtgg aacgaggctg atgccacagt   19680
agcaggaggc agagtcttaa aaaagaccac ccctatgaga ccttgctatg atcctatgc   19740 caaacctact aatgccaatg gcggtcaagg gatcatggtg gccaatgatc agggagcgct   19800
tgaatctaaa gttgagatgc aattttctc caccacaacg tctcttaatg taagggaagg   19860
tgaaaacaat cttcagccaa aagtagtgct atacagcgaa gatgttaact tggaatcccc   19920
tgacactcat ttgtcttaca aacctaaaaa ggatgacacc aactctaaaa tcatgttggg   19980
tcagcaagcc atgcccaaca gacccaacct cattgctttt agggacaact ttattggact   20040
tatgtactac aacagcacag gcaacatggg agtgctggca ggacaggcct cccagctaaa   20100
cgctgtggta gacttgcaag acagaaacac agagctgtca taccaactga tgcttgattc   20160
cattggagac agatcaagat actttttccat gtggaaccag gcagtggaca gctatgaccc   20220
agatgtcaga atcattgaaa accatggggt tgaagatgag ctgcccaact attgctttcc   20280
cctgggcggt attggaatta cagacacata ccagtgcata aaaccaaccg cagctgctaa   20340
taacactaca tggtctaagg atgaagaatt tagtgatcgc aatgaaatag gggtgggaaa   20400
caacttcgcc atggagatca acatccaggc caacctctgg aggaacttcc tctatgcgaa   20460 cgtgggctc tacctgccag acaagctcaa gtacaacccc accaacgtgg acatctctga   20520
caaccccaac acctatgact acatgaacaa gcgtgtggtg gctcccggcc tggtggactg   20580
ctttgtcaat gtgggagcca ggtggtccct ggactacatg gacaacgtca acccccttcaa   20640 ccaccaccgc aatgcgggtc tgcgctaccg ctccatgatc ctgggcaacg ggcgctacgt   20700
gcccttccac attcaggtgc cccagaagtt ctttgccatc aagaacctcc tcctcctgcc   20760
gggctcctac acttacgagt ggaacttcag gaaggatgtc aacatggtcc tgcagagctc   20820
tctgggcaat gaccttaggg tggacggggc cagcatcaag tttgacagcg tcaccctcta   20880
tgctaccttc ttccccatgg ctcacaacac cgcctccacg ctcgaggcca tgctgaggaa   20940
cgacaccaac gaccagtcct tcaatgacta cctctctggg gccaacatgc tctacccat   21000 ccccgccaag gccaccaacg tgcccatctc cattccctct cgcaactggg ccgccttcag   21060
```

```
aggctgggcc tttacccgcc ttaagaccaa ggaaaccccc tccctgggct cgggttttga    21120
cccctacttt gtctactcgg gatccatccc ctacctggat ggcaccttct acctcaacca    21180
cacttttaag aagatatcca tcatgtatga ctcctccgtc agctggccgg gcaatgaccg    21240
cctgctcacc cccaatgagt tcgaggtcaa gcgcgccgtg gacggcgagg gctacaacgt    21300
ggcccagtgc aacatgacca aggactggtt cctggtgcag atgctggcca actacaacat    21360
aggctaccag ggcttctaca tcccagagag ctacaaggac aggatgtact ccttcttcag    21420
aaatttccaa cccatgagca ggcaggtggt ggacgagacc aaatacaagg actatcaggc    21480
cattggcatc actcaccagc acaacaactc gggattcgtg ggctacctgg ctcccaccat    21540
gcgcgagggg caggcctacc ccgccaactt ccctacccg ttgataggca aaccgcggt    21600
cgacagcgtc acccagaaaa agttcctctg cgaccgcacc ctctggcgca tcccttctc    21660
tagcaacttc atgtccatgg gtgcgctcac ggacctgggc cagaacctgc tctatgccaa    21720
ctccgcccat gcgctggaca tgacttttga ggtggacccc atggacgagc ccaccttct    21780
ctatattgtg tttgaagtgt tcgacgtggt cagagtgcac cagccgcacc gcggtgtcat    21840
cgagaccgtg tacctgcgca cgcccttctc ggccggcaac gccaccacct aaggagacag    21900
cgccgccgcc tgcatgacgg gttccaccga gcaagagctc agggccatcg ccagagacct    21960
gggatgcgga ccctattttt tgggcaccta tgacaaacgc ttcccgggct tcatctcccg    22020
agacaagctc gcctgcgcca tcgtcaacac ggccgcgcgc gagaccgggg gcgtgcactg    22080
gctggccttt ggctgggacc cgcgctccaa aacctgctac ctcttcgacc cctttggctt    22140
ctccgatcag cgcctcagac agatctatga gtttgagtac gaggggctgc tgcgccgcag    22200
cgcgcttgcc tcctcgcccg accgctgcat cacccttgag aagtccaccg agaccgtgca    22260
ggggccccac tcggccgcct gcggtctctt ctgctgcatg ttttgcacg cctttgtgcg    22320
ctggccccag agtcccatgg atcgcaaccc caccatgaac ttgctcaagg gagtgcccaa    22380
cgccatgctc cagagccccc aggtccagcc caccctgcgc cacaaccagg aacagctcta    22440
ccgcttcctg gagcgccact cccctactt ccgcagtcac agcgcgcaca tccgggggc    22500
cacctctttc tgccacttgc aagaaaacat gcaagacgga aaatgatgta cagctcgctt    22560
tttaataaat gtaaagactg tgcacttat ttatacacgg gctctttctg gttatttatt    22620
caacaccgcc gtcgccatct agaaatcgaa agggttctgc cgcgcgtcgc cgtgcgccac    22680
gggcagagac acgttgcgat actggaagcg gctcgcccac ttaaactcgg gcaccaccat    22740
gcggggcagt ggttcctcgg ggaagttctc gccccacagg gtgcgggtca gctgcagcgc    22800
gctcaggagg tcgggagccg agatcttgaa gtcgcagttg gggccggaac cctgcgcgcg    22860
cgagttgcgc tacacggggt tgcagcactg gaacaccagc agggccggat tatgcacgct    22920
ggccagcagg ctctcgtcgc tgatcatgtc gctgtccaga tcctccgcgt tgctcagggc    22980
gaacggggtc atcttgcaga cctgcctgcc caggaaaggc ggcagccggg gcttgccgtt    23040
gcagtcgcag cgcaggggca tcagcaggtg cccgcggccc gactgcgcct gcgggtacag    23100
cgcgcgcatg aaggcttcga tctgcctgaa agccacctgc gtcttggctc cctccgaaaa    23160
gaacatccca caggacttgc tggagaactg gttcgcggga cagctggcat cgtgcaggca    23220
gcagcgcgcg tcggtgttgg cgatctgcac cacgttgcga ccccaccggt tcttcactat    23280
cttggccttg gaagcctgct ccttcagcgc gcgctggccg ttctcgctgg tcacatccat    23340
ctctatcacc tgctccttgt tgatcatgtt tgtaccgtgc agacacttca ggtcgccctc    23400
```

```
cgtctgggtg cagcggtgct cccacagcgc gcaaccggtg ggctcccaat ttttgtgggt   23460
cacccccgcg taggcctgca ggtaggcctg caagaagcgc cccatcatgg ccacaaaggt   23520
cttctggctc gtaaaggtca gctgcaggcc gcgatgctct tcgttcagcc aggtcttgca   23580
gatggcggcc agcgcctcgg tctgctcggg cagcatccta aaatttgtct tcaggtcgtt   23640
atccacgtgg tacttgtcca tcatggcgcg cgccgcctcc atgcccttct cccaggcgga   23700
caccatgggc aggcttaggg ggtttatcac ttccaccggc gaggacaccg tactttcgat   23760
ttcttcttcc tcccctctt cccggcgcgc gcccacgctg ctgcgcgctc tcaccgcctg   23820
caccaagggg tcgtcttcag gcaagcgccg caccgagcgc ttgccgccct tgacctgctt   23880
aatcagcacc ggcgggttgc tgaagcccac catggtcagc gccgcctgct cttcttcgtc   23940
ttcgctgtct accactatct ctggggaagg gcttctccgc tctgcggcgg cgcgcttctt   24000 tttttcttg ggagcggccg tgatggagtc cgccacggcg acgaggtcg agggcgtggg    24060 gctgggggtg cgcggtacca gggcctcgtc gccctcggac tcttcctctg actccaggcg   24120
gcggcggagt cgcttctttg ggggcgcgcg cgtcagcggc ggcggagacg gggacgggga   24180
cggggacggg acgccctcca caggggtgg tcttcgcgca gacccgcggc cgcgctcggg    24240
ggtcttctcg agctggtctt ggtcccgact ggccattgta tcctcctcct cctaggcaga   24300
gagacataag gagtctatca tgcaagtcga gaaggaggag agcttaaccc cccctctga   24360 gaccgccgat gcgcccgccg tcgccgtcgc ccccgctgcc gccgacgcgc cgccacacc    24420 gagcgacacc cccgcggacc ccccgccga cgcacccctg ttcgaggaag cggccgtgga    24480
gcaggacccg gctttgtct cggcagagga ggatttgcga gaggaggagg ataaggagaa    24540
gaagccctca gtgccaaaag atgataaaga gcaagacgag cacgacgcag atgcacacca   24600
gggtgaagtc gggcggggg acggagggca tgacggcgcc gactacctag acgaaggaa     24660 cgacgtgctc ttgaagcacc tgcatcgtca gtgcgccatt gtttgcgacg ctctgcagga   24720
gcgcagcgaa gtgcccctca gcgtggcgga ggtcagccac gcctacgagc tcagcctctt   24780
ctccccccgg gtgccccccc ccgccgcga aaacggcaca tgcgagccca cccgcgcct    24840 caacttctac cccgcctttg tggtacccga ggtcctggcc acctatcaca tcttctttca   24900
aaattgcaag atccccctct cgtgccgcgc caaccgtagc cgcgccgata agatgctggc   24960
cctgcgccag ggcgaccaca tacctgatat cgccgctttg gaagatgtac caaagatctt   25020
cgagggtctg ggtcgcaacg agaagcgggc agcaaactct ctgcaacagg aaaacagcga   25080
aaatgagagt cacaccgggg tactggtgga gctcgagggc gacaacgccc gcctggcggt   25140
ggtcaagcgc agcatcgagg tcacccactt tgcctacccc gcgctaaacc tgcccccaa    25200 agtcatgaac gcggccatgg acgggctgat catgcgccgc ggccggcccc tcgctccaga   25260
tgcaaacttg catgaggaga ccgaggacgg ccagcccgtg gtcagcgacg agcagctggc   25320
gcgctggctg gagaccgcgg accccgccga actggaggag cggcgcaaga tgatgatggc   25380
cgtggtgctg gtcaccgtag agctggagtg tctgcagcgc ttcttcggcg accccgagat   25440
gcagagaaag gtcgaggaga ccctgcacta caccttccgc cagggctacg tgcgccaggc   25500
ttgcaagatc tccaacgtgg agctcagcaa cctggtgtcc tacctgggca tcttgcatga   25560
gaaccgcctc gggcagagcg tgctgcactc caccctgcgc ggggaggcgc gccgcgacta   25620
cgtgcgcgac tgcgtttacc tcttcctctg ctacacctgg cagacggcca tggggtctg    25680 gcagcagtgc ctggaggagc gcaacctcaa ggagctggag aagctcctgc agcgcgcgct   25740
caaagatctc tggacgggct acaacgagcg ctcggtggcc gccgcgctgg ccgacctcat   25800
```

```
cttccccgag cgcctgctca aaaccctcca gcaggggctg cccgacttca ccagccaaag   25860
catgttgcaa aacttcagga actttatcct ggagcgttct ggcatcctac ccgccacctg   25920
ctgcgccctg cccagcgact ttgtccccct cgtgtaccgc gagtgccccc cgccgctgtg   25980
gggtcactgc tacctgttcc aactggccaa ctacctgtcc taccacgcgg acctcatgga   26040
ggactccagc ggcgaggggc tcatggagtg ccactgccgc tgcaacctct gcacgcccca   26100
ccgctccctg gtctgcaaca cccaactgct cagcgagagt cagattatcg gtaccttcga   26160
gctacagggt ccgtcctcct cagacgagaa gtccgcggct ccggggctaa aactcactcc   26220
ggggctgtgg acttccgcct acctgcgcaa atttgtacct gaagactacc acgcccacga   26280
gatcaggttt tacgaagacc aatcccgccc gcccaaggcg gagctgaccg cctgcgtcat   26340
cacccagggc gagatcctag gccaattgca agccatccaa aaagcccgcc aagacttttt   26400
gctgaagaag ggtcgggggg tgtatctgga cccccagtcg ggtgaggagc tcaacccggt   26460 tccccgctg ccgccgccgc gggaccttgc ttcccaggat aagcatcgcc atggctccca   26520
gaaagaagca gcagcggccg ccactgccgc caccccacat gctggaggaa gaggaggaat   26580
actgggacag tcaggcagag gaggtttcgg acgaggagga gccggagacg gagatggaag   26640
agtgggagga ggacagctta gacgaggagg cttccgaagc cgaagaggca gacgcaacac   26700
cgtcaccctc ggccgcagcc ccctcgcagg cgccccgaa gtccgctccc agcatcagca   26760
gcaacagcag cgctataacc tccgctcctc caccgccgcg acccacggcc gaccgcagac   26820
ccaaccgtag atgggacacc accggaaccg gggccggtaa gtcctccggg agaggcaagc   26880
aagcgcagcg ccaaggctac cgctcgtggc gcgctcacaa gaacgccata gtcgcttgct   26940
tgcaagactg cgggggggaac atctccttcg cccgccgctt cctgctcttc caccacggtg   27000
tggccttccc ccgtaacgtc ctgcattact accgtcatct ctacagcccc tactgcggcg   27060
gcagtgagcc agagacggtc ggcggcggcg gcggcgcccg tttcggcgcc taggaagacc   27120
cagggcaaga cttcagccaa gaaactcgcg gcggccgcgg cgaacgcggt cgcggggggcc   27180 ctgcgcctga cggtgaacga acccctgtcg accccgcgaac tgaggaaccg aatcttcccc   27240
actctctatg ccatcttcca gcagagcaga gggcaggatc aggaactgaa agtaaaaaac   27300
aggtctctgc gctccctcac ccgcagctgt ctgtatcaca agagcgaaga ccagcttcgg   27360
cgcacgctgg aggacgctga ggcactcttc agcaaatact gcgcgctcac tcttaaggac   27420
tagctccgcg cccttctcga atttaggcgg gaacgcctac gtcatcgcag cgccgccgtc   27480
atgagcaagg acattcccac gccatacatg tggagctatc agccgcagat gggactcgcg   27540
gcgggcgcct cccaagacta ctccacccgc atgaactggc tcagtgccgg cccacacatg   27600
atctcacagg ttaatgatat ccgcacccat cgaaaccaaa tattggtgga gcaggcggca   27660
attaccacca cgccccgcaa taatcccaac cccagggagt ggcccgcgtc cctggtgtat   27720
caggaaattc ccgccccac caccgtacta cttccgcgtg attcccaggc cgaagtccaa   27780
atgactaact caggggcaca gctcgcgggc ggctgtcgtc acagggtgcg gcctcctcgc   27840
cagggtataa ctcacctgga gatccgaggc agaggtattc agctcaacga cgagtcggtg   27900
agctcctcgc tcggtctcag acctgacggg accttccaga tagccggagc cggccgatct   27960
tccttcacgc cccgccaggc gtacctgact ctgcaaagct cgtcctcggc gccgcgctcg   28020
ggcggcatcg ggactctcca gttcgtgcag gagtttgtgc cctcggtcta cttcaacccc   28080
ttctcgggct ctcccggtcg ctacccggac cagttcatct cgaactttga cgccgcgagg   28140
```

```
gactcggtgg acggctacga ctgaatgtcg ggtggacccg gtgcagagca acttcgcctg   28200
aagcacctcg accactgccg ccgccctcag tgctttgccc gctgtcagac cggtgagttc   28260
cagtactttt ccctgcccga ctcgcacccg gacggcccgg cgcacggggt gcgcttttc    28320 atcccgagtc aggtgcgctc taccctaatc agggagttta ccgcccgtcc cctactggcg   28380
gagttggaaa aggggccttc tatcctaacc attgcctgca tctgctctaa ccctggattg   28440
caccaagatc tttgctgtca tttgtgtgct gagtataata aaggctgaga tcagaatcta   28500
ctcgggctcc tgtcgccatc ctgtcaacgc caccgtccaa gcccggcccg atcagcccga   28560
ggtgaacctc acctgcggtc tgcaccggcg cctgaggaaa tacctagctt ggtactacaa   28620
cagcactccc tttgtggttt acaacagctt tgaccaggac ggggtctcac tgagggataa   28680
cctctcgaac ctgagctact ccatcaggaa gaacagcacc ctcgagctac ttcctcctta   28740
cctgcccggg acttaccagt gtgtcaccgg tccctgcacc cacacccacc tgttgatcgt   28800
aaacgactct cttccgagaa cagacctcaa taactcctct tcgcagttcc ccagaacagg   28860
aggtgagctc aggaaacccc gggtaaagaa gggtggacga gagttaacac ttgtggggtt   28920
tctggtgtat gtgacgctgg tggtggctct tttgattaag gcttttcctt ccatgtctga   28980 actctcccctc ttcttttatg aacaactcga ctagtgctaa cggacccta cccaacgaat    29040 cgggattgaa tatcggtaac caggttgcag tttcactttt gattaccttc atagtcctct   29100
tcctgctagt gctgtcgctt ctgtgcctgc ggatcggggg ctgctgcatc cacgtttata   29160
tctggtgctg gctgtttaga aggttcggag accatcgcag gtagaataaa catgctgctg   29220
cttaccctct ttgtcctggc gctggccgcc agctgccaag ccttttccga ggctgactt    29280 atagagcccc agtgtaatgt gacttttaaa gcccatgcac agcgttgtca tactataatc   29340
aaatgtgcca ccgaacacga tgaataccctt atccagtata agataaatc acacaaagtg   29400 gcacttgttg acatctggaa acccgaagac cctttggaat acaatgtgac cgttttccag   29460
ggtgacctct tcaaaattta caattacact ttcccatttg accagatgtg tgactttgtc   29520
atgtacatgg aaaagcagca caagctgtgg cctccgactc cccagggctg tgtggaaaat   29580
ccaggctctt tctgcatgat ctctctctgt gtaactgtgc tggcactaat actcacgctt   29640
ttgtatatca gatttaaatc aaggcaaagc ttcattgatg aaaagaaaat gccttaatcg   29700
ctttcacgct tgattgctaa caccgggttt ttatccgcag aatgattgga atcaccctac   29760
taatcacctc cctccttgcg attgcccatg ggttggaacg aatcgaagtc cctgtggggg   29820
ccaatgttac cctggtgggg cctgtcggca atgctacatt aatgtgggaa aaatatacta   29880
aaaatcaatg ggtctcttac tgcactaaca aaaatagcca caagcccaga gccatctgcg   29940
atgggcaaaa tctaaccttg attgatgttc aattgctgga tgcgggctac tattatgggc   30000
agctgggtac aatgattaat tactggagac cccacagaga ttacatgctc cacgtagtaa   30060
agggtcccct tagcagccca cccactacca cctctactac ccccactacc accactactc   30120
ccaccaccag cactgccgcc cagcctcctc atagcagaac aaccactttt atcaattcca   30180
agtcccactc cccccacatt gccggcgggc cctccgcctc agactccgaa accaccgaga   30240
tctgcttctg caaatgctct gacgccattg cccaggattt ggaagatcac gaggaagatg   30300
agcatgactt cgcagatgca tgccaggcat cagagccaga agcgctgccg gtggccctca   30360
aacagtatgc agaccccac accacccccg accttcctcc accttccag aagccaagtt    30420 tcctggggga aaatgaaact ctgcctctct ccatactcgc tctgacatct gttgctatgt   30480
tgaccgctct gctggtgctt ctatgctcta tatgctacct gatctgctgc agaaagaaaa   30540
```

```
aatctcacgg ccatgctcac cagcccctca tgcactttcc cttaccctcca gagctgggcg    30600 accacaaact ttaagtctgc agtaactatc tgcccatccc ttgtcagtcg acagcgatga    30660
gccccactaa tctaacggcc tctggactta caacatcgtc tcttaatgag accaccgctc    30720
ctcaagacct gtacgatggt gtctccgcgc tggttaacca gtgggatcac ctgggcatat    30780
ggtggctcct cataggagca gtgaccctgt gcctaatcct ggtctggatc atctgctgca    30840
tcaaaagcag aagacccagg cggcggccca tctacaggcc ctttgtcatc acacctgaag    30900
atgatgatga caccacttcc aggctgcaga ggctaaagca gctactcttc tcttttacag    30960
catggtaaat tgaatcatgc ctcgcatttt catctacttg tctctccttc cacttttct     31020 gggctcttct acattggccg ctgtgtccca catcgaggta gactgcctca cgcccttcac    31080
agtctacctg cttttcggct ttgtcatctg caccttttgtc tgcagcgtta tcactgtagt   31140
gatctgcttc atacagtgca tcgactacgt ctgcgtgcgg gtggcttact ttagacacca    31200
cccccagtat cgcaacaggg acatagcggc tctcctaaga cttgtttaaa atcatggcca    31260
aattaactgt gattggtctt ctgatcatct gctgcgtcct agccgcgatt gggactcaag    31320
ctcctaccac caccagcgct cccagaaaga gacatgtatc ctgcagcttc aagcgtccct    31380
ggaatatacc ccaatgcttt actgatgaac ctgaaatctc tttggcttgg tacttcagcg    31440 tcaccgcccct tcttatcttc tgcagtacgg ttattgccct tgccatctac ccttcccttg   31500
acctgggctg gaatgctgtc aactctatgg aatatcccac cttcccagaa ccagacctgc    31560
cagacctggt tgttctaaac gcgtttcctc ctcctgctcc cgttcaaaat cagtttcgcc    31620
ctccgtcccc cacgcccact gaggtcagct actttaatct aacaggcgga gatgactgaa    31680
aacctagacc tagaaatgga cggtctctgc agcgagcaac gcacactaga gaggcgccgg    31740
caaaaagagc tcgagcgtct taaacaagag ctccaagacg cggtggccat acaccagtgc    31800
aaaaaaggtg tcttctgtct ggtaaaacag gccacgctca cctatgaaaa acaggtgac     31860 acccaccgcc taggatacaa gctgcccaca cagcgccaaa agttcgccct catgataggc    31920
gaacaaccca tcaccgtgac ccagcactcc gtggagacag aaggctgcat acatgctccc    31980
tgtaggggcg ctgactgcct ctacaccttg atcaaaaccc tctgcggtct cagagacctt    32040
atccctttca attaatcata actgtaatca ataaaaaatc acttacttga aatctgatag    32100
caagcctctg tccaattttt tcagcaacac ttccttcccc tcctcccaac tctggtactc    32160
taggcgcctc ctagctgcaa acttcctcca cagtctgaag ggaatgtcag attcctcctc    32220
ctgtccctcc gcaccacga tcttcatgtt gttgcagatg aaacgcgcga gatcgtctga    32280
cgagaccttc aaccccgtgt accccctacga taccgagatc gctccgactt ctgtccctt    32340 ccttacccct cctttgtgt catccgcagg aatgcaagaa atccagctg ggtgctgtc      32400 cctgcacttg tcagagcccc ttaccaccca caatgggggcc ctgactctaa aaatgggggg   32460
cggcctgacc ctggacaagg aagggaatct cacttcccaa acatcacca gtgtcgatcc    32520 ccctctcaaa aaaagcaaga acaacatcag ccttcagacc gccgcacccc tcgccgtcag    32580
ctccggggcc ctaacacttt ttgccactcc cccctagcg gtcagtggtg acaaccttac    32640
tgtgcagtct caggcccctc tcactttgga agactcaaaa ctaactctgg ccaccaaagg    32700 accccctaact gtgtccgaag gcaaacttgt cctagaaaca gaggctcccc tgcatgcaag    32760
tgacagcagc agcctgggcc ttagcgttac ggccccactt agcattaaca atgcagcct     32820 aggactagat ctgcaggcac ccattgtctc tcaaaatgga aaactggctc taaatgtagc    32880
```

```
aggcccccta gctgtggcca atggcattaa tgctttgaca gtaggcacag gcaaaggtat   32940
tggtctaaat gaaaccagca ctcacttgca agcaaagttg gtcgccccc  taggctttga   33000 taccaatggc aacattaagc taagcgttgc aggaggcatg agactaaata atgacacact   33060
tatactagat gtaaactacc catttgaagc tcaaggccaa ctaagtctaa gagtgggcca   33120
gggtccgctg tatgtagatt ctagcagcca taacctgacc attagatgcc ttagaggatt   33180
atacataaca tcgtctaata accaaaccgg tctagaggcc aacataaaac taacaaaagg   33240
ccttgtctat gatggaaatg ccatagcagt caatgttggt caaggattgc aatacagcac   33300
tactgccaca tcggaaggtg tgtatcctat acagtctaag ataggtttgg gaatggaata   33360
tgataccaac ggagccatga tgacaaaact aggctctgga ctaagctttg acaattcagg   33420
agccattgta gtgggaaaca aaatgatga  caggcttact ctgtggacta caccagaccc   33480
atctcctaac tgtagaattt attctgaaaa agatactaaa ctaaccttgg tgctgactaa   33540
gtgtggcagc caaatcctag gcacagtatc tgcccttgct gtcagaggca gccttgcgcc   33600
catcactaat gcatccagca tagtccaaat atttctaaga tttgatgaaa atggactatt   33660
gatgagcaac tcatcgctag acggtgatta ctggaattac agaaatgggg actccactaa   33720
tagcacacca tatacaaatg cagtaggctt tatgcctaat ctagcagcct atcctaaagg   33780
tcaggctaca gctgcaaaaa gcagtattgt aagccaggta tacatggatg gtgacactac   33840
taaacctata acactaaaaa taaacttcaa tggcattgat gaaacaacag aaaataccc   33900 tgttagtaaa tattccatga cattctcatg gagctggccc accgcaagct acataggcca   33960
cacttttgca acaaactctt ttactttctc ctacatcgcc caagaataaa gaaagcacag   34020
agatgcttgt tttgatttca aaattgtgtg ctttttattta ttttcagctt acagtatttc   34080
cagtagtcat tcgaataaag cttaatcaaa ctgcatgaga acccttccac atagcttaaa   34140
ttagcaccag tgcaaatgga gaaaattcaa cataccttt  ttatccagat atcagagaac   34200
tctagtggtc agttttcccc caccctccca gctcacagaa tacacagtcc tttccccccg   34260
gctggcttta acaacacta tctcattggt aacagacata ttcttaggtg taataatcca   34320
cacggtctct tggcgggcca agcgctggtc ggtgatgtta ataaactccc caggcagctc   34380
tttcaagttc acgtcgctgt ccaactgctg aagcgctcgc ggctccgact gcgcctctag   34440
cggaggcaac ggcaacaccc gatccttgat ctataaagga gtagagtcat aatcccccat   34500
aagaataggg cggtgatgca gcaacaaggc gcgcagcaac tcctgccgcc gcctctccgt   34560
acgacaggaa tgcaacggcg tggtggtctc ctccgcgata atccgcaccg ctcgcagcat   34620
cagcatcctc gtcctccggg cacagcagcg catcctgatc tcactgagat cggcgcagta   34680
agtgcagcac aaaaccaaga tgttatttaa gatcccacag tgcaaagcac tgtacccaaa   34740
gctcatggcg ggaaggacag cccccacgtg accatcatac cagatcctta ggtaaatcaa   34800
atgacgacct ctcataaaca cgctggacat gtacatcacc tccttgggca tgcgctgatt   34860
caccacctct cgataccaca agcatcgctg attaattaaa gaccctcaa  gcaccatcct   34920 gaaccaggaa gccagcacct gaccccccgc caggcactgc agggaccccg gtgaattgca   34980
gtggcagtga agactccagc gctcgtagcc gtgaaccata gagccggtca ttatatccac   35040
attggcacaa cacaaacaca ctttcataca ctttttcatg attagcagct cctctctagt   35100
caggaccata tcccaaggaa tcacccactc ttgaatcaag gtaaatccca cacagcaggg   35160
caggcctctc acataactca cgttatgcat agtgagcgtg tcgcaatctg gaataccgg   35220 atgatcttcc atcaccgaag ctcgcgtctc cgtctcaaag ggaggtaaac ggtccctcgt   35280
```

```
gtagggacag tggcgggata atcgagatcg tgttgaacgt agagtcatgc caaagggaac   35340
agcggacgta ctcatatttc ctccagcaga accaagtgcg cgcgtggcag ctatccctgc   35400
gtcttctgtc tcgccgcctg ccccgctcgg tgtagtagtt gtaatacagc cactccctca   35460
gaccgtcaag gcgctccctg gcgtccggat ctataacaac accgtcctgc agcgccgccc   35520
tgatgacatc caccaccgta gagtatgcca agcccagcca ggaaatgcat tcactttgac   35580
agcgagagat aggaggagcg ggaagagatg gaagaaccat gatagtaaaa gacttttatt   35640
ccaatcgatc ctctacaatg tcaaagtgta gatctataag atgacactgg tctcctccgc   35700
tgagtcgatc aaaaataaca gctaaaccac aaacaacacg attggtcaaa tgctccacaa   35760
gggcttgcag cataaaatcg cctcgaaagt ccaccgcaag cataacatca agccaccgc    35820 ccctatcatg atctataata aaaccccac agctatccac cagacccata agttttcat     35880 ctctccatcg tgaaaaaata tttacaagct cctcctttaa atcacctcca accaattgaa   35940
aaagttgagc caaccgcccc tccaccttca ttttcagcaa cgcatcatg attgcaaaaa    36000 ttcaggctcc tgagacacct gtataagatt gagaagcgga acgttaacgt caatgtttcg   36060
ctcgcgaaga tcgcgcctca gtgcaagcat gatataatcc cacaggtcgg agcggatcag   36120
cgaggacatc tccccgccag gaaccaactc aacggagcct atgctgatta taatacgcat   36180
attcggggct atgctgacca gcacggcccc caaataggcg tactgcatag gcggcgacaa   36240
aaagtgaaca gtttgggtta aaaaatcagg caaacagtcg cgcaaaaaag caagaacatc   36300
ataaccatgc tcatgcaaat agatgcaagt aagctcagga acgaccacag aaaaatgcac   36360
aatttttctc tcaaacatga ctgcgagccc tgcaaaaaat aaaaagaaa cattacacaa    36420 gagtagcctg tcttacgatg ggatagacta ctctaaccaa cataagacgg cccacaacat   36480
cgcccgcgtg gccataaaaa aaattgtccg tgtgattaaa aagaagcaca gatagctggc   36540
cagtcatatc cggagtcatc acgtgtgaac ccgtgtagac ccccgggttg gacacatcgg   36600
ccaaacaaag aaagcggcca atgtacccag gaggaatcat aacactaaga cgaagataca   36660
acagaataac cccatgaggg ggaataacaa agttagtagg tgaataaaaa cgataaacac   36720
ccgaaactcc ctcctgcgta ggcaaaatag caccctcccc ttccaaaaca acatatagcg   36780
cttccacagc agccatgaca aaagactcaa aacactcaaa agactcagtc ttaccaggaa   36840
aataaaagca ctctcacagc accagcacta atcagagtgt gaagagggcc aagtgccgaa   36900
cgagtatata taggaataaa aaatgacgta aatgtgtaaa ggtcagaaaa cgcccagaaa   36960
aatacacaga ccaacgcccg aaacgaaaac ccgcgaaaaa atacccagaa cttcctcaac   37020
aaccgccact tccggtttct cacggtacgt cacttccgca agaaaagcaa aactacattt   37080
cccacatgtg taaaaacgaa accccgcccc ttgtaactgc ccacaactta catcatcaaa   37140
acataaactc ctacgtcacc cgcccgcct ctccccgccc acctcattat catattggcc    37200
acaatccaaa ataaggtata ttattgatga tg                                37232

<210> SEQ ID NO 23
<211> LENGTH: 37213
<212> TYPE: DNA
<213> ORGANISM: Gorilla beringei beringei

<400> SEQUENCE: 23
ataatatacc ttattttgga ttgtggccaa tatgataatg aggtgggcgg ggagaggcgg    60
ggcgggtgac gtaggacgcg cgagtagggt tgggaggtgt ggcggaagtg tggcatttgc   120
```

```
aagtgggagg agctcacatg caagcttccg tcgcggaaaa tgtgacgttt ttgatgagcg    180
ccgcctacct ccggaagtgc caattttcgc gcgcttttca ccggatatcg tagtaatttt    240
gggcgggacc atgtaagatt tggccatttt cgcgcgaaaa gtgaaacggg gaagtgaaaa    300
ctgaataata gggcgttagt catagcgcgt aatatttacc gagggccgag ggactttgac    360
cgattacgtg gaggactcgc ccaggtgttt tttacgtgaa tttccgcgtt ccgggtcaaa    420
gtctccgttt ttattgtcac cgtcatttga cgcggagggt atttaaaccc gctgcgctcc    480
tcaagaggcc actcttgagt gccagcgaga agagttttct cctctgctcc gcttcggtga    540
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagttttttgt ctaggtgggc   1080 ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctcccccctg aaattcaccc   1320 agtggttcct ctgggtatac ataaacctgt tgctgttaaa gtttgcgggc gacgccctgc   1380
agtacagtgc attgaggact tgcttcacga tcccgaggaa cctttggact tgagccttaa   1440 acgcccctagg caataaaccc cacctaagta ataaaccccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca ataccctatac tatttggagg   1740 tatctgtggg gctctactca ggccaagttg gtttccagaa ttaagcagga ttacaagtgc   1800
gattttgaag agcttttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca aacaaatgg    2040 aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
```

```
tgcggcccga ttgcaagtat aagattacta agttggttaa tattagaaac tgctgctata    2580
tttctgggaa cggggccgaa gtggagatag atactcagga cagggtggct tttaggtgtt    2640
gcatgataaa catgtggccc gggatactgg ggatggatgg ggtggtattc atgaatgtga    2700
ggtttacggg ccccaacttt aatggcacgg tgttcatggg caacaccaac ttgctcctgc    2760
atggtgcgag tttctatggg tttaataaca cctgtataga ggcctggacc gatgtaaagg    2820
ttcgaggttg ttccttttat agctgttgga aggcggtggt gtgtcgccct aaaagcaggg    2880
gttctgtgaa aaaatgcttg tttgaaaggt gcaccttagg catcctctct gagggcaact    2940
ccagggtgcg ccataatgtg gcttcgaact gcggttgctt catgcaagtg aaggggggtga   3000 gcgttatcaa gcataactcg gtgtgtggaa actgcgagga tcgcgcctcc cagatgctga    3060
cctgctttga tggcaactgt cacctgttga agaccattca tataagcagc caccccagaa    3120
aggcctggcc cgtgtttgag cataacatct tgacccgctg ctccttgcat ctggggggtca   3180 ggaggggtat gttcctgcct taccagtgta actttagcca cactaaaatc ctgctggaac    3240
ccgagtgcat gaccaaggtc agcctgaatg gtgtgtttga tgtgactctg aaaatctgga    3300
aggtgctgag gtatgatgag accaggacca ggtgccgacc ctgcgagtgc ggcggcaagc    3360
acatgagaaa tcagcctgtg atgttggatg tgaccgagga gcttaggcct gaccatctgg    3420
tgctggcctg caccagggcc gagtttgggt ctagcgatga ggataccgat tgaggtgggt    3480
aaggtgggcg tggctagaag ggtggggcgt gtataaattg ggggtctaag ggtctctctg    3540
ttttgtcttg caacagccgc cgccatgagc gacaccggca acagctttga tggaagcatc    3600
tttagcccct atctgacagt gcgcatgcct cactgggctg gagtgcgtca gaatgtgatg    3660
ggttccaacg tggatggacg ccccgttctg ccttcaaatt cgtctacaat ggcctacgcg    3720
accgtgggag gaactccgct ggacgccgcg acctccgccg ccgcctccgc cgccgccgcg    3780
accgcgcgca gcatggctac ggaccttttac agctctttgg tggcgagcgg cgcggcctct    3840
cgcgcgtctg ctcgggatga gaaactgacc gctctgctgc ttaaactgga agacttgacc    3900
cgggagctgg gtcaactgac ccagcaggtc tccagcttgc gtgagagcag ccttgcctcc    3960
ccctaatggc ccataatata aataaaagcc agtctgtttg gattaagcaa gtgtatgttc    4020
tttatttaac tctccgcgcg cggtaagccc gggaccagcg gtctcggtcg tttagggtgc    4080
ggtggattct ttccaacacg tggtacaggt ggctctggat gtttagatac atgggcatga    4140
gtccatccct ggggtggagg tagcaccact gcagagcttc gtgctcgggg gtggtgttgt    4200
atatgatcca gtcgtagcag gagcgctggg cgtggtgctg aaaaatgtcc ttaagcaaga    4260
ggcttatagc taggggagg cccttggtgt aagtgtttac aaatctgctc agttgggagg    4320
ggtgcatccg gggggatata atgtgcatct tggactggat ttttaggttg gctatgttcc    4380
cacccagatc ccttctggga ttcatgttgt gcaggaccac cagcacggta tatccagtgc    4440
acttgggaaa tttatcgtgg agcttagacg ggaatgcatg gaagaacttg agacgccct    4500 tgtggcctcc cagatttttcc atacattcgt ccatgatgat ggcaatgggc ccgtgggaag    4560
ctgcctgagc aaaaatgttt ctgggatcgc tcacatcgta gttatgttcc agggtgaggt    4620
catcatagga catctttacg aatcgggggc ggagggtccc ggactggggg atgatggtac    4680
cctcgggccc cggggcgtag ttcccctcac agatctgcat ctcccaggct ttcatttcag    4740
agggagggat catatccacc tgcggagcga tgaaaaacac agtttctggc gcaggggaga    4800
ttaactggga tgagagcagg tttctgagca gctgtgactt tccacagccg gtgggcccat    4860
```

```
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgccagaag gcgctcgccg cccagcgaaa gcagctcttg caaggaagca aaattttca    5040
gcggttttag gccgtcggcc gtgggcatgt ttttcagcgt ctgggtcagc agttccagcc   5100
tgtcccacag ctcggtgatg tgctctacgg catctcgatc cagcagatct cctcgtttcg   5160
cgggttgggg cggctttcgc tgtagggcac cagccgatgg gcgtccagcg gggcagagt    5220
catgtccttc catgggcgca gggtcctcgt cagggtggtc tgggtcacgg tgaaggggtg   5280
cgctccgggt tgggcgctgg ccaggtgcg cttgaggctg gttctgctgg tgctgaatcg    5340
ctgccgctct tcgccctgcg cgtcggccag gtagcatttg accatggtct cgtagtcgag   5400
accctcggcg gcgtgcccct tggcgcgag ctttccttg gaggtggcgc cgcacgaggg     5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgctttttg atgcgtttct tacctcggct   5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt ccccctcctc   5880
cgcgtccaga aaagtgattg gcttgtaggt gtaggacacg tgaccggggg ttcccgacgg   5940
gggggtataa aaggggggtgg cgcccttc atcttcactc tcttccgcat cgctgtctgc    6000
gagggccagc tgctggggta agtattccct ctcgaaggcg ggcatgacct cagcgctcag   6060
gttgtcagtt tctaaaaatg aggaggattt gatgttcacc tgtccggagg tgatacctt    6120
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcaggc gctcgttggt   6420
ccagcagagg cggccgccct tgcgcgagca aagggggggt aggggtcca gctggtcctc    6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg aggggcgggc cccagggcat ggggtgggtg agcgcggagg cgtacatgcc   6660
gcagatgtca tacacgtaca ggggttccct gaggatgccg aggtaggtgg ggtagcagcg   6720
ccccccgcgg atgctggcgc gcacgtagtc atagagctcg tgggaggggg ccagcatgtt   6780
gggcccgagg ttggtgcgct ggggcgctc ggcgcggaag gcgatctgcc tgaagatggc    6840
atgggagttg gaggagatgg tgggccgctg gaagacgttg aagcttgctt cttgcaagcc   6900
caccgagtcc ctgacgaagg aggcgtagga ctcgcgcagc ttgtgcacca gctcggcggt   6960
gacctggacg tcgagcgcgc agtagtcgag ggtctcgcgg atgatgtcat acttatcctc   7020
cccttctt ttccacagct cgcggttgag gacgaactct tcgcggtctt ccagtactc      7080
ttgaggggga aacccgtccg tgtccgaacg gtaagagcct agcatgtaga actggttgac   7140
ggcctggtag gggcaacagc ccttctccac gggcagcgcg taggcctgcg ccgccttgcg   7200
gagggaggtg tgggtgaggg cgaaagtgtc cctgaccatg actttgaggt attgatgttt   7260
```

```
gaagtctgtg tcatcgcagc cgccctgttc ccacaggggtg tagtccgtgc gcttttttgga    7320
gcgcgggttg ggcagggaga aggtgaggtc attgaagagg atcttccccg ctcgaggcat    7380
gaagtttctg gtgatgcgaa agggccctgg gaccgaggag cggttgttga tgacctgggc    7440
ggccaggacg atctcgtcaa agccgtttat gttgtggccc acgatgtaga gctccaaaaa    7500
gcggggctgg cccttgatgg agggggagctt tttgagttcc tcgtaggtga gctcctcggg    7560
cgattccagg ccgtgctcct ccagggccca gtcttgcaag tgagggttgg ccgccaggaa    7620
ggatcgccag aggtcgcggg ccatgagggt ctgcaggcgg tcgcggaagg ttctgaactg    7680
tcgccccacg gccatctttt cggggtgat gcagtagaag gtgaggggt ctttctccca    7740
ggggtcccat ctgagctctc gggcgaggtc gcgcgcggcg gcgaccagag cctcgtcgcc    7800
ccccagtttc atgaccagca tgaagggcac gagctgcttg ccaaaggctc ccatccaagt    7860
gtaggtctct acatcgtagg tgacaaagag gcgctccgtg cgaggatgag agccgatcgg    7920
gaagaactgg atctcccgcc accagttgga ggattggctg ttgatgtggt gaaagtagaa    7980
gtcccgtctg cgggccgagc actcgtgctg gcttttgtaa aagcgaccgc agtactggca    8040
gcgctgcacg ggttgtatat cttgcacgag gtgaacctgg cgacctctga cgaggaagcg    8100
cagcgggaat ctaagtcccc cgcctggggt cccgtgtggc tggtggtctt ctactttggt    8160
tgtctggccg ccagcatctg tctcctggag ggcgatggtg gagcagacca ccacgccgcg    8220
agagccgcag gtccagatct cggcgctcgg cgggcggagt tgatgacga catcgcgcac    8280
attggagctg tccatggtct ccagctcccg cggcggcagg tcagctggga gttcctggag    8340
gttcacctcg cagagacggg tcaaggcgcg ggcagtgttg agatggtatc tgatttcaag    8400
gggcgtgttg gcggcggagt cgatggcttg caggaggccg cagccccggg gggccacgat    8460
ggttccccgc ggggcgcgag gggaggcgga agctgggggt gtgttcagaa gcggtgacgc    8520
gggcgggccc ccggaggtag gggggttcc ggccccacag gcatgggcgg caggggcacg    8580
tcttcgccgc gcgcgggcag gggctggtgc tggctccgaa gagcgcttgc gtgcgcgacg    8640
acgcgacggt tggtgtcctg tatctgacgc ctctgagtga agaccacggg tcccgtgacc    8700
ttgaacctga aagagagttc gacagaatca atctcggcat cgttgacagc ggcctggcgc    8760
aggatctcct gcacgtcgcc cgagttgtcc tggtaggcga tctctgccat gaactgctcg    8820
atctcttctt cctggagatc tcctcgtccg gcgcgctcca cggtggccgc caggtcgttg    8880
gagatgcgac ccatgagctg tgagaaggcg ttgagcccgc cctcgttcca gacccggctg    8940
tagaccacgc ccccctcggc gtcgcgagcg cgcatgacca cctgggccag gttgagctcc    9000
acgtgtcgcg tgaagacggc gtagttgcgc aggcgctgga aaaggtagtt cagggtggtg    9060
gcggtgtgct cggcgacgaa gaagtacatg acccagcgcc gcaacgtgga ttcattgatg    9120
tcccccaagg cctccaggcg ctccatggcc tcgtagaagt ccacggcgaa gttgaaaaac    9180
tgggagttgc gagcggacac ggtcaactcc tcctccagaa gacggatgag ctcggcgaca    9240
gtgttgcgca cctcgcgctc gaaggccacg ggggcgcttt cttcctcttc cacctcttct    9300
tccatgatcg cttcttcttc ttcctcagcc gggacgggag ggggcggcgg cggcggggga    9360
ggggcgcggc ggcggcggcg gcgcaccggg aggcggtcga tgaagcgctc gatcatctcc    9420
ccccgcatgc ggcgcatggt ctcggtgacg gcgcggccgt tctcccgggg gcgcagctcg    9480
aagacgccgc ctctcatctc gccgcggggc gagcggccgt gaggtagcga gacgcgctg    9540
actatgcatc ttaacaattg ctgtgtaggt acaccgccga gggacctgat tgagtccaga    9600
```

```
tccaccggat ccgaaaacct tggaggaaa gcgtctatcc agtcgcagtc gcaaggtagg    9660
ctgagcaccg tggcgggcgg gggcgggtct ggagagttcc tggcggagat gctgctgatg    9720
atgtaattaa agtaggcggt cttgagaagg cggatggtgg acaggagcac catgtctttg    9780
ggtccggcct gttggatgcg gaggcggtcg gccatgcccc aggcctcgtt ctgacaccgg    9840
cgcaggtctt tgtagtagtc ttgcatgagt cttccaccg gcacctcttc tccttcctct    9900
tctccatctc gccggtggtt tctcgcgccc cccatgcgcg tgaccccaaa gcccctgagc    9960
ggctgcagca gggccaggtc ggcgaccacg cgctcggcca agatggcctg ctgcacctga   10020
gtgagggtcc tctcgaagtc atccatgtcc acgaagcggt ggtaggcgcc cgtgttgatg   10080
gtgtaggtgc agttggccat gacggaccag ttgacggtct ggtgtcccgg ctgcgagagc   10140
tccgtgtacc gcaggcgcga gaaggcgcgg gaatcgaaca cgtagtcgtt gcaagtccgc   10200
accagatact ggtagcccac caggaagtgc ggcggaggtt ggcgatagag gggccagcgc   10260
tgggtggcgg gggcgccggg cgccaggtct ccagcatga ggcggtggta ccgtagatg   10320 tacctggaca tccaggtgat gccggcgcg gtggtggtgg cgcgcgcgta gtcgcggacc   10380
cggttccaga tgtttcgcag gggcgagaag tgttccatgg tcggcacgct ctggccggtg   10440
aggcgcgcgc agtcgttgac gctctataca cacacaaaaa cgaaagcgtt tacagggctt   10500
tcgttctgta gcctggagga aagtaaatgg gttgggttgc ggtgtgcccc ggttcgagac   10560
caagctgagc tcggccggct gaagccgcag ctaacgtggt attggcagtc ccgtctcgac   10620
ccaggccctg tatcctccag gatacggtcg agagcccttt tgctttcttg gccaagcgcc   10680
cgtggcgcga tctgggatag atggtcgcga tgagaggaca aaagcggctc gcttccgtag   10740
tctggagaaa caatcgccag ggttgcgttg cggcgtaccc cggttcgagc ccctatggcg   10800
gcttgaatcg gccggaaccg cggctaacga gggccgtggc agcccgtcc tcaggacccc   10860 gccagccgac ttctccagtt acgggagcga gccccttttg ttttttattt tttagatgca   10920
tcccgtgctg cggcagatgc gcccctcgcc ccggcccgat cagcagcagc aacagcaggc   10980
atgcagaccc ccctctcccc tttccgcccc ggtcaccacg gccgcggcgg ccgtgtcggg   11040 cgcgggggc gcgctggagt cagatgagcc accgcggcgg cgacctaggc agtatctgga   11100
cttggaagag ggcgagggac tggcgcggct gggggcgaac tctccagagc gccacccgcg   11160
ggtgcagttg aaaagggacg cgcgcgaggc gtacctgccg cggcagaacc tgtttcgcga   11220 ccgcggggc gaggagcccg aggagatgcg agactgcagg ttccaagcgg ggcgcgagct   11280
gcggcgcggg ctggacagac agcgcctgct gcgcgaggag gactttgagc ccgacacgca   11340
gacgggcatc agccccgcgc gcgcgcacgt agccgcggcc gacctggtga ccgcctacga   11400
gcagacggta aaccaggagc gcaacttcca aaagagcttc aacaaccacg tgcgcacgct   11460
ggtggcgcgc gaggaggtga ccctgggtct catgcatctg tgggacctgg tggaggcgat   11520
cgtgcagaac cccagcagca agccctgac cgcgcagctg ttcctggtgg tgcagcacag   11580
cagggacaac gaggccttca gggaggcgct gctgaacatc accgagccgg aggggcgctg   11640
gctcctggac ctgataaaca tcctgcagag catagtggtg caggagcgca gcctgagcct   11700
ggccgagaag gtgcgggcca tcaactactc tatgctgagc ctgggcaagt tctacgcccg   11760
caagatctac aagaccccct acgtgcccat agacaaggag gtgaagatag acagcttcta   11820
catgcgcatg gcgctgaagg tgctgacccct gagcgacgac ctgggagtgt accgcaacga   11880
gcgcatccac aaggccgtga gcgccagccg gggcgcgag ctgagcgacc gcgagctgat   11940
gcacagtctg cagcgcgcgc tgaccggcgc gggcgagggc gacagggagg tcgagtccta   12000
```

```
cttcgacatg ggggccgacc tgcactggca gccgagccgc cgcgccctgg aggcggcggg   12060
ggcgtacggc ggccccctgg cggccgatga ccaggaagag gaggactatg agctagagga   12120
gggcgagtac ctggaggact gacctggctg gtggtgtttt ggtatagatg caagatccga   12180
acgtggcgga cccggcggtc cgggcggcgc tgcaaagcca gccgtccggc attaactcct   12240
ctgacgactg ggccgcggcc atgggtcgca tcatggccct gaccgcgcgc aaccccgagg   12300 cttttcaggca gcagcctcag gccaaccggc tggcggccat cttggaagcg gtagtgcccg   12360
cgcgctccaa ccccacccac gagaaggtgc tggccatagt caacgcgctg gcggagagca   12420
gggccatccg cgcggacgag gccggactgg tgtacgatgc gctgctgcag cgggtggcgc   12480
ggtacaacag cggcaacgtg cagaccaacc tggaccgcct ggtgacggac gtgcgcgagg   12540
ccgtggcgca gcgcgagcgc ttgcatcagg acggtaacct gggctcgctg gtggcgctaa   12600
acgccttcct cagcacccag ccggccaacg taccgcgggg gcaggaggac tacaccaact   12660
ttttgagcgc gctgcggctg atggtgaccg aggtccctca gagcgaggtg taccagtcgg   12720
ggcccgacta cttcttccag accagcagac agggcttgca aaccgtgaac ctgagccagg   12780 cttttcaagaa cctgcggggg ctgtggggag tgaaggcgcc caccggcgac cgggctacgg   12840
tgtccagcct gctaaccccc aactcgcgcc tgctgctgct gctgatcgcg cccttcacgg   12900
acagcgggag cgtctcgcgg gagacctatc tgggccacct gctgacgctg taccgcgagg   12960
ccatcgggca ggcgcaggtg gacgagcaca ccttccaaga gatcaccagc gtgagccacg   13020
cgctggggca ggaggacacg ggcagcctgc aggcgaccct gaactacctg ctgaccaaca   13080
ggcggcagaa gattcccacg ctgcacagcc tgacccagga ggaggagcgc atcttgcgct   13140
acgtgcagca gagcgtgagc ctgaacctga tgcgcgacgg cgtgacgccc agcgtggcgc   13200
tggacatgac cgcgcgcaac atggaaccgg gcatgtacgc ctcccaccgg ccgtttatca   13260
accgcctgat ggactacttg catcgggcgg cggccgtgaa ccccgagtac ttcactaatg   13320
ccattctgaa tccccactgg atgccccctc cgggttttcta caacggggac tttgaggtgc   13380
ccgaggtcaa cgacgggttc ctctgggatg acatggatga cagtgtgttc tcacccaacc   13440
cgctgcgcgc cgcgtctctg cgattgaagg agggctctga cagggaagga ccgaggagtc   13500
tggcctcctc cctggctctg ggagcggtgg gcgccacggg cgcggcgcg cggggcagta   13560 gcccccttccc cagcctggca gactctctga cagcggggcg ggtgagcagg ccccgcttgc   13620
taggcgagga ggagtatctg aacaactccc tgctgcagcc cgcgagggac aagaacgctc   13680
agcggcagca gtttcccaac aatgggatag agagcctggt ggacaagatg tccagatgga   13740
agacgtatgc gcaggagtac aaggagtggg aggaccgcca gccgcggccc ttgccgcccc   13800
ctaggcagcg ctgcagcgg cgcgcgtcca accgccgctg gaggcagggg cccgaggacg   13860
atgatgactc tgcagatgac agcagcgtgt ggaccctggg cgggagcggg aaccccttttt   13920 cgcacctgcg cccacgcctg ggcaagatgt tttaaagaaa aaaaaaaata aaactcacca   13980
aggccatggc gacgagcgtt ggttttttgt tccctttcctt agtatgcggc gcgcggcgat   14040
gttcgaggag gggcctcccc cctcttacga gagcgcgatg gggatttctc ctgcggcgcc   14100
cctgcagcct ccctacgtgc ctcctcggta cctgcaacct acaggggga gaaatagcat   14160 ctgttactct gagctgcagc ccctgtacga taccaccaga ctgtacctgg tggacaacaa   14220
gtccgcggac gtgccctccc tgaactacca gaacgaccac agcgatttt tgaccacggt   14280 gatccaaaac aacgacttca ccccaaccga ggccagcacc cagaccataa acctggataa   14340
```

```
caggtcgaac tggggcggcg acctgaagac catcttgcac accaacatgc ccaacgtgaa    14400
cgagttcatg ttcaccaact cttttaaggc gcgggtgatg gtggcgcgcg agcaggggga    14460
ggcgaagtac gagtgggtgg acttcacgct gcccgagggc aactactcag agaccatgac    14520
tctcgacctg atgaacaatg cgatcgtgga acactatctg aaagtgggca ggcagaacgg    14580
ggtgaaggaa agcgatatcg gggtcaagtt tgacaccaga aacttccgtc tgggctggga    14640
ccccgtgacc gggctggtca tgccggggt ctacaccaac gaggcctttc atcccgacat     14700
agtgcttctg cccggctgtg gggtggactt cacccagagc cggctgagca acctgctggg    14760
cattcgcaag cggcagcctt tccaggaggg tttcaagatc acctatgagg atctgaaggg    14820
gggcaacatt cccgcgctcc ttgatctgga cgcctacgag gagagcttga aacccgagga    14880
gagcgctggc gacagcggcg agagtggcga ggagcaagcc ggcggcggtg gcggcgcgtc    14940
ggtagaaaac gaaagtacgc ccgcagtggc ggcggacgct gcggaggtcg agccggaggc    15000
catgcagcag gacgcagagg agggcgcaca ggagggcgcg cagaaggaca tgaacgatgg    15060
ggagatcagg ggagacacat cgccacccg ggcgaagaa aaagaggcag aggcggcggc       15120
ggcggcgacg gcggaggccg aaaccgaggt tgaggcagag gcagagcccg agaccgaagt    15180
tatggaagac atgaatgatg gagaacgtag gggcgacacg ttcgccaccc ggggcgaaga    15240
gaaggcggcg gaggcagaag ccgcggctga ggaggcggct gcggctgcgg ccaagactga    15300
ggctgcggct aaggctgagg tcgaagccaa tgttgcggtt gaggctcagg ctgaggagga    15360
ggcggcggct gaagcagtta aggaaaaggc ccaggcagag caggaagaga aaaaacctgt    15420
cattcaacct ctaaaagaag atagcaaaaa gcgcagttac aacgtcatcg agggcagcac    15480
ctttacccag taccgcagct ggtacctggc gtacaactac ggcgacccgg tcaaggggt     15540 gcgctcgtgg accctgctct gcacgccgga cgtcacctgc ggctccgagc agatgtactg    15600
gtcgctgccg aacatgatgc aagacccggt gaccttccgc tccacgcggc aggttagcaa    15660
cttcccggtg gtgggcgccg aactgctgcc cgtgcactcc aagagttttt acaacgagca    15720
ggccgtctac tcccagctga tccgccaggc cacctctctg acccacgtgt tcaatcgctt    15780
tcccgagaac cagatttttgg cgcgcccgcc ggccccacc atcaccaccg tgagtgaaaa    15840
cgttcctgcc ctcacagatc acgggacgct accgctgcgc aacagcatct caggagtcca    15900
gcgagtgacc attactgacg ccagacgccg gacctgcccc tacgtttaca aggccttggg    15960
catagtctcg ccgcgcgtcc tctccagtcg cacttttaa aacacatcta cccacacgtt      16020
ccaaaatcat gtccgtactc atctcaccca gcaacaacac cggctggggg ctgcgcgcgc    16080
ccagcaagat gtttggaggg gcgaggaagc gctccgacca gcaccctgtg cgcgtgcgcg    16140
gccactaccg cgcgccctgg ggagcgcaca agcgcgggcg cacagggcgc accactgtgg    16200
acgacgtcat tgactccgta gtggagcaag cgcgccacta cacacccggc gcgccgaccg    16260
cccccgccgt gtccaccgtg gaccaggcga tcgaaagcgt ggtacagggc gcgcggcact    16320
atgccaacct taaaagtcgc cgccgccgcg tggcccgccg ccatcgccgg agaccccggg    16380
ccaccgccgc cgcgcgccct actaaggctc tgctcaggcg cgccaggcga actggccacc    16440
gggccgccat gagggccgca cggcggggctg ccgctgccgc aagcgtcgtg gccccgcggg   16500
cacgaaggcg cgcggccgct gccgccgccg ccgccatttc cagcttggcc tcgacgcggc    16560
gcggtaacat atactgggtg cgcgactcgg taaccggcac gcgggtaccc gtgcgctttc    16620 gcccccgcg gaattagcac aagacaacat acacactgag tctcctgctg ttgtgtatcc     16680
cagcggcgac cgtcagcagc ggcgacatgt ccaagcgcaa aattaaagaa gagatgctcc    16740
```

```
aggtcatcgc gccggagatc tatgggcccc cgaagaagga ggaggatgat tacaagcccc   16800
gcaagctaaa gcgggtcaaa aagaaaaaga aagatgatga tgacgaggcg gtggagtttg   16860
tccgccgcat ggcacccagg cgccccgtgc agtggaaggg ccggcgcgtg cagcgcgttt   16920
tgcgccccgg caccgcggtg gtcttcacgc ccggcgagcg ctccacgcgc actttcaagc   16980
gggtgtacga tgaggtgtac ggcgacgagg acctgttgga gcaggccaac cagcgctttg   17040
gggagtttgc atatgggaaa cggccccgcg agagtctaaa agaggacctg ctggcgctac   17100
cgctggacga gggcaatccc accccgagtc tgaagccggt aaccctgcaa caggtgctgc   17160
ctttgagcgc gcccagcgag cataagcgag ggttgaagcg cgaaggcggg gacctggcgc   17220
ccaccgtgca gttgatggtg cccaagcggc agaagctgga ggacgtgctg gagaaaatga   17280
aagtagagcc cgggatccag cccgagatca aggtccgccc catcaagcag gtggcgcccg   17340
gcgtgggagt ccagaccgtg gacgttagga ttcccacgga ggagatggaa acccaaaccg   17400
ccactccctc ttcggcggcc agcgccacca ccggcaccgc ttcggtagag gtgcagacgg   17460 accctggct accgccacc gctgttgccg ccgccgcccc ccgttcgcgc gggcgcaaga   17520
gaaattatcc agcggccagc gcgctcatgc cccagtacgc actgcatcca tccatcgtgc   17580 ccaccccgg ctaccgcggg tactcgtacc gcccgcgcag atcagccggc actcgcggcc   17640
gccgccgccg tgcgaccaca accagccgcc gccgtcgccg ccgccgccag ccagtgctga   17700
cccccgtgtc tgtaaggaag gtggctcgct cggggagcac gctggtggtg cccagagcgc   17760
gctaccaccc cagcatcgtt taaagccggt ctctgtatgg ttcttgcaga tatggccctc   17820
acttgtcgcc tccgcttccc ggtgccggga taccgaggaa gaactcaccg ccgcagaggc   17880
atggcgggca gcgtctccg cggcggccgt cgccatcgcc ggcgcgcaaa aagcaggcgc   17940
atgcgcggcg gtgtgctgcc tctgctaatc ccgctaatcg ccgcggcgat cggtgccgta   18000
cccgggatcg cctccgtggc cctgcaggcg tcccagaaac gttgactctt gcaaccttgc   18060
aagcttgcat tttttggagg aaaaataaaa aaaagtctag actctcacgc tcgcttggtc   18120
ctgtgactat tttgtagaaa aaaagatgga agacatcaac tttgcgtcgc tggccccgcg   18180
tcacggctcg cgcccgttca tgggagactg gacagatatc ggcaccagca atatgagcgg   18240
tggcgccttc agctggggca gtctgtggag cggccttaaa aatttttggtt ccaccattaa   18300 gaactatggc aacaaagcgt ggaacagcag cacgggccag atgctgagag acaagttgaa   18360
agagcagaac ttccaggaga aggtggcgca gggcctggcc tctggcatca gcggggtggt   18420
ggacatagct aaccaggccg tgcagaaaaa gataaacagt catctggacc cccgtcctca   18480
ggtggaggaa atgcctccag cgatggagac ggtgtctccc gagggcaaag gcgaaaagcg   18540
cccgcggccc gacagagaag agaccctggt gtcacacacc gaggagccgc cctcttacga   18600
ggaggcagtc aaggccggcc tgcccaccac tcgccccata gccccatgg ccaccggtgt   18660 ggtgggccac aggcaacaca ctcccgcaac actagatctg cccccgccgt ccgagccgcc   18720
gcgccagcca aaggcggcga cggtgcccgc tccctccact tccgccgcca acagagtgcc   18780
cctgcgccgc gccgcgagcg gccccgggc ctcgcgagtt agcggcaact ggcagagcac   18840
actgaacagc atcgtgggcc tgggagtgag gagtgtgaag cgccgccgtt gctactgaat   18900
gagcaagcta gctaacgtgt tgtatgtgtg tatgcgtcct atgtcgccgc cagaggagct   18960
gttgagccgc cggcgccgtc tgcactccag cgaatttcaa gatggcgacc ccatcgatga   19020
tgcctcagtg gtcgtacatg cacatctcgg gccaggacgc ttcggagtac ctgagccccg   19080
```

```
ggctggtgca gttcgcccgc gccacagaca cctacttcaa catgagtaac aagttcagga  19140
accccactgt ggcgcccacc cacgatgtga ccacggaccg gtcgcagcgc ctgacgctgc  19200
ggttcatccc cgtggatcgg gaggacaccg cctactctta caaggcgcgg ttcacgctgg  19260
ccgtgggcga caaccgcgtg ctggacatgg cctccactta ctttgacatc aggggggtgc  19320
tggacagggg ccccaccttc aagccctact cgggtactgc ctacaactcc ctggccccca  19380
agggcgctcc caattcttgc gagtgggaac aagatgaacc agctcaggca gcaatagctg  19440
aagatgaaga agaacttgaa gaagaacaag ctcaggacga acaggcgccc actaagaaaa  19500
cccatgtata cgcccaggca cctctttctg gtgaaaaaat tactaaggat ggtttgcaaa  19560
taggtgtgga tgccacacag gcgggagata accctatata tgctgataaa acattccaac  19620
ccgaacctca gataggtgag tctcagtgga acgaggctga tgccacagta gcaggaggca  19680
gagtcttaaa aaagaccacc cctatgagac cttgctatgg atcctatgcc aaacctacta  19740
atgccaatgg cggtcaaggg atcatggtgg ccaatgatca gggagcgctt gaatctaaag  19800
ttgagatgca atttttctcc accacaacgt ctcttaatgt aagggaaggt gaaaacaatc  19860
ttcagccaaa agtagtgcta tacagcgaag atgttaactt ggaatcccct gacactcatt  19920
tgtcttacaa acctaaaaag gatgacacca actctaaaat catgttgggt cagcaagcca  19980
tgcccaacag acccaacctc attgctttta gggacaactt tattggactt atgtactaca  20040
acagcacagg caacatggga gtgctggcag gacaggcctc ccagctaaac gctgtggtag  20100
acttgcaaga cagaaacaca gagctgtcat accaactgat gcttgattcc attggagaca  20160
gatcaagata cttttccatg tggaaccagg cagtggacag ctatgaccca gatgtcagaa  20220
tcattgaaaa ccatggggtt gaagatgagc tgcccaacta ttgctttccc ctgggcggta  20280
ttggaattac agacacatac cagtgcataa aaccaaccgc agctgctaat aacactacat  20340
ggtctaagga tgaagaattt agtgatcgca atgaaatagg ggtgggaaac aacttcgcca  20400
tggagatcaa catccaggcc aacctctgga ggaacttcct ctatgcgaac gtggggctct  20460
acctgccaga caagctcaag tacaaccccca ccaacgtgga catctctgac aaccccaaca  20520
cctatgacta catgaacaag cgtgtggtgg ctcccggcct ggtggactgc tttgtcaatg  20580
tgggagccag gtggtccctg gactacatgg acaacgtcaa ccccttcaac caccaccgca  20640
atgcgggtct cgctaccgc tccatgatcc tgggcaacgg cgctacgtg cccttccaca  20700
ttcaggtgcc ccagaagttc tttgccatca agaacctcct cctcctgccg ggctcctaca  20760
cttacgagtg gaacttcagg aaggatgtca acatggtcct gcagagctct ctgggcaatg  20820
accttagggt ggacgggcc agcatcaagt ttgacagcgt caccctctat gctaccttct  20880
tccccatggc tcacaacacc gcctccacgc tcgaggccat gctgaggaac gacaccaacg  20940
accagtcctt caatgactac ctctctgggg ccaacatgct ctaccccatc cccgccaagg  21000
ccaccaacgt gcccatctcc attccctctc gcaactgggc cgccttcaga ggctgggcct  21060
ttacccgcct taagaccaag gaaacccccct cctgggctc gggttttgac ccctacttgg  21120
tctactcggg atccatcccc tacctggatg gcaccttcta cctcaaccac acttttaaga  21180
agatatccat catgtatgac tcctccgtca gctggccggg caatgaccgc tgctcaccc  21240
ccaatgagtt cgaggtcaag cgcgccgtgg acggcgaggg ctacaacgtg cccagtgca  21300
acatgaccaa ggactggttc ctggtgcaga tgctggccaa ctacaacata ggctaccagg  21360
gcttctacat cccagagagc tacaaggaca ggatgtactc cttcttcaga aatttccaac  21420
ccatgagcag gcaggtggtg gacgagacca atacaaggga ctatcaggcc attggcatca  21480
```

```
ctcaccagca caacaactcg ggattcgtgg gctacctggc tcccaccatg cgcgagggc    21540
aggcctaccc cgccaacttc ccctacccgt tgataggcaa accgcggtc gacagcgtca    21600
cccagaaaaa gttcctctgc daccgcaccc tctggcgcat ccccttctct agcaacttca   21660
tgtccatggg tgcgctcacg gacctgggcc agaacctgct ctatgccaac tccgcccatg   21720
cgctggacat gacttttgag gtggacccca tggacgagcc caccttctc tatattgtgt    21780
ttgaagtgtt cgacgtggtc agagtgcacc agccgcaccg cggtgtcatc gagaccgtgt   21840
acctgcgcac gcccttctcg gccggcaacg ccaccaccta aggagacagc gccgccgcct   21900
gcatgacggg ttccaccgag caagagctca gggccatcgc cagagacctg ggatgcggac   21960
cctattttt gggcacctat gacaaacgct tcccgggctt catctcccga dacaagctcg    22020
cctgcgccat cgtcaacacg gccgcgcgcg agaccggggg cgtgcactgg ctggcctttg   22080
gctgggaccc gcgctccaaa acctgctacc tcttcgaccc cttttggcttc tccgatcagc  22140
gcctcagaca gatctatgag tttgagtacg aggggctgct cgccgcagc gcgcttgcct    22200
cctcgcccga ccgctgcatc acccttgaga agtccaccga gaccgtgcag gggccccact   22260
cggccgcctg cggtctcttc tgctgcatgt tttgcacgc cttttgtgcgc tggccccaga   22320
gtcccatgga tcgcaacccc accatgaact tgctcaaggg agtgcccaac gccatgctcc   22380
agagcccca ggtccagccc accctgcgcc acaaccagga acagctctac cgcttcctgg    22440
agcgccactc cccctacttc cgcagtcaca gcgcgcacat ccggggggcc acctctttct   22500
gccacttgca agaaaacatg caagacggaa aatgatgtac agctcgcttt ttaataaatg   22560
taaagactgt gcactttatt tatacacggg ctctttctgg ttatttattc aacaccgccg   22620
tcgccatcta gaaatcgaaa gggttctgcc gcgcgtcgcc gtgcgccacg ggcagagaca   22680
cgttgcgata ctggaagcgg ctcgcccact taaactcggg caccaccatg cggggcagtg   22740
gttcctcggg gaagttctcg ccccacaggg tgcgggtcag ctgcagcgcg ctcaggaggt   22800
cgggagccga gatcttgaag tcgcagttgg ggccggaacc ctgcgcgcgc gagttgcggt   22860
acacgggggtt gcagcactgg aacaccagca gggccggatt atgcacgctg gccagcaggc  22920
tctcgtcgct gatcatgtcg ctgtccagat cctccgcgtt gctcagggcg aacgggtca    22980
tcttgcagac ctgcctgccc aggaaaggcg gcagcccggg cttgccgttg cagtcgcagc   23040
gcaggggcat cagcaggtgc ccgcggcccg actgcgcctg cgggtacagc gcgcgcatga   23100
aggcttcgat ctgcctgaaa gccacctgcg tcttggctcc ctccgaaaag aacatcccac   23160
aggacttgct ggagaactgg ttcgcgggac agctggcatc gtgcaggcag cagcgcgcgt   23220
cggtgttggc gatctgcacc acgttgcgac cccaccggtt cttcactatc ttggccttgg   23280
aagcctgctc cttcagcgcg cgctggccgt tctcgctggt cacatccatc tctatcacct   23340
gctccttgtt gatcatgttt gtaccgtgca gacacttcag gtcgccctcc gtctgggtgc   23400
agcggtgctc ccacagcgcg caaccggtgg gctcccaatt tttgtgggtc accccgcgt    23460
aggcctgcag gtaggcctgc aagaagcgcc ccatcatggc cacaaaggtc ttctggctcg   23520
taaaggtcag ctgcaggccg cgatgctctt cgttcagcca ggtcttgcag atggcggcca   23580
gcgcctcggt ctgctcgggc agcatcctaa aatttgtctt caggtcgtta tccacgtggt   23640
acttgtccat catggcgcgc gccgcctcca tgcccttctc ccaggcggac accatgggca   23700
ggcttagggg gtttatcact tccaccgcg aggacaccgt actttcgatt tcttcttcct    23760
ccccctcttc ccggcgcgcg cccacgctgc tgcgcgctct caccgcctgc accaaggggt   23820
```

```
cgtcttcagg caagcgccgc accgagcgct tgccgccctt gacctgctta atcagcaccg   23880
gcgggttgct gaagcccacc atggtcagcg ccgcctgctc ttcttcgtct tcgctgtcta   23940
ccactatctc tggggaaggg cttctccgct ctgcggcggc gcgcttcttt ttttcttgg    24000 gagcggccgt gatggagtcc gccacggcga cggaggtcga gggcgtgggg ctggggtgc    24060 gcggtaccag ggcctcgtcg ccctcggact cttcctctga ctccaggcgg cggcggagtc   24120
gcttctttgg gggcgcgcgc gtcagcggcg cggagacgg ggacggggac ggggacggga    24180
cgccctccac aggggtggt cttcgcgcag acccgcggcc gcgctcgggg gtcttctcga    24240
gctggtcttg gtcccgactg gccattgtat cctcctcctc ctaggcagag agacataagg   24300
agtctatcat gcaagtcgag aaggaggaga gcttaaccac cccctctgag accgccgatg   24360
cgcccgccgt cgccgtcgcc cccgctgccg ccgacgcgcc cgccacaccg agcgacaccc   24420
ccgcggaccc ccccgccgac gcaccctgt tcgaggaagc ggccgtggag caggacccgg    24480
gctttgtctc ggcagaggag gatttgcgag aggaggagga taaggagaag aagccctcag   24540
tgccaaaaga tgataaagag caagacgagc acgacgcaga tgcacaccag ggtgaagtcg   24600
ggcgggggga cggagggcat gacgcgccg actacctaga cgaagggaac gacgtgctct    24660
tgaagcacct gcatcgtcag tgcgccattg tttgcgacgc tctgcaggag cgcagcgaag   24720
tgcccctcag cgtggcggag gtcagccacg cctacgagct cagcctcttc tccccccggg   24780
tgcccccccg ccgccgcgaa aacggcacat gcgagcccaa cccgcgcctc aacttctacc   24840
ccgcctttgt ggtacccgag gtcctggcca cctatcacat cttctttcaa aattgcaaga   24900
tccccctctc gtgccgcgcc aaccgtagcc gcgccgataa gatgctggcc ctgcgccagg   24960
gcgaccacat acctgatatc gccgctttgg aagatgtacc aaagatcttc gagggtctgg   25020
gtcgcaacga gaagcgggca gcaaactctc tgcaacagga aaacagcgaa aatgagagtc   25080
acaccggggt actggtggag ctcgagggcg acaacgcccg cctggcggtg gtcaagcgca   25140
gcatcgaggt cacccacttt gcctaccccg cgctaaacct gccccccaaa gtcatgaacg   25200
cggccatgga cgggctgatc atgcgccgcg gccggcccct cgctccagat gcaaacttgc   25260
atgaggagac cgaggacggc cagcccgtgg tcagcgacga gcagctggcg cgctggctgg   25320
agaccgcgga ccccgccgaa ctggaggagc ggcgcaagat gatgatggcc gtggtgctgg   25380
tcaccgtaga gctggagtgt ctgcagcgct tcttcggcga ccccgagatg cagagaaagg   25440
tcgaggagac cctgcactac accttccgcc agggctacgt gcgccaggct tgcaagatct   25500
ccaacgtgga gctcagcaac ctggtgtcct acctgggcat cttgcatgag aaccgcctcg   25560
ggcagagcgt gctgcactcc accctgcgcg gggaggcgcg ccgcgactac gtgcgcgact   25620
gcgtttacct cttcctctgc tacacctggc agacggccat gggggtctgg cagcagtgcc   25680
tggaggagcg caacctcaag gagctggaga agctcctgca gcgcgcgctc aaagatctct   25740
ggacgggcta caacgagcgc tcggtggccg ccgcgctggc cgacctcatc ttccccgagc   25800
gcctgctcaa aaccctccag caggggctgc ccgacttcac cagccaaagc atgttgcaaa   25860
acttcaggaa ctttatcctg gagcgttctg gcatcctacc cgccacctgc tgcgccctgc   25920
ccagcgactt tgtcccccct cgtgtaccgcg agtgcccccc gccgctgtgg ggtcactgct   25980
acctgttcca actggccaac tacctgtcct accacgcgga cctcatggag gactccagcg   26040
gcgaggggct catggagtgc cactgccgct gcaacctctg cacgcccac cgctccctgg    26100 tctgcaacac ccaactgctc agcgagagtc agattatcgg taccttcgag ctacagggtc   26160
cgtcctcctc agacgagaag tccgcggctc cggggctaaa actcactccg gggctgtgga   26220
```

```
cttccgccta cctgcgcaaa tttgtacctg aagactacca cgcccacgag atcaggtttt    26280
acgaagacca atcccgcccg cccaaggcgg agctgaccgc ctgcgtcatc acccagggcg    26340
agatcctagg ccaattgcaa gccatccaaa aagcccgcca agacttttg ctgaagaagg    26400 gtcgggggt gtatctggac ccccagtcgg gtgaggagct caacccggtt cccccgctgc     26460
cgccgccgcg ggaccttgct tcccaggata agcatcgcca tggctcccag aaagaagcag    26520
cagcggccgc cactgccgcc accccacatg ctggaggaag aggaggaata ctggacagt     26580 caggcagagg aggtttcgga cgaggaggag ccggagacgg agatggaaga gtgggaggag    26640
gacagcttag acgaggaggc ttccgaagcc gaagaggcag acgcaacacc gtcaccctcg    26700
gccgcagccc cctcgcaggc gccccgaag tccgctccca gcatcagcag caacagcagc      26760
gctataacct ccgctcctcc accgccgcga cccacggccg accgcagacc caaccgtaga    26820
tgggacacca ccggaaccgg ggccggtaag tcctccggga gaggcaagca agcgcagcgc    26880
caaggctacc gctcgtggcg cgctcacaag aacgccatag tcgcttgctt gcaagactgc    26940 gggggaaca tctccttcgc ccgccgcttc ctgctcttcc accacggtgt ggccttcccc     27000
cgtaacgtcc tgcattacta ccgtcatctc tacagcccct actgcggcgg cagtgagcca    27060
gagacggtcg gcggcggcgg cggcgcccgt ttcggcgcct aggaagaccc agggcaagac    27120
ttcagccaag aaactcgcgg cggcgcggc gaacgcggtc gcggggcccc tgcgcctgac      27180
ggtgaacgaa cccctgtcga cccgcgaact gaggaaccga atcttcccca ctctctatgc    27240
catcttccag cagagcagag ggcaggatca ggaactgaaa gtaaaaaaca ggtctctgcg    27300
ctccctcacc cgcagctgtc tgtatcacaa gagcgaagac cagcttcggc gcacgctgga    27360
ggacgctgag gcactcttca gcaaatactg cgcgctcact cttaaggact agctccgcgc    27420
ccttctcgaa tttaggcggg aacgcctacg tcatcgcagc gccgccgtca tgagcaagga    27480
cattcccacg ccatacatgt ggagctatca gccgcagatg ggactcgcgg cgggcgcctc    27540
ccaagactac tccacccgca tgaactggct cagtgccggc ccacacatga tctcacaggt    27600
taatgatatc cgcacccatc gaaaccaaat attggtggag caggcggcaa ttaccaccac    27660
gccccgcaat aatcccaacc ccagggagtg gcccgcgtcc ctggtgtatc aggaaattcc    27720 cggcccacc accgtactac ttccgcgtga ttcccaggcc gaagtccaaa tgactaactc     27780
aggggcacag ctcgcgggcg gctgtcgtca cagggtgcgg cctcctcgcc agggtataac    27840
tcacctggag atccgaggca gaggtattca gctcaacgac gagtcggtga gctcctcgct    27900
cggtctcaga cctgacggga ccttccagat agccggagcc ggccgatctt ccttcacgcc    27960
ccgccaggcg tacctgactc tgcaaagctc gtcctcggcg ccgcgctcgg gcggcatcgg    28020
gactctccag ttcgtgcagg agtttgtgcc ctcggtctac ttcaacccct ctcgggctc     28080 tcccggtcgc tacccggacc agttcatctc gaactttgac gccgcgaggg actcggtgga    28140
cggctacgac tgaatgtcgg gtggaccgg tgcagagcaa cttcgcctga agcacctcga     28200
ccactgccgc cgccctcagt gctttgcccg ctgtcagacc ggtgagttcc agtactttc     28260 cctgcccgac tcgcacccgg acggccggc gcacggggtg cgcttttca tcccgagtca     28320 ggtgcgctct accctaatca gggagtttac cgcccgtccc ctactggcgg agttggaaaa    28380
ggggccttct atcctaacca ttgcctgcat ctgctctaac cctggattgc accaagatct    28440
ttgctgtcat ttgtgtgctg agtataataa aggctgagat cagaatctac tcgggctcct    28500
gtcgccatcc tgtcaacgcc accgtccaag cccggcccga tcagcccgag gtgaacctca    28560
```

```
cctgcggtct gcaccggcgc ctgaggaaat acctagcttg gtactacaac agcactccct    28620
ttgtggttta caacagcttt gaccaggacg gggtctcact gagggataac ctctcgaacc    28680
tgagctactc catcaggaag aacagcaccc tcgagctact tcctccttac ctgcccggga    28740
cttaccagtg tgtcaccggt ccctgcaccc acacccacct gttgatcgta aacgactctc    28800
ttccgagaac agacctcaat aactcctctt cgcagttccc cagaacagga ggtgagctca    28860
ggaaaccccg ggtaaagaag ggtggacgag agttaacact tgtggggttt ctggtgtatg    28920
tgacgctggt ggtggctctt ttgattaagg cttttccttc catgtctgaa ctctccctct    28980
tcttttatga acaactcgac tagtgctaac gggaccctac ccaacgaatc gggattgaat    29040
atcggtaacc aggttgcagt ttcacttttg attaccttca tagtcctctt cctgctagtg    29100
ctgtcgcttc tgtgcctgcg gatcggggc tgctgcatcc acgtttatat ctggtgctgg    29160
ctgtttagaa ggttcggaga ccatcgcagg tagaataaac atgctgctgc ttaccctctt    29220
tgtcctggcg ctggccgcca gctgccaagc cttttccgag gctgacttta tagagcccca    29280
gtgtaatgtg acttttaaag cccatgcaca gcgttgtcat actataatca aatgtgccac    29340
cgaacacgat gaataccttta tccagtataa agataaatca cacaaagtgg cacttgttga    29400
catctggaaa cccgaagacc cttttggaata caatgtgacc gttttccagg gtgacctctt    29460
caaaatttac aattacactt tcccatttga ccagatgtgt gactttgtca tgtacatgga    29520
aaagcagcac aagctgtggc ctccgactcc ccagggctgt gtggaaaatc caggctcttt    29580
ctgcatgatc tctctctgtg taactgtgct ggcactaata ctcacgcttt tgtatatcag    29640
atttaaatca aggcaaagct tcattgatga aaagaaaatg ccttaatcgc tttcacgctt    29700
gattgctaac accgggtttt tatccgcaga atgattggaa tcaccctact aatcacctcc    29760
ctccttgcga ttgcccatgg gttggaacga atcgaagtcc ctgtggggc caatgttacc    29820 ctggtggggc ctgtcggcaa tgctacatta atgtgggaaa aatatactaa aaatcaatgg    29880
gtctcttact gcactaacaa aaatagccac aagcccagag ccatctgcga tgggcaaaat    29940
ctaaccttga ttgatgttca attgctggat gcgggctact attatgggca gctgggtaca    30000
atgattaatt actggagacc ccacagagat tacatgctcc acgtagtaaa gggtcccctt    30060
agcagcccac ccactaccac ctctactacc cccactacca ccactactcc caccaccagc    30120
actgccgccc agcctcctca tagcagaaca accacttttta tcaattccaa gtcccactcc    30180
ccccacattg ccggcgggcc ctccgcctca gactccgaaa ccaccgagat ctgcttctgc    30240
aaatgctctg acgccattgc ccaggatttg gaagatcacg aggaagatga gcatgacttc    30300
gcagatgcat gccaggcatc agagccagaa gcgctgccgg tgggcctcaa acagtatgca    30360
gaccccacca ccacccccga ccttcctcca ccttcccaga gccaagtttt cctgggggaa    30420
aatgaaactc tgcctctctc catactcgct ctgacatctg ttgctatgtt gaccgctctg    30480
ctggtgcttc tatgctctat atgctacctg atctgctgca gaaagaaaaa atctcacggc    30540
catgctcacc agcccctcat gcacttccct taccctccag agctgggcga ccacaaactt    30600
taagtctgca gtaactatct gcccatccct tgtcagtcga cagcgatgag ccccactaat    30660
ctaacggcct ctggacttac aacatcgtct cttaatgaga ccaccgctcc tcaagacctg    30720
tacgatggtg tctccgcgct ggttaaccag tgggatcacc tgggcatatg gtggctcctc    30780
ataggagcag tgaccctgtg cctaatcctg gtctggatca tctgctgcat caaaagcaga    30840
agacccaggc ggcggcccat ctacaggccc tttgtcatca cacctgaaga tgatgatgac    30900
accacttcca ggctgcagag gctaaagcag ctactcttct cttttacagc atggtaaatt    30960
```

```
gaatcatgcc tcgcatttc atctacttgt ctctccttcc acttttctg ggctcttcta    31020 cattggccgc tgtgtcccac atcgaggtag actgcctcac gcccttcaca gtctacctgc    31080
ttttcggctt tgtcatctgc accttttgtct gcagcgttat cactgtagtg atctgcttca    31140
tacagtgcat cgactacgtc tgcgtgcggg tggcttactt tagacaccac ccccagtatc    31200
gcaacaggga catagcggct ctcctaagac ttgtttaaaa tcatggccaa attaactgtg    31260
attggtcttc tgatcatctg ctgcgtccta gccgcgattg ggactcaagc tcctaccacc    31320
accagcgctc ccagaaagag acatgtatcc tgcagcttca agcgtccctg gaatataccc    31380
caatgcttta ctgatgaacc tgaaatctct ttggcttggt acttcagcgt caccgcccctt    31440 cttatcttct gcagtacggt tattgccctt gccatctacc cttcccttga cctgggctgg    31500
aatgctgtca actctatgga atatcccacc ttcccagaac cagacctgcc agacctggtt    31560
gttctaaacg cgtttcctcc tcctgctccc gttcaaaatc agtttcgccc tccgtccccc    31620
acgcccactg aggtcagcta ctttaatcta acaggcggag atgactgaaa acctagacct    31680
agaaatggac ggtctctgca gcgagcaacg cacactagag aggcgccggc aaaaagagct    31740
cgagcgtctt aaacaagagc tccaagacgc ggtggccata caccagtgca aaaaaggtgt    31800
cttctgtctg gtaaaacagg ccacgctcac ctatgaaaaa acaggtgaca cccaccgcct    31860
aggatacaag ctgcccacac agcgccaaaa gttcgccctc atgataggcg aacaacccat    31920
caccgtgacc cagcactccg tggagacaga aggctgcata catgctccct gtaggggcgc    31980
tgactgcctc tacaccttga tcaaaaccct ctgcggtctc agagacctta tccctttcaa    32040
ttaatcataa ctgtaatcaa taaaaaatca cttacttgaa atctgatagc aagcctctgt    32100
ccaatttttt cagcaacact tccttccct cctcccaact ctggtactct aggcgcctcc    32160
tagctgcaaa cttcctccac agtctgaagg gaatgtcaga ttcctcctcc tgtccctccg    32220
cacccacgat cttcatgttg ttgcagatga acgcgcgag atcgtctgac gagaccttca    32280
accccgtgta ccctacgat accgagatcg ctccgacttc tgtccctttc cttaccctc    32340 cctttgtgtc atccgcagga atgcaagaaa atccagctgg ggtgctgtcc ctgcacttgt    32400
cagagcccct taccacccac aatggggccc tgactctaaa aatgggggc ggcctgaccc    32460 tggacaagga agggaatctc acttcccaaa acatcaccag tgtcgatccc cctctcaaaa    32520
aaagcaagaa caacatcagc cttcagaccg ccgcacccct cgccgtcagc tccggggccc    32580
taacactttt tgccactccc cccctagcgg tcagtggtga caaccttact gtgcagtctc    32640
aggcccctct cactttggaa gactcaaaac taactctggc caccaaagga cctaactg    32700 tgtccgaagg caaacttgtc ctagaaacag aggctcccct gcatgcaagt gacagcagca    32760
gcctgggcct tagcgttacg gccccactta gcattaacaa tgcagcccta ggactagatc    32820
tgcaggcacc cattgtctct caaaatggaa aactggctct aaatgtagca ggcccctag    32880 ctgtggccaa tggcattaat gctttgacag taggcacagg caaaggtatt ggtctaaatg    32940
aaaccagcac tcacttgcaa gcaaagttgg tcgccccct aggctttgat accaatggca    33000
acattaagct aagcgttgca ggaggcatga gactaaataa tgacacactt atactagatg    33060
taaactaccc atttgaagct caaggccaac taagtctaag agtgggccag ggtccgctgt    33120
atgtagattc tagcagccat aacctgacca ttagatgcct tagaggatta tacataacat    33180
cgtctaataa ccaaaccggt ctagaggcca acataaaact aacaaaaggc cttgtctatg    33240
atggaaatgc catagcagtc aatgttggtc aaggattgca atacagcact actgccacat    33300
```

| | |
|---|---|
| cggaaggtgt gtatcctata cagtctaaga taggtttggg aatggaatat gataccaacg | 33360 |
| gagccatgat gacaaaacta ggctctggac taagctttga caattcagga gccattgtag | 33420 |
| tgggaaacaa aaatgatgac aggcttactc tgtggactac accagaccca tctcctaact | 33480 |
| gtagaattta ttctgaaaaa gatactaaac taaccttggt gctgactaag tgtggcagcc | 33540 |
| aaatcctagg cacagtatct gcccttgctg tcagaggcag ccttgcgccc atcactaatg | 33600 |
| catccagcat agtccaaata tttctaagat ttgatgaaaa tggactattg atgagcaact | 33660 |
| catcgctaga cggtgattac tggaattaca gaaatgggga ctccactaat agcacaccat | 33720 |
| atacaaatgc agtaggcttt atgcctaatc tagcagccta tcctaaaggt caggctacag | 33780 |
| ctgcaaaaag cagtattgta agccaggtat acatggatgg tgacactact aaacctataa | 33840 |
| cactaaaaat aaacttcaat ggcattgatg aaacaacaga aaataccct gttagtaaat | 33900 |
| attccatgac attctcatgg agctggccca ccgcaagcta cataggccac acttttgcaa | 33960 |
| caaactcttt tacttctcc tacatcgccc aagaataaag aaagcacaga gatgcttgtt | 34020 |
| ttgatttcaa aattgtgtgc ttttatttat tttcagctta cagtatttcc agtagtcatt | 34080 |
| cgaataaagc ttaatcaaac tgcatgagaa cccttccaca tagcttaaat tagcaccagt | 34140 |
| gcaaatggag aaaattcaac ataccttttt tatccagata tcagagaact ctagtggtca | 34200 |
| gttttccccc accctcccag ctcacagaat acacagtcct ttccccccgg ctggctttaa | 34260 |
| acaacactat ctcattggta acagacatat tcttaggtgt aataatccac acggtctctt | 34320 |
| ggcgggccaa gcgctggtcg gtgatgttaa taaactcccc aggcagctct ttcaagttca | 34380 |
| cgtcgctgtc caactgctga agcgctcgcg gctccgactg cgcctctagc ggaggcaacg | 34440 |
| gcaacacccg atccttgatc tataaaggag tagagtcata atcccccata agaatagggc | 34500 |
| ggtgatgcag caacaaggcg cgcagcaact cctgccgccg cctctccgta cgacaggaat | 34560 |
| gcaacggcgt ggtggtctcc tccgcgataa tccgcaccgc tcgcagcatc agcatcctcg | 34620 |
| tcctccggga cagcagcgc atcctgatct cactgagatc ggcgcagtaa gtgcagcaca | 34680 |
| aaaccaagat gttatttaag atcccacagt gcaaagcact gtacccaaag ctcatggcgg | 34740 |
| gaaggacagc ccccacgtga ccatcatacc agatccttag gtaaatcaaa tgacgacctc | 34800 |
| tcataaacac gctggacatg tacatcacct ccttgggcat gcgctgattc accacctctc | 34860 |
| gataccacaa gcatcgctga ttaattaaag accctcaag caccatcctg aaccaggaag | 34920 |
| ccagcacctg acccccgcc aggcactgca gggaccccgg tgaattgcag tggcagtgaa | 34980 |
| gactccagcg ctcgtagccg tgaaccctag agccggtcat tatatccaca ttggcacaac | 35040 |
| acaaacacac tttcatacac tttttcatga ttagcagctc ctctctagtc aggaccatat | 35100 |
| cccaaggaat cacccactct tgaatcaagg taaatcccac acagcagggc aggcctctca | 35160 |
| cataactcac gttatgcata gtgagcgtgt cgcaatctgg aaataccgga tgatcttcca | 35220 |
| tcaccgaagc tcgcgtctcc gtctcaaagg gaggtaaacg gtcccctgtg tagggacagt | 35280 |
| ggcgggataa tcgagatcgt gttgaacgta gagtcatgcc aaagggaaca gcggacgtac | 35340 |
| tcatatttcc tccagcagaa ccaagtgcgc gcgtggcagc tatccctgcg tcttctgtct | 35400 |
| cgccgcctgc cccgctcggt gtagtagttg taatacagcc actccctcag accgtcaagg | 35460 |
| cgctccctgg cgtccggatc tataacaaca ccgtcctgca gcgccgccct gatgacatcc | 35520 |
| accaccgtag agtatgccaa gcccagccag gaaatgcatt cactttgaca gcgagagata | 35580 |
| ggaggagcgg gaagagatgg aagaaccatg atagtaaaag acttttattc caatcgatcc | 35640 |
| tctacaatgt caaagtgtag atctataaga tgacactggt ctcctccgct gagtcgatca | 35700 |

```
aaaataacag ctaaaccaca aacaacacga ttggtcaaat gctccacaag ggcttgcagc    35760
ataaaatcgc ctcgaaagtc caccgcaagc ataacatcaa agccaccgcc cctatcatga    35820
tctataataa aaaccccaca gctatccacc agacccataa agttttcatc tctccatcgt    35880
gaaaaaatat ttacaagctc ctcctttaaa tcacctccaa ccaattgaaa aagttgagcc    35940
aaaccgccct ccaccttcat tttcagcaag cgcatcatga ttgcaaaaat tcaggctcct    36000
gagacacctg tataagattg agaagcggaa cgttaacgtc aatgtttcgc tcgcgaagat    36060
cgcgcctcag tgcaagcatg atataatccc acaggtcgga gcggatcagc gaggacatct    36120
ccccgccagg aaccaactca acggagccta tgctgattat aatacgcata ttcgggggcta    36180 tgctgaccag cacggccccc aaataggcgt actgcatagg cggcgacaaa agtgaacag    36240 tttgggttaa aaaatcaggc aaacagtcgc gcaaaaaagc aagaacatca taaccatgct    36300
catgcaaata gatgcaagta agctcaggaa cgaccacaga aaaatgcaca attttttctct    36360 caaacatgac tgcgagccct gcaaaaaata aaaagaaac attacacaag agtagcctgt    36420
cttacgatgg gatagactac tctaaccaac ataagacggg ccacaacatc gcccgcgtgg    36480
ccataaaaaa aattgtccgt gtgattaaaa agaagcacag atagctggcc agtcatatcc    36540
ggagtcatca cgtgtgaacc cgtgtagacc cccgggttgg acacatcggc caaacaaaga    36600
aagcggccaa tgtacccagg aggaatcata acactaagac gaagatacaa cagaataacc    36660
ccatgagggg gaataacaaa gttagtaggt gaataaaaac gataaacacc cgaaactccc    36720
tcctgcgtag gcaaaatagc accctccccct tccaaaacaa catatagcgc ttccacagca    36780
gccatgacaa aagactcaaa acactcaaaa gactcagtct taccaggaaa ataaaagcac    36840
tctcacagca ccagcactaa tcagagtgtg aagagggcca agtgccgaac gagtatatat    36900
aggaataaaa aatgacgtaa atgtgtaaag gtcagaaaac gcccagaaaa atacacagac    36960
caacgcccga aacgaaaacc cgcgaaaaaa tacccagaac ttcctcaaca accgccactt    37020
ccggtttctc acggtacgtc acttccgcaa gaaaagcaaa actacatttc ccacatgtgt    37080
aaaaacgaaa ccccgcccct tgtaactgcc cacaacttac atcatcaaaa cataaactcc    37140
tacgtcaccc gccccgcctc tccccgccca cctcattatc atattggcca caatccaaaa    37200
taaggtatat tat                                                      37213
```

<210> SEQ ID NO 24  
<211> LENGTH: 37216  
<212> TYPE: DNA  
<213> ORGANISM: Gorilla beringei beringei

<400> SEQUENCE: 24

```
ataatatacc ttattttgga ttgtggccaa tatgataatg aggtgggcgg ggagaggcgg        60
ggcgggtgac gtaggacgcg cgagtagggt tgggaggtgt ggcggaagtg tggcatttgc       120
aagtgggagg agctcacatg caagcttccg tcgcggaaaa tgtgacgttt ttgatgagcg       180
ccgcctacct ccggaagtgc caattttcgc gcgcttttca ccggatatcg tagtaatttt       240
gggcgggacc atgtaagatt tggccatttt cgcgcgaaaa gtgaacggg gaagtgaaaa       300 ctgaataata gggcgttagt catagcgcgt aatatttacc gagggccgag ggactttgac       360
cgattacgtg gaggactcgc ccaggtgttt tttacgtgaa tttccgcgtt ccgggtcaaa       420
gtctccgttt ttattgtcac cgtcatttga cgcggagggt atttaaaccc gctgcgctcc       480
tcaagaggcc actcttgagt gccagcgaga agagttttct cctctgctcc gcttcggtga       540
```

```
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagttttttgt ctaggtgggc   1080 tttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctcccctg aaattcaccc    1320 agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca ataccttac tatttggagg   1740 tatctgtggg gctctactca ggccaagttg gtttccagaa ttaagcagga ttacaagtgc   1800
gattttgaag agcttttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca aacaaatgg    2040 aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgttttcca gaactgagac gggtcctgac tatcagggag gatggtcagt   2280
ttgtgaagaa gtttaagagg gatcggggtg agggagatga tgaggcggct agcaatttag   2340 ctttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcaccttagg catcctctct gagggcaact   2940
```

```
ccagggtgcg ccataatgtg gcttcgaact gcggttgctt catgcaagtg aaggggtga       3000 gcgttatcaa gcataactcg gtgtgtggaa actgcgagga tcgcgcctcc cagatgctga      3060
cctgctttga tggcaactgt cacctgttga agaccattca tataagcagc caccccagaa      3120
aggcctggcc cgtgtttgag cataacatct tgacccgctg ctccttgcat ctggggtca       3180 ggaggggtat gttcctgcct taccagtgta actttagcca cactaaaatc ctgctggaac      3240
ccgagtgcat gaccaaggtc agcctgaatg gtgtgtttga tgtgactctg aaaatctgga     3300
aggtgctgag gtatgatgag accaggacca ggtgccgacc ctgcgagtgc ggcggcaagc     3360
acatgagaaa tcagcctgtg atgttggatg tgaccgagga gcttaggcct gaccatctgg     3420
tgctggcctg caccagggcc gagtttgggt ctagcgatga ggataccgat tgaggtgggt     3480
aaggtgggcg tggctagaag ggtggggcgt gtataaattg ggggtctaag ggtctctctg     3540 tttgtcttg caacagccgc cgccatgagc gacaccggca acagctttga tggaagcatc       3600
tttagcccct atctgacagt gcgcatgcct cactgggctg gagtgcgtca gaatgtgatg      3660
ggttccaacg tggatggacg ccccgttctg ccttcaaatt cgtctacaat ggcctacgcg     3720
accgtgggag gaactccgct ggacgccgcg acctccgccg ccgcctccgc cgccgccgcg     3780
accgcgcgca gcatggctac ggacctttac agctcttttgg tggcgagcgg cgcggcctct   3840
cgcgcgtctg ctcgggatga gaaactgacc gctctgctgc ttaaactgga agacttgacc    3900
cgggagctgg gtcaactgac ccagcaggtc tccagcttgc gtgagagcag ccttgcctcc    3960
ccctaatggc ccataatata aataaaagcc agtctgtttg gattaagcaa gtgtatgttc    4020
tttatttaac tctccgcgcg cggtaagccc gggaccagcg gtctcggtcg tttagggtgc     4080
ggtggattct ttccaacacg tggtacaggt ggctctggat gtttagatac atggcatga    4140 gtccatccct ggggtggagg tagcaccact gcagagcttc gtgctcgggg gtggtgttgt     4200
atatgatcca gtcgtagcag gagcgctggg cgtggtgctg aaaaatgtcc ttaagcaaga   4260
ggcttatagc taggggagg cccttggtgt aagtgtttac aaatctgctc agttgggagg      4320
ggtgcatccg gggggatata atgtgcatct tggactggat ttttaggttg gctatgttcc    4380
cacccagatc ccttctggga ttcatgttgt gcaggaccac cagcacggta tatccagtgc    4440
acttgggaaa tttatcgtgg agcttagacg ggaatgcatg gaagaacttg gagacgccct     4500
tgtggcctcc cagattttcc atacattcgt ccatgatgat ggcaatgggc ccgtgggaag    4560
ctgcctgagc aaaaatgttt ctgggatcgc tcacatcgta gttatgttcc agggtgaggt   4620
catcatagga catcttacg aatcggggc ggagggtccc ggactggggg atgatggtac      4680
cctcgggccc cggggcgtag ttcccctcac agatctgcat ctcccaggct ttcatttcag    4740
agggagggat catatccacc tgcggagcga tgaaaaacac agtttctggc gcaggggaga    4800
ttaactggga tgagagcagg tttctgagca gctgtgactt tccacagccg gtgggcccat   4860
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgccagaag gcgctcgccg cccagcgaaa gcagctcttg caaggaagca aaattttca    5040 gcggttttag gccgtcggcc gtgggcatgt ttttcagcgt ctgggtcagc agttccagcc    5100
tgtcccacag ctcggtgatg tgctctacgg catctcgatc cagcagatct cctcgtttcg   5160
cgggttgggg cggcttcgc tgtagggcac cagccgatgg gcgtccagcg gggcagagt     5220 catgtccttc catgggcgca gggtcctcgt cagggtggtc tgggtcacgg tgaaggggtg    5280
```

```
cgctccgggt tgggcgctgg ccagggtgcg cttgaggctg gttctgctgg tgctgaatcg   5340
ctgccgctct tcgccctgcg cgtcggccag gtagcatttg accatggtct cgtagtcgag   5400
accctcggcg gcgtgcccct tggcgcggag ctttcccttg gaggtggcgc cgcacgaggg   5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgctttttg atgcgtttct tacctcggct   5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt cccctcctc   5880
cgcgtccaga aaagtgattg gcttgtaggt gtaggacacg tgaccggggg ttcccgacgg   5940
gggggtataa aaggggtggg cgcccctttc atcttcactc tcttccgcat cgctgtctgc   6000
gagggccagc tgctggggta agtattccct ctcgaaggcg gcatgaccct cagcgctcag   6060
gttgtcagtt tctaaaaatg aggaggattt gatgttcacc tgtccggagg tgatacccttt  6120
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcaggc gctcgttggt   6420
ccagcagagg cggccgccct tgcgcgagca aagggggggt aggggggtcca gctggtcctc   6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg aggggcgggc cccagggcat ggggtgggtg agcgcggagg cgtacatgcc   6660
gcagatgtca tacacgtaca ggggttccct gaggatgccg aggtaggtgg ggtagcagcg   6720
ccccccgcgg atgctggcgc gcacgtagtc atagagctcg tgggaggggg ccagcatgtt   6780
gggcccgagg ttggtgcgct gggggcgctc ggcgcggaag gcgatctgcc tgaagatggc   6840
atgggagttg gaggagatgg tgggccgctg gaagacgttg aagcttgctt cttgcaagcc   6900
caccgagtcc ctgacgaagg aggcgtagga ctcgcgcagc ttgtgcacca gctcggcggt   6960
gacctggacg tcgagcgcgc agtagtcgag ggtctcgcgg atgatgtcat acttatcctc   7020
ccccttcttt ttccacagct cgcggttgag gacgaactct tcgcggtctt ccagtactc   7080
ttggagggga aacccgtccg tgtccgaacg gtaagagcct agcatgtaga actggttgac   7140
ggcctggtag gggcaacagc ccttctccac gggcagcgcg taggcctgcg ccgccttgcg   7200
gagggaggtc tgggtgaggg cgaaagtgtc cctgaccatg actttgaggt attgatgttt   7260
gaagtctgtg tcatcgcagc cgccctgttc ccacagggtg tagtccgtgc gcttttttgga  7320
gcgcgggttg ggcagggaga aggtgaggtc attgaagagg atcttccccg ctcgaggcat   7380
gaagtttctg gtgatgcgaa agggccctgg gaccgaggag cggttgttga tgacctgggc   7440
ggccaggacg atctcgtcaa agccgtttat gttgtggccc acgatgtaga gctccaaaaa   7500
gcggggctgg cccttgatgg aggggagctt tttgagttcc tcgtaggtga gctcctcggg   7560
cgattccagg ccgtgctcct ccagggccca gtccttgcaag tgagggttgg ccgccaggaa   7620
ggatcgccag aggtcgcggg ccatgagggt ctgcaggcgg tcgcggaagg ttctgaactg   7680
```

-continued

```
tcgccccacg gccatctttt cggggqtgat gcagtagaag gtgagggggt ctttctccca   7740
ggggtcccat ctgagctctc gggcgaggtc gcgcgcggcg gcgaccagag cctcgtcgcc   7800
ccccagtttc atgaccagca tgaagggcac gagctgcttg ccaaaggctc ccatccaagt   7860
gtaggtctct acatcgtagg tgacaaagag gcgctccgtg cgaggatgag agccgatcgg   7920
gaagaactgg atctcccgcc accagttgga ggattggctg ttgatgtggt gaaagtagaa   7980
gtcccgtctg cgggccgagc actcgtgctg gcttttgtaa agcgaccgc agtactggca    8040
gcgctgcacg ggttgtatat cttgcacgag gtgaacctgg cgacctctga cgaggaagcg   8100
cagcgggaat ctaagtcccc cgcctggggt cccgtgtggc tggtggtctt ctactttggt   8160
tgtctggccg ccagcatctg tctcctggag ggcgatggtg agcagaccca ccacgccgcg   8220
agagccgcag gtccagatct cggcgctcgg cgggcggagt ttgatgacga catcgcgcac   8280
attggagctg tccatggtct ccagctcccg cggcggcagg tcagctggga gttcctggag   8340
gttcacctcg cagagacggg tcaaggcgcg gcagtgttg agatggtatc tgatttcaag    8400
ggcgtgttg gcggcggagt cgatggcttg caggaggccg cagccccggg gggccacgat    8460
ggttccccgc ggggcgcgag gggaggcgga agctgggggt gtgttcagaa gcggtgacgc   8520
gggcgggccc ccggaggtag ggggggttcc ggccccacag gcatgggcgg caggggcacg   8580
tcttcgccgc gcgcgggcag gggctggtgc tggctccgaa gagcgcttgc gtgcgcgacg   8640
acgcgacggt tggtgtcctg tatctgacgc ctctgagtga agaccacggg tcccgtgacc   8700
ttgaacctga aagagagttc gacagaatca atctcggcat cgttgacagc ggcctggcgc   8760
aggatctcct gcacgtcgcc cgagttgtcc tggtaggcga tctctgccat gaactgctcg   8820
atctcttctt cctggagatc tcctcgtccg gcgcgctcca cggtggccgc caggtcgttg   8880
gagatgcgac ccatgagctg tgagaaggcg ttgagcccgc cctcgttcca gacccggctg   8940
tagaccacgc cccctcggc gtcgcgagcg cgcatgacca cctgggccag gttgagctcc    9000
acgtgtcgcg tgaagacggc gtagttgcgc aggcgctgga aaaggtagtt cagggtggtg   9060
gcggtgtgct cggcgacgaa gaagtacatg acccagcgcc gcaacgtgga ttcattgatg   9120
tcccccaagg cctccaggcg ctccatggcc tcgtagaagt ccacggcgaa gttgaaaaac   9180
tgggagttgc gagcggacac ggtcaactcc tcctccagaa gacggatgag ctcggcgaca   9240
gtgttgcgca cctcgcgctc gaaggccacg ggggcgctt cttcctcttc cacctcttct    9300
tccatgatcg cttcttcttc ttcctcagcc gggacgggag ggggcggcgg cggcggggga   9360
ggggcgcggc ggcggcggcg gcgcaccggg aggcggtcga tgaagcgctc gatcatctcc   9420
ccccgcatgc ggcgcatggt ctcggtgacg gcgcggccgt tctcccgggg gcgcagctcg   9480
aagacgccgc ctctcatctc gccgcgggc gagcggccgt gaggtagcga gacggcgctg    9540
actatgcatc ttaacaattg ctgtgtaggt acaccgccga gggacctgat tgagtccaga   9600
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt cttttccaccg gcacctcttc tccttcctct   9900
tctccatctc gccggtggtt tctcgcgccg cccatgcgcg tgaccccaaa gcccctgagc   9960
ggctgcagca gggccaggtc ggcgaccacg cgctcggcca agatggcctg ctgcacctga  10020
```

```
gtgagggtcc tctcgaagtc atccatgtcc acgaagcggt ggtaggcgcc cgtgttgatg    10080
gtgtaggtgc agttggccat gacggaccag ttgacggtct ggtgtcccgg ctgcgagagc    10140
tccgtgtacc gcaggcgcga gaaggcgcgg gaatcgaaca cgtagtcgtt gcaagtccgc    10200
accagatact ggtagcccac caggaagtgc ggcggaggtt ggcgatagag gggccagcgc    10260
tgggtggcgg gggcgccggg cgccaggtct tccagcatga ggcggtggta tccgtagatg    10320
tacctggaca tccaggtgat gccggcgcg gtggtggtgg cgcgcgcgta gtcgcggacc     10380
cggttccaga tgtttcgcag gggcgagaag tgttccatgg tcggcacgct ctggccggtg    10440
aggcgcgcgc agtcgttgac gctctataca cacacaaaaa cgaaagcgtt tacagggctt    10500
tcgttctgta gcctggagga agtaaatgg gttgggttgc ggtgtgcccc ggttcgagac     10560
caagctgagc tcggccggct gaagccgcag ctaacgtggt attggcagtc ccgtctcgac    10620
ccaggccctg tatcctccag gatacggtcg agagcccttt tgctttcttg gccaagcgcc    10680
cgtggcgcga tctgggatag atggtcgcga tgagaggaca aaagcggctc gcttccgtag    10740
tctggagaaa caatcgccag ggttgcgttg cggcgtaccc cggttcgagc ccctatggcg    10800
gcttgaatcg gccggaaccg cggctaacga gggccgtggc agcccccgtcc tcaggacccc    10860
gccagccgac ttctccagtt acgggagcga gcccctttttg tttttattt tttagatgca    10920
tcccgtgctg cggcagatgc gcccctcgcc ccggcccgat cagcagcagc aacagcaggc    10980
atgcagaccc ccctctcccc tttccgcccc ggtcaccacg gccgcggcgg ccgtgtcggg    11040
cgcgggggc gcgctggagt cagatgagcc accgcggcgg cgacctaggc agtatctgga    11100
cttgaagag ggcgagggac tggcgcggct ggggcgaac tctccagagc gccacccgcg       11160
ggtgcagttg aaaagggacg cgcgcgaggc gtacctgccg cggcagaacc tgtttcgcga    11220
ccgcgggggc gaggagcccg aggagatgcg agactgcagg ttccaagcgg ggcgcgagct    11280
gcggcgcggg ctggacagac agcgcctgct gcgcgaggag gactttgagc ccgacacgca    11340
gacgggcatc agccccgcgc gcgcgcacgt agccgcggcc gacctggtga ccgcctacga    11400
gcagacggta aaccaggagc gcaacttcca aaagagcttc aacaaccacg tgcgcacgct    11460
ggtgcgcgc gaggaggtga ccctgggtct catgcatctg tgggacctgg tggaggcgat     11520
cgtgcagaac cccagcagca agccctgac cgcgcagctg ttcctggtgg tgcagcacag     11580
cagggacaac gaggccttca gggaggcgct gctgaacatc accgagccgg aggggcgctg    11640
gctcctggac ctgataaaca tcctgcagag catagtggtg caggagcgca gcctgagcct    11700
ggccgagaag gtggcggcca tcaactactc tatgctgagc ctgggcaagt tctacgcccg    11760
caagatctac aagaccccct acgtgccat agacaaggag gtgaagatag acagcttcta     11820
catgcgcatg gcgctgaagg tgctgaccct gagcgacgac ctgggagtgt accgcaacga    11880
gcgcatccac aaggccgtga cgccagccg gcggcgcgag ctgagcgacc gcgagctgat     11940
gcacagtctg cagcgcgcgc tgaccggcgc gggcgagggc gacagggagg tcgagtccta    12000
cttcgacatg ggggccgacc tgcactggca gccgagccgc cgcgccctgg aggcggcggg    12060
ggcgtacggc ggcccctgg cggccgatga ccaggaagag gaggactatg agctagagga     12120
gggcgagtac ctgaggact gacctggctg gtggtgtttt ggtatagatg caagatccga     12180
acgtggcgga cccggcggtc cgggcggcgc tgcaaagcca gccgtccggc attaactcct    12240
ctgacgactg ggccgcggcc atgggtcgca tcatggccct gaccgcgcgc aaccccgagg    12300
cttttcaggca gcagcctcag gccaaccggc tggcggccat cttggaagcg gtagtgcccg   12360
cgcgctccaa ccccacccac gagaaggtgc tggccatagt caacgcgctg gcggagagca    12420
```

```
gggccatccg cgcggacgag gccggactgg tgtacgatgc gctgctgcag cgggtggcgc   12480
ggtacaacag cggcaacgtg cagaccaacc tggaccgcct ggtgacggac gtgcgcgagg   12540
ccgtggcgca gcgcgagcgc ttgcatcagg acggtaacct gggctcgctg gtggcgctaa   12600
acgccttcct cagcacccag ccggccaacg taccgcgggg gcaggaggac tacaccaact   12660
ttttgagcgc gctgcggctg atggtgaccg aggtccctca gagcgaggtg taccagtcgg   12720
ggcccgacta cttcttccag accagcagac agggcttgca aaccgtgaac ctgagccagg   12780
cttttcaagaa cctgcggggg ctgtggggag tgaaggcgcc caccggcgac cgggctacgg   12840
tgtccagcct gctaaccccc aactcgcgcc tgctgctgct gctgatcgcg cccttcacgg   12900
acagcgggag cgtctcgcgg gagacctatc tgggccacct gctgacgctg taccgcgagg   12960
ccatcgggca ggcgcaggtg gacgagcaca ccttccaaga gatcaccagc gtgagccacg   13020
cgctggggca ggaggacacg ggcagcctgc aggcgaccct gaactacctg ctgaccaaca   13080
ggcggcagaa gattcccacg ctgcacagcc tgacccagga ggaggagcgc atcttgcgct   13140
acgtgcagca gagcgtgagc ctgaacctga tgcgcgacgg cgtgacgccc agcgtggcgc   13200
tggacatgac cgcgcgcaac atggaaccgg gcatgtacgc ctcccaccgg ccgtttatca   13260
accgcctgat ggactacttg catcgggcgg cggccgtgaa ccccgagtac ttcactaatg   13320
ccattctgaa tccccactgg atgcccccte cgggtttcta caacggggac tttgaggtgc   13380
ccgaggtcaa cgacgggttc ctctgggatg acatggatga cagtgtgttc tcacccaacc   13440
cgctgcgcgc cgcgtctctg cgattgaagg agggctctga cagggaagga ccgaggagtc   13500
tggcctcctc cctggctctg ggagcggtgg gcgccacggg cgcggcggcg cggggcagta   13560
gcccettccc cagcctggca gactctctga cagcgggcg ggtgagcagg ccccgcttgc   13620
taggcgagga ggagtatctg aacaactccc tgctgcagcc cgcgagggac aagaacgctc   13680
agcggcagca gtttcccaac aatgggatag agagcctggt ggacaagatg tccagatgga   13740
agacgtatgc gcaggagtac aaggagtggg aggaccgcca gccgcggccc ttgccgcccc   13800
ctaggcagcg ctggcagcgg cgcgcgtcca accgccgctg gaggcagggg cccgaggacg   13860
atgatgactc tgcagatgac agcagcgtgt tggacctggg cgggagcggg aacccctttt   13920
cgcacctgcg cccacgcctg ggcaagatgt tttaaaagaa aaaaaaaat aaaactcacc   13980
aaggccatgg cgacgagcgt tggttttttg ttcccttcct tagtatgcgg cgcgcggcga   14040
tgttcgagga ggggcctccc ccctcttacg agagcgcgat ggggatttct cctgcggcgc   14100
ccctgcagcc tccctacgtg cctcctcggt acctgcaacc tacagggggg agaaatagca   14160
tctgttactc tgagctgcag cccctgtacg ataccaccag actgtacctg gtggacaaca   14220
agtccgcgga cgtggcctcc ctgaactacc agaacgacca cagcgatttt ttgaccacgg   14280
tgatccaaaa caacgacttc accccaaccg aggccagcac ccagaccata aacctggata   14340
acaggtcgaa ctgggcggc gacctgaaga ccatcttgca caccaacatg cccaacgtga   14400
acgagttcat gttcaccaac tctttttaagg cgcgggtgat ggtggcgcgc gagcaggggg   14460
aggcgaagta cgagtgggtg gacttcacgc tgcccgaggg caactactca gagaccatga   14520
ctctcgacct gatgaacaat gcgatcgtgg aacactatct gaaagtgggc aggcagaacg   14580
gggtgaagga aagcgatatc ggggtcaagt ttgacaccag aaacttccgt ctgggctggg   14640
accccgtgac cgggctggtc atgccggggg tctacaccaa cgaggccttt catcccgaca   14700
tagtgcttct gcccggctgt ggggtggact tcacccagag ccggctgagc aacctgctgg   14760
```

-continued

```
gcattcgcaa gcggcagcct ttccaggagg gtttcaagat cacctatgag gatctgaagg   14820
ggggcaacat tcccgcgctc cttgatctgg acgcctacga ggagagcttg aaacccgagg   14880
agagcgctgg cgacagcggc gagagtggcg aggagcaagc cggcggcggt ggcggcgcgt   14940
cggtagaaaa cgaaagtacg cccgcagtgg cggcggacgc tgcggaggtc gagccggagg   15000
ccatgcagca ggacgcagag gagggcgcac aggagggcgc gcagaaggac atgaacgatg   15060
gggagatcag gggagacaca ttcgccaccc ggggcgaaga aaaagaggca gaggcggcgg   15120
cggcggcgac ggcggaggcc gaaaccgagg ttgaggcaga ggcagagccc gagaccgaag   15180
ttatggaaga catgaatgat ggagaacgta ggggcgacac gttcgccacc cggggcgaag   15240
agaaggcggc ggaggcagaa gccgcggctg aggaggcggc tgcggctgcg gccaagactg   15300
aggctgcggc taaggctgag gtcgaagcca atgttgcggt tgaggctcag gctgaggagg   15360
aggcggcggc tgaagcagtt aaggaaaagg cccaggcaga gcaggaagag aaaaaacctg   15420
tcattcaacc tctaaaagaa gatagcaaaa agcgcagtta caacgtcatc gagggcagca   15480
cctttaccca gtaccgcagc tggtacctgg cgtacaacta cggcgacccg gtcaaggggg   15540
tgcgctcgtg gaccctgctc tgcacgccgg acgtcacctg cggctccgag cagatgtact   15600
ggtcgctgcc gaacatgatg caagacccgg tgaccttccg ctccacgcgg caggttagca   15660
acttcccggt ggtgggcgcc gaactgctgc ccgtgcactc caagagtttt tacaacgagc   15720
aggccgtcta ctcccagctg atccgccagg ccacctctct gacccacgtg ttcaatcgct   15780
ttcccgagaa ccagattttg gcgcgcccgc cggcccccac catcaccacc gtgagtgaaa   15840
acgttcctgc cctcacagat cacggggacg taccgctgcg caacagcatc tcaggagtcc   15900
agcgagtgac cattactgac gccagacgcc ggacctgccc ctacgtttac aaggccttgg   15960
gcatagtctc gccgcgcgtc ctctccagtc gcactttttta aaacacatct acccacacgt   16020
tccaaaatca tgtccgtact catctcaccc agcaacaaca ccggctgggg gctgcgcgcg   16080
cccagcaaga tgtttggagg ggcgaggaag cgctccgacc agcaccctgt gcgcgtgcgc   16140
ggccactacc gcgcgccctg gggagcgcac aagcgcgggc gcacagggcg caccactgtg   16200
gacgacgtca ttgactccgt agtggagcaa gcgcgccact acacacccgg cgcgccgacc   16260
gcccccgccg tgtccaccgt ggaccaggcg atcgaaagcg tggtacaggg cgcgcggcac   16320
tatgccaacc ttaaaagtcg ccgccgccgc gtggcccgcc gccatcgccg gagacccccgg   16380 gccaccgccg ccgcgcgcct tactaaggct ctgctcaggc gcgccaggcg aactggccac   16440
cgggccgcca tgagggccgc acggcgggct gccgctgccg caagcgtcgt ggccccgcgg   16500
gcacgaaggc gcgcggccgc tgccgccgcc gccgccattt ccagcttggc ctcgacgcgg   16560
cgcggtaaca tatactgggt gcgcgactcg gtaaccggca cgcgggtacc cgtgcgcttt   16620 cgcccccgc ggaattagca caagacaaca tacacactga gtctcctgct gttgtgtatc   16680
ccagcggcga ccgtcagcag cggcgacatg tccaagcgca aaattaaaga agagatgctc   16740
caggtcatcg cgccggagat ctatgggccc ccgaagaagg aggaggatga ttacaagccc   16800
cgcaagctaa agcgggtcaa aaagaaaaag aaagatgatg atgacgaggc ggtggagttt   16860
gtccgccgca tggcacccag gcgccccgtg cagtggaagg gccggcgcgt gcagcgcgtt   16920
ttgcgccccg gcaccgcggt ggtcttcacg cccggcgagc gctccacgcg cactttcaag   16980
cgggtgtacg atgaggtgta cggcgacgag gacctgttgg agcaggccaa ccagcgcttt   17040
ggggagtttg catatgggaa acggccccgc gagagtctaa aagaggacct gctgcgctsa   17100
ccgctggacg agggcaatcc cacccccgagt ctgaagccgg taaccctgca acaggtgctg   17160
```

```
cctttgagcg cgcccagcga gcataagcga gggttgaagc gcgaaggcgg ggacctggcg   17220
cccaccgtgc agttgatggt gcccaagcgg cagaagctgg aggacgtgct ggagaaaatg   17280
aaagtagagc ccgggatcca gcccgagatc aaggtccgcc ccatcaagca ggtggcgccc   17340
ggcgtgggag tccagaccgt ggacgttagg attcccacgg aggagatgga aacccaaacc   17400
gccactccct cttcggcggc cagcgccacc accggcaccg cttcggtaga ggtgcagacg   17460
gaccCCtggc tacccgccac cgctgttgcc gccgccgccc ccgttcgcg cgggcgcaag    17520 agaaattatc cagcggccag cgcgctcatg ccccagtacg cactgcatcc atccatcgtg   17580 cccaccccg gctaccgcgg gtactcgtac cgcccgcgca gatcagccgg cactcgcggc    17640
cgccgccgcc gtgcgaccac aaccagccgc cgccgtcgcc gccgccgcca gccagtgctg   17700 accccccgtgt ctgtaaggaa ggtggctcgc tcggggagca cgctggtggt gcccagagcg  17760
cgctaccacc ccagcatcgt ttaaagccgg tctctgtatg gttcttgcag atatggccct   17820
cacttgtcgc ctccgcttcc cggtgccggg ataccgagga gaactcacc gccgcagagg    17880 catggcgggc agcggtctcc gcggcggccg tcgccatcgc cggcgcgcaa aaagcaggcg   17940
catgcgcggc ggtgtgctgc ctctgctaat cccgctaatc gccgcggcga tcggtgccgt   18000
acccgggatc gcctccgtgg ccctgcaggc gtcccagaaa cgttgactct tgcaaccttg   18060
caagcttgca ttttttggag gaaaaaataa aaaaaaagtc tagactctca cgctcgcttg   18120
gtcctgtgac tattttgtag aaaaaaagat ggaagacatc aactttgcgt cgctggcccc   18180
gcgtcacggc tcgcgcccgt tcatgggaga ctggacagat atcggcacca gcaatatgag   18240
cggtggcgcc ttcagctggg gcagtctgtg gagcggcctt aaaaattttg gttccaccat   18300
taagaactat ggcaacaaag cgtggaacag cagcacgggc cagatgctga gagacaagtt   18360
gaaagagcag aacttccagg agaaggtggc gcagggcctg gcctctggca tcagcggggt   18420
ggtggacata gctaaccagg ccgtgcagaa aaagataaac agtcatctgg accccgtcc    18480 tcaggtggag gaaatgcctc cagcgatgga gacggtgtct cccgagggca aggcgaaaa    18540 gcgcccgcgg cccgacagag aagagaccct ggtgtcacac accgaggagc cgccctctta   18600
cgaggaggca gtcaaggccg gcctgcccac cactcgcccc atagccccca tggccaccgg   18660
tgtggtgggc cacaggcaac acactcccgc aacactagat ctgccccgc cgtccgagcc    18720 gccgcgccag ccaaaggcgg cgacggtgcc cgctccctcc acttccgccg ccaacagagt   18780 gccctgcgc cgcgccgcga gcggccccg ggcctcgcga gttagcggca actggcagag    18840
cacactgaac agcatcgtgg gcctgggagt gaggagtgtg aagcgccgcc gttgctactg   18900
aatgagcaag ctagctaacg tgttgtatgt gtgtatgcgt cctatgtcgc cgccagagga   18960
gctgttgagc cgccggcgcc gtctgcactc cagcgaattt caagatggcg accccatcga   19020
tgatgcctca gtggtcgtac atgcacatct cgggccagga cgcttcggag tacctgagcc   19080
ccgggctggt gcagttcgcc cgcgccacag acacctactt caacatgagt aacaagttca   19140
ggaaccccac tgtggcgccc acccacgatg tgaccacgga ccggtcgcag cgcctgacgc   19200
tgcggttcat ccccgtggat cgggaggaca ccgcctactc ttacaaggcg cggttcacgc   19260
tggccgtggg cgacaaccgc gtgctggaca tggcctccac ttactttgac atcaggggg    19320 tgctggacag ggccccacc ttcaagccct actcgggtac tgcctacaac tccctggccc   19380
ccaagggcgc tcccaattct tgcgagtggg aacaagatga accagctcag gcagcaatag   19440
ctgaagatga agaagaactt gaagaagaac aagctcagga cgaacaggcg cccactaaga   19500
```

```
aaacccatgt atacgcccag gcacctcttt ctggtgaaaa aattactaag gatggtttgc   19560
aaataggtgt ggatgccaca caggcgggag ataaccctat atatgctgat aaaacattcc   19620
aacccgaacc tcagataggt gagtctcagt ggaacgaggc tgatgccaca gtagcaggag   19680
gcagagtctt aaaaaagacc accccctatga gaccttgcta tggatcctat gccaaaccta   19740
ctaatgccaa tggcggtcaa gggatcatgg tggccaatga tcagggagcg cttgaatcta   19800
aagttgagat gcaattttc tccaccacaa cgtctcttaa tgtaagggaa ggtgaaaaca   19860
atcttcagcc aaaagtagtg ctatacagcg aagatgttaa cttggaatcc cctgacactc   19920
atttgtctta caaacctaaa aaggatgaca ccaactctaa aatcatgttg ggtcagcaag   19980
ccatgcccaa cagacccaac ctcattgctt ttagggacaa cttttattgga cttatgtact   20040 acaacagcac aggcaacatg ggagtgctgg caggacaggc ctcccagcta aacgctgtgg   20100
tagacttgca agacagaaac acagagctgt cataccaact gatgcttgat tccattggag   20160
acagatcaag atacttttcc atgtggaacc aggcagtgga cagctatgac ccagatgtca   20220
gaatcattga aaaccatggg gttgaagatg agctgcccaa ctattgcttt cccctgggcg   20280
gtattggaat tacagacaca taccagtgca taaaaccaac cgcagctgct aataacacta   20340
catggtctaa ggatgaagaa tttagtgatc gcaatgaaat aggggtggga aacaacttcg   20400
ccatggagat caacatccag gccaacctct ggaggaactt cctctatgcg aacgtggggc   20460
tctacctgcc agacaagctc aagtacaacc ccaccaacgt ggacatctct gacaacccca   20520
acacctatga ctacatgaac aagcgtgtgg tggctcccgg cctggtggac tgctttgtca   20580
atgtgggagc caggtggtcc ctggactaca tggacaacgt caacccccttc aaccaccacc   20640 gcaatgcggg tctgcgctac cgctccatga tcctgggcaa cggggcgctac gtgcccttcc   20700 acattcaggt gccccagaag ttctttgcca tcaagaacct cctcctcctg ccgggctcct   20760
acacttacga gtggaacttc aggaaggatg tcaacatggt cctgcagagc tctctgggca   20820
atgaccttag ggtggacggg gccagcatca agtttgacag cgtcaccctc tatgctacct   20880 tcttcccat ggctcacaac accgcctcca cgctcgaggc catgctgagg aacgacacca   20940
acgaccagtc cttcaatgac tacctctctg gggccaacat gctctacccc atccccgcca   21000
aggccaccaa cgtgcccatc tccattccct ctcgcaactg ggccgccttc agaggctggg   21060
cctttacccg ccttaagacc aaggaaaccc cctccctggg ctcgggtttt gaccccactc   21120
ttgtctactc gggatccatc ccctacctgg atggcacctt ctacctcaac cacacttttta   21180 agaagatatc catcatgtat gactcctccg tcagctggcc gggcaatgac cgcctgctca   21240 ccccccaatga gttcgaggtc aagcgcgccg tggacggcga gggctacaac gtggcccagt   21300
gcaacatgac caaggactgg ttcctggtgc agatgctggc caactacaac ataggctacc   21360
agggcttcta catcccagag agctacaagg acaggatgta ctccttcttc agaaatttcc   21420
aacccatgag caggcaggtg gtggacgaga ccaaatacaa ggactatcag gccattggca   21480
tcactcacca gcacaacaac tcgggattcg tgggctacct ggctcccacc atgcgcgagg   21540
ggcaggccta cccccgccaac ttcccctacc cgttgatagg caaaaccgcg gtcgacagcg   21600
tcacccagaa aaagttcctc tgcgaccgca ccctctggcg catcccccttc tctagcaact   21660 tcatgtccat gggtgcgctc acggacctgg gccagaacct gctctatgcc aactccgccc   21720
atgcgctgga catgacttttt gaggtggacc ccatggacga gcccaccctt ctctatattg   21780
tgtttgaagt gttcgacgtg gtcagagtgc accagccgca ccgcggtgtc atcgagaccg   21840
tgtacctgcg cacgcccttc tcggccggca acgccaccac ctaaggagac agcgccgccg   21900
```

```
cctgcatgac gggttccacc gagcaagagc tcagggccat cgccagagac ctgggatgcg   21960
gaccctattt tttgggcacc tatgacaaac gcttcccggg cttcatctcc cgagacaagc   22020
tcgcctgcgc catcgtcaac acggccgcgc gcgagaccgg gggcgtgcac tggctggcct   22080
ttggctggga cccgcgctcc aaaacctgct acctcttcga cccctttggc ttctccgatc   22140
agcgcctcag acagatctat gagtttgagt acgaggggct gctgcgccgc agcgcgcttg   22200
cctcctcgcc cgaccgctgc atcacccttg agaagtccac cgagaccgtg caggggcccc   22260
actcggccgc ctgcggtctc ttctgctgca tgttttttgca cgcctttgtg cgctggcccc   22320
agagtcccat ggatcgcaac cccaccatga acttgctcaa gggagtgccc aacgccatgc   22380
tccagagccc ccaggtccag cccaccctgc gccacaacca ggaacagctc taccgcttcc   22440
tggagcgcca ctccccctac ttccgcagtc acagcgcgca catccggggg gccacctctt   22500
tctgccactt gcaagaaaac atgcaagacg gaaaatgatg tacagctcgc ttttttaataa   22560 atgtaaagac tgtgcacttt atttatacac gggctctttc tggttattta ttcaacaccg   22620
ccgtcgccat ctagaaatcg aaagggttct gccgcgcgtc gccgtgcgcc acgggcagag   22680
acacgttgcg atactggaag cggctcgccc acttaaactc gggcaccacc atgcggggca   22740
gtggttcctc ggggaagttc tcgccccaca gggtgcgggt cagctgcagc gcgctcagga   22800
ggtcgggagc cgagatcttg aagtcgcagt tggggccgga accctgcgcg cgcgagttgc   22860
ggtacacggg gttgcagcac tggaacacca gcagggccgg attatgcacg ctggccagca   22920
ggctctcgtc gctgatcatg tcgctgtcca gatcctccgc gttgctcagg gcgaacgggg   22980
tcatcttgca gacctgcctg cccaggaaag gcggcagccc gggcttgccg ttgcagtcgc   23040
agcgcagggg catcagcagg tgcccgcggc ccgactgcgc ctgcgggtac agcgcgcgca   23100
tgaaggcttc gatctgcctg aaagccacct gcgtcttggc tccctccgaa aagaacatcc   23160
cacaggactt gctggagaac tggttcgcgg gacagctggc atcgtgcagg cagcagcgcg   23220
cgtcggtgtt ggcgatctgc accacgttgc gaccccaccg gttcttcact atcttggcct   23280
tggaagcctg ctccttcagc gcgcgctggc cgttctcgct ggtcacatcc atctctatca   23340
cctgctcctt gttgatcatg tttgtaccgt gcagacactt caggtcgccc tccgtctggg   23400
tgcagcggtg ctcccacagc gcgcaaccgg tgggctccca attttgtgg gtcaccccg   23460 cgtaggcctg caggtaggcc tgcaagaagc gccccatcat ggccacaaag gtcttctggc   23520
tcgtaaaggt cagctgcagg ccgcgatgct cttcgttcag ccaggtcttg cagatggcgg   23580
ccagcgcctc ggtctgctcg ggcagcatcc taaaatttgt cttcaggtcg ttatccacgt   23640
ggtacttgtc catcatggcg cgcgccgcct ccatgccctt ctcccaggcg acaccatgg   23700 gcaggcttag ggggtttatc acttccaccg gcgaggacac cgtactttcg atttcttctt   23760
cctccccctc ttcccggcgc gcgcccacgc tgctgcgcgc tctcaccgcc tgcaccaagg   23820
ggtcgtcttc aggcaagcgc cgcaccgagc gcttgccgcc cttgacctgc ttaatcagca   23880
ccggcgggtt gctgaagccc accatggtca gcgccgcctg ctcttcttcg tcttcgctgt   23940
ctaccactat ctctggggaa gggcttctcc gctctgcggc ggcgcgcttc ttttttttct   24000
tgggagcggc cgtgatggag tccgccacgg cgacggaggt cgaggcgtg gggctggggg   24060 tgcgcggtac cagggcctcg tcgccctcgg actcttcctc tgactccagg cggcggcgga   24120
gtcgcttctt tgggggcgcg cgcgtcagcg gcggcggaga cggggacggg gacgggacg   24180 ggacgccctc cacagggggt ggtcttcgcg cagacccgcg gccgcgctcg gggtcttct   24240
```

```
cgagctggtc ttggtcccga ctggccattg tatcctcctc ctcctaggca gagagacata    24300
aggagtctat catgcaagtc gagaaggagg agagcttaac caccccctct gagaccgccg    24360
atgcgcccgc cgtcgccgtc gccccgctg ccgccgacgc gccgccaca ccgagcgaca      24420 cccccgcgga ccccccgcc gacgcacccc tgttcgagga gcggccgtg gagcaggacc      24480 cgggctttgt ctcggcagag gaggatttgc gagaggagga ggataaggag aagaagccct    24540
cagtgccaaa agatgataaa gagcaagacg agcacgacgc agatgcacac cagggtgaag    24600
tcgggcgggg ggacggaggg catgacggcg ccgactacct agacgaaggg aacgacgtgc    24660
tcttgaagca cctgcatcgt cagtgcgcca ttgtttgcga cgctctgcag gagcgcagcg    24720
aagtgcccct cagcgtggcg gaggtcagcc acgcctacga gctcagcctc ttctcccccc    24780
gggtgccccc ccgccgccgc gaaaacggca catgcgagcc caacccgcgc ctcaacttct    24840
accccgcctt tgtggtaccc gaggtcctgg ccacctatca catcttcttt caaaattgca    24900 agatcccccct ctcgtgccgc gccaaccgta gccgcgccga taagatgctg gccctgcgcc   24960
agggcgacca catacctgat atcgccgctt tggaagatgt accaaagatc ttcgagggtc    25020
tgggtcgcaa cgagaagcgg gcagcaaact ctctgcaaca ggaaaacagc gaaaatgaga    25080
gtcacaccgg ggtactggtg gagctcgagg gcgacaacgc ccgcctggcg gtggtcaagc    25140
gcagcatcga ggtcacccac tttgcctacc ccgcgctaaa cctgccccc aaagtcatga     25200 acgcggccat ggacgggctg atcatgcgcc gcggccggcc cctcgctcca gatgcaaact    25260
tgcatgagga gaccgaggac ggccagcccg tggtcagcga cgagcagctg gcgcgctggc    25320
tggagaccgc ggaccccgcc gaactggagg agcggcgcaa gatgatgatg gccgtggtgc    25380
tggtcaccgt agagctggag tgtctgcagc gcttcttcgg cgaccccgag atgcagagaa    25440
aggtcgagga gaccctgcac tacaccttcc gccagggcta cgtgcgccag gcttgcaaga    25500
tctccaacgt ggagctcagc aacctggtgt cctacctggg catcttgcat gagaaccgcc    25560
tcgggcagag cgtgctgcac tccacccctgc gcggggaggc gcgccgcgac tacgtgcgcg    25620
actgcgttta cctcttcctc tgctacacct ggcagacggc catgggggtc tggcagcagt    25680
gcctggagga gcgcaacctc aaggagctgg agaagctcct gcagcgcgcg ctcaaagatc    25740
tctggacggg ctacaacgag cgctcggtgg ccgccgcgct ggccgacctc atcttccccg    25800
agcgcctgct caaaaccctc cagcagggc tgcccgactt caccagccaa agcatgttgc     25860
aaaacttcag gaactttatc ctggagcgtt ctggcatcct acccgccacc tgctgcgccc    25920
tgcccagcga ctttgtcccc ctcgtgtacc gcgagtgccc ccgccgctg tggggtcact     25980 gctacctgtt ccaactggcc aactacctgt cctaccacgc ggacctcatg gaggactcca    26040
gcggcgaggg gctcatggag tgccactgcc gctgcaacct ctgcacgccc caccgctccc    26100
tggtctgcaa cacccaactg ctcagcgaga gtcagattat cggtaccttc gagctacagg    26160
gtccgtcctc ctcagacgag aagtccgcgg ctccgggget aaaactcact ccggggctgt    26220
ggacttccgc ctacctgcgc aaatttgtac ctgaagacta ccacgccac gagatcaggt     26280 tttacgaaga ccaatcccgc ccgcccaagg cggagctgac cgcctgcgtc atcacccagg    26340
gcgagatcct aggccaattg caagccatcc aaaaagcccg ccaagacttt ttgctgaaga    26400
agggtcgggg ggtgtatctg gacccccagt cgggtgagga gctcaacccg gttccccgc     26460 tgccgccgcc gcgggacctt gcttcccagg ataagcatcg ccatggctcc cagaaagaag    26520
cagcagcggc cgccactgcc gccacccac atgctggagg aagaggagga atactgggac     26580
agtcaggcag aggaggtttc ggacgaggag gagccggaga cggagatgga agagtgggag    26640
```

```
gaggacagct tagacgagga ggcttccgaa gccgaagagg cagacgcaac accgtcaccc   26700
tcggccgcag cccctcgca ggcgcccccg aagtccgctc ccagcatcag cagcaacagc   26760
agcgctataa cctccgctcc tccaccgccg cgacccacgg ccgaccgcag acccaaccgt   26820
agatgggaca ccaccggaac cggggccggt aagtcctccg ggagaggcaa gcaagcgcag   26880
cgccaaggct accgctcgtg gcgcgctcac aagaacgcca tagtcgcttg cttgcaagac   26940
tgcgggggga acatctcctt cgcccgccgc ttcctgctct tccaccacgg tgtggccttc   27000
ccccgtaacg tcctgcatta ctaccgtcat ctctacagcc cctactgcgg cggcagtgag   27060
ccagagacgt tcggcggcgg cggcggcgcc cgtttcggcg cctaggaaga cccagggcaa   27120
gacttcagcc aagaaactcg cggcggccgc ggcgaacgcg gtcgcggggg ccctgcgcct   27180
gacggtgaac gaaccctgt cgacccgcga actgaggaac cgaatcttcc ccactctcta   27240
tgccatcttc cagcagagca gagggcagga tcaggaactg aaagtaaaaa acaggtctct   27300
gcgctccctc acccgcagct gtctgtatca caagagcgaa gaccagcttc ggcgcacgct   27360
ggaggacgct gaggcactct tcagcaaata ctgcgcgctc actcttaagg actagctccg   27420
cgccttctc gaatttaggc gggaacgcct acgtcatcgc agcgccgccg tcatgagcaa   27480
ggacattccc acgccataca tgtggagcta tcagccgcag atgggactcg cggcgggcgc   27540
ctcccaagac tactccaccc gcatgaactg gctcagtgcc ggcccacaca tgatctcaca   27600
ggttaatgat atccgcaccc atcgaaacca aatattggtg gagcaggcgg caattaccac   27660
cacgccccgc aataatccca accccaggga gtggcccgcg tccctggtgt atcaggaaat   27720
tcccggcccc accaccgtac tacttccgcg tgattcccag gccgaagtcc aaatgactaa   27780
ctcaggggca cagctcgcgg gcggctgtcg tcacagggtg cggcctcctc gccagggtat   27840
aactcacctg gagatccgag gcagaggtat tcagctcaac gacgagtcgg tgagctcctc   27900
gctcggtctc agacctgacg ggaccttcca gatagccgga gccggccgat cttccttcac   27960
gccccgccag gcgtacctga ctctgcaaag ctcgtcctcg gcgccgcgct cgggcggcat   28020
cgggactctc cagttcgtgc aggagtttgt gccctcggtc tacttcaacc ccttctcggg   28080
ctctcccggt cgctacccgg accagttcat ctcgaacttt gacgccgcga gggactcggt   28140
ggacggctac gactgaatgt cgggtggacc cggtgcagag caacttcgcc tgaagcacct   28200
cgaccactgc cgccgccctc agtgcttgc ccgctgtcag accggtgagt tccagtactt   28260
ttccctgccc gactcgcacc cggacggccc ggcgcacggg gtgcgctttt tcatcccgag   28320
tcaggtcgcg tctaccctaa tcagggagtt taccgcccgt cccctactgg cggagttgga   28380
aaagggggcct tctatcctaa ccattgcctg catctgctct aaccctggat gcaccaaga   28440
tctttgctgt catttgtgtg ctgagtataa taaaggctga gatcagaatc tactcggct   28500
cctgtcgcca tcctgtcaac gccaccgtcc aagcccggcc cgatcagccc gaggtgaacc   28560
tcacctgcgg tctgcaccgg cgcctgagga aataccaagc ttggtactac aacagcactc   28620
cctttgtggt ttacaacagc tttgaccagg acggggtctc actgagggat aacctctcga   28680
acctgagcta ctccatcagg aagaacagca ccctcgagct acttcctcct tacctgcccg   28740
ggacttacca gtgtgtcacc ggtccctgca cccacaccca cctgttgatc gtaaacgact   28800
ctcttccgag aacagacctc aataactcct cttcgcagtt ccccagaaca ggaggtgagc   28860
tcaggaaacc ccgggtaaag aagggtggac gagagttaac acttgtgggg tttctggtgt   28920
atgtgacgct ggtggtggct cttttgatta aggcttttcc ttccatgtct gaactctccc   28980
```

```
tcttcttttta tgaacaactc gactagtgct aacgggaccc tacccaacga atcgggattg    29040
aatatcggta accaggttgc agtttcactt ttgattacct tcatagtcct cttcctgcta    29100
gtgctgtcgc ttctgtgcct gcggatcggg ggctgctgca tccacgttta tatctggtgc    29160
tggctgttta gaaggttcgg agaccatcgc aggtagaata aacatgctgc tgcttaccct    29220
ctttgtcctg gcgctggccg ccagctgcca agccttttcc gaggctgact ttatagagcc    29280
ccagtgtaat gtgactttta aagcccatgc acagcgttgt catactataa tcaaatgtgc    29340
caccgaacac gatgaatacc ttatccagta taaagataaa tcacacaaag tggcacttgt    29400
tgacatctgg aaacccgaag acctttgga atacaatgtg accgttttcc agggtgacct    29460
cttcaaaatt tacaattaca ctttcccatt tgaccagatg tgtgactttg tcatgtacat    29520
ggaaaagcag cacaagctgt ggcctccgac tccccagggc tgtgtggaaa atccaggctc    29580
tttctgcatg atctctctct gtgtaactgt gctggcacta atactcacgc ttttgtatat    29640
cagatttaaa tcaaggcaaa gcttcattga tgaaaagaaa atgccttaat cgctttcacg    29700
cttgattgct aacaccgggt ttttatccgc agaatgattg gaatcaccct actaatcacc    29760
tccctccttg cgattgccca tgggttggaa cgaatcgaag tccctgtggg ggccaatgtt    29820
accctggtgg ggcctgtcgg caatgctaca ttaatgtggg aaaaatatac taaaaatcaa    29880
tgggtctctt actgcactaa caaaaatagc cacaagccca gagccatctg cgatgggcaa    29940
aatctaacct tgattgatgt tcaattgctg gatgcgggct actattatgg gcagctgggt    30000
acaatgatta attactggag accccacaga gattacatgc tccacgtagt aaagggtccc    30060
cttagcagcc cacccactac cacctctact accccacta ccaccactac tcccaccacc    30120
agcactgccg cccagcctcc tcatagcaga caaccactt ttatcaattc caagtcccac    30180
tccccccaca ttgccggcgg gccctccgcc tcagactccg aaaccaccga gatctgcttc    30240
tgcaaatgct ctgacgccat gcccaggat ttggaagatc acgaggaaga tgagcatgac    30300
ttcgcagatg catgccaggc atcagagcca gaagcgctgc cggtggccct caaacagtat    30360
gcagaccccc acaccacccc cgaccttcct ccaccttccc agaagccaag tttcctgggg    30420
gaaaatgaaa ctctgcctct ctccatactc gctctgacat ctgttgctat gttgaccgct    30480
ctgctggtgc ttctatgctc tatatgctac ctgatctgct gcagaaagaa aaaatctcac    30540
ggccatgctc accagcccct catgcacttc ccttaccctc cagagctggg cgaccacaaa    30600
ctttaagtct gcagtaacta tctgcccatc ccttgtcagt cgacagcgat gagccccact    30660
aatctaacgg cctctggact tacaacatcg tctcttaatg agaccaccgc tcctcaagac    30720
ctgtacgatg gtgtctccgc gctggttaac cagtgggatc acctgggcat atggtggctc    30780
ctcataggag cagtgaccct gtgcctaatc tggtctgga tcatctgctg catcaaaagc    30840
agaagaccca ggcggcggcc catctacagg ccctttgtca tcacacctga agatgatgat    30900
gacaccactt ccaggctgca gaggctaaag cagctactct tctcttttac agcatggtaa    30960
attgaatcat gcctcgcatt ttcatctact tgtctctcct tccactttt ctgggctctt    31020
ctacattggc cgctgtgtcc cacatcgagg tagactgcct cacgcccttc acagtctacc    31080
tgcttttcgg ctttgtcatc tgcacctttg tctgcagcgt tatcactgta gtgatctgct    31140
tcatacagtg catcgactac gtctgcgtgc gggtggctta ctttagacac caccccagt    31200
atcgcaacag ggacatagcg gctctcctaa gacttgttta aaatcatggc caaattaact    31260
gtgattggtc ttctgatcat ctgctgcgtc ctagccgcga ttgggactca agctcctacc    31320
accaccagcg ctcccagaaa gagacatgta tcctgcagct tcaagcgtcc ctggaatata    31380
```

```
ccccaatgct ttactgatga acctgaaatc tctttggctt ggtacttcag cgtcaccgcc   31440
cttcttatct tctgcagtac ggttattgcc cttgccatct acccttccct tgacctgggc   31500
tggaatgctg tcaactctat ggaatatccc accttcccag aaccagacct gccagacctg   31560
gttgttctaa acgcgtttcc tcctcctgct cccgttcaaa atcagtttcg ccctccgtcc   31620
cccacgccca ctgaggtcag ctactttaat ctaacaggcg gagatgactg aaaacctaga   31680
cctagaaatg gacggtctct gcagcgagca acgcacacta gagaggcgcc ggcaaaaaga   31740
gctcgagcgt cttaaacaag agctccaaga cgcggtggcc atacaccagt gcaaaaaagg   31800
tgtcttctgt ctggtaaaac aggccacgct cacctatgaa aaaacaggtg cacccaccg   31860 cctaggatac aagctgccca cacagcgcca aaagttcgcc ctcatgatag gcgaacaacc   31920
catcaccgtg acccagcact ccgtggagac agaaggctgc atacatgctc cctgtagggg   31980
cgctgactgc ctctacacct tgatcaaaac cctctgcggt ctcagagacc ttatcccttt   32040
caattaatca taactgtaat caataaaaaa tcacttactt gaaatctgat agcaagcctc   32100
tgtccaattt tttcagcaac acttccttcc cctcctccca actctggtac tctaggcgcc   32160
tcctagctgc aaacttcctc cacagtctga agggaatgtc agattcctcc tcctgtccct   32220
ccgcacccac gatcttcatg ttgttgcaga tgaaacgcgc gagatcgtct gacgagacct   32280
tcaaccccgt gtaccctac gataccgaga tcgctccgac ttctgtccct ttccttaccc   32340 ctcccttttgt gtcatccgca ggaatgcaag aaaatccagc tggggtgctg tccctgcact   32400
tgtcagagcc ccttaccacc cacaatgggg ccctgactct aaaaatgggg ggcggcctga   32460
ccctggacaa ggaagggaat ctcacttccc aaaacatcac cagtgtcgat cccctctca   32520 aaaaagcaa gaacaacatc agccttcaga ccgccgcacc cctcgccgtc agctccgggg   32580
ccctaacact ttttgccact ccccccctag cggtcagtgg tgacaacctt actgtgcagt   32640
ctcaggcccc tctcactttg gaagactcaa aactaactct ggccaccaaa ggacccctaa   32700
ctgtgtccga aggcaaactt gtcctagaaa cagaggctcc cctgcatgca agtgacagca   32760
gcagcctggg ccttagcgtt acggccccac ttagcattaa caatgacagc ctaggactag   32820
atctgcaggc acccattgtc tctcaaaatg gaaaactggc tctaaatgta gcaggccccc   32880
tagctgtggc caatggcatt aatgctttga cagtaggcac aggcaaaggt attggtctaa   32940
atgaaaccag cactcacttg caagcaaagt tggtcgcccc cctaggcttt gataccaatg   33000
gcaacattaa gctaagcgtt gcaggaggca tgagactaaa taatgacaca cttatactag   33060
atgtaaacta cccatttgaa gctcaaggcc aactaagtct aagagtgggc cagggtccgc   33120
tgtatgtaga ttctagcagc cataacctga ccattagatg ccttagagga ttatacataa   33180
catcgtctaa taaccaaacc ggtctagagg ccaacataaa actaacaaaa gccttgtct   33240 atgatggaaa tgccatagca gtcaatgttg gtcaaggatt gcaatacagc actactgcca   33300
catcggaagg tgtgtatcct atacagtcta agataggttt gggaatgaa tatgatacca   33360 acggagccat gatgacaaaa ctaggctctg gactaagctt tgacaattca ggagccattg   33420
tagtgggaaa caaaaatgat gacaggctta ctctgtggac tacaccagac ccatctccta   33480
actgtagaat ttattctgaa aaagatacta aactaacctt ggtgctgact aagtgtggca   33540
gccaaatcct aggcacagta tctgcccttg ctgtcagagg cagccttgcg cccatcacta   33600
atgcatccag catagtccaa atatttctaa gatttgatga aaatggacta ttgatgagca   33660
actcatcgct agacggtgat tactggaatt acagaaatgg ggactccact aatagcacac   33720
```

```
catatacaaa tgcagtaggc tttatgccta atctagcagc ctatcctaaa ggtcaggcta    33780
cagctgcaaa aagcagtatt gtaagccagg tatacatgga tggtgacact actaaaccta    33840
taacactaaa aataaacttc aatggcattg atgaaacaac agaaaatacc cctgttagta    33900
aatattccat gacattctca tggagctggc ccaccgcaag ctacataggc cacactttg     33960
caacaaactc ttttactttc tcctacatcg cccaagaata aagaaagcac agagatgctt    34020
gttttgattt caaaattgtg tgcttttatt tattttcagc ttacagtatt tccagtagtc    34080
attcgaataa agcttaatca aactgcatga gaacccttcc acatagctta aattagcacc    34140
agtgcaaatg gagaaaattc aacataccct ttttatccag atatcagaga actctagtgg    34200
tcagttttcc cccacccctcc cagctcacag aatacacagt cctttccccc cggctggctt    34260
taaacaacac tatctcattg gtaacagaca tattcttagg tgtaataatc cacacggtct    34320
cttggcgggc caagcgctgg tcggtgatgt taataaactc cccaggcagc tctttcaagt    34380
tcacgtcgct gtccaactgc tgaagcgctc gcggctccga ctgcgcctct agcggaggca    34440
acggcaacac ccgatccttg atctataaag gagtagagtc ataatccccc ataagaatag    34500
ggcggtgatg cagcaacaag gcgcgcagca actcctgccg ccgcctctcc gtacgacagg    34560
aatgcaacgg cgtggtggtc tcctccgcga taatccgcac cgctcgcagc atcagcatcc    34620
tcgtcctccg ggcacagcag cgcatcctga tctcactgag atcggcgcag taagtgcagc    34680
acaaaccaa gatgttattt aagatcccac agtgcaaagc actgtaccca aagctcatgg    34740
cgggaaggac agcccccacg tgaccatcat accagatcct taggtaaatc aaatgacgac    34800
ctctcataaa cacgctggac atgtacatca cctccttggg catgcgctga ttcaccacct    34860
ctcgatacca caagcatcgc tgattaatta aagacccctc aagcaccatc ctgaaccagg    34920
aagccagcac ctgaccccccc gccaggcact gcagggaccc cggtgaattg cagtggcagt    34980
gaagactcca gcgctcgtag ccgtgaacca tagagccggt cattatatcc acattggcac    35040
aacacaaaca cactttcata cacttttttca tgattagcag ctcctctcta gtcaggacca    35100
tatcccaagg aatcacccac tcttgaatca aggtaaatcc cacacagcag ggcaggcctc    35160
tcacataact cacgttatgc atagtgagcg tgtcgcaatc tggaaatacc ggatgatctt    35220
ccatcaccga agctcgcgtc tccgtctcaa agggaggtaa acggtccctc gtgtagggac    35280
agtggcggga taatcgagat cgtgttgaac gtagagtcat gccaaaggga acagcggacg    35340
tactcatatt tcctccagca gaaccaagtg cgcgcgtggc agctatccct gcgtcttctg    35400
tctcgccgcc tgccccgctc ggtgtagtag ttgtaataca gccactccct cagaccgtca    35460
aggcgctccc tggcgtccgg atctataaca acaccgtcct gcagcgccgc cctgatgaca    35520
tccaccaccg tagagtatgc caagcccagc caggaaatgc attcactttg acagcgagag    35580
ataggaggag cgggaagaga tggaagaacc atgatagtaa aagacttta ttccaatcga    35640
tcctctacaa tgtcaaagtg tagatctata agatgacact ggtctcctcc gctgagtcga    35700
tcaaaaataa cagctaaacc acaaacaaca cgattggtca aatgctccac aagggcttgc    35760
agcataaaat cgcctcgaaa gtccaccgca agcataacat caaagccacc gccctatca    35820
tgatctataa taaaaacccc acagctatcc accagaccca taagttttc atctctccat    35880
cgtgaaaaaa tatttacaag ctcctccttt aaatcacctc caaccaattg aaaaagttga    35940
gccaaaccgc cctccacctt catttttcagc aagcgcatca tgattgcaaa aattcaggct    36000
cctgagacac ctgtataaga ttgagaagcg gaacgttaac gtcaatgttt cgctcgcgaa    36060
gatcgcgcct cagtgcaagc atgatataat cccacaggtc ggagcggatc agcgaggaca    36120
```

```
tctccccgcc aggaaccaac tcaacggagc ctatgctgat tataatacgc atattcgggg    36180
ctatgctgac cagcacggcc cccaaatagg cgtactgcat aggcggcgac aaaaagtgaa    36240
cagtttgggt taaaaaatca ggcaaacagt cgcgcaaaaa agcaagaaca tcataaccat    36300
gctcatgcaa atagatgcaa gtaagctcag gaacgaccac agaaaatgc acaattttc    36360 tctcaaacat gactgcgagc cctgcaaaaa ataaaaaaga acattacac aagagtagcc    36420 tgtcttacga tgggatagac tactctaacc aacataagac gggccacaac atcgcccgcg    36480
tggccataaa aaaattgtc cgtgtgatta aaagaagca cagatagctg gccagtcata    36540
tccggagtca tcacgtgtga accccgtgtag acccccgggt tggacacatc ggccaaacaa    36600
agaaagcggc caatgtaccc aggaggaatc ataacactaa gacgaagata caacagaata    36660 acccccatgag ggggaataac aaagttagta ggtgaataaa aacgataaac acccgaaact    36720
ccctcctgcg taggcaaaat agcaccctcc ccttccaaaa caacatatag cgcttccaca    36780
gcagccatga caaaagactc aaaacactca aagactcag tcttaccagg aaaataaaag    36840
cactctcaca gcaccagcac taatcagagt gtgaagaggg ccaagtgccg aacgagtata    36900
tataggaata aaaaatgacg taaatgtgta aaggtcagaa aacgcccaga aaaatacaca    36960
gaccaacgcc cgaaacgaaa acccgcgaaa aaatacccag aacttcctca caaccgcca    37020 cttccggttt ctcacggtac gtcacttccg caagaaaagc aaaactacat ttcccacatg    37080
tgtaaaaacg aaaccccgcc ccttgtaact gcccacaact tacatcatca aaacataaac    37140
tcctacgtca cccgcccgc ctctccccgc ccacctcatt atcatattgg ccacaatcca    37200
aaataaggta tattat                                                     37216

<210> SEQ ID NO 25
<211> LENGTH: 34029
<212> TYPE: DNA
<213> ORGANISM: Gorilla beringei beringei

<400> SEQUENCE: 25
catcatcaat aatataccttt attttggatt gtggccaata tgataatgag gtgggcgggg     60
agaggcgggg cgggtgacgt aggacgcgcg agtagggttg ggaggtgtgg cggaagtgtg    120
gcatttgcaa gtgggaggag ctcacatgca agcttccgtc gcggaaaatg tgacgttttt    180
gatgagcgcc gcctacctcc ggaagtgcca atttcgcgc gcttttcacc ggatatcgta    240
gtaattttgg gcgggaccat gtaagatttg gccattttcg cgcgaaaagt gaacgggga    300 agtgaaaact gaataatagg gcgttagtca tagtgcgtaa tatttaccga gggccgaggg    360
actttgaccg attacgtgga ggactcgccc aggtgttttt tacgtgaatt tccgcgttcc    420
gggtcaaagt ctccgttta ttgtcaccgt catttgacgc ttaggcctga ccatctggtg    480
ctggcctgca ccagggccga gtttgggtct agcgatgagg ataccgattg aggtgggtaa    540
ggtgggcgtg gctagaaggg tggggcgtgt ataaattggg ggtctaaggg tctctctgtt    600
ttgtcttgca acagccgccg ccatgagcga caccggcaac agctttgatg gaagcatctt    660
tagcccctat ctgacagtgc gcatgcctca ctgggctgga gtgcgtcaga atgtgatggg    720
ttccaacgtg gatggacgcc ccgttctgcc ttcaaattcg tctacaatgg cctacgcgac    780
cgtgggagga actccgctgg acgccgcgac ctccgccgcc gcctccgccg ccgccgcgac    840
cgcgcgcagc atggctacgg accttttacag ctctttggtg gcgagcggcg cggcctctcg    900
cgcgtctgct cgggatgaga aactgaccgc tctgctgctt aaactggaag acttgacccg    960
```

```
ggagctgggt caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagcccgg gaccagcggt ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcggggggt ggtgttgtat   1260 atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata ccagtgcac   1500 ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacgaa tcgggggcgg agggtcccgg actgggggat gatggtaccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa attttttcagc   2100 ggttttaggc cgtcggccgt gggcatgttt ttcagcgtct gggtcagcag ttccagcctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aagggggtgcg   2340 ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgcccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgccccat gctttttgat gcgtttctta cctcggctct   2700
ccatgaggcg gtgtcccttc tcggtgacga agaggctgtc cgtgtccccg tagaccgact   2760 tcagggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc cctcctccg   2940 cgtccagaaa agtgattggc ttgtaggtgt aggacacgtg accgggggtt cccgacgggg   3000
gggtataaaa gggggtgggc gccctttcat cttcactctc ttccgcatcg ctgtctgcga   3060
gggccagctg ctggggtaag tattccctct cgaaggcggg catgacctca gcgctccagt   3120
tgtcagtttc taaaaatgag gaggatttga tgttcacctg tccggaggtg atacctttga   3180
gggtacctgg gtccatctgg tcagaaaaca ctatttttt gttgtcaagc ttggtggcga   3240
acgacccgta gagggcgttg gagagcagct tggcgatgga gcgcagggtc tggttttttgt   3300 cgcggtcggc tcgctccttg gccgcgatgt tgagttgcac gtactcgcgg gccacgcact   3360
```

```
tccactcggg gaagacggtg gtgcgctcgt ctgggattag gcgcaccctc cagcctcggt    3420
tgtgcagggt gaccatgtcg acgctggtgg cgacctcgcc gcgcaggcgc tcgttggtcc    3480
agcagaggcg gccgcccttg cgcgagcaga agggggtag ggggtccagc tggtcctcgt    3540 ttgggggtc cgcgtcgatg gtgaagaccc cggggagcaa gcgcgggtca aagtagtcga    3600
tcttgcaagc ttgcatgtcc agagcccgct gccattcgcg ggcggcgagc gcgcgctcgt    3660
aggggttgag gggcgggccc cagggcatgg ggtgggtgag cgcggaggcg tacatgccgc    3720
agatgtcata cacgtacagg ggttccctga ggatgccgag gtaggtgggg tagcagcgcc    3780
ccccgcggat gctggcgcgc acgtagtcat agagctcgtg ggagggggcc agcatgttgg    3840
gcccgaggtt ggtgcgctgg gggcgctcgg cgcggaaggc gatctgcctg aagatggcat    3900
gggagttgga ggagatggtg ggccgctgga agacgttgaa gcttgcttct tgcaagccca    3960
ccgagtccct gacgaaggag gcgtaggact cgcgcagctt gtgcaccagc tcggcggtga    4020
cctggacgtc gagcgcgcag tagtcgaggg tctcgcggat gatgtcatac ttatcctccc    4080
ccttcttttt ccacagctcg cggttgagga cgaactcttc gcggtctttc cagtactctt    4140 ggagggaaa cccgtccgtg tccgaacggt aagagcctag catgtagaac tggttgacgg    4200
cctggtaggg gcaacagccc ttctccacgg gcagcgcgta ggcctgcgcc gccttgcgga    4260
gggaggtgtg ggtgagggcg aaagtgtccc tgaccatgac tttgaggtat tgatgtttga    4320
agtctgtgtc atcgcagccg ccctgttccc acagggtgta gtccgtgcgc tttttggagc    4380
gcgggttggg cagggagaag gtgaggtcat tgaagaggat cttccccgct cgaggcatga    4440
agtttctggt gatgcgaaag ggccctggga ccgaggagcg gttgttgatg acctgggcgg    4500
ccaggacgat ctcgtcaaag ccgtttatgt tgtggcccac gatgtagagc tccaaaaagc    4560
ggggctggcc cttgatggag gggagctttt tgagttcctc gtaggtgagc tcctcgggcg    4620
attccaggcc gtgctcctcc agggcccagt cttgcaagtg agggttggcc gccaggaagg    4680
atcgccagag gtcgcgggcc atgagggtct gcaggcggtc gcggaaggtt ctgaactgtc    4740
gccccacggc catctttttcg ggggtgatgc agtagaaggt gaggggtct ttctcccagg    4800 ggtcccatct gagctctcgg gcgaggtcgc gcgcggcggc gaccagagcc tcgtcgcccc    4860
ccagtttcat gaccagcatg aagggcacga gctgcttgcc aaaggctccc atccaagtgt    4920
aggtctctac atcgtaggtg acaaagaggc gctccgtgcg aggatgagag ccgatcggga    4980
agaactggat ctcccgccac cagttggagg attggctgtt gatgtggtga aagtagaagt    5040
cccgtctgcg ggccgagcac tcgtgctggc ttttgtaaaa gcgaccgcag tactggcagc    5100
gctgcacggg ttgtatatct tgcacgaggt gaacctggcg acctctgacg aggaagcgca    5160 gcggaatct aagtccccg cctggggtcc cgtgtggctg gtgtcttct actttggttg    5220 tctggccgcc agcatctgtc tcctggaggg cgatggtgga gcagaccacc acgccgcgag    5280
agccgcaggt ccagatctcg cgcgctcggcg ggcggagttt gatgacgaca tcgcgcacat    5340
tggagctgtc catggtctcc agctcccgcg gcggcaggtc agctgggagt tcctggaggt    5400
tcacctcgca gagacgggtc aaggcgcggg cagtgttgag atggtatctg atttcaaggg    5460
gcgtgttggc ggcggagtcg atggcttgca ggaggccgca gccccggggg ccacgatgg    5520 ttccccgcgg ggcgcgaggg gaggcggaag ctgggggtgt gttcagaagc ggtgacgcgg    5580
gcgggccccc ggaggtaggg ggggttccgg ccccacaggc atgggcggca ggggcacgtc    5640
ttcgccgcgc gcgggcaggg gctggtgctg gctccgaaga gcgcttgcgt gcgcgacgac    5700
```

```
gcgacggttg gtgtcctgta tctgacgcct ctgagtgaag accacgggtc ccgtgacctt    5760
gaacctgaaa gagagttcga cagaatcaat ctcggcatcg ttgacagcgg cctggcgcag    5820
gatctcctgc acgtcgcccg agttgtcctg gtaggcgatc tctgccatga actgctcgat    5880
ctcttcttcc tggagatctc ctcgtccggc gcgctccacg gtggccgcca ggtcgttgga    5940
gatgcgaccc atgagctgtg agaaggcgtt gagcccgccc tcgttccaga cccggctgta    6000
gaccacgccc ccctcggcgt cgcgagcgcg catgaccacc tgggccaggt tgagctccac    6060
gtgtcgcgtg aagacggcgt agttgcgcag gcgctggaaa aggtagttca gggtggtggc    6120
ggtgtgctcg gcgacgaaga agtacatgac ccagcgccgc aacgtggatt cattgatgtc    6180
ccccaaggcc tccaggcgct ccatggcctc gtagaagtcc acggcgaagt tgaaaaactg    6240
ggagttgcga gcggacacgg tcaactcctc ctccagaaga cggatgagct cggcgacagt    6300
gttgcgcacc tcgcgctcga aggccacggg gggcgcttct tcctcttcca cctcttcttc    6360
catgatcgct tcttcttctt cctcagccgg acgggaggg ggcggcggcg gcggggagg    6420 ggcgcggcg cggcggcggc gcaccgggag gcggtcgatg aagcgctcga tcatctcccc    6480
ccgcatgcgg cgcatggtct cggtgacggc gcggccgttc tcccggggc gcagctcgaa    6540 gacgccgcct ctcatctcgc cgcggggcga gcggccgtga ggtagcgaga cggcgctgac    6600
tatgcatctt aacaattgct gtgtaggtac accgccgagg gacctgattg agtccagatc    6660
caccggatcc gaaaaccttt ggaggaaagc gtctatccag tcgcagtcgc aaggtaggct    6720
gagcaccgtg gcgggcgggg gcgggtctgg agagttcctg gcggagatgc tgctgatgat    6780
gtaattaaag taggcggtct tgagaaggcg gatggtggac aggagcacca tgtctttggg    6840
tccggcctgt tggatgcgga ggcggtcggc catgccccag gcctcgttct gacaccggcg    6900
caggtctttg tagtagtctt gcatgagtct ttccaccggc acctcttctc cttcctcttc    6960
tccatctcgc cggtggtttc tcgcgccgcc catgcgcgtg accccaaagc ccctgagcgg    7020
ctgcagcagg gccaggtcgg cgaccacgcg ctcggccaag atggcctgct gcacctgagt    7080
gagggtcctc tcgaagtcat ccatgtccac gaagcggtgg taggcgcccg tgttgatggt    7140
gtaggtgcag ttggccatga cggaccagtt gacggtctgg tgtcccggct gcgagagctc    7200
cgtgtaccgc aggcgcgaga aggcgcggga atcgaacacg tagtcgttgc aagtccgcac    7260
cagatactgg tagcccacca ggaagtgcgg cggaggttgg cgatagaggg gccagcgctg    7320
ggtggcgggg gcgccgggcg ccaggtcttc cagcatgagg cggtggtatc cgtagatgta    7380
cctggacatc caggtgatgc cggcggcggt ggtggtggcg cgcgcgtagt cgcggacccg    7440
gttccagatg tttcgcaggg gcgagaagtg ttccatggtc ggcacgctct ggccggtgag    7500
gcgcgcgcag tcgttgacgc tctatacaca cacaaaaacg aaagcgttta cagggctttc    7560
gttctgtagc ctggaggaaa gtaaatgggt tgggttgcgg tgtgccccgg ttcgagacca    7620
agctgagctc ggccggctga agccgcagct aacgtggtat tggcagtccc gtctcgaccc    7680
aggccctgta tcctccagga tacggtcgag agcccttttg ctttcttggc caagcgcccg    7740
tggcgcgatc tgggatagat ggtcgcgatg agaggacaaa agcggctcgc ttccgtagtc    7800
tggagaaaca atcgccaggg ttgcgttgcg gcgtaccccg gttcgagccc ctatggcggc    7860
ttgaatcggc cggaaccgcg gctaacgagg gccgtggcag cccgtcctc aggaccccgc    7920 cagccgactt ctccagttac gggagcgagc ccctttgtt ttttattttt tagatgcatc    7980
ccgtgctgcg gcagatgcgc ccctcgcccc ggcccgatca gcagcagcaa cagcaggcat    8040
gcagaccccc ctctccccctt tccgccccgg tcaccacggc cgcggcggcc gtgtcgggcg    8100
```

```
cgggggcgc gctggagtca gatgagccac cgcggcggcg acctaggcag tatctggact    8160
tggaagaggg cgagggactg gcgcggctgg gggcgaactc tccagagcgc cacccgcggg    8220
tgcagttgaa aagggacgcg cgcgaggcgt acctgccgcg gcagaacctg tttcgcgacc    8280
gcgggggcga ggagcccgag gagatgcgag actgcaggtt ccaagcgggg cgcgagctgc    8340
ggcgcgggct ggacagacag cgcctgctgc gcgaggagga ctttgagccc gacacgcaga    8400
cgggcatcag ccccgcgcgc gcgcacgtag ccgcggccga cctggtgacc gcctacgagc    8460
agacggtaaa ccaggagcgc aacttccaaa agagcttcaa caaccacgtg cgcacgctgg    8520
tggcgcgcga ggaggtgacc ctgggtctca tgcatctgtg ggacctggtg gaggcgatcg    8580
tgcagaaccc cagcagcaag cccctgaccg cgcagctgtt cctggtggtg cagcacagca    8640
gggacaacga ggccttcagg gaggcgctgc tgaacatcac cgagccggag gggcgctggc    8700
tcctggacct gataaacatc ctgcagagca tagtggtgca ggagcgcagc ctgagcctgg    8760
ccgagaaggt ggcggccatc aactactcta tgctgagcct gggcaagttc tacgcccgca    8820
agatctacaa gaccccctac gtgcccatag acaaggaggt gaagatagac agcttctaca    8880
tgcgcatggc gctgaaggtg ctgaccctga gcgacgacct gggagtgtac cgcaacgagc    8940
gcatccacaa ggccgtgagc gccagccggc ggcgcgagct gagcgaccgc gagctgatgc    9000
acagtctgca gcgcgcgctg accggcgcgg gcgagggcga cagggaggtc gagtcctact    9060
tcgacatggg ggccgacctg cactggcagc cgagccgccg cgccctggag gcggcggggg    9120
cgtacggcgg cccccctggcg gccgatgacc aggaagagga ggactatgag ctagaggagg    9180
gcgagtacct ggaggactga cctggctggt ggtgttttgg tatagatgca agatccgaac    9240
gtggcggacc cggcggtccg ggcggcgctg caaagccagc cgtccggcat taactcctct    9300
gacgactggg ccgcggccat gggtcgcatc atggccctga ccgcgcgcaa ccccgaggct    9360
ttcaggcagc agcctcaggc caaccggctg cggccatct tggaagcggt agtgcccgcg    9420
cgctccaacc ccacccacga aaggtgctg gccatagtca acgcgctggc ggagagcagg    9480
gccatccgcg cggacgaggc cggactggtg tacgatgcgc tgctgcagcg ggtggcgcgg    9540
tacaacagcg gcaacgtgca gaccaacctg gaccgcctgg tgacggacgt gcgcgaggcc    9600
gtggcgcagc gcgagcgctt gcatcaggac ggtaacctgg gctcgctggt ggcgctaaac    9660
gccttcctca gcacccagcc ggccaacgta ccgcgggggc aggaggacta caccaacttt    9720
ttgagcgcgc tgcggctgat ggtgaccgag gtccctcaga gcgaggtgta ccagtcgggg    9780
cccgactact tcttccagac cagcagacag ggcttgcaaa ccgtgaacct gagccaggct    9840
ttcaagaacc tgcgggggct gtggggagtg aaggcgccca ccggcgaccg ggctacggtg    9900
tccagcctgc taaccccaa ctcgcgcctg ctgctgctgc tgatcgcgcc cttcacggac    9960
agcgggagcg tctcgcggga gacctatctg ggccacctgc tgacgctgta ccgcgaggcc   10020
atcgggcagg cgcaggtgga cgagcacacc ttccaagaga tcaccagcgt gagccacgcg   10080
ctggggcagg aggacacggg cagcctgcag gcgaccctga actacctgct gaccaacagg   10140
cggcagaaga ttcccacgct gcacagcctg acccaggagg aggagcgcat cttgcgctac   10200
gtgcagcaga gcgtgagcct gaacctgatg cgcgacggcg tgacgccag cgtggcgctg   10260
gacatgaccg cgcgcaacat ggaaccgggc atgtacgcct cccaccggcc gtttatcaac   10320
cgcctgatgg actacttgca tcgggcgcg ccgtgaacc ccgagtactt cactaatgcc   10380
attctgaatc cccactggat gccccctccg ggtttctaca acgggacttt tgaggtgccc   10440
```

```
gaggtcaacg acgggttcct ctgggatgac atggatgaca gtgtgttctc acccaacccg   10500
ctgcgcgccg cgtctctgcg attgaaggag ggctctgaca gggaaggacc gaggagtctg   10560
gcctcctccc tggctctggg agcggtgggc gccacgggcg cggcggcgcg gggcagtagc   10620
cccttcccca gcctggcaga ctctctgaac agcgggcggg tgagcaggcc ccgcttgcta   10680
ggcgaggagg agtatctgaa caactccctg ctgcagcccg cgagggacaa gaacgctcag   10740
cggcagcagt ttcccaacaa tgggatagag agcctggtgg acaagatgtc cagatggaag   10800
acgtatgcgc aggagtacaa ggagtgggag gaccgccagc cgcggcccct gccgcccct    10860 aggcagcgct ggcagcggcg cgcgtccaac cgccgctgga ggcaggggcc cgaggacgat   10920
gatgactctg cagatgacag cagcgtgttg gacctgggcg ggagcgggaa ccccttttcg   10980
cacctgcgcc cacgcctggg caagatgttt taaaagaaaa aaaaaataaa actcaccaag   11040
gccatggcga cgagcgttgg ttttttgttc ccttccttag tatgcggcgc gcggcgatgt   11100
tcgaggaggg gcctccccc tcttacgaga gcgcgatggg gatttctcct gcggcgcccc    11160
tgcagcctcc ctacgtgcct cctcggtacc tgcaacctac aggggggaga aatagcatct   11220
gttactctga gctgcagccc ctgtacgata ccaccagact gtacctggtg acaacaagt    11280 ccgcggacgt ggcctccctg aactaccaga acgaccacg cgattttttg accacggtga    11340
tccaaaacaa cgacttcacc ccaaccgagg ccagcaccca gaccataaac ctggataaca   11400
ggtcgaactg gggcggcgac ctgaagacca tcttgcacac caacatgccc aacgtgaacg   11460
agttcatgtt caccaactct tttaaggcgc gggtgatggt ggcgcgcgag caggggaggg   11520
cgaagtacga gtgggtggac ttcacgctgc ccgagggcaa ctactcagag accatgactc   11580
tcgacctgat gaacaatgcg atcgtggaac actatctgaa agtgggcagg cagaacgggg   11640
tgaaggaaag cgatatcggg gtcaagtttg acaccagaaa cttccgtctg ggctgggacc   11700
ccgtgaccgg gctggtcatg ccgggggtct acaccaacga ggcctttcat cccgacatag   11760
tgcttctgcc cggctgtggg gtggacttca cccagagccg gctgagcaac ctgctgggca   11820
ttcgcaagcg gcagcctttc caggaggggtt tcaagatcac ctatgaggat ctgaaggggg   11880
gcaacattcc cgcgctcctt gatctggacg cctacgagga gagcttgaaa cccgaggaga   11940
gcgctggcga cagcggcgag agtggcgagg agcaagccgg cggcggtggc ggcgcgtcgg   12000
tagaaaacga aagtacgccc gcagtggcgg cggacgctgc ggaggtcgag ccggaggcca   12060
tgcagcagga cgcagaggag ggcgcacagg agggcgcgca gaaggacatg aacgatgggg   12120
agatcagggg agacacattc gccacccggg gcgaagaaaa agaggcagag gcggcggcgg   12180
cggcgacggc ggaggccgaa accgaggttg aggcagaggc agagcccgag accgaagtta   12240
tggaagacat gaatgatgga gaacgtaggg gcgacacgtt cgccacccgg ggcgaagaga   12300
aggcggcgga ggcagaagcc gcggctgagg aggcggctgc ggctgcggcc aagactgagg   12360
ctgcggctaa ggctgaggtc gaagccaatg ttgcggttga ggctcaggct gaggaggagg   12420
cggcggctga agcagttaag gaaaaggccc aggcagagca ggaagagaaa aaacctgtca   12480
ttcaacctct aaaagaagat agcaaaaagc gcagttacaa cgtcatcgag ggcagcacct   12540
ttacccagta ccgcagctgg tacctggcgt acaactacgg cgaccggtc aaggggtgc     12600 gctcgtggac cctgctctgc acgccggacg tcacctgcgg ctccgagcag atgtactggt   12660
cgctgccgaa catgatgcaa gacccggtga ccttccgctc cacgcggcag gttagcaact   12720 tccccggtgggt gggcgccgaa ctgctgcccg tgcactccaa gagttttta acgagcagg    12780 ccgtctactc ccagctgatc cgccaggcca cctctctgac ccacgtgttc aatcgctttc   12840
```

```
ccgagaacca gattttggcg cgcccgccgg cccccaccat caccaccgtg agtgaaaacg   12900
ttcctgccct cacagatcac gggacgctac cgctgcgcaa cagcatctca ggagtccagc   12960
gagtgaccat tactgacgcc agacgccgga cctgcccta cgtttacaag gccttgggca    13020
tagtctcgcc gcgcgtcctc tccagtcgca ctttttaaaa cacatctacc cacacgttcc   13080
aaaatcatgt ccgtactcat ctcacccagc aacaacaccg ctgggggct gcgcgcgccc    13140 agcaagatgt ttggaggggc gaggaagcgc tccgaccagc accctgtgcg cgtgcgcggc   13200
cactaccgcg cgccctgggg agcgcacaag cgcgggcgca cagggcgcac cactgtggac   13260
gacgtcattg actccgtagt ggagcaagcg cgccactaca caccccggcgc gccgaccgcc   13320 cccgccgtgt ccaccgtgga ccaggcgatc gaaagcgtgg tacagggcgc gcggcactat   13380 gccaaccta aaagtcgccg ccgccgcgtg gccgccgcc atcgccggag accccgggcc     13440
accgccgccg cgcgccttac taaggctctg ctcaggcgcg ccaggcgaac tggccaccgg   13500
gccgccatga gggccgcacg gcgggctgcc gctgccgcaa gcgtcgtggc cccgcgggca   13560
cgaaggcgcg cggccgctgc cgccgccgcc gccatttcca gcttggcctc gacgcggcgc   13620
ggtaacatat actgggtgcg cgactcggta accggcacgc gggtacccgt gcgctttcgc   13680
cccccgcgga attagcacaa gacaacatac acactgagtc tcctgctgtt gtgtatccca   13740
gcggcgaccg tcagcagcgg cgacatgtcc aagcgcaaaa ttaaagaaga gatgctccag   13800
gtcatcgcgc cggagatcta tgggcccccg aagaaggagg aggatgatta caagcccgc    13860 aagctaaagc gggtcaaaaa gaaaagaaa gatgatgatg acgaggcggt ggagtttgtc    13920
cgccgcatgg cacccaggcg ccccgtgcag tggaagggcc ggcgcgtgca gcgcgttttg   13980
cgccccggca ccgcggtggt cttcacgccc ggcgagcgct ccacgcgcac tttcaagcgg   14040
gtgtacgatg aggtgtacgg cgacgaggac ctgttggagc aggccaacca gcgctttggg   14100
gagtttgcat atgggaaacg gccccgcgag agtctaaaag aggacctgct ggcgctaccg   14160
ctggacgagg gcaatcccac cccgagtctg aagccggtaa ccctgcaaca ggtgctgcct   14220
ttgagcgcgc ccagcgagca taagcgaggg ttgaagcgcg aaggcggga cctggcgccc    14280 accgtgcagt tgatggtgcc caagcggcag aagctggagg acgtgctgga gaaaatgaaa   14340
gtagagcccg ggatccagcc cgagatcaag gtccgcccca tcaagcaggt ggcgcccggc   14400
gtgggagtcc agaccgtgga cgttaggatt cccacggagg agatgaaac ccaaaccgcc    14460 actccctctt cggcggccag cgccaccacc ggcaccgctt cggtagaggt gcagacggac   14520
ccctggctac ccgccaccgc tgttgccgcc gccgccccc gttcgcgcgg gcgcaagaga    14580
aattatccag cggccagcgc gctcatgccc cagtacgcac tgcatccatc catcgtgccc   14640
acccccggct accgcgggta ctcgtaccgc ccgcgcagat cagccggcac tcgcggccgc   14700
cgccgccgtg cgaccacaac cagccgccgc cgtcgccgcc gccgccagcc agtgctgacc   14760
cccgtgtctg taaggaaggt ggctcgctcg gggagcacgc tggtggtgcc cagagcgcgc   14820
taccacccca gcatcgttta aagccggtct ctgtatggtt cttgcagata tggccctcac   14880
ttgtcgcctc cgcttccgg tgccgggata ccgaggaaga actcaccgcc gcagaggcat    14940
ggcgggcagc ggtctccgcg gcggccgtcg ccatcgccgg cgcgcaaaaa gcaggcgcat   15000
gcgcggcggt gtgctgcctc tgctaatccc gctaatcgcc gcggcgatcg gtgccgtacc   15060
cgggatcgcc tccgtggccc tgcaggcgtc ccagaaacgt tgactcttgc aaccttgcaa   15120
gcttgcattt tttggaggaa aaataaaaaa aagtctagac tctcacgctc gcttggtcct   15180
```

```
gtgactattt tgtagaaaaa aagatggaag acatcaactt tgcgtcgctg ccccgcgtc    15240 acggctcgcg cccgttcatg ggagactgga cagatatcgg caccagcaat atgagcggtg   15300
gcgccttcag ctggggcagt ctgtggagcg gccttaaaaa ttttggttcc accattaaga   15360
actatggcaa caaagcgtgg aacagcagca cgggccagat gctgagagac aagttgaaag   15420
agcagaactt ccaggagaag gtggcgcagg gcctggcctc tggcatcagc ggggtggtgg   15480
acatagctaa ccaggccgtg cagaaaaaga taaacagtca tctggacccc cgtcctcagg   15540
tggaggaaat gcctccagcg atggagacgg tgtctcccga gggcaaaggc gaaaagcgcc   15600
cgcggcccga cagagaagag accctggtgt cacacaccga ggagccgccc tcttacgagg   15660
aggcagtcaa ggccggcctg cccaccactc gccccatagc ccccatggcc accggtgtgg   15720
tgggccacag gcaacacact cccgcaacac tagatctgcc cccgccgtcc gagccgccgc   15780
gccagccaaa ggcggcgacg tgcccgctc cctccacttc cgccgccaac agagtgcccc    15840
tgcgccgcgc cgcgagcggc ccccgggcct cgcgagttag cggcaactgg cagagcacac   15900
tgaacagcat cgtgggcctg ggagtgagga gtgtgaagcg ccgccgttgc tactgaatga   15960
gcaagctagc taacgtgttg tatgtgtgta tgcgtcctat gtcgccgcca gaggagctgt   16020
tgagccgccg cgccgtctg cactccagcg aatttcaaga tggcgacccc atcgatgatg     16080
cctcagtggt cgtacatgca catctcgggc caggacgctt cggagtacct gagccccggg   16140
ctggtgcagt tcgcccgcgc cacagacacc tacttcaaca tgagtaacaa gttcaggaac   16200
cccactgtgg cgcccaccca cgatgtgacc acggaccggt cgcagcgcct gacgctgcgg   16260
ttcatccccg tggatcggga ggacaccgcc tactcttaca aggcgcggtt cacgctggcc   16320
gtgggcgaca accgcgtgct ggacatggcc tccacttact ttgacatcag gggggtgctg   16380
gacaggggcc ccaccttcaa gccctactcg ggtactgcct acaactccct ggcccccaag   16440
ggcgctccca attcttgcga gtgggaacaa gatgaaccag ctcaggcagc aatagctgaa   16500
gatgaagaag aacttgaaga agaacaagct caggacgaac aggcgcccac taagaaaacc   16560
catgtatacg cccaggcacc tctttctggt gaaaaaatta ctaaggatgg tttgcaaata   16620
ggtgtggatg ccacacaggc gggagataac cctatatatg ctgataaaac attccaaccc   16680
gaacctcaga taggtgagtc tcagtggaac gaggctgatg ccacagtagc aggaggcaga   16740
gtcttaaaaa agaccacccc tatgagacct tgctatggat cctatgccaa acctactaat   16800
gccaatggcg gtcaagggat catggtggcc aatgatcagg gagcgcttga atctaaagtt   16860
gagatgcaat ttttctccac cacaacgtct cttaatgtaa gggaaggtga aaacaatctt   16920
cagccaaaag tagtgctata cagcgaagat gttaacttgg aatcccctga cactcatttg   16980
tcttacaaac ctaaaaagga tgacaccaac tctaaaatca tgttgggtca gcaagccatg   17040
cccaacagac ccaacctcat tgcttttagg gacaactta ttggacttat gtactacaac     17100
agcacaggca acatgggagt gctggcagga caggcctccc agctaaacgc tgtggtagac   17160
ttgcaagaca gaaacacaga gctgtcatac caactgatgc ttgattccat ggagacagga   17220
tcaagatact tttccatgtg gaaccaggca gtggacagct atgacccaga tgtcagaatc   17280
attgaaaacc atgggggttga agatgagctg cccaactatt gctttcccct gggcggtatt   17340
ggaattacag acacatacca gtgcataaaa ccaaccgcag ctgctaataa cactacatgg   17400
tctaaggatg aagaatttag tgatcgcaat gaaatagggg tgggaaacaa cttcgccatg   17460
gagatcaaca tccaggccaa cctctggagg aacttcctct atgcgaacgt ggggctctac   17520
ctgccagaca agctcaagta caacccccacc aacgtggaca tctctgacaa ccccaacacc   17580
```

```
tatgactaca tgaacaagcg tgtggtggct cccggcctgg tggactgctt tgtcaatgtg   17640
ggagccaggt ggtccctgga ctacatggac aacgtcaacc ccttcaacca ccaccgcaat   17700
gcgggtctgc gctaccgctc catgatcctg ggcaacgggc gctacgtgcc cttccacatt   17760
caggtgcccc agaagttctt tgccatcaag aacctcctcc tcctgccggg ctcctacact   17820
tacgagtgga acttcaggaa ggatgtcaac atggtcctgc agagctctct gggcaatgac   17880
cttagggtgg acggggccag catcaagttt gacagcgtca ccctctatgc taccttcttc   17940
cccatggctc acaacaccgc ctccacgctc gaggccatgc tgaggaacga caccaacgac   18000
cagtccttca tgactacct ctctgggcc aacatgctct accccatccc cgccaaggcc   18060
accaacgtgc ccatctccat tccctctcgc aactgggccg ccttcagagg ctgggccttt   18120
acccgcctta agaccaagga aaccccctcc ctgggctcgg gttttgaccc ctactttgtc   18180
tactcgggat ccatccccta cctggatggc accttctacc tcaaccacac ttttaagaag   18240
atatccatca tgtatgactc ctccgtcagc tggccgggca atgaccgcct gctcaccccc   18300
aatgagttcg aggtcaagcg cgccgtggac ggcgagggct acaacgtggc ccagtgcaac   18360
atgaccaagg actggttcct ggtgcagatg ctggccaact acaacatagg ctaccagggc   18420
ttctacatcc agagagcta caaggacagg atgtactcct tcttcagaaa tttccaaccc   18480
atgagcaggc aggtggtgga cgagaccaaa tacaaggact atcaggccat tggcatcact   18540
caccagcaca acaactcggg attcgtgggc tacctggctc ccaccatgcg cgaggggcag   18600
gcctaccccg ccaacttccc ctacccgttg ataggcaaaa ccgcggtcga cagcgtcacc   18660
cagaaaaagt tcctctgcga ccgcaccctc tggcgcatcc ccttctctag caacttcatg   18720
tccatgggtg cgctcacgga cctgggccag aacctgctct atgccaactc cgcccatgcg   18780
ctggacatga cttttgaggt ggaccccatg gacgagccca cccttctcta tattgtgttt   18840
gaagtgttcg acgtggtcag agtgcaccag ccgcaccgcg tgtcatcga gaccgtgtac   18900 ctgcgcacgc ccttctcggc cggcaacgcc accacctaag agacagcgc cgccgcctgc   18960 atgacgggtt ccaccgagca agagctcagg gccatcgcca gagacctggg atgcggaccc   19020
tattttttgg gcacctatga caaacgcttc ccgggcttca tctcccgaga caagctcgcc   19080
tgcgccatcg tcaacacggc cgcgcgcgag accggggggcg tgcactggct ggcctttggc   19140 tgggaccccgc gctccaaaac ctgctacctc ttcgacccct ttggcttctc cgatcagcgc   19200
ctcagacaga tctatgagtt tgagtacgag gggctgctgc ccgcagcgc gcttgcctcc   19260 tcgcccgacc gctgcatcac ccttgagaag tccaccgaga ccgtgcaggg gccccactcg   19320
gccgcctgcg gtctcttctg ctgcatgttt ttgcacgcct ttgtgcgctg gccccagagt   19380
cccatggatc gcaaccccac catgaacttg ctcaaggag tgcccaacgc catgctccag   19440
agcccccagg tccagcccac cctgcgccac aaccaggaac agctctaccg cttcctggag   19500
cgccactccc cctacttccg cagtcacagc gcgcacatcc gggggccac tctctttctgc   19560 cacttgcaag aaaacatgca agacggaaaa tgatgtacag ctcgcttttt aataaatgta   19620
aagactgtgc actttatta tacacggggct cttttctggtt atttattcaa caccgccgtc   19680
gccatctaga aatcgaaagg gttctgccgc gcgtcgccgt gcgccacggg cagagacacg   19740
ttgcgatact ggaagcggct cgcccactta aactcgggca ccaccatgcg gggcagtggt   19800
tcctcgggga agttctcgcc ccacagggtg cgggtcagct gcagcgcgct caggaggtcg   19860
ggagccgaga tcttgaagtc gcagttgggg ccggaaccct gcgcgcgcga gttgcggtac   19920
```

```
acggggttgc agcactggaa caccagcagg gccggattat gcacgctggc cagcaggctc    19980
tcgtcgctga tcatgtcgct gtccagatcc tccgcgttgc tcagggcgaa cggggtcatc    20040
ttgcagacct gcctgcccag gaaaggcggc agcccgggct tgccgttgca gtcgcagcgc    20100
aggggcatca gcaggtgccc gcggcccgac tgccgctgcg ggtacagcgc gcgcatgaag    20160
gcttcgatct gcctgaaagc cacctgcgtc ttggctccct ccgaaaagaa catcccacag    20220
gacttgctgg agaactggtt cgcgggacag ctggcatcgt gcaggcagca gcgcgcgtcg    20280
gtgttggcga tctgcaccac gttgcgaccc caccggttct tcactatctt ggccttggaa    20340
gcctgctcct tcagcgcgcg ctggccgttc tcgctggtca catccatctc tatcacctgc    20400
tccttgttga tcatgtttgt accgtgcaga cacttcaggt cgccctccgt ctgggtgcag    20460
cggtgctccc acagcgcgca accggtgggc tcccaatttt tgtgggtcac ccccgcgtag    20520
gcctgcaggt aggcctgcaa gaagcgcccc atcatggcca caaaggtctt ctggctcgta    20580
aaggtcagct gcaggccgcg atgctcttcg ttcagccagg tcttgcagat ggcggccagc    20640
gcctcggtct gctcgggcag catcctaaaa tttgtcttca ggtcgttatc cacgtggtac    20700
ttgtccatca tggcgcgcgc cgcctccatg cccttctccc aggcggacac catgggcagg    20760
cttagggggt ttatcacttc caccggcgag gacaccgtac tttcgatttc ttcttcctcc    20820
ccctcttccc ggcgcgcgcc cacgctgctg cgcgctctca ccgcctgcac caaggggtcg    20880
tcttcaggca agcgccgcac cgagcgcttg ccgcccttga cctgcttaat cagcaccggc    20940
gggttgctga agcccaccat ggtcagcgcc gcctgctctt cttcgtcttc gctgtctacc    21000
actatctctg gggaagggct tctccgctct gcggcggcgc gcttctttttt tttcttggga    21060
gcggccgtga tggagtccgc cacggcgacg gaggtcgagg gcgtggggct gggggtgcgc    21120
ggtaccaggg cctcgtcgcc ctcggactct tcctctgact ccaggcggcg gcggagtcgc    21180
ttctttgggg gcgcgcgcgt cagcggcggc ggagacgggg acggggacgg ggacgggacg    21240
ccctccacag ggggtggtct tcgcgcagac ccgcggccgc gctcgggggt cttctcgagc    21300
tggtcttggt cccgactggc cattgtatcc tcctcctcct aggcagagag acataaggag    21360
tctatcatgc aagtcgagaa ggaggagagc ttaaccaccc cctctgagac cgccgatgcg    21420
cccgccgtcg ccgtcgcccc cgctgccgcc gacgcgcccg ccacaccgag cgacaccccc    21480
gcggacccccc ccgccgacgc acccctgttc gaggaagcgg ccgtggagca ggacccgggc    21540
tttgtctcgg cagaggagga tttgcgagag gaggaggata aggagaagaa gccctcagtg    21600
ccaaaagatg ataaagagca agacgagcac gacgcagatg cacaccaggg tgaagtcggg    21660
cgggggacg gagggcatga cggcgccgac tacctagacg aagggaacga cgtgctcttg    21720
aagcacctgc atcgtcagtg cgccattgtt tgcgacgctc tgcaggagcg cagcgaagtg    21780
cccctcagcg tggcggaggt cagccacgcc tacgagctca gcctcttctc cccccgggtg    21840
ccccccccgcc gccgcgaaaa cggcacatgc gagcccaacc cgcgcctcaa cttctacccc    21900
gcctttgtgg tacccgaggt cctggccacc tatcacatct tctttcaaaa ttgcaagatc    21960
cccctctcgt gccgcgccaa ccgtagccgc gccgataaga tgctggccct gcgccagggc    22020
gaccacatac ctgatatcgc cgcttttggaa gatgtaccaa agatcttcga gggtctgggt    22080
cgcaacgaga agcgggcagc aaactctctg caacaggaaa acagcgaaaa tgagagtcac    22140
accggggtac tggtggagct cgagggcgac aacgcccgcc tggcggtggt caagcgcagc    22200
atcgaggtca cccactttgc ctaccccgcg ctaaacctgc cccccaaagt catgaacgcg    22260
gccatggacg ggctgatcat gcgccgcggc cggcccctcg ctccagatgc aaacttgcat    22320
```

```
gaggagaccg aggacggcca gcccgtggtc agcgacgagc agctggcgcg ctggctggag    22380
accgcggacc ccgccgaact ggaggagcgg cgcaagatga tgatggccgt ggtgctggtc    22440
accgtagagc tggagtgtct gcagcgcttc ttcggcgacc ccgagatgca gagaaaggtc    22500
gaggagaccc tgcactacac cttccgccag ggctacgtgc gccaggcttg caagatctcc    22560
aacgtggagc tcagcaacct ggtgtcctac ctgggcatct tgcatgagaa ccgcctcggg    22620
cagagcgtgc tgcactccac cctgcgcggg gaggcgcgcc gcgactacgt gcgcgactgc    22680
gtttacctct tcctctgcta cacctggcag acggccatgg gggtctggca gcagtgcctg    22740
gaggagcgca acctcaagga gctggagaag ctcctgcagc gcgcgctcaa agatctctgg    22800
acgggctaca acgagcgctc ggtggccgcc gcgctggccg acctcatctt ccccgagcgc    22860
ctgctcaaaa ccctccagca ggggctgccc gacttcacca gccaaagcat gttgcaaaac    22920
ttcaggaact ttatcctgga gcgttctggc atcctacccg ccacctgctg cgccctgccc    22980
agcgactttg tccccctcgt gtaccgcgag tgccccccgc cgctgtgggg tcactgctac    23040
ctgttccaac tggccaacta cctgtcctac cacgcggacc tcatggagga ctccagcggc    23100
gaggggctca tggagtgcca ctgccgctgc aacctctgca cgccccaccg ctccctggtc    23160
tgcaacaccc aactgctcag cgagagtcag attatcggta ccttcgagct acagggtccg    23220
tcctcctcag acgagaagtc cgcggctccg gggctaaaac tcactccggg gctgtggact    23280
tccgcctacc tgcgcaaatt tgtacctgaa gactaccacg cccacgagat caggttttac    23340
gaagaccaat cccgcccgcc caaggcgagc ctgaccgcct gcgtcatcac ccagggcgag    23400
atcctaggcc aattgcaagc catccaaaaa gcccgccaag actttttgct gaagaagggt    23460
cggggggtgt atctggaccc ccagtcgggt gaggagctca acccggttcc cccgctgccg    23520
ccgccgcggg accttgcttc ccaggataag catcgccatg ctcccagaa agaagcagca    23580 gcggccgcca ctgccgccac cccacatgct ggaggaagag gaggaatact gggacagtca    23640
ggcagaggag gtttcggacg aggaggagcc ggagacggag atggaagagt gggaggagga    23700
cagcttagac gaggaggctt ccgaagccga agaggcagac gcaacaccgt caccctcggc    23760
cgcagccccc tcgcaggcgc ccccgaagtc cgctcccagc atcagcagca acagcagcgc    23820
tataacctcc gctcctccac cgccgcgacc cacggccgac cgcagaccca accgtagatg    23880
ggacaccacc ggaaccgggg ccggtaagtc ctccgggaga ggcaagcaag cgcagcgcca    23940
aggctaccgc tcgtggcgcg ctcacaagaa cgccatagtc gcttgcttgc aagactgcgg    24000
ggggaacatc tccttcgccc gccgcttcct gctcttccac cacggtgtgg ccttcccccg    24060
taacgtcctg cattactacc gtcatctcta cagcccctac tgcggcggca gtgagccaga    24120
gacggtcggc ggcggcggcg gcgccgcttt cggcgcctag gaagaccag ggcaagactt    24180 cagccaagaa actcgcggcg gccgcggcga acgcggtcgc ggggccctg cgcctgacgg    24240 tgaacgaacc cctgtcgacc cgcgaactga ggaaccgaat cttccccact ctctatgcca    24300
tcttccagca gagcagaggg caggatcagg aactgaaagt aaaaaacagg tctctgcgct    24360
ccctcacccg cagctgtctg tatcacaaga gcgaagacca gcttcggcgc acgctggagg    24420
acgctgaggc actcttcagc aaatactgcg cgctcactct taaggactag ctccgcgccc    24480
ttctcgaatt taggcgggaa cgcctacgtc atcgcagcgc cgccgtcatg agcaaggaca    24540
ttcccacgcc atacatgtgg agctatcagc cgcagatggg actcgcggcg ggcgcctccc    24600
aagactactc cacccgcatg aactggctca gtgccggccc acacatgatc tcacaggtta    24660
```

| | |
|---|---|
| atgatatccg cacccatcga aaccaaatat tggtggagca ggcggcaatt accaccacgc | 24720 |
| cccgcaataa tcccaacccc agggagtggc ccgcgtccct ggtgtatcag gaaattcccg | 24780 |
| gccccaccac cgtactactt ccgcgtgatt cccaggccga agtccaaatg actaactcag | 24840 |
| gggcacagct cgcgggcggc tgtcgtcaca gggtgcggcc tcctcgccag gtataactc | 24900 |
| acctggagat ccgaggcaga ggtattcagc tcaacgacga gtcggtgagc tcctcgctcg | 24960 |
| gtctcagacc tgacgggacc ttccagatag ccggagccgg ccgatcttcc ttcacgcccc | 25020 |
| gccaggcgta cctgactctg caaagctcgt cctcggcgcc gcgctcgggc ggcatcggga | 25080 |
| ctctccagtt cgtgcaggag tttgtgccct cggtctactt caaccccttc tcgggctctc | 25140 |
| ccggtcgcta cccggaccag ttcatctcga actttgacgc cgcgagggac tcggtggacg | 25200 |
| gctacgactg aatgtcgggt ggacccggtg cagagcaact tcgcctgaag cacctcgacc | 25260 |
| actgccgccg ccctcagtgc tttgcccgct gtcagaccgg tgagttccag tacttttccc | 25320 |
| tgcccgactc gcaccggac ggccggcgc acggggtgcg cttttcatc ccgagtcagg | 25380 |
| tgcgctctac cctaatcagg gagtttaccg cccgtcccct actggcggag ttggaaaagg | 25440 |
| ggccttctat cctaaccatt gcctgcatct gctctaaccc tggattgcac caagatcttt | 25500 |
| gctgtcattt gtgtgctgag tataataaag gctgagatca gaatctactc gggctcctgt | 25560 |
| cgccatcctg tcaacgccac cgtccaagcc cggcccgatc agcccgaggt gaacctcacc | 25620 |
| tgcggtctgc accggcgcct gaggaaatac ctagcttggt actacaacag cactcccttt | 25680 |
| gtggtttaca acagctttga ccaggacggg gtctcactga gggataaacct ctcgaacctg | 25740 |
| agctactcca tcaggaagaa cagcaccctc gagctacttc ctccttacct gcccgggact | 25800 |
| taccagtgtg tcaccggtcc ctgcacccac acccacctgt tgatcgtaaa cgactctctt | 25860 |
| ccgagaacag acctcaataa ctcctcttcg cagttcccca gaacaggagg tgagctcagg | 25920 |
| aaaccccggg taaagaaggg tggacgagag ttaacacttg tgggggtttct ggtgtatgtg | 25980 |
| acgctggtgt tggctctttt gattaaggct tttccttcca tgtctgaact ctccctcttc | 26040 |
| ttttatgaac aactcgacta gtgctaacgg gaccctaccc aacgaatcgg gattgaatat | 26100 |
| cggtaaccag gttgcagttt cacttttgat taccttcata gtcctcttcc tgctagtgct | 26160 |
| gtcgcttctg tgcctgcgga tcgggggctg ctgcatccac gtttatatct ggtgctggct | 26220 |
| gtttagaagg ttcggagacc atcgcaggta gaataaacat gctgctgctt accctctttg | 26280 |
| tcctggcgct ggccgccagc tgccaagcct tttccgaggc tgactttata gagccccagt | 26340 |
| gtaatgtgac ttttaaagcc catgcacagc gttgtcatac tataatcaaa tgtgccaccg | 26400 |
| aacacgatga ataccttatc cagtataaag ataaatcaca caaagtggca cttgttgaca | 26460 |
| tctggaaacc cgaagaccct ttggaataca atgtgaccgt tttccagggt gacctcttca | 26520 |
| aaatttacaa ttacactttc ccatttgacc agatgtgtga ctttgtcatg tacatggaaa | 26580 |
| agcagcacaa gctgtggcct ccgactcccc agggctgtgt ggaaaatcca ggctctttct | 26640 |
| gcatgatctc tctctgtgta actgtgctgg cactaatact cacgcttttg tatatcagat | 26700 |
| ttaaatcaag gcaaagcttc attgatgaaa agaaaatgcc ttaatcgctt tcacgcttga | 26760 |
| ttgctaacac cgggttttta tccgcagaat gattggaatc accctactaa tcacctccct | 26820 |
| ccttgcgatt gcccatgggt tggaacgaat cgaagtccct gtgggggcca atgttaccct | 26880 |
| ggtggggcct gtcggcaatg ctacattaat gtgggaaaaa tatactaaaa atcaatgggt | 26940 |
| ctcttactgc actaacaaaa atagccacaa gcccagagcc atctgcgatg gcaaaatct | 27000 |
| aaccttgatt gatgttcaat tgctggatgc gggctactat tatgggcagc tgggtacaat | 27060 |

```
gattaattac tggagacccc acagagatta catgctccac gtagtaaagg gtcccttag   27120 cagcccaccc actaccacct ctactacccc cactaccacc actactccca ccaccagcac   27180
tgccgcccag cctcctcata gcagaacaac cacttttatc aattccaagt cccactcccc   27240
ccacattgcc ggcgggccct ccgcctcaga ctccgaaacc accgagatct gcttctgcaa   27300
atgctctgac gccattgccc aggatttgga agatcacgag gaagatgagc atgacttcgc   27360
agatgcatgc caggcatcag agccagaagc gctgccggtg gccctcaaac agtatgcaga   27420
cccccacacc accccgacc ttcctccacc ttcccagaag ccaagtttcc tgggggaaaa   27480
tgaaactctg cctctctcca tactcgctct gacatctgtt gctatgttga ccgctctgct   27540
ggtgcttcta tgctctatat gctacctgat ctgctgcaga agaaaaaat ctcacggcca   27600 tgctcaccag cccctcatgc acttccctta ccctccagag ctgggcgacc acaaacttta   27660
agtctgcagt aactatctgc ccatcccttg tcagtcgaca gcgatgagcc ccactaatct   27720
aacggcctct ggacttacaa catcgtctct taatgagacc accgctcctc aagacctgta   27780
cgatggtgtc tccgcgctgg ttaaccagtg ggatcacctg gcatatggt ggctcctcat   27840 aggagcagtg accctgtgcc taatcctggt ctggatcatc tgctgcatca aaagcagaag   27900
acccaggcgg cggcccatct acaggccctt tgtcatcaca cctgaagatg atgatgacac   27960
cacttccagg ctgcagaggc taaagcagct actcttctct tttacagcat ggtaaattga   28020
atcatgcctc gcatttcat ctacttgtct ctccttccac tttttctggg ctcttctaca   28080
ttggccgctg tgtcccacat cgaggtagac tgcctcacgc ccttcacagt ctacctgctt   28140
ttcggctttg tcatctgcac ctttgtctgc agcgttatca ctgtagtgat ctgcttcata   28200
cagtgcatcg actacgtctg cgtgcgggtg gcttacttta gacaccaccc ccagtatcgc   28260
aacagggaca tagcggctct cctaagactt gtttaaaatc atggccaaat taactgtgat   28320
tggtcttctg atcatctgct gcgtcctagc cgcgattggg actcaagctc ctaccaccac   28380
cagcgctccc agaaagagac atgtatcctg cagcttcaag cgtccctgga atataccca   28440 atgctttact gatgaacctg aaatctcttt ggcttggtac ttcagcgtca ccgcccttct   28500
tatcttctgc agtacggtta ttgcccttgc catctacct tcccttgacc tgggctggaa   28560
tgctgtcaac tctatggaat atcccacctt cccagaacca gacctgccag acctggttgt   28620
tctaaacgcg tttcctcctc ctgctcccgt tcaaaatcag tttcgccctc cgtccccac   28680 gcccactgag gtcagctact taatctaac aggcggagat gactgaaaac ctagacctag   28740
aaatggacgt tctctgcagc gagcaacgca cactagagag gcgccggcaa aaagagctcg   28800
agcgtcttaa acaagagctc caagacgcgg tggccataca ccagtgcaaa aaaggtgtct   28860
tctgtctggt aaaacaggcc acgctcacct atgaaaaaac aggtgacacc caccgcctag   28920
gatacaagct gcccacacag cgccaaaagt tcgccctcat gataggcgaa caacccatca   28980
ccgtgaccca gcactccgtg gagacagaag gctgcataca tgctccctgt aggggcgctg   29040
actgcctcta caccttgatc aaaaaccctct gcggtctcag agaccttatc cctttcaatt   29100
aatcataact gtaatcaata aaaaatcact tacttgaaat ctgatagcaa gcctctgtcc   29160
aattttttca gcaacacttc cttcccctcc tcccaactct ggtactctag gcgcctccta   29220
gctgcaaact tcctccacag tctgaaggga atgtcagatt cctcctcctg tccctccgca   29280
cccacgatct tcatgttgtt gcagatgaaa gcgcgcgagat cgtctgacga gaccttcaac   29340
cccgtgtacc cctacgatac cgagatcgct ccgacttctg tccctttcct tacccctccc   29400
```

```
tttgtgtcat ccgcaggaat gcaagaaaat ccagctgggg tgctgtccct gcacttgtca   29460
gagcccctta ccacccacaa tggggccctg actctaaaaa tgggggggcgg cctgaccctg   29520
gacaaggaag ggaatctcac ttcccaaaac atcaccagtg tcgatccccc tctcaaaaaa   29580
agcaagaaca acatcagcct tcagaccgcc gcaccctcg ccgtcagctc cggggccta    29640
acactttttg ccactccccc cctagcggtc agtggtgaca accttactgt gcagtctcag   29700
gcccctctca ctttggaaga ctcaaaacta actctggcca ccaaaggacc cctaactgtg   29760
tccgaaggca aacttgtcct agaaacagag gctcccctgc atgcaagtga cagcagcagc   29820
ctgggcctta gcgttacggc cccacttagc attaacaatg acagcctagg actagatctg   29880
caggcaccca ttgtctctca aaatggaaaa ctggctctaa atgtagcagg ccccctagct   29940
gtggccaatg gcattaatgc tttgacagta ggcacaggca aaggtattgg tctaaatgaa   30000
accagcactc acttgcaagc aaagttggtc gccccctag gctttgatac caatggcaac   30060
attaagctaa gcgttgcagg aggcatgaga ctaaataatg acacacttat actagatgta   30120
aactacccat ttgaagctca aggccaacta agtctaagag tgggccaggg tccgctgtat   30180
gtagattcta gcagccataa cctgaccatt agatgcctta gaggattata cataacatcg   30240
tctaataacc aaaccggtct agaggccaac ataaaactaa caaaaggcct tgtctatgat   30300
ggaaatgcca tagcagtcaa tgttggtcaa ggattgcaat acagcactac tgccacatcg   30360
gaaggtgtgt atcctataca gtctaagata ggtttgggaa tggaatatga taccaacgga   30420
gccatgatga caaaactagg ctctggacta agctttgaca attcaggagc cattgtagtg   30480
ggaaacaaaa atgatgacag gcttactctg tggactacac cagacccatc tcctaactgt   30540
agaatttatt ctgaaaaaga tactaaaacta accttggtgc tgactaagtg tggcagccaa   30600
atcctaggca cagtatctgc ccttgctgtc agaggcagcc ttgcgcccat cactaatgca   30660
tccagcatag tccaaatatt tctaagattt gatgaaaatg gactattgat gagcaactca   30720
tcgctagacg gtgattactg gaattacaga aatggggact ccactaatag cacaccatat   30780
acaaatgcag taggctttat gcctaatcta gcagcctatc ctaaaggtca ggctacagct   30840
gcaaaaagca gtattgtaag ccaggtatac atggatggtg acactactaa acctataaca   30900
ctaaaaataa acttcaatgg cattgatgaa acaacagaaa ataccctgt tagtaaatat    30960
tccatgacat tctcatggag ctggcccacc gcaagctaca taggccacac ttttgcaaca   31020
aactctttta ctttctccta catcgcccaa gaataaagaa agcacagaga tgcttgtttt   31080
gatttcaaaa ttgtgtgctt ttatttattt tcagcttaca gtatttccag tagtcattcg   31140
aataaagctt aatcaaactg catgagaacc cttccacata gcttaaatta gcaccagtgc   31200
aaatggagaa aagcctcgag gtcgttgcgc ggccgggatc ggtgatcacc gatccagaca   31260
tgataagata cattgatgag tttggacaaa ccacaactag aatgcagtga aaaaaatgct   31320
ttatttgtga aatttgtgat gctattgctt tatttgtaac cattataagc tgcaataaac   31380
aagttcccgg atcgcgatcc ggcccgaggc tgtagccgac gatggtgcgc caggagagtt   31440
gttgattcat tgtttgcctc cctgctgcgg ttttcaccg aagttcatgc cagtccagcg    31500
tttttgcagc agaaaagccg ccgacttcgg tttgcggtcg cgagtgaaga tcccttcctt    31560
gttaccgcca acgcgcaata tgccttgcga ggtcgcaaaa tcggcgaaat tccatacctg   31620
ttcaccgacg acggcgctga cgcgatcaaa gacgcggtga tacatatcca gccatgcaca   31680
ctgatactct tcactccaca tgtcggtgta cattgagtgc agcccggcta acgtatccac   31740
gccgtattcg gtgatgataa tcggctgatg cagtttctcc tgccaggcca gaagttcttt    31800
```

```
ttccagtacc ttctctgccg tttccaaatc gccgctttgg acataccatc cgtaataacg    31860
gttcaggcac agcacatcaa agagatcgct gatggtatcg gtgtgagcgt cgcagaacat    31920
tacattgacg caggtgatcg gacgcgtcgg gtcgagttta cgcgttgctt ccgccagtgg    31980
cgcgaaatat tcccgtgcac cttgcggacg ggtatccggt tcgttggcaa tactccacat    32040
caccacgctt gggtggtttt tgtcacgcgc tatcagctct ttaatcgcct gtaagtgcgc    32100
ttgctgagtt tccccgttga ctgcctcttc gctgtacagt tctttcggct tgttgcccgc    32160
ttcgaaacca atgcctaaag agaggttaaa gccgacagca gcagtttcat caatcaccac    32220
gatgccatgt tcatctgccc agtcgagcat ctcttcagcg taagggtaat gcgaggtacg    32280
gtaggagttg gccccaatcc agtccattaa tgcgtggtcg tgcaccatca gcacgttatc    32340
gaatcctttg ccacgcaagt ccgcatcttc atgacgacca aagccagtaa agtagaacgg    32400
tttgtggtta atcaggaact gttcgccctt cactgccact gaccggatgc cgacgcgaag    32460
cgggtagata tcacactctg tctggctttt ggctgtgacg cacagttcat agagataacc    32520
ttcacccggt tgccagaggt gcggattcac cacttgcaaa gtcccgctag tgccttgtcc    32580
agttgcaacc acctgttgat ccgcatcacg cagttcaacg ctgacatcac cattggccac    32640
cacctgccag tcaacagacg cgtggttaca gtcttgcgcg acatgcgtca ccacggtgat    32700
atcgtccacc caggtgttcg gcgtggtgta gagcattacg ctgcgatgga ttccggcata    32760
gttaaagaaa tcatggaagt aagactgctt tttcttgccg ttttcgtcgg taatcaccat    32820
tcccggcggg atagtctgcc agttcagttc gttgttcaca caaacggtga tacgtacact    32880
tttcccggca ataacatacg gcgtgacatc ggcttcaaat ggcgtatagc cgccctgatg    32940
ctccatcact tcctgattat tgacccacac tttgccgtaa tgagtgaccg catcgaaacg    33000
cagcacgata cgctggcctg cccaaccttt cggtataaag acttcgcgct gataccagac    33060
gttgcccgca taattacgaa tatctgcatc ggcgaactga tcgttaaaac tgcctggcac    33120
agcaattgcc cggctttctt gtaacgcgct ttcccaccaa cgctgatcaa ttccacagtt    33180
ttcgcgatcc agactgaatg cccacaggcc gtcgagtttt ttgatttcac gggttggggt    33240
ttctacagga cggaccatgc gttcgacctt tctcttcttt tttgggccca tgatggcaga    33300
tccgtatagt gagtcgtatt agctggttct ttccgcctca gaagccatag agcccaccgc    33360
atccccagca tgcctgctat tgtcttccca atcctccccc ttgctgtcct gccccacccc    33420
accccccaga atagaatgac acctactcag acaatgcgat gcaatttcct cattttatta    33480
ggaaaggaca gtgggagtgg caccttccag ggtcaaggaa ggcacggggg agggcaaac    33540 aacagatggc tggcaactag aaggcacagt cgaggctgat cagcgagctc tagatgcatg    33600
ctcgagcggc cgcacgtcgt accggcaatt gccgcggcaa ttgccgacgc cgcgtaacta    33660
taacggtcct aaggtagcga gagggccaag tgccgaacga gtatatatag gaataaaaaa    33720
tgacgtaaat gtgtaaaggt cagaaaacgc ccagaaaaat acacagacca acgcccgaaa    33780
cgaaaacccg cgaaaaaata cccagaactt cctcaacaac cgccacttcc ggtttctcac    33840
ggtacgtcac ttccgcaaga aaagcaaaac tacatttccc acatgtgtaa aaacgaaacc    33900 ccgcccttg taactgccca caacttacat catcaaaaca taaactccta cgtcacccgc    33960
cccgcctctc cccgcccacc tcattatcat attggccaca atccaaaata aggtatatta    34020
ttgatgatg                                                            34029
```